United States Patent
Beauprez et al.

(10) Patent No.: US 10,858,684 B2
(45) Date of Patent: Dec. 8, 2020

(54) MUTANT MICROORGANISMS RESISTANT TO LACTOSE KILLING

(71) Applicant: Inbiose N.V., Zwijnaarde (BE)

(72) Inventors: Joeri Beauprez, Bredene (BE); Sofie De Maeseneire, Destelbergen (BE); Eric Timmermans, Ghent (BE)

(73) Assignee: INBIOSE N.V., Zwijnaarde (BE)

( * ) Notice: Subject to any disclaimer, the term of this patent is extended or adjusted under 35 U.S.C. 154(b) by 203 days.

(21) Appl. No.: 15/505,809

(22) PCT Filed: Nov. 12, 2015

(86) PCT No.: PCT/EP2015/076449
§ 371 (c)(1),
(2) Date: Feb. 22, 2017

(87) PCT Pub. No.: WO2016/075243
PCT Pub. Date: May 19, 2016

(65) Prior Publication Data
US 2018/0066294 A1    Mar. 8, 2018

(30) Foreign Application Priority Data
Nov. 14, 2014    (EP) .................... 14193151

(51) Int. Cl.
| | | |
|---|---|---|
| *C12P 19/12* | (2006.01) | |
| *C07K 14/245* | (2006.01) | |
| *C12N 15/52* | (2006.01) | |
| *C12N 15/10* | (2006.01) | |
| *C12N 15/81* | (2006.01) | |

(52) U.S. Cl.
CPC ............ *C12P 19/12* (2013.01); *C07K 14/245* (2013.01); *C12N 15/10* (2013.01); *C12N 15/81* (2013.01)

(58) Field of Classification Search
None
See application file for complete search history.

(56) References Cited

U.S. PATENT DOCUMENTS 5,858,752 A    1/1999    Seed et al.

FOREIGN PATENT DOCUMENTS

| WO | 2012/112777 A2 | 8/2012 |
| WO | 2013/087884 A1 | 6/2013 |

OTHER PUBLICATIONS

Aerts et al. (2010) "A constitutive expression system for high throughput screening," Engineering in Life Sciences. 11(1):10-19.
Alper et al. (2005) "Tuning genetic control through promoter engineering," Proc. Natl. Acad. Sci. USA. 102(36):12678-12683.
Beauprez (2010) "Metabolic modelling and engineering of *Escherichia coil* for succinate production," Ph.D. Dissertation. Ghent University. Ghent, Belgium.
Blazeck et al. (May 17, 2012) "Controlling promoter strength and regulation in *Saccharomyces cerevisiae* using synthetic hybrid promoters," Biotechnology and Bioengineering 109:2884-2895.
Blount et al. (Mar. 19, 2012) "Rational Diversification of a Promoter Providing Fine-Tuned Expression and Orthogonal Regulation for Synthetic Biology," PLoS ONE. 7:e33279. pp. 1-11.
Bode (2006) "Recent Advances on Structure, Metabolism, and Function of Human Milk Oligosaccharides," The Journal of Nutrition 136:2127-2130.
Bode (Apr. 18, 2012) "Human milk oligosaccharides: Every baby needs a sugar mama," Glycobiology 22:1147-1162.
Cabantous et al. (2005) "Protein tagging and detection with engineered self-assembling fragments of green fluorescent protein," Nat Biotech 23:102-107.
Canton et al. (2008) "Refinement and standardization of synthetic biological parts and devices," Nat Biotech 26:787-793.
Chen et al. (2009) "Advances in the Biology and Chemistry of Sialic Acids," ACS Chemical Biology 5:163-176.
Coussement et al. (Mar. 2, 2014) "One step DNA assembly for combinatorial metabolic engineering," Metabolic Engineering 23:70-77.
Curran et al. (Jul. 12, 2013) "Use of expression-enhancing terminators in *Saccharomyces cerevisiae* to increase mRNA half-life and improve gene expression control for metabolic engineering applications," Metabolic Engineering 19:88-97.
Davis (1997) "Biomedical applications of nanotechnology—implications for drug targeting and gene therapy," Trends in Biotechnology 15:217-224.
De Mey et al. (2007) "Construction and model-based analysis of a promoter library for *E. coli*: an indispensable tool for metabolic engineering," BMC Biotechnology 7:34-48.
Drozdikova et al. (May 10, 2015) "Production of squalene by lactose-fermenting yeast *Kluyveromyces lactis* with reduced squalene epoxidase activity," Letters in Applied Microbiology 61:77-84.
Dumon et al. (2001) "In vivo fucosylation of lactoN-neotetraose and lactoN-neohexaose by heterologous expression of Helicobacter pylori a-1,3 fucosyltransferase in engineered *Escherichia coli*," Glycoconjugate Journal 18:465-474.
Dykhuizen et al. (1978) "Transport by the lactose permease of *Escherichia coli* as the basis of lactose killing," Journal of Bacteriology 135:876-882.
Eames et al. (May 18, 2012) "Cost-Benefit Tradeoffs in Engineered lac Operons," Science. 336(6083):911-915.
Filonov et al. (Oct. 22, 2014) "Broccoli: Rapid Selection of an RNA Mimic of Green Fluorescent Protein by Fluorescence-Based Selection and Directed Evolution," Journal of the American Chemical Society. 136(46):16299-16308.

(Continued)

*Primary Examiner* — Channing S Mahatan
(74) *Attorney, Agent, or Firm* — Lathrop GPM LLP; James H. Velema, Esq.

(57) ABSTRACT

The present invention relates to a method to produce mutated microorganisms which resist the phenomenon of lactose killing and to the microorganisms obtainable via said method. Such engineered microorganisms can be applied for the production of specialty products, such as but not limited to specialty carbohydrates, glycolipids and galactosylated compounds.

35 Claims, 68 Drawing Sheets
Specification includes a Sequence Listing.

(56) References Cited

OTHER PUBLICATIONS

Ghazi et al. (1983) "Comparison of lactose uptake in resting and energized *Escherichia coli* cells: high rates of respiration inactivate the lac carrier," Journal of Bacteriology 154:92-103.
Hammer et al. (2006) "Synthetic promoter libraries—tuning of gene expression," Trends in Biotechnology 24:53-55.
Koizumi et al. (1998) "Large-scale production of UDP-galactose and globotriose by coupling metabolically engineered bacteria," Nat Biotech 16:847-850.
Kojima et al. (2005) "Eukaryotic Translational Coupling in UAAUG Stop-Start Codons for the Bicistronic RNA Translation of the Non-Long Terminal Repeat Retrotransposon SART1," Molecular and Cellular Biology 25:7675-7686.
Levin-Karp et al. (Apr. 16, 2013) "Quantifying Translational Coupling in *E coli* Synthetic Operons Using RBS Modulation and Fluorescent Reporters," ACS Synthetic Biology 2:327-336.
Lodi et al. (2005) "Lactose-induced cell death of β-galactosidase mutants in Kluyveromyces lactis," FEMS Yeast Research. 5(8):727-734.
Mendez-Perez et al. (May 3, 2012) "A translation-coupling DNA cassette for monitoring protein translation in *Escherichia coil*," Metabolic Engineering 14:298-305.
Mutalik et al. (Mar. 10, 2013) "Precise and reliable gene expression via standard transcription and translation initiation elements," Nat Methods 10:354-360.—with supplementary information.
Nakamura et al. (2000) "Codon usage tabulated from international DNA sequence databases: status for the year 2000," Nucleic Acids Research 28:292.
Pechmann et al. (Dec. 23, 2012) "Evolutionary conservation of codon optimality reveals hidden signatures of cotranslational folding," Nat Struct Mol Biol 20:237-243.
Peijnenburg et al. (1990) "Translational coupling in a penP-lacZ gene fusion in Bacillus subtilis and *Escherichia coil*: Use of AUA as a restart codon," Mol Gen Genet. 221:267-272.

Pothoulakis et al. (Aug. 30, 2013) "The Spinach RNA Aptamer as a Characterization Tool for Synthetic Biology," ACS Synthetic Biology 3:182-187.
Rhodius et al. (Dec. 8, 2011) "Predicting the strength of UP-elements and full-length *E. coil* SigmaE promoters," Nucleic Acids Research 40:2907-2924.
Rubio-Texeira et al. (2006) "Endless versatility in the biotechnological applications of Kluyveromyces LAC genes," Biotechnology Advances. 24(2):212-225.
Salis et al. (2009) "Automated design of synthetic ribosome binding sites to control protein expression," Nat Biotech 27:946-950.
Supek (2010) "On Relevance of Codon Usage to Expression of Synthetic and Natural Genes in *Escherichia coli*," Genetics 185:1129-1134.
Timblin et al. (1984) "Lactose inhibits the growth of Rhizobium meliloti cells that contain an actively expressed *Escherichia coli* lactose operon," Journal of Bacteriology 158:1204-1207.
Varki (1992) "Diversity in the sialic acids," Glycobiology 2:25-40.
Waldo et al. (1999) "Rapid protein-folding assay using green fluorescent protein," Nat Biotech 17:691-695.
Welch et al. (2009) "Design Parameters to Control Synthetic Gene Expression in *Escherichia coli*," PLoS ONE 4:e7002. pp. 1-10.
Wilson et al. (1981) "Inhibition of growth of *Escherichia coli* by lactose and other galactosides," Biochimica et Biophysica Acta (BBA)—Biomembranes 649:377-384.
Yanase et al. (1988) "Fermentation of lactose by Zymomonas mobilis carrying a Lac+ recombinant plasmid," Journal of Fermentation Technology 66:409-415.
Zhou et al. (Mar. 7, 2013) "Non-optimal codon usage affects expression, structure and function of clock protein FRQ," Nature 495:111-115.
International Search Report with Written Opinion corresponding to International Patent Application No. PCT/EP2015/076449, dated Feb. 29, 2016.
Luong, J.H., "Kinetics of ethanol inhibition in alcohol fermentation", Biotechnology and Bioengineering, Mar. 1985 27(3): 280-5.
Mathews, et al., "The Lactose Operon: Early Evidence for Transcriptional Control of Gene Expression," Biochemistry 2nd Ed., the Benjamin/Cummings Publishing Co, Inc., 1996, pp. 973-991.

Sequence of the lactose permease gene with a mutant promoter and untranslated region AGCGCAACGCAATTAATGTGAGTTAGCTCACTCATTAGGCACCCCAGGCTTGTGTAGGCTG
GAGCTGCTTCGAAGTTCCTATACTTTCTAGAGAATAGGAACTTCGGAATAGGAACTAAGGA
GGATATTCATATGGACCGATATCCCGGGCGGCCGCTCTAGAAGAAGCTTGGGATCCGTCGA
CCTCGAATTCGGAGGAAACAAAGATGTACTATTTAAAAAACACAAACTTTTGGATGTTCGG
TTTATTCTTTTTCTTTTACTTTTTTATCATGGGAGCCTACTTCCCGTTTTCCCGATTTGG
CTACATGACATCAACCATATCAGCAAAAGTGATACGGGTATTATTTTGCCGCTATTTCTC
TGTTCTCGCTATTATTCCAACCGCTGTTTGGTCTGCTTTCTGACAAACTCGGGCTGCGCAA
ATACCTGCTGTGGATTATTACCGGCATGTTAGTGATGTTTGCGCCGTTCTTTATTTTATC
TTCGGGCCACTGTTACAATACAACATTTAGTAGGATCGATTGTTGGTGGTATTTATCTAG
GCTTTTGTTTTAACGCCGGTGCGCCAGCAGTAGAGGCATTTATTGAGAAAGTCAGCCGTCG
CAGTAATTTCGAATTTGGTCGCGCGCGGATGTTTGGCTGTGTTGGCTGGGCGCTGTGTGCC
TCGATTGTCGGCATCATGTTCACCATCAATAATCAGTTTGTTTCTGGCTGGGCTCTGGCT
GTGCACTCATCCTCGCCGTTTACTCTTTTCGCCAAAACGGATGCGCCCTCTTCTGCCAC
GGTTGCCAATGCGGTAGGTGCCAACCATTCGGCATTTAGCCTTAAGCTGGCACTGGAACTG
TTCAGACAGCCAAAACTGTGGTTTTGTCACTGTATGTTATTGGCGTTTCCTGCACCTACG
ATGTTTTTGACCAACAGTTTGCTAATTTCTTTACTTCGTTCTTTGCTACCGGTGAACAGGG
TACGCGGGTATTTGGCTACGTAACGACAATGGGCGAATTACTTAACGCCTCGATTATGTTC
TTTGCGCCACTGATCATTAATCGCATCGGTGGGAAAAACGCCCTGCTGCTGGCTGGCACTA
TTATGTCTGTACGTATTATTGGCTCATCGTTCGCCACCTCAGCGCTGGAAGTGGTTATTCT
GAAAACGCTGCATATGTTTGAAGTACCGTTCCTGCTGGTGGGCTGCTTTAAATATATTACC
AGCCAGTTTGAAGTGCGTTTTTCAGCGACGATTTATCTGGTCTGTTTCTGCTTCTTTAAGC
AACTGGCGATGATTTTTATGTCTGTACTGGCGGGCAATATGTATGAAAGCATCGGTTTCCA
GGGCGCTTATCTGGTGCTGGGTCTGGTGGCGCTGGGCTTCACCTTAATTTCCGTGTTCACG
CTTAGCGGCCCCGGCCCGCTTTCCTGCTGCGTCGTCAGGTGAATGAAGTCGCTTAA (SEQ ID N° 1)

Figure 3

Sequence of the lactose permease gene translational coupled to the lacZ gene

```
ATGTACTATTTAAAAAACACAAACTTTTGGATGTTCGGTTTATTCTTTTTCTTTTACTTTT
TTATCATGGGAGCCTACTTCCCGTTTTTCCCGATTTGGCTACATGACATCAACCATATCAG
CAAAAGTGATACGGGTATTATTTTTGCCGCTATTTCTCTGTTCTCGCTATTATTCCAACCG
CTGTTTGGTCTGCTTTCTGACAAACTCGGGCTGCGCAAATACCTGCTGTGGATTATTACCG
GCATGTTAGTGATGTTTGCGCCGTTCTTTATTTTATCTTCGGGCCACTGTTACAATACAA
CATTTTAGTAGGATCGATTGTTGGTGGTATTTATCTAGGCTTTTGTTTAACGCCGGTGCG
CCAGCAGTAGAGGCATTTATTGAGAAAGTCAGCCGTCGCAGTAATTTCGAATTTGGTCGCG
CGCGGATGTTTGGCTGTGTTGGCTGGGCGCTGTGTGCCTCGATTGTCGGCATCATGTTCAC
CATCAATAATCAGTTTGTTTTCTGGCTGGGCTCTGGCTGTGCACTCATCCTCGCCGTTTTA
CTCTTTTTCGCCAAAACGGATGCGCCCTCTTCTGCCACGGTTGCCAATGCGGTAGGTGCCA
ACCATTCGGCATTTAGCCTTAAGCTGGCACTGGAACTGTTCAGACAGCCAAAACTGTGGTT
TTTGTCACTGTATGTTATTGGCGTTTCCTGCACCTACGATGTTTTTGACCAACAGTTTGCT
AATTTCTTTACTTCGTTCTTTGCTACCGGTGAACAGGGTACGCGGGTATTTGGCTACGTAA
CGACAATGGGCGAATTACTTAACGCCTCGATTATGTTCTTTGCGCCACTGATCATTAATCG
CATCGGTGGGAAAAACGCCCTGCTGCTGGCTGGCACTATTATGTCTGTACGTATTATTGGC
TCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTC
AGCGACGATTTATCTGGTCTGTTTCTGCTTCTTTAAGCAACTGGCGATGATTTTATGTCT
GTACTGGCGGGCAATATGTATGAAAGCATCGGTTTCCAGGGCGCTTATCTGGTGCTGGGTC
TGGTGGCGCTGGGCTTCACCTTAATTTCCGTGTTCACGCTTAGCGGCCCCGGCCCGCTTTC
CCTGCTGCGTCGTCAGGTGAATGAAGTCGCTGATAAAAACTGGAGGCGTCATAGGGGATCC
CGTCGTTTTACAACGTCGTGACTGGGAAAACCCTGGCGTTACCCAACTTAATCGCCTTGCA
GCACATCCCCCTTTCGCCAGCTGGCGTAATAGCGAAGAGGCCCGCACCGATCGCCCTTCCC
AACAGTTGCGCAGCCTGAATGGCGAATGGCGCTTTGCCTGGTTTCCGGCACCAGAAGCGGT
GCCGGAAAGCTGGCTGGAGTGCGATCTTCCTGAGGCCGATACTGTCGTCGTCCCCTCAAAC
TGGCAGATGCACGGTTACGATGCGCCCATCTACACCAACGTGACCTATCCCATTACGGTCA
ATCCGCCGTTTGTTCCCACGGAGAATCCGACGGGTTGTTACTCGCTCACATTTAATGTTGA
TGAAAGCTGGCTACAGGAAGGCCAGACGCGAATTATTTTTGATGGCGTTAACTCGGCGTTT
CATCTGTGGTGCAACGGGCGCTGGGTCGGTTACGGCCAGGACAGTCGTTTGCCGTCTGAAT
TTGACCTGAGCGCATTTTTACGCGCCGGAGAAAACCGCCTCGCGGTGATGGTGCTGCGCTG
GAGTGACGGCAGTTATCTGGAAGATCAGGATATGTGGCGGATGAGCGGCATTTTCCGTGAC
GTCTCGTTGCTGCATAAACCGACTACACAAATCAGCGATTTCCATGTTGCCACTCGCTTTA
ATGATGATTTCAGCCGCGCTGTACTGGAGGCTGAAGTTCAGATGTGCGGCGAGTTGCGTGA
CTACCTACGGGTAACAGTTTCTTTATGGCAGGGTGAAACGCAGGTCGCCAGCGGCACCGCG
CCTTTCGGCGGTGAAATTATCGATGAGCGTGGTGGTTATGCCGATCGCGTCACACTACGTC
TGAACGTCGAAAACCCGAAACTGTGGAGCGCCGAAATCCCGAATCTCTATCGTGCGGTGGT
TGAACTGCACACCGCCGACGGCACGCTGATTGAAGCAGAAGCCTGCGATGTCGGTTTCCGC
GAGGTGCGGATTGAAAATGGTCTGCTGCTGCTGAACGGCAAGCCGTTGCTGATTCGAGGCG
TTAACCGTCACGAGCATCATCCTCTGCATGGTCAGGTCATGGATGAGCAGACGATGGTGCA
GGATATCCTGCTGATGAAGCAGAACAACTTTAACGCCGTGCGCTGTTCGCATTATCCGAAC
CATCCGCTGTGGTACACGCTGTGCGACCGCTACGGCCTGTATGTGGTGGATGAAGCCAATA
TTGAAACCCACGGCATGGTGCCAATGAATCGTCTGACCGATGATCCGCGCTGGCTACCGGC
```

Figure 4

```
GATGAGCGAACGCGTAACGCGAATGGTGCAGCGCGATCGTAATCACCCGAGTGTGATCATC
TGGTCGCTGGGGAATGAATCAGGCCACGGCGCTAATCACGACGCGCTGTATCGCTGGATCA
AATCTGTCGATCCTTCCCGCCCGGTGCAGTATGAAGGCGGCGGAGCCGACACCACGGCCAC
CGATATTATTTGCCCGATGTACGCGCGCGTGGATGAAGACCAGCCCTTCCCGGCTGTGCCG
AAATGGTCCATCAAAAAATGGCTTTCGCTACCTGGAGAGACGCGCCCGCTGATCCTTTGCG
AATACGCCCACGCGATGGGTAACAGTCTTGGCGGTTTCGCTAAATACTGGCAGGCGTTTCG
TCAGTATCCCCGTTTACAGGGCGGCTTCGTCTGGGACTGGGTGGATCAGTCGCTGATTAAA
TATGATGAAAACGGCAACCCGTGGTCGGCTTACGGCGGTGATTTTGGCGATACGCCGAACG
ATCGCCAGTTCTGTATGAACGGTCTGGTCTTTGCCGACCGCACGCCGCATCCAGCGCTGAC
GGAAGCAAAACACCAGCAGCAGTTTTTCCAGTTCCGTTTATCCGGGCAAACCATCGAAGTG
ACCAGCGAATACCTGTTCCGTCATAGCGATAACGAGCTCCTGCACTGGATGGTGGCGCTGG
ATGGTAAGCCGCTGGCAAGCGGTGAAGTGCCTCTGGATGTCGCTCCACAAGGTAAACAGTT
GATTGAACTGCCTGAACTACCGCAGCCGGAGAGCGCCGGGCAACTCTGGCTCACAGTACGC
GTAGTGCAACCGAACGCGACCGCATGGTCAGAAGCCGGGCACATCAGCGCCTGGCAGCAGT
GGCGTCTGGCGGAAAACCTCAGTGTGACGCTCCCCGCCGCGTCCCACGCCATCCCGCATCT
GACCACCAGCGAAATGGATTTTTGCATCGAGCTGGGTAATAAGCGTTGGCAATTTAACCGC
CAGTCAGGCTTTCTTTCACAGATGTGGATTGGCGATAAAAACAACTGCTGACGCCGCTGC
GCGATCAGTTCACCCGTGCACCGCTGGATAACGACATTGGCGTAAGTGAAGCGACCCGCAT
TGACCCTAACGCCTGGGTCGAACGCTGGAAGGCGGCGGGCCATTACCAGGCCGAAGCAGCG
TTGTTGCAGTGCACGGCAGATACACTTGCTGATGCGGTGCTGATTACGACCGCTCACGCGT
GGCAGCATCAGGGGAAAACCTTATTTATCAGCCGGAAAACCTACCGGATTGATGGTAGTGG
TCAAATGGCGATTACCGTTGATGTTGAAGTGGCGAGCGATACACCGCATCCGGCGCGGATT
GGCCTGAACTGCCAGCTGGCGCAGGTAGCAGAGCGGGTAAACTGGCTCGGATTAGGGCCGC
AAGAAAACTATCCCGACCGCCTTACTGCCGCCTGTTTTGACCGCTGGGATCTGCCATTGTC
AGACATGTATACCCGTACGTCTTCCCGAGCGAAAACGGTCTGCGCTGCGGGACGCGCGAA
TTGAATTATGGCCCACACCAGTGGCGCGGCGACTTCCAGTTCAACATCAGCCGCTACAGTC
AACAGCAACTGATGGAAACCAGCCATCGCCATCTGCTGCACGCGGAAGAAGGCACATGGCT
GAATATCGACGGTTTCCATATGGGGATTGGTGGCGACGACTCCTGGAGCCCGTCAGTATCG
GCGGAATTCCAGCTGAGCGCCGGTCGCTACCATTACCAGTTGGTCTGGTGTCAAAAATAAG
CTGGTTTGAAGGGTATTGGTCGGTCAGTTTCACCTGATTTACGTAAAAACCCGCTTCGGCG
GGTTTTTGCTTTTGGAGGGGCAGAAAGATGAATGACTGTC   (SEQ ID N° 2)
```

Figure 4 (cont.)

Sequence of the lactose permease gene *lacY* translational coupled to the cat gene

```
ATGTACTATTTAAAAAACACAAACTTTTGGATGTTCGGTTTATTCTTTTCTTTTACTTTT
TTATCATGGGAGCCTACTTCCCGTTTTCCCGATTTGGCTACATGACATCAACCATATCAG
CAAAAGTGATACGGGTATTATTTTTGCCGCTATTTCTCTGTTCTCGCTATTATTCCAACCG
CTGTTTGGTCTGCTTTCTGACAAACTCGGGCTGCGCAAATACCTGCTGTGGATTATTACCG
GCATGTTAGTGATGTTTGCGCCGTTCTTTATTTTATCTTCGGGCCACTGTTACAATACAA
CATTTAGTAGGATCGATTGTTGGTGGTATTTATCTAGGCTTTTGTTTTAACGCCGGTGCG
CCAGCAGTAGAGGCATTTATTGAGAAAGTCAGCCGTCGCAGTAATTTCGAATTGGTCGCG
CGCGGATGTTTGGCTGTGTTGGCTGGGCGCTGTGCCTCGATTGTCGGCATCATGTTCAC
CATCAATAATCAGTTTGTTTCTGGCTGGGCTCTGGCTGTGCACTCATCCTCGCCGTTTTA
CTCTTTTTCGCCAAAACGGATGCGCCCTCTTCTGCCACGGTTGCCAATGCGGTAGGTGCCA
ACCATTCGGCATTTAGCCTTAAGCTGGCACTGGAACTGTTCAGACAGCCAAAACTGTGGTT
TTTGTCACTGTATGTTATTGGCGTTTCCTGCACCTACGATGTTTTGACCAACAGTTTGCT
AATTTCTTTACTTCGTTCTTTGCTACCGGTGAACAGGGTACGCGGGTATTTGGCTACGTAA
CGACAATGGGCGAATTACTTAACGCCTCGATTATGTTCTTTGCGCCACTGATCATTAATCG
CATCGGTGGGAAAAACGCCCTGCTGCTGGCTGGCACTATTATGTCTGTACGTATTATTGGC
TCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTC
AGCGACGATTTATCTGGTCTGTTTCTGCTTCTTTAAGCAACTGGCGATGATTTTATGTCT
GTACTGGCGGGCAATATGTATGAAAGCATCGGTTTCCAGGGCGCTTATCTGGTGCTGGGTC
TGGTGGCGCTGGGCTTCACCTTAATTTCCGTGTTCACGCTTAGCGGCCCCGGCCCGCTTTC
CCTGCTGCGTCGTCAGGTGAATGAAGTCGCTCATCATCACCACCATCATTAGGATGGTGGT
GATGATAATGGAGAAAAAATCACTGGATATACCACCGTTGATATATCCCAATGGCATCGT
AAAGAACATTTTGAGGCATTTCAGTCAGTTGCTCAATGTACCTATAACCAGACCGTTCAGC
TGGATATTACGGCCTTTTTAAAGACCGTAAAGAAAAATAAGCACAAGTTTTATCCGGCCTT
TATTCACATTCTTGCCCGCCTGATGAATGCTCATCCGGAGTTCCGTATGGCAATGAAAGAC
GGTGAGCTGGTGATATGGGATAGTGTTCACCCTTGTTACACCGTTTTCCATGAGCAAACTG
AAACGTTTTCATCGCTCTGGAGTGAATACCACGACGATTTCCGGCAGTTTCTACACATATA
TTCGCAAGATGTGGCGTGTTACGGTGAAAACCTGGCCTATTTCCCTAAAGGGTTTATTGAG
AATATGTTTTTCGTCAGCGCCAATCCCTGGGTGAGTTTCACCAGTTTTGATTTAAACGTGG
CCAATATGGACAACTTCTTCGCCCCCGTTTTCACTATGGGCAAATATTATACGCAAGGCGA
CAAGGTGCTGATGCCGCTGGCGATTCAGGTTCATCATGCCGTTTGTGATGGCTTCCATGTC
GGCAGAATGCTTAATGAATTACAACAGTACTGCGATGAGTGGCAGGGCGGGCGTAAGGAT
CCAAAGGTACCTCTAGAGTCGACCTGCAGGCCTTCGTAAATCTGGCGAGTGGGGAACTGCC
AGACATCAAATAAACAAAAGGCTCAGTCGGAAGACTGGGCCTTTTGTTTTATCTGTTGTT
TGTCGGTGAACACTCTCCC  (SEQ ID N° 3)
```

Sequence of the *K. marxianus* lactose permease gene translational coupled to the aph 1 gene

```
ATGGCAGATCATTCGAGCAGCTCATCTTCGCTGCAGAAGAAGCCAATTAATACTATCGAGC
ATAAAGACACTTTGGGCAATGATCGGGATCACAAGGAAGCCTTGAACAGTGATAATGATAA
TACTTCTGGATTGAAAATCAATGGTGTCCCCATCGAGGACGCTAGAGAGGAAGTGCTCTTA
CCAGGTTACTTGTCGAAGCAATATTACAAATTGTACGGTTTATGTTTATAACATATCTGT
GTGCTACTATGCAAGGTTATGATGGGGCTTTAATGGGTTCTATCTATACCGAAGATGCATA
TTTGAAATACTACCATTTGGATATTAACTCATCCTCTGGTACTGGTCTAGTGTTCTCTATT
TTCAACGTTGGTCAAATTTGCGGTGCATTCTTTGTTCCTCTTATGGATTGGAAAGGTAGAA
AACCTGCTATTTTAATTGGGTGTCTGGGTGTTGTTATTGGTGCTATTATTCGTCTTTAAC
AACAACAAGAGTGCATTAATTGGTGGTAGATGGTTCGTGGCCTTTTCGCTACAATCGCT
AATGCAGCAGCTCCAACATACTGTGCAGAAGTGGCTCCAGCTCACTTAAGAGGTAAGGTTG
CAGGTCTTTATAACACCCTTTGGTCTGTCGGTTCCATTGTTGCTGCCTTTAGCACTTACGG
TACCAACAAAACTTCCCTAACTCCTCCAAGGCTTTTAAGATTCCATTATACTTACAAATG
ATGTTCCAGGTCTTGTGTGTATATTGGTTGGTTAATCCCAGAATCTCCAAGATGGTTGG
TTGGTGTTGGCCGTGAGGAAGAAGCTCGTGAATTCATTATCAAATACCACTTAAATGGCGA
TAGAACTCATCCATTATTGGATATGGAGATGGCAGAAATAATAGAATCTTTCCATGGTACA
GATTTATCAAACCCTCTAGAAATGTTAGATGTAAGGAGCTTATTCAGAACGAGATCGGATA
GGTACAGAGCAATGTTGGTTATACTTATGGCTTGGTTCGGTCAATTTTCCGGTAACAATGT
GTGTTCGTACTATTTGCCTACCATGTTGAGAAATGTTGGTATGAAGAGTGTCTCATTGAAT
GTGTTAATGAATGGTGTTTATTCCATCGTCACTTGGATTTCTTCAATTTGCGGTGCATTCT
TTATTGATAAGATTGGTAGAAGGGAAGGTTTCCTTGGTTCTATCTCAGGTGCTGCATTAGC
ATTGACAGGTCTATCTATCTGTACTGCTCGTTATGAGAAGACTAAGAAGAAGAGTGCTTCC
AATGGTGCATTGGTGTTCATTTATCTCTTTGGTGGTATCTTTTCTTTTGCTTTCACTCCAA
TGCAATCCATGTACTCAACAGAAGTGTCTACAAACTTGACGAGATCTAAGGCCCAACTCCT
CAACTTTGTGGTTTCTGGTGTTGCCCAATTTGTTAATCAATTTGCTACTCCAAAGGCAATG
AAGAATATCAAATATTGGTTCTATGTGTTCTACGTTTTCTTCGATATTTCGAATTTATTG
TTATCTACTTCTTCTTCGTTGAAACTAAGGGTAGAAGCTTAGAAGAATTAGAAGTTGTCTT
TGAAGCTCCAAACCCAAGAAAGGCATCCGTTGATCAAGCATTCTTGGCTCAAGTCAGGGCA
ACTTTGGTCCAACGAAATGACGTTAGAGTTGCAAATGCTCAAAATTTGAAAGAGCAAGAGC
CTCTAAAGAGCGATGCTGATCATGTCGAAAAGCTTTCAGAGGCAGAATCTGTTAGAGCAGA
AGGAAGGGGTTCTTTGTTGACTTGTGGAGATGTTGAGGAGAATCCAGGACCAGGTAAGGAA
AAGACTCACGTTTCGAGGCCGCGATTAAATTCCAACATGGATGCTGATTTATATGGGTATA
AATGGGCTCGCGATAATGTCGGGCAATCAGGTGCGACAATCTATCGATTGTATGGGAAGCC
CGATGCGCCAGAGTTGTTTCTGAAACATGGCAAAGGTAGCGTTGCCAATGATGTTACAGAT
GAGATGGTCAGACTAAACTGGCTGACGGAATTATGCCTCTTCCGACCATCAAGCATTTTA
TCCGTACTCCTGATGATGCATGGTTACTCACCACTGCGATCCCCGGCAAAACAGCATTCCA
GGTATTAGAAGAATATCCTGATTCAGGTGAAAATATTGTTGATGCGCTGGCAGTGTTCCTG
CGCCGGTTGCATTCGATTCCTGTTTGTAATTGTCCTTTAACAGCGATCGCGTATTTCGTC
TCGCTCAGGCGCAATCACGAATGAATAACGGTTTGGTTGATGCGAGTGATTTGATGACGA
GCGTAATGGCTGGCCTGTTGAACAAGTCTGGAAAGAAATGCATAAGCTTTTGCCATTCTCA
CCGGATTCAGTCGTCACTCATGGTGATTTCTCACTTGATAACCTTATTTTTGACGAGGGGA
AATTAATAGGTTGTATTGATGTTGGACGAGTCGGAATCGCAGACCGATACCAGGATCTTGC
CATCCTATGGAACTGCCTCGGTGAGTTTTCTCCTTCATTACAGAAACGGCTTTTTCAAAAA
TATGGTATTGATAATCCTGATATGAATAAATTGCAGTTTCATTTGATGCTCGATGAGTTTT
TCTAA   (SEQ ID N° 4)
```

Figure 6

Sequence of a lactose permease gene coupled with an aptamer sequence

```
ATGTACTATTTAAAAAACACAAACTTTTGGATGTTCGGTTTATTCTTTTTCTTTTACTTTTT
TATCATGGGAGCCTACTTCCCGTTTTTCCCGATTTGGCTACATGACATCAACCATATCAGCA
AAAGTGATACGGGTATTATTTTTGCCGCTATTTCTCTGTTCTCGCTATTATTCCAACCGCTG
TTTGGTCTGCTTTCTGACAAACTCGGGCTGCGCAAATACCTGCTGTGGATTATTACCGGCAT
GTTAGTGATGTTTGCGCCGTTCTTTATTTTTATCTTCGGGCCACTGTTACAATACAACATTT
TAGTAGGATCGATTGTTGGTGGTATTTATCTAGGCTTTTGTTTAACGCCGGTGCGCCAGCA
GTAGAGGCATTTATTGAGAAAGTCAGCCGTCGCAGTAATTTCGAATTTGGTCGCGCGCGGAT
GTTTGGCTGTGTTGGCTGGGCGCTGTGCCTCGATTGTCGGCATCATGTTCACCATCAATA
ATCAGTTTGTTTCTGGCTGGGCTCTGGCTGTGCACTCATCCTCGCCGTTTTACTCTTTTC
GCCAAAACGGATGCGCCCTCTTCTGCCACGGTTGCCAATGCGGTAGGTGCCAACCATTCGGC
ATTTAGCCTTAAGCTGGCACTGGAACTGTTCAGACAGCCAAAACTGTGGTTTTTGTCACTGT
ATGTTATTGGCGTTTCCTGCACCTACGATGTTTTTGACCAACAGTTTGCTAATTTCTTTACT
TCGTTCTTTGCTACCGGTAACAGGGTACGCGGGTATTTGGCTACGTAACGACAATGGGCGA
ATTACTTAACGCCTCGATTATGTTCTTTGCGCCACTGATCATTAATCGCATCGGTGGGAAAA
ACGCCCTGCTGCTGGCTGGCACTATTATGTCTGTACGTATTATTGGCTCATCGTTCGCCACC
TCAGCGCTGGAAGTGGTTATTCTGAAAACGCTGCATATGTTTGAAGTACCGTTCCTGCTGGT
GGGCTGCTTTAAATATATTACCAGCCAGTTTGAAGTGCGTTTTCAGCGACGATTTATCTGG
TCTGTTTCTGCTTCTTTAAGCAACTGGCGATGATTTTATGTCTGTACTGGCGGGCAATATG
TATGAAAGCATCGGTTTCCAGGGCGCTTATCTGGTGCTGGGTCTGGTGGCGCTGGGCTTCAC
CTTAATTTCCGTGTTCACGCTTAGCGGCCCCGGCCCGCTTTCCCTGCTGCGTCGTCAGGTGA
ATGAAGTCGCTGATAACTCTACGACAACCTCTTCACAGCCAATCTCGCCCGGATAGCTCAGT
CGGTAGAGCAGCGGCCGGACGCAACTGAATGAAATGGTGAAGGACGGGTCCAGGTGTGGCTG
CTTCGGCAGTGCAGCTTGTTGAGTAGAGTGTGAGCTCCGTAACTAGTCGCGTCCGGCCGCGG
GTCCAGGGTTCAAGTCCCTGTTCGGGCGCCA  (SEQ ID N° 5)
```

Figure 7

**pCXP14-FT_*H. pylori***

CGCGTTGGATGCAGGCATGCAAGCTTGGCTGTTTTGGCGGATGAGAGAAGATTTTCAGCC
TGATACAGATTAAATCAGAACGCAGAAGCGGTCTGATAAAACAGAATTTGCCTGGCGGCA
GTAGCGCGGTGGTCCCACCTGACCCCATGCCGAACTCAGAAGTGAAACGCCGTAGCGCCG
ATGGTAGTGTGGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGTGAACGCTCTC
CTGAGTAGGACAAATCCGCCGGGAGCGGATTTGAACGTTGCGAAGCAACGGCCCGGAGGG
TGGCGGGCAGGACGCCCGCCATAAACTGCCAGGCATCAAATTAAGCAGAAGGCCATCCTG
ACGGATGGCCTTTTTGCGTTTCTACAAACTCTTTTTGTTTATTTTTCTAAATACATTCAA
ATATGTATCCGCTCATGAGACAATAACCCTGATAAATGCTTCAATAATATTGAAAAAGGA
AGAGTATGAGTATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTAT
TATCCCGTGTTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGACACCA
CGATGCCTACAGCAATGGCAACAACGTTGCGCAAACTATTAACTGGCGAACTACTTACTC
TAGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTA
TCTACACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTAGA
TTGATTTAAAACTTCATTTTTAATTTAAAAGGATCTAGGTGAAGATCCTTTTTGATAATC
TCATGACCAAAATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTAGTGTAGCCGT
AGTTAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGCGGAGCCTAT
GGAAAAACGCCAGCAACGCGGCCTTTTTACGGTTCCTGGCCTTTTGCTGGCCTTTTGCTC
ACATGTTCTTTCCTGCGTTATCCCCTGATTCTGTGGATAACCGTATTACCGCCTTTGAGT
GAGCTGATACCGCTCGCCGCAGCCGAACGACCGAGCGCAGCGAGTCAGTGAGCGAGGAAG
CGGAAGAGCGCCTGATGCGGTATTTTCTCCTTACGCATCTGTGCGGTATTTCACACCGCA
TATGGTGCACTCTCAGTACAATCTGCTCTGATGCCGCATAGTTAAGCCAGTATACACTCC

Figure 10

```
GCTATCGCTACGTGACTGGGTCATGGCTGCGCCCCGACACCCGCCAACACCCGCTGACGC
GCCCTGACGGGCTTGTCTGCTCCCGGCATCCGCTTACAGACAAGCTGTGACCGTCTCCGG
GAGAGCTCGATATCCCGGGCGGCCGCCTTCATTCTATAAGTTTCTTGACATCTTGGCCGG
CATATGGTATAATAGGGAAATTTCCATGGCGGCCGCTCTAGAAGAAGCTTGGGATCCGTC
GACCTCGAATTCGGAGGAAACAAAGATGGCCTTTAAAGTTGTTCAGATTTGTGGTGGTCT
GGGCAATCAGATGTTTCAGTATGCATTTGCAAAAGCCTGCAGAAACATAGCAATACACC
GGTTCTGCTGGATATTACCAGCTTTGATTGGAGCAATCGTAAATGCAGCTGGAACTGTT
TCCGATTGATCTGCCGTATGCAAGCGAAAAGAAATTGCAATTGCCAAAATGCAGCATCT
GCCGAAACTGGTTCGTAATGTTCTGAAATGCATGGGTTTTGATCGTGTGAGCCAAGAAAT
CGTGTTTGAATATGAACCGAAACTGCTGAAAACCAGCCGTCTGACCTATTTTTATGGCTA
TTTTCAGGATCCGCGTTATTTTGATGCAATTAGTCCGCTGATCAAACAGACCTTTACCCT
GCCTCCGCCTCCGGAAAATGGTAATAACAAAAAAAAAGAAGAAGAGTATCATCGTAAACT
GGCACTGATTCTGGCAGCAAAAAATAGCGTGTTTGTGCATATTCGTCGCGGTGATTATGT
TGGTATTGGTTGTCAGCTGGGCATCGATTATCAGAAAAAAGCACTGGAATACATGGCAAA
ACGTGTTCCGAATATGGAACTGTTTGTGTTTTGCGAGGACCTGGAATTTACCCAGAATCT
GGATCTGGGCTATCCGTTTATGGATATGACCACCCGTGATAAAGAGGAAGAGGCATATTG
GGATATGCTGCTGATGCAGAGCTGTAAACATGGTATTATTGCCAACAGCACCTATAGTTG
GTGGGCAGCATATCTGATTAATAACCCGGAAAAAATCATTATTGGTCCGAAACATTGGCT
GTTTGGCCATGAAAACATCCTGTGTAAAGAATGGGTGAAAATCGAAAGCCACTTTGAAGT
GAAAAGCCAGAAATATAATGCCTAATAAGAGCTCCCAA   (SEQ ID N° 6)
```

Figure 10 (cont.)

Sequence of the *K. marxianus* lactose permease coding sequence with a mutant promoter (p1), Kozak, and terminator combination

```
TATTTTAGATTCCTGACTTCAACTCAAGACGCACAGATATTATAACATCTGCAGAATAGGCATT
TGCAAGAATTACTCGTGAGTAAGGAAAGAGTGAGGAACTATCGCATACCTGCATTTAAAGATGC
CGATTTGGGCGCGAATCCTTTATTTTGGCTTCACCCTCATACTATTATCAGGGCCAGAAAAAGG
AAGTGTTTCCCTCCTTCTTGAATTGATGTTACCCTCATAAAGCACGTGGCCTCTTATCGAGAAA
GAAATTACCGTCGCTCGTGATTTGTTTGCAAAAGAACAAAACTGAAAAAACCCAGACACGCTC
GACTTCCTCTCTTCCTATTGATTGCAGCTTCCAATTTCGTCACACAACAAGGTCCTAGCGACGG
CTCACAGGTTTTGTAACAAGCAATCGAAGGTTCTGGAATGGCGGGAAGGGTTTAGTACCACAT
GCTATGATGCCCACTGTGATCACCAGAGCAAGTTCGTTCGATCGTACTGTTACTCTCTCTCTT
TCAAACAGAATTGTCCGAATCGTGTGACAACAACAGCCTGTTCTCACACACTCTTTTCTTCTAA
CCAAGGGGTGGTTTAGTTTAGTAGAACCTCGTGAAACTTACATTTACATATATATAAACTTGC
ATAAATTGGTCAATGCAAGAAATACATATTTGGTCTTTTCTAATTCGTAGTTTTTCAAGTTCT
TAGATGCTTTCTTTTTCTCTTTTTTACAGATCATCAAGGAAGTAATTATCTACTTTTTACAAC
AAATATAAAAAAAATGGCAGATCATTCGAGCAGCTCATCTTCGCTGCAGAAGAAGCCAATTAAT
ACTATCGAGCATAAAGACACTTTGGGCATTGATCTGGATCACAAGGAAGCCTTGAACAGTGATA
ATGATAATACTTCTGGATTGAAAATCAATGGTGTCCCCATCGAGGACGCTAGAGAGGAAGTGCT
CTTACCAGGTTACTTGTCGAAGCAATATTACAAATTGTACAGTTTATGTTTTGTAACATATCTG
TGTGCTACTATGCAAGGTTATGATGGGGCTTTAATGGGTTCTATCTATACCGAAAATGCATATT
TGGAATACTACCATTTGGATATTAACTCATCCAGTGGTACTGGTCTAGTGTTCTATTTTCAA
CGTTGGTCAAATTTGCGGTGCATTCTTTGTTCCTCTTATGGATTGGAAAGGTAGAAAACCTGCT
ATTTTAATTGGGTGTCTGGGTGTTGTTATTGGTGGTATTATTACGTCTGTAACAACAACAAAGA
GTGCATTAATTGGTGGTAGATGGTTCATGGCCTTTTCGCTACAATCGCTAATTCAGCAGCTCC
AGCATACTGTGCAGAAGTGGCTCCAGCTCACTTAAGAGGTAAGGTTGCAGGTCTTTATAACACC
CTTTGGTCTGTCGGTTCCATTGTTGCTGCCTTTACCACTCTCGGTACCAACAAAAACTTCCCTA
ACTCCTCCAAGGCTTTTAAGATTCCATTATACTTACAAATGATGTTCCCAGGTCTTGTGTGTAT
ATTTGGTTGGTTAATCCCAGAATCTCCAAGATGGTTGGTTGGTGTTGGCCGTGAGGAAGAAGCT
CGTGAATTCATTATCAAATACCACTTAAATGGCGATAGAACTCATCCATTATTGGATATGGAGA
TGGCAGAAATAATAGAATCTTTCCATGGTACAGATTTATCAAACCCTCTAGAAATGTTAGATGT
AAGGATCTTATTCAGAACGAGATCGGATAGGTACAGAGCAATGTTGGTTATACTTATGGCTTGG
TTCGGTCAATTTTCCGGTAACAATGTGTGTTCGTACTATTTGCCTACCATGTTGAGAAATGTTG
GTATGAAGAGTGTCTCATTGAATGTGTTAATGAATGGTGTTTATTCCATCGTCTCTTGGATTTC
TTCAATTTGCGGTGCATTCTTTATTGATAAGATTGGTAGAAGGGAAGGTTTCCTTGGTTCTATC
TCAGGTGCTGCATTAGCATTGACAGGTCTATCTATCTGTACTGCTCGTTATGAGAAGACTAAGA
AGAAGAGTGCTTCCAATGGTGCATTGGTGTTCATTATCTCTTTGGTGTTATCTTTTCTTTTGC
TTTCACTCCAATGCAATCCATGTACTCAACAGAAGTGTCTACAAACTTGACGAGATCTAAGGCC
CAACTCCTCAACGGTGTGGTTTCTGGTGTTGCCCAATTTGTTAATCAATTTGCTACTCCAAAGG
CAATGAAGAATATCAAATATTGGTTCTATGTGTTCTACGTTTTCTTCGATATTTCGAATTTAT
TGTTATCTACTTCTTCTTCGTTGAAACTAAGGGTAGAAGCTTAGAAGAATTAGAAGCTGTCTTT
GAAGCTCCAAACCCAAGAAGGCATCCGTTGATCAAGCATTCTTGGCTCAAGCCAGGGCAACTT
TGGTCCAACAAAATGACGTTAGAGTTGCAAATGCTCAAAATTTGAAAGAGCAAGAGCTTCTAAA
GAGCGATGCTGATCATGTCGAAAAGCTTTCAGAGGCAGAATCTGTTTAAAGAGTCTTTTGTAAC
GACCCGTCTCCACCAACTTGGTATGCTTGAAATCTCAAGGCCATTACACATTCAGTTATGTGA
ACGAAAGGTCTTTATTTAACGTAGCATAAACTAAAT (SEQ ID N° 7)
```

Figure 13

Sequence of the *K. marxianus* lactose permease coding sequence with a mutant promoter (p2), Kozak, and terminator combination

```
AGGAATAAGGATACTTCAAGACTAGATTCCCCCCTGCATTCCCATCAGAACCGTAAACCTTGGC
GCTTTCCTTGGGAAGTATTCAAGAAGTGCCTTGTCCGGTTTCTGTGGCTCACAAACCAGCGCGC
CCGATATGGCTTTCTTTTCACTTATGAATGTACCAGTACGGGACAATTAGAACGCTCCTGTAAC
AATCTCTTTGCAAATGTGGGGTTACATTCTAACCATGTCACACTGCTGACGAAATTCAAAGTAA
AAAAAAATGGGACCACGTCTTGAGAACGATAGATTTTCTTTATTTTACATTGAACAGTCGTTGT
CTCAGCGCGCTTTATGTTTTCATTCATACTTCATATTATAAAATAACAAAAGAAGAATTTCATA
TTCACGCCCAAGAAATCAGGCTGCTTTCCAAATGCAATTGACACTTCATTAGCCATCACACAAA
ACTCTTTCTTGCTGGAGCTTCTTTTAAAAAAGACCTCAGTACACCAAACACGTTACCCGACCTC
GTTATTTTACGACAACTATGATAAAATTCTGAAGAAAAATAAAAAAATTTTCATACTTCTTGC
TTTTATTTAAACCATTGAATGATTTCTTTGAACAAAACTACCTGTTTCACCAAAGGAAATAGA
AAGAAAAAATCAATTAGAAGAAAACAAAAAACAAAATGGCAGATCATTCGAGCAGCTCATCTTC
GCTGCAGAAGAAGCCAATTAATACTATCGAGCATAAAGACACTTTGGGCATTGATCTGGATCAC
AAGGAAGCCTTGAACAGTGATAATGATAATACTTCTGGATTGAAAATCAATGGTGTCCCCATCG
AGGACGCTAGAGAGGAAGTGCTCTTACCAGGTTACTTGTCGAAGCAATATTACAAATTGTACAG
TTTATGTTTTGTAACATATCTGTGTGCTACTATGCAAGGTTATGATGGGCTTTAATGGGTTCT
ATCTATACCGAAAATGCATATTTGGAATACTACCATTTGGATATTAACTCATCCAGTGGTACTG
GTCTAGTGTTCTCTATTTTCAACGTTGGTCAAATTTGCGGTGCATTCTTTGTTCCTCTTATGGA
TTGGAAAGGTAGAAAACCTGCTATTTTAATTGGGTGTCTGGGTGTTGTTATTGGTGGTATTATT
ACGTCTGTAACAACAACAAAGAGTGCATTAATTGGTGGTAGATGGTTCATGGCCTTTTCGCTA
CAATCGCTAATTCAGCAGCTCCAGCATACTGTGCAGAAGTGGCTCCAGCTCACTTAAGAGGTAA
GGTTGCAGGTCTTTATAACACCCTTTGGTCTGTCGGTTCCATTGTTGCTGCCTTTACCACTCTC
GGTACCAACAAAAACTTCCCTAACTCCTCCAAGGCTTTTAAGATTCCATTATACTTACAAATGA
TGTTCCCAGGTCTTGTGTGTATATTTGGTTGGTTAATCCCAGAATCTCCAAGATGGTTGGTTGG
TGTTGGCCGTGAGGAAGAAGCTCGTGAATTCATTATCAAATACCACTTAAATGGCGATAGAACT
CATCCATTATTGGATATGGAGATGGCAGAAATAATAGAATCTTTCCATGGTACAGATTTATCAA
ACCCTCTAGAAATGTTAGATGTAAGGATCTTATTCAGAACGAGATCGGATAGGTACAGAGCAAT
GTTGGTTATACTTATGGCTTGGTTCGGTCAATTTTCCGGTAACAATGTGTGTTCGTACTATTTG
CCTACCATGTTGAGAAATGTTGGTATGAAGAGTGTCTCATTGAATGTGTTAATGAATGGTGTTT
ATTCCATCGTCTCTTGGATTTCTTCAATTTGCGGTGCATTCTTTATTGATAAGATTGGTAGAAG
GGAAGGTTTCCTTGGTTCTATCTCAGGTGCTGCATTAGCATTGACAGGTCTATCTATCTGTACT
GCTCGTTATGAGAAGACTAAGAAGAAGAGTGCTTCCAATGGTGCATTGGTGTTCATTTATCTCT
TTGGTGTTATCTTTTCTTTTGCTTTCACTCCAATGCAATCCATGTACTCAACAGAAGTGTCTAC
AAACTTGACGAGATCTAAGGCCCAACTCCTCAACGGTGTGGTTTCTGGTGTTGCCCAATTTGTT
AATCAATTTGCTACTCCAAAGGCAATGAAGAATATCAAATATTGGTTCTATGTGTTCTACGTTT
TCTTCGATATTTTCGAATTTATTGTTATCTACTTCTTCTTCGTTGAAACTAAGGGTAGAAGCTT
AGAAGAATTAGAAGCTGTCTTTGAAGCTCCAAACCCAAGAAAGGCATCCGTTGATCAAGCATTC
TTGGCTCAAGCCAGGGCAACTTTGGTCCAACAAAATGACGTTAGAGTTGCAAATGCTCAAAATT
TGAAAGAGCAAGAGCTTCTAAAGAGCGATGCTGATCATGTCGAAAGCTTTCAGAGGCAGAATC
TGTTTAAAGAGTCTTTTGTAACGACCCCGTCTCCACCAACTTGGTATGCTTGAAATCTCAAGGC
CATTACACATTCAGTTATGTGAACGAAAGGTCTTTATTTAACGTAGCATAAACTAAAT (SEQ
ID N° 8)
```

Figure 14

Example of a promoter, Kozak, *K. marxianus* β-galactosidase coding sequence and terminator combination

```
TATTTTAGATTCCTGACTTCAACTCAAGACGCACAGATATTATAACATCTGCAGAATAGGCATT
TGCAAGAATTACTCGTGAGTAAGGAAAGAGTGAGGAACTATCGCATACCTGCATTTAAAGATGC
CGATTTGGGCGCGAATCCTTTATTTTGGCTTCACCCTCATACTATTATCAGGGCCAGAAAAAGG
AAGTGTTTCCCTCCTTCTTGAATTGATGTTACCCTCATAAAGCACGTGGCCTCTTATCGAGAAA
GAAATTACCGTCGCTCGTGATTTGTTTGCAAAAGAACAAAACTGAAAAACCCAGACACGCTC
GACTTCCTCTCTTCCTATTGATTGCAGCTTCCAATTTCGTCACACAACAAGGTCCTAGCGACGG
CTCACAGGTTTTGTAACAAGCAATCGAAGGTTCTGGAATGGCGGGAAAGGGTTTAGTACCACAT
GCTATGATGCCCACTGTGATCACCAGAGCAAAGTTCGTTCGATCGTACTGTTACTCTCTCTCTT
TCAAACAGAATTGTCCGAATCGTGTGACAACAACAGCCTGTTCTCACACACTCTTTTCTTCTAA
CCAAGGGGGTGGTTTAGTTTAGTAGAACCTCGTGAAACTTACATTTACATATATATAAACTTGC
ATAAATTGGTCAATGCAAGAAATACATATTTGGTCTTTTCTAATTCGTAGTTTTTTCAAGTTCT
TAGATGCTTTCTTTTTCTCTTTTTTTACAGATCATCAAGGAAGTAATTATCTACTTTTTACAAC
AAATATAAAAAAATGTCTTGCCTTATTCCTGAGAATTTAAGGAACCCCAAAAAGGTTCACGAA
AATAGATTGCCTACTAGGGCTTACTACTATGATCAGGATATTTTCGAATCTCTCAATGGGCCTT
GGGCTTTTGCGTTGTTTGATGCACCTCTTGACGCTCCGGATGCTAAGAATTTAGACTGGGAAAC
GGCAAAGAAATGGAGCACCATTTCTGTGCCATCCCATTGGGAACTTCAGGAAGACTGGAAGTAC
GGTAAACCAATTTACACGAACGTACAGTACCCTATCCCAATCGACATCCCAAATCCTCCCACTG
TAAATCCTACTGGTGTTTATGCTAGAACTTTTGAATTAGATTCGAAATCGATTGAGTCGTTCGA
GCACAGATTGAGATTTGAGGGTGTGGACAATTGTTACGAGCTTTATGTTAATGGTCAATATGTG
GGTTTCAATAAGGGGTCCCGTAACGGGGCTGAATTTGATATCCAAAAGTACGTTTCTGAGGGCG
AAAACTTAGTGGTCGTCAAGGTTTTCAAGTGGTCCGATTCCACTTATATCGAGGACCAAGATCA
ATGGTGGCTCTCTGGTATTTACAGAGACGTTTCTTTACTAAAATTGCCTAAGAAGGCCCATATT
GAAGACGTTAGGGTCACTACAACTTTTGTGGACTCTCAGTATCAGGATGCAGAGCTTTCTGTGA
AAGTTGATGTCCAGGGTTCTTCTTATGATCACATCAATTTCACACTTTACGAACCTGAAGATGG
ATCTAAAGTTTACGATGCAAGCTCTTTGTTGAACGAGGAGAATGGGAACACGACTTTTTCAACT
AAAGAATTTATTTCCTTCTCCACCAAAAAGAACGAAGAAACAGCTTTCAAGATCAACGTCAAGG
CCCCAGAACATTGGACCGCAGAAAATCCTACTTTGTACAAGTACCAGTTGGATTTAATTGGATC
TGATGGCAGTGTGATTCAATCTATTAAGCACCATGTTGGTTTCAGACAAGTGGAGTTGAAGGAC
GGTAACATTACTGTTAATGGCAAAGACATTCTCTTTAGAGGTGTCAACAGACATGATCACCATC
CAAGGTTCGGTAGAGCTGTGCCATTAGATTTTGTTGTTAGGGACTTGATTCTAATGAAGAAGTT
TAACATCAATGCTGTTCGTAACTCGCATTATCCAAACCATCCTAAGGTGTATGACCTCTTCGAT
AAGCTGGGCTTCTGGGTCATTGACGAGGCAGATCTTGAAACTCATGGTGTTCAAGAGCCATTTA
ATCGTCATACGAACTTGGAGGCTGAATATCCAGATACTAAAAATAAACTCTACGATGTTAATGC
CCATTACTTATCAGATAATCCAGAGTACGAGGTCGCGTACTTAGACAGAGCTTCCCAACTTGTC
CTAAGAGATGTCAATCATCCTTCGATTATTATCTGGTCCTTGGGTAACGAAGCTTGTTATGGCA
GAAACCACAAAGCCATGTACAAGTTAATTAAACAATTGGATCCTACCAGACTTGTGCATTATGA
GGGTGACTTGAACGCTTTGAGTGCAGATATCTTTAGTTTCATGTACCCAACATTTGAAATTATG
GAAAGGTGGAGGAAGAACCACACTGATGAAAATGGTAAGTTTGAAAAGCCTTTGATCTTGTGTG
```

Figure 15

```
AGTACGGCCATGCAATGGGTAACGGTCCTGGCTCTTTGAAAGAATATCAAGAGTTGTTCTACAA
GGAGAAGTTTTACCAAGGTGGCTTTATCTGGGAATGGGCAAATCACGGTATTGAATTCGAAGAT
GTTAGTACTGCAGATGGTAAGTTGCATAAAGCTTATGCTTATGGTGGTGACTTTAAGGAAGAGG
TTCATGACGGAGTGTTCATCATGGATGGTTTGTGTAACAGTGAGCATAATCCTACTCCGGGCCT
TGTAGAGTATAAGAAGGTTATTGAACCCGTTCATATTAAAATTGCGCACGGATCTGTAACAATC
ACAAATAAGCACGACTTCATTACGACAGACCACTTATTGTTTATCGACAAGGACACGGGAAAGA
CAATCGACGTTCCATCTTTAAAGCCAGAAGAATCTGTTACTATTCCTTCTGATACAACTTATGT
TGTTGCCGTGTTGAAAGATGATGCTGGTGTTCTAAAGGCAGGTCATGAAATTGCCTGGGCCAA
GCTGAACTTCCATTGAAGGTACCCGATTTTGTTACAGAGACAGCAGAAAAAGCTGCGAAGATCA
ACGACGGTAAACGTTATGTCTCAGTTGAATCCAGTGGATTGCATTTATCTTGGACAAATTGTT
GGGTAAAATTGAAAGCCTAAAGGTCAAGGGTAAGGAAATTTCCAGCAAGTTTGAGGGTTCTTCA
ATCACTTTCTGGAGACCTCCAACGAATAATGATGAACCTAGGGACTTTAAGAACTGGAAGAAGT
ACAATATTGATTTAATGAAGCAAAACATCCATGGAGTGAGTGTCGAAAAAGGTTCTAATGGTTC
TCTAGCTGTAGTCACGGTTAACTCTCGTATATCCCCAGTTGTATTTTACTATGGGTTTGAGACT
GTTCAGAAGTACACGATCTTTGCTAACAAAATAAACTTGAACACTTCTATGAAGCTTACTGGCG
AATATCAGCCTCCTGATTTCCCAAGAGTTGGGTACGAATTCTGGCTAGGAGATAGTTATGAATC
ATTTGAATGGTTAGGTCGCGGGCCCGGCGAATCATATCCGGATAAGAAGGAATCTCAAAGATTC
GGTCTTTACGATTCCAAAGATGTAGAGGAATTCGTATATGACTATCCTCAAGAAAATGGAAATC
ATACAGATACCCACTTTTTGAACATCAAATTTGAAGGTGCAGGAAAACTATCGATCTTCCAAAA
GGAGAAGCCATTTAACTTCAAGATTTCAGACGAATACGGGGTTGATGAAGCTGCCCACGCTTGT
GACGTTAAAAGATACGGCAGACACTATCTAAGGTTGGACCATGCAATCCATGGTGTTGGTAGCG
AAGCATGCGGACCTGCTGTTCTGGACCAGTACAGATTGAAAGCTCAAGATTTCAACTTTGAGTT
TGATCTCGCTTTTGAATAAGCCGGCCATTGAATTGAATTGAAATCGATAGATCAATTTTTTTCT
TTTCTCTTTCCCCATCCTTTACGCTAAATAATAGTTTATTTTATTTTTTGAATATTTTTTATT
TATATACGTATATATAGACTATTATTTATCTTTTAATGATTATTAAGATTTTTATTAAAAAAAA
ATTCGCACCTCTTTTAATGCCTTTATGCAGTTTTTTTTCCCATTCGATATTTCTATGTTCGGG
TTCAGCGTATTTTAAGTTTAATAACTCGAAAATTCTGCGTTTCGA (SEQ ID N° 9)
```

Figure 15 (cont.)

Sequence of the HR1 rDNA

```
TTAATCTCAGCAGATCGTAACAACAAGGCTACTCTACTGCTTACAATACCCCGTTGTACATCTA
AGTCGTATACAAATGATTTATCCCCACGCAAAATGACATTGCAATTCGCCAGCAAGCACCCAAG
GCCTTTCCGCCAAGTGCACCGTTGCTAGCCTGCTATGGTTCAGCGACGCCACAAGGACGCCTTA
TTCGTATCCATCTATATTGTGTGGAGCAAAGAAATCACCGCGTTCTAGCATGGATTCTGACTTA
GAGGCGTTCAGCCATAATCCAGCGGATGGTAGCTTCGCGGCAATGCCTGATCAGACAGCCGCAA
AAACCAATTATCCGAATGAACTGTTCCTCTCGTACTAAGTTCAATTACTATTGCGGTAACATTC
ATCAGTAGGGTAAAACTAACCTGTCTCACGACGGTCTAAACCCAGCTCACGTTCCCTATTAGTG
GGTGAACAATCCAACGCTTACCGAATTCTGCTTCGGTATGATAGGAAGAGCCGACATCGAAGAA
TCAAAAAGCAATGTCGCTATGAACGCTTGACTGCCACAAGCCAGTTATCCCTGTGGTAACTTTT
CTGGCACCTCTAGCCTCAAATTCCGAGGGACTAAAGGATCGATAGGCCACACTTTCATGGTTTG
TATTCACACTGAAAATCAAAATCAAGGGGGCTTTTACCCTTTTGTTCTACTGGAGATTTCTGTT
CTCCATGAGCCCCCCTTAGGACATCTGCGTTATCGTTTAACAGATGTGCCGCCCCAGCCAAACT
CCCCACCTGACAATGTCTTCAACCCGGATCAGCCCCGAATGGGACCTTGAATGCTAGAACGTGG
AAAATGAATTCCAGCTCCGCTTCATTGAATAAGTAAAGAAACTATAAAGGTAGTGGTATTTCAC
TGGCGCCGAAGCTCCCACTTATTCTACACCCTCTATGTCTCTTCACAATGTCAAACTAGAGTCA
AGCTCAACAGGGTCTTCTTTCCCCGCTGATTCTGCCAAGCCCGTTCCCTTGGCTGTGGTTTCGC
TAGATAGTAGATAGGGACAGTGGGAATCTCGTTAATCCATTCATGCGCGTCACTAATTAGATGA
CGAGGCATTTGGCTACCTTAAGAGAGTCATAGTTACTCCCGCCGTTTACCCGCGCTTGGTTGAA
TTTCTTCACTTTGACATTCAGAGCACTGGGCAGAA (SEQ ID N° 10)
```

Figure 16

Sequence of the HR2 rDNA
```
AGTAGTCCGCCTAGCAGAGCAAGCCCCACCAAGCAGTCCACAAGCACGCCCGCTGCGTCTGACC
AAGGCCCTCACTACCCGACCCTTAGAGCCAATCCTTATCCCGAAGTTACGGATCTATTTTGCCG
ACTTCCCTTATCTACATTATTCTATCAACTAGAGGCTGTTCACCTTGGAGACCTGCTGCGGTTA
TCAGTACGACCTGGCATGAAAACTATTCCTTCCTGTGGATTTTCACGGGCCGTCACAAGCGCAC
CGGAGCCAGCAAAGGTGCTGGCCTCTTCCAGCCATAAGACCCCATCTCCGGATAAACCAATTCC
GGGGTGATAAGCTGTTAAGAAGAAAAGATAACTCCTCCCAGGGCTCGCGCCGACGTCTCCACAT
TCAGTTACGTTACCGTGAAGAATCCATATCCAGGTTCCGGAATCTTAACCGGATTCCCTTTCGA
TGGTGGCCTGCATAAAATCAGGCCTTTGAAACGGAGCTTCCCCATCTCTTAGGATCGACTAACC
CACGTCCAACTGCTGTTGACGTGGAACCTTTCCCCACTTCAGTCTTCAAAGTTCTCATTTGAAT
ATTTGCTACTACCACCAAGATCTGCACTAGAGGCCGTTCGACCCGACCTTACGGTCTAGGCTTC
GTCACTGACCTCCACGCCTGCCTACTCGTCAGGGCATCATATCAACCCTGACGGTAGAGTATAG
GTAACACGCTTGAGCGCCATCCATTTTCAGGGCTAGTTCATTCGGCCGGTGAGTTGTTACACAC
TCCTTAGCGGATTCCGACTTCCATGGCCACCGTCCGGCTGTCTAGATGAACTAACACCTTTTGT
GGTGTCTGATGAGCGTGTATTCCGGCACCTTAACTCTACGTTCGGTTCATCCCGCATCGCCAGT
TCTGCTTACCAAAAATGGCCCACTAAAAGCTCTTCATTCAAATGTCCACGTTCAATTAAGTAAC
AAGGACTTCTTACATATTTAAAGTTTGAGAATAGGTCAAGGTCATTTCGACCCCGGAACCTCTA
ATCATTCGCTTTACCTCATAAAACTGATACGAGCTTCTGCTATCCTGAGGGAAACTTCGGCAGG
AACCAGCTACTAGATGGTTCGATTAGTCTTTCGCCCCTATACCCAAATTCGACGATCGATTTGC
ACGTCAGAACCGCTACGAGCCTCCACCAGAGTTTCCTCTGGCTTCACCCTATTCAGGCATAGTT
CACCATCTTTCGGGTCCCAACAGCTATGCTCTTACTCAAATCCATCCGAAGACATCAGGATCGG
TCGATTGTGCACCTCTTGCGAGGCCCCAACCTACGTTCACTTTCATTACGCGTATGGGTTTTAC
ACCCAAACACTCGCATAGACGTTAGACTCCTTGGTCCGTGTTTCAAGACGGGCGGCATATAACC
ATTATGCCAGCATCCTTGACTTACGTCGCAGTCCTCAGTCCAGCTGGCAGTATTCCCACAGGC
TATAATACTTACCGAGGCAAGCTACATTCCTATGGATTTATCCTGCCACCAAAACTGATGCTGG
CCCAGTGAAATGCGAGATTCCCTACCCACAAGGAGCAGAGGGCACAAAACACCATGTCTGATC
AAATGCCCTTCCCTTTCAACAATTTCACGTACTTTTCACTCTCTTTTCAAAGTTCTTTTCATC
TTTCCATCACTGTACTTGTTCGCTATCGGTCTCTCGCCAATATTTAGCTTTAGATGGAATTTAC
CACCCACTTAGAGCTGCATTCCCAAACAACTCGACTCTTCGAAGGCACTTTACAAAGAACCGCA
CTCCTCGCCACACGGGATTCTCACCCTCTATGACGTCCTGTTCCAAGGAACATAGACAAGGAAC
GGCCCCAAAGTTGCCCTCTCCAAATTACAACTCGGGCACCGAAGGTACCAGATTTCAAATTTGA
GCTTTTGCCGCTTCACTCGCCGTTACTAAGGCAATCCCGGTTGGTTTCTTTTCCTCCGCTTATT
GATATGCTTAAGTTCAGCGGGTACTC (SEQ ID N° 11)
```

Figure 17

Examples of selected sequences that originate from the lactose killing screening methodology as describe in the examples

```
> Cas 1.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCTTACTGTCGGGAATTCGCGTTGGCCAATTCATTAATGGTATAAGGTTCTTGACATCTTA
CAATCAATATGGTATAATAATTTAGTTAGGGCCCAAGTTCACTTAAAAAGGAGATCAACAATGA
AAGCAATTTTCGTACTGAAACATCTTAATCATGCGTAGGATTTTTTCTATGTACTATTTAAAAA
ACACAAACTTTTGGATGTTCGGTTTATTCTTTTTCTTTTACTTTTTTATCATGGGAGCCTACTT
CCCGTTTTTCCCGATTTGGCTACATGACATCAACCATATCAGCAAAAGTGATACGGGTATTATT
TTTGCCGCTATTTCTCTGTTCTCGCTATTATTCCAACCGCTGTTTGGTCTGCTTTCTGACAAAC
TCGGGCTGCGCAAATACCTGCTGTGGATTATTACCGGCATGTTAGTGATGTTTGCGCCGTTCTT
TATTTTATCTTCGGGCCACTGTTACAATACAACATTTAGTAGGATCGATTGTTGGTGGTATT
TATCTAGGCTTTTGTTTAACGCCGGTGCGCCAGCAGTAGAGGCATTTATTGAGAAAGTCAGCC
GTCGCAGTAATTTCGAATTTGGTCGCGCGGATGTTTGGCTGTGTTGGCTGGGCGCTGTGTGC
CTCGATTGTCGGCATCATGTTCACCATCAATAATCAGTTTGTTTTCTGGCTGGGCTCTGGCTGT
GCACTCATCCTCGCCGTTTTACTCTTTTTCGCCAAAACGGATGCGCCCTCTTCTGCCACGGTTG
CCAATGCGGTAGGTGCCAACCATTCGGCATTTAGCCTTAAGCTGGCACTGGAACTGTTCAGACA
GCCAAAACTGTGGTTTTGTCACTGTATGTTATTGGCGTTTCCTGCACCTACGATGTTTTTGAC
CAACAGTTTGCTAATTTCTTTACTTCGTTCTTTGCTACCGGTGAACAGGGTACGCGGGTATTTG
GCTACGTAACGACAATGGGCGAATTACTTAACGCCTCGATTATGTTCTTTGCGCCACTGATCAT
TAATCGCATCGGTGGGAAAAACGCCCTGCTGCTGGCTGGCACTATTATGTCTGTACGTATTATT
GGCTCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTCAGC
GACGATTTATCTGGTCTGTTTCTGCTTCTTTAAGCAACTGGCGATGATTTTATGTCTGTACTG
GCGGGCAATATGTATGAAAGCATCGGTTTCCAGGGCGCTTATCTGGTGCTGGGTCTGGTGGCGC
TGGGCTTCACCTTAATTTCCGTGTTCACGCTTAGCGGCCCCGGCCCGCTTTCCCTGCTGCGTCG
TCAGGTGAATGAAGTCGCTTAA (SEQ ID N° 12)
```

Figure 18

> Cas 2.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACACTT
ACTGTCGGGAATTCGCGTTGGCCAATTAATTAATGGTATAAGGTTCTTGACATCTTACAATCAA
TATGGTATAATAATTTAGTTAGGGCCCAAGTTCACTTAAAAAGGAGATCAACAATGAAAGCAAT
TTTCGTACTGAAACATCTTAATCATGCGTAGGATTTTTCTATGTACTATTTAAAAAACACAAA
CTTTTGGATGTTCGGTTTATTCTTTTCTTTTACTTTTTATCATGGGAGCCTACTTCCCGTTT
TTCCCGATTTGGCTACATGACATCAACCATATCAGCAAAAGTGATACGGGTATTATTTTGCCG
CTATTTCTCTGTTCTCGCTATTATTCCAACCGCTGTTTGGTCTGCTTTCTGACAAACTCGGGCT
GCGCAAATACCTGCTGTGGATTATTACCGGCATGTTAGTGATGTTTGCGCCGTTCTTTATTTTT
ATCTTCGGGCCACTGTTACAATACAACATTTAGTAGGATCGATTGTTGGTGGTATTTATCTAG
GCTTTTGTTTTAACGCCGGTGCGCCAGCAGTAGAGGCATTTATTGAGAAAGTCAGCCGTCGCAG
TAATTTCGAATTTGGTCGCGCGCGGATGTTTGGCTGTGTTGGCTGGCGCTGTGTGCCTCGATT
GTCGGCATCATGTTCACCATCAATAATCAGTTTGTTTTCTGGCTGGGCTCTGGCTGTGCACTCA
TCCTCGCCGTTTTACTCTTTTTCGCCAAAACGGATGCGCCCTCTTCTGCCACGGTTGCCAATGC
GGTAGGTGCCAACCATTCGGCATTTAGCCTTAAGCTGGCACTGGAACTGTTCAGACAGCCAAAA
CTGTGGTTTTTGTCACTGTATGTTATTGGCGTTTCCTGCACCTACGATGTTTTTGACCAACAGT
TTGCTAATTTCTTTACTTCGTTCTTTGCTACCGGTGAACAGGGTACGCGGGTATTTGGCTACGT
AACGACAATGGGCGAATTACTTAACGCCTCGATTATGTTCTTTGCGCCACTGATCATTAATCGC
ATCGGTGGGAAAAACGCCCTGCTGCTGGCTGGCACTATTATGTCTGTACGTATTATTGGCTCAT
CGTTCGCCACCTCAGCGCTGGAAGTGGTTATTCTGAAAACGCTGCATATGTTTGAAGTACCGTT
CCTGCTGGTGGCTGCTTTAAATATATTACCAGCCAGTTTGAAGTGCGTTTTTCAGCGACGATT
TATCTGGTCTGTTTCTGCTTCTTTAAGCAACTGGCGATGATTTTATGTCTGTACTGGCGGGCA
ATATGTATGAAAGCATCGGTTTCCAGGGCGCTTATCTGGTGCTGGGTCTGGTGGCGCTGGGCTT
CACCTTAATTTCCGTGTTCACGCTTAGCGGCCCCGGCCCGCTTTCCTGCTGCGTCGTCAGGTG
AATGAAGTCGCTTAA (SEQ ID N° 13)

Figure 18 – cont

> Cas 3.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCAATTTTCGTACATGTACTATTTAAAAAACACAAACTTTTGGATGTTCGGTTTATTCTTT
TTCTTTTACTTTTTTATCATGGGAGCCTACTTCCCGTTTTTCCCGATTTGGCTACATGACATCA
ACCATATCAGCAAAAGTGATACGGGTATTATTTTTGCCGCTATTTCTCTGTTCTCGCTATTATT
CCAACCGCTGTTTGGTCTGCTTTCTGACAAACTCGGGCTGCGCAAATACCTGCTGTGGATTATT
ACCGGCATGTTAGTGATGTTTGCGCCGTTCTTTATTTTTATCTTCGGGCCACTGTTACAATACA
ACATTTTAGTAGGATCGATTGTTGGTGGTATTTATCTAGGCTTTTGTTTTAACGCCGGTGCGCC
AGCAGTAGAGGCATTTATTGAGAAAGTCAGCCGTCGCAGTAATTTCGAATTTGGTCGCGCGCGG
ATGTTTGGCTGTGTTGGCTGGGCGCTGTGTGCCTCGATTGTCGGCATCATGTTCACCATCAATA
ATCAGTTTGTTTCTGGCTGGGCTCTGGCTGTGCACTCATCCTCGCCGTTTTACTCTTTTTCGC
CAAAACGGATGCGCCCTCTTCTGCCACGGTTGCCAATGCGGTAGGTGCCAACCATTCGGCATTT
AGCCTTAAGCTGGCACTGGAACTGTTCAGACAGCCAAAACTGTGGTTTTTGTCACTGTATGTTA
TTGGCGTTTCCTGCACCTACGATGTTTTTGACCAACAGTTTGCTAATTTCTTTACTTCGTTCTT
TGCTACCGGTGAACAGGGTACGCGGGTATTTGGCTACGTAACGACAATGGGCGAATTACTTAAC
GCCTCGATTATGTTCTTTGCGCCACTGATCATTAATCGCATCGGTGGGAAAAACGCCCTGCTGC
TGGCTGGCACTATTATGTCTGTACGTATTATTGGCTCATCGTTCGCCACCTCAGCGCTGGAAGT
GGTTATTCTGAAAACGCTGCATATGTTTGAAGTACCGTTCCTGCTGGTGGGCTGCTTTAAATAT
ATTACCAGCCAGTTTGAAGTGCGTTTTTCAGCGACGATTTATCTGGTCTGTTTCTGCTTCTTTA
AGCAACTGGCGATGATTTTTATGTCTGTACTGGCGGGCAATATGTATGAAAGCATCGGTTTCCA
GGGCGCTTATCTGGTGCTGGGTCTGGTGGCGCTGGGCTTCACCTTAATTTCCGTGTTCACGCTT
AGCGGCCCCGGCCCGCTTTCCCTGCTGCGTCGTCAGGTGAATGAAGTCGCTTAA     (SEQ ID N° 14)

Figure 18 – cont

> Cas 4.
CCCGTCTTACTGTCGGGAATTCGCGTTGGCCAATTAATTAATGGTATAAGGTTCTTGACATCTT
ACAATCAATATGGTATAATAATTTAGTTAGGGCCCAAGTTCACTTAAAAAGGAGATCAACAATG
AAAGCTTACTGTCGGGAATTCGCGTTGGCCGATTCATTAATGGTATAAGGTTCTTGACATCTTA
CAATCAATATGGTATAATAATTTAGTTAGGGCCCAAGTTCACTTAAAAAGGAGATCAACAATGA
AAGCAATTTTCGTACTGAAACATCTTAATCATGCGTAGGATTTTTCTATGTACTATTTAAAAA
ACACAAACTTTTGGATGTTCGGTTTATTCTTTTCTTTTACTTTTTTATCATGGGAGCCTACTT
CCCGTTTTTCCCGATTTGGCTACATGACATCAACCATATCAGCAAAAGTGATACGGGTATTATT
TTTGCCGCTATTTCTCTGTTCTCGCTATTATTCCAACCGCTGTTTGGTCTGCTTTCTGACAAAC
TCGGGCTGCGCAAATACCTGCTGTGGATTATTACCGGCATGTTAGTGATGTTTGCGCCGTTCTT
TATTTTTATCTTCGGGCCACTGTTACAATACAACATTTTAGTAGGATCGATTGTTGGTGGTATT
TATCTAGGCTTTTGTTTTAACGCCGGTGCGCCAGCAGTAGAGGCATTTATTGAGAAAGTCAGCC
GTCGCAGTAATTTCGAATTTGGTCGCGCGCGGATGTTTGGCTGTGTTGGCTGGGCGCTGTGTGC
CTCGATTGTCGGCATCATGTTCACCATCAATAATCAGTTTGTTTCTGGCTGGGCTCTGGCTGT
GCACTCATCCTCGCCGTTTTACTCTTTTTCGCCAAAACGGATGCGCCCTCTTCTGCCACGGTTG
CCAATGCGGTAGGTGCCAACCATTCGGCATTTAGCCTTAAGCTGGCACTGGAACTGTTCAGACA
GCCAAAACTGTGGTTTTTGTCACTGTATGTTATTGGCGTTTCCTGCACCTACGATGTTTTTGAC
CAACAGTTTGCTAATTTCTTTACTTCGTTCTTTGCTACCGGTGAACAGGGTACGCGGGTATTTG
GCTACGTAACGACAATGGGCGAATTACTTAACGCCTCGATTATGTTCTTTGCCCACTGATCAT
TAATCGCATCGGTGGGAAAAACGCCCTGCTGCTGGCTGGCACTATTATGTCTGTACGTATTATT
GGCTCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTCAGC
GACGATTTATCTGGTCTGTTTCTGCTTCTTTAAGCAACTGGCGATGATTTTATGTCTGTACTG
GCGGGCAATATGTATGAAAGCATCGGTTTCCAGGGCGCTTATCTGGTGCTGGGTCTGGTGGCGC
TGGGCTTCACCTTAATTTCCGTGTTCACGCTTAGCGGCCCCGGCCCGCTTTCCTGCTGCGTCG
TCAGGTGAATGAAGTCGCTTAA (SEQ ID N° 15)

Figure 18 – cont

> Cas 5.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCTTACTGTCGGGAATTCGCGTTGGCCGATTCTTATAAATCATTATCTTCTTGACATTTTA
GAAACAATATGGTATAATATAACGATAAGGGCCCAAGTTCACTTAAAAAGGAGATCAACAATGA
AAGCAATTTTCGTACTGAAACATCTTAATCATGCGTAGGATTTTTTCTATGTACTATTTAAAAA
ACACAAACTTTTGGATGTTCGGTTTATTCTTTTCTTTTACTTTTTTATCATGGGAGCCTACTT
CCCGTTTTTCCCGATTTGGCTACATGACATCAACCATATCAGCAAAAGTGATACGGGTATTATT
TTTGCCGCTATTTCTCTGTTCTCGCTATTATTCCAACCGCTGTTTGGTCTGCTTTCTGACAAAC
TCGGGCTGCGCAAATACCTGCTGTGGATTATTACCGGCATGTTAGTGATGTTTGCGCCGTTCTT
TATTTTATCTTCGGGCCACTGTTACAATACAACATTTAGTAGGATCGATTGTTGGTGGTATT
TATCTAGGCTTTTGTTTAACGCCGGTGCGCCAGCAGTAGAGGCATTTATTGAGAAAGTCAGCC
GTCGCAGTAATTTCGAATTTGGTCGCGCGCGGATGTTTGGCTGTGTTGGCTGGGCGCTGTGTGC
CTCGATTGTCGGCATCATGTTCACCATCAATAATCAGTTTGTTTCTGGCTGGGCTCTGGCTGT
GCACTCATCCTCGCCGTTTTACTCTTTTTCGCCAAAACGGATGCGCCCTCTTCTGCCACGGTTG
CCAATGCGGTAGGTGCCAACCATTCGGCATTTAGCCTTAAGCTGGCACTGGAACTGTTCAGACA
GCCAAAACTGTGGTTTTTGTCACTGTATGTTATTGGCGTTTCCTGCACCTACGATGTTTTGAC
CAACAGTTTGCTAATTTCTTTACTTCGTTCTTTGCTACCGGTGAACAGGGTACGCGGGTATTTG
GCTACGTAACGACAATGGGCGAATTACTTAACGCCTCGATTATGTTCTTTGCGCCACTGATCAT
TAATCGCATCGGTGGGAAAAACGCCCTGCTGCTGGCTGGCACTATTATGTCTGTACGTATTATT
GGCTCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTCAGC
GACGATTTATCTGGTCTGTTTCTGCTTCTTTAAGCAACTGGCGATGATTTTTATGTCTGTACTG
GCGGGCAATATGTATGAAAGCATCGGTTTCCAGGGCGCTTATCTGGTGCTGGGTCTGGTGGCGC
TGGGCTTCACCTTAATTTCCGTGTTCACGCTTAGCGGCCCCGGCCCGCTTTCCCTGCTGCGTCG
TCAGGTGAATGAAGTCGCTTAA (SEQ ID N° 16)

Figure 18 – cont

> Cas 6.
CCCGTCTTACTGTCGGGAATTCGCGTTGGCCGATTCGAATTCGCGTTGGCCGATTCGAATTCGC
GTTGGCCGATTCTTATTAACAATATCCTTCTTGACATTTTGCAGGGATTGTGATATAATCAATA
AGTATGGGCCCAAGTTCACTTAAAAAGGAGATCAACAATGAAAGCAATTTTCGTACTGAAACAT
CTTAATCATGCGTAGGATTTTTTCTATGTACTATTTAAAAAACACAAACTTTTGGATGTTCGGT
TTATTCTTTTTCTTTTACTTTTTTATCATGGGAGCCTACTTCCCGTTTTTCCCGATTTGGCTAC
ATGACATCAACCATATCAGCAAAAGTGATACGGGTATTATTTTTGCCGCTATTTCTCTGTTCTC
GCTATTATTCCAACCGCTGTTTGGTCTGCTTTCTGACAAACTCGGGCTGCGCAAATACCTGCTG
TGGATTATTACCGGCATGTTAGTGATGTTTGCGCCGTTCTTTATTTTATCTTCGGGCCACTGT
TACAATACAACATTTTAGTAGGATCGATTGTTGGTGGTATTTATCTAGGCTTTTGTTTTAACGC
CGGTGCGCCAGCAGTAGAGGCATTTATTGAGAAAGTCAGCCGTCGCAGTAATTTCGAATTTGGT
CGCGCGCGGATGTTTGGCTGTGTTGGCTGGGCGCTGTGTGCCTCGATTGTCGGCATCATGTTCA
CCATCAATAATCAGTTTGTTTTCTGGCTGGGCTCTGGCTGTGCACTCATCCTCGCCGTTTTACT
CTTTTTCGCCAAAACGGATGCGCCCTCTTCTGCCACGGTTGCCAATGCGGTAGGTGCCAACCAT
TCGGCATTTAGCCTTAAGCTGGCACTGGAACTGTTCAGACAGCCAAAACTGTGGTTTTTGTCAC
TGTATGTTATTGGCGTTTCCTGCACCTACGATGTTTTTGACCAACAGTTTGCTAATTTCTTTAC
TTCGTTCTTTGCTACCGGTGAACAGGGTACGCGGGTATTTGGCTACGTAACGACAATGGGCGAA
TTACTTAACGCCTCGATTATGTTCTTTGCGCCACTGATCATTAATCGCATCGGTGGGAAAAACG
CCCTGCTGCTGGCTGGCACTATTATGTCTGTACGTATTATTGGCTCATCGTTCGCCACCTCAGC
GCTGGAAGTGGTTATTCTGAAAACGCTGCATATGTTTGAAGTACCGTTCCTGCTGGTGGGCTGC
TTTAAATATATTACCAGCCAGTTTGAAGTGCGTTTTTCAGCGACGATTTATCTGGTCTGTTTCT
GCTTCTTTAAGCAACTGGCGATGATTTTATGTCTGTACTGGCGGGCAATATGTATGAAAGCAT
CGGTTTCCAGGGCGCTTATCTGGTGCTGGGTCTGGTGGCGCTGGGCTTCACCTTAATTTCCGTG
TTCACGCTTAGCGGCCCCGGCCCGCTTTCCCTGCTGCGTCGTCAGGTGAATGAAGTCGCTTAA
(SEQ ID N° 17)

Figure 18 – cont

> Cas 7.
CCCGTCTTACTGTCGGGAATTCGCGTTGGCCGATTCGAATTCGCGTTGGCCGATTCGAATTCGC
GTTGGCCGATTCGAATTCGCGTTGGCCGATTCGAATTCGCGTTGGCCAATTAATTAATGGTATA
AGGTTCTTGACATCTTACAATCAATATGGTATAATAATTTAGTTAGGGCCCAAGTTCACTTAAA
AAGGAGATCAACACTTACTGTCGGGAATTCGCGTTGGCCAATTAATTAATGGTATAAGGTTCTT
GACATCTTACAATCAATATGGTATAAATAATTTAGTTAGGGCCCAAGTTCACTTAAAAGGAGA
TCAACAATGAAAGCAATTTTCGTACTGAAACATCTTAATCATGCGTAGGATTTTTCTATGTAC
TATTTAAAAAACACAAACTTTTGGATGTTCGGTTATTCTTTTCTTTTACTTTTTATCATGG
GAGCCTACTTCCCGTTTTTCCCGATTTGGCTACATGACATCAACCATATCAGCAAAAGTGATAC
GGGTATTATTTTTGCCGCTATTTCTCTGTTCTCGCTATTATTCCAACCGCTGTTTGGTCTGCTT
TCTGACAAACTCGGGCTGCGCAAATACCTGCTGTGGATTATTACCGGCATGTTAGTGATGTTTG
CGCCGTTCTTTATTTTATCTTCGGGCCACTGTTACAATACAACATTTTAGTAGGATCGATTGT
TGGTGGTATTTATCTAGGCTTTTGTTTAACGCCGGTGCGCCAGCAGTAGAGGCATTTATTGAG
AAAGTCAGCCGTCGCAGTAATTTCGAATTTGGTCGCGCGCGGATGTTTGGCTGTGTTGGCTGGG
CGCTGTGTGCCTCGATTGTCGGCATCATGTTCACCATCAATAATCAGTTTGTTTCTGGCTGGG
CTCTGGCTGTGCACTCATCCTCGCCGTTTTACTCTTTTCGCCAAAACGGATGCGCCCTCTTCT
GCCACGGTTGCCAATGCGGTAGGTGCCAACCATTCGGCATTTAGCCTTAAGCTGGCACTGGAAC
TGTTCAGACAGCCAAAACTGTGGTTTTTGTCACTGTATGTTATTGGCGTTTCCTGCACCTACGA
TGTTTTTGACCAACAGTTTGCTAATTTCTTTACTTCGTTCTTTGCTACCGGTGAACAGGGTACG
CGGGTATTTGGCTACGTAACGACAATGGGCGAATTACTTAACGCCTCGATTATGTTCTTTGCGC
CACTGATCATTAATCGCATCGGTGGGAAAAACGCCCTGCTGCTGGCTGGCACTATTATGTCTGT
ACGTATTATTGGCTCATCGTTCGCCACCTCAGCGCTGGAAGTGGTTATTCTGAAAACGCTGCAT
ATGTTTGAAGTACCGTTCCTGCTGGTGGGCTGCTTTAAATATATTACCAGCCAGTTTGAAGTGC
GTTTTTCAGCGACGATTTATCTGGTCTGTTTCTGCTTCTTTAAGCAACTGGCGATGATTTTTAT
GTCTGTACTGGCGGGCAATATGTATGAAAGCATCGGTTTCCAGGGCGCTTATCTGGTGCTGGGT
CTGGTGGCGCTGGGCTTCACCTTAATTTCCGTGTTCACGCTTAGCGGCCCCGGCCCGCTTTCCC
TGCTGCGTCGTCAGGTGAATGAAGTCGCTTAA (SEQ ID N° 18)

Figure 18 – cont

> Cas 8.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCTTACTGTCGGGAATTCGCGTTGGCCGATTCATTAATGGTATAAGGTTCTTGACATCTTA
CAATCAATATGGTATAATAATTTAGTTAGGGCCCAAGTTCACTTAAAAAGGAGATCAACAATGA
AAGCAATTTTCGTACTGAAACATCTTAATCATGCGTAGGATTTTTCTATGTACTATTTAAAAA
ACACAAACTTTTGGATGTTCGGTTTATTCTTTTTCTTTTACTTTTTATCATGGGAGCCTACTT
CCCGTTTTTCCCGATTTGGCTACATGACATCAACCATATCAGCAAAAGTGATACGGGTATTATT
TTTGCCGCTATTTCTCTGTTCTCGCTATTATTCCAACCGCTGTTTGGTCTGCTTTCTGACAAAC
TCGGGCTGCGCAAATACCTGCTGTGGATTATTACCGGCATGTTAGTGATGTTTGCGCCGTTCTT
TATTTTATCTTCGGGCCACTGTTACAATACAACATTTTAGTAGGATCGATTGTTGGTGGTATT
TATCTAGGCTTTTGTTTAACGCCGGTGCGCCAGCAGTAGAGGCATTTATTGAGAAAGTCAGCC
GTCGCAGTAATTTCGAATTTGGTCGCGCGCGGATGTTTGGCTGTGTTGGCTGGGCGCTGTGTGC
CTCGATTGTCGGCATCATGTTCACCATCAATAATCAGTTTGTTTTCTGGCTGGGCTCTGGCTGT
GCACTCATCCTCGCCGTTTTACTCTTTTTCGCCAAAACGGATGCGCCCTCTTCTGCCACGGTTG
CCAATGCGGTAGGTGCCAACCATTCGGCATTTAGCCTTAAGCTGGCACTGGAACTGTTCAGACA
GCCAAAACTGTGGTTTTTGTCACTGTATGTTATTGGCGTTTCCTGCACCTACGATGTTTTTGAC
CAACAGTTTGCTAATTTCTTTACTTCGTTCTTTGCTACCGGTGAACAGGGTACGCGGGTATTTG
GCTACGTAACGACAATGGGCGAATTACTTAACGCCTCGATTATGTTCTTTGCGCCACTGATCAT
TAATCGCATCGGTGGGAAAAACGCCCTGCTGCTGGCTGGCACTATTATGTCTGTACGTATTATT
GGCTCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTCAGC
GACGATTTATCTGGTCTGTTTCTGCTTCTTTAAGCAACTGGCGATGATTTTATGTCTGTACTG
GCGGGCAATATGTATGAAAGCATCGGTTTCCAGGGCGCTTATCTGGTGCTGGGTCTGGTGGCGC
TGGGCTTCACCTTAATTTCCGTGTTCACGCTTAGCGGCCCCGGCCCGCTTTCCCTGCTGCGTCG
TCAGGTGAATGAAGTCGCTTAA (SEQ ID N° 19)

Figure 18 – cont

> Cas 9.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCAGGCTTACCCGTCTTACTGTCGGGAATTCGCGTTGGCCGATTCATTAATGGTATAAGGT
TCTTGACATCTTACAATCAATATGGTATAATAATTTAGTTAGGGCCCAAGTTCACTTAAAAAGG
AGATCAACAATGAAAGCAATTTTCGTACTGAAACATCTTAATCATGCGTAGGATTTTTCTATG
TACTATTTAAAAAACACAAACTTTTGGATGTTCGGTTTATTCTTTTTCTTTTACTTTTTTATCA
TGGGAGCCTACTTCCCGTTTTTCCCGATTTGGCTACATGACATCAACCATATCAGCAAAAGTGA
TACGGGTATTATTTTTGCCGCTATTTCTCTGTTCTCGCTATTATTCCAACCGCTGTTTGGTCTG
CTTTCTGACAAACTCGGGCTGCGCAAATACCTGCTGTGGATTATTACCGGCATGTTAGTGATGT
TTGCGCCGTTCTTTATTTTTATCTTCGGGCCACTGTTACAATACAACATTTTAGTAGGATCGAT
TGTTGGTGGTATTTATCTAGGCTTTTGTTTTAACGCCGGTGCGCCAGCAGTAGAGGCATTTATT
GAGAAAGTCAGCCGTCGCAGTAATTTCGAATTGGTCGCGCGCGGATGTTTGGCTGTGTTGGCT
GGGCGCTGTGTGCCTCGATTGTCGGCATCATGTTCACCATCAATAATCAGTTTGTTTCTGGCT
GGGCTCTGGCTGTGCACTCATCCTCGCCGTTTACTCTTTTTCGCCAAAACGGATGCGCCCTCT
TCTGCCACGGTTGCCAATGCGGTAGGTGCCAACCATTCGGCATTTAGCCTTAAGCTGGCACTGG
AACTGTTCAGACAGCCAAAACTGTGGTTTTGTCACTGTATGTTATTGGCGTTTCCTGCACCTA
CGATGTTTTTGACCAACAGTTTGCTAATTTCTTTACTTCGTTCTTTGCTACCGGTGAACAGGGT
ACGCGGGTATTTGGCTACGTAACGACAATGGGCGAATTACTTAACGCCTCGATTATGTTCTTTG
CGCCACTGATCATTAATCGCATCGGTGGGAAAAACGCCCTGCTGCTGGCTGGCACTATTATGTC
TGTACGTATTATTGGCTCATCGTTCGCCACCTCAGCGCTGGAAGTGGTTATTCTGAAAACGCTG
CATATGTTTGAAGTACCGTTCCTGCTGGTGGGCTGCTTTAAATATATTACCAGCCAGTTTGAAG
TGCGTTTTTCAGCGACGATTTATCTGGTCTGTTTCTGCTTCTTTAAGCAACTGGCGATGATTTT
TATGTCTGTACTGGCGGGCAATATGTATGAAAGCATCGGTTTCCAGGGCGCTTATCTGGTGCTG
GGTCTGGTGGCGCTGGGCTTCACCTTAATTTCCGTGTTCACGCTTAGCGGCCCCGGCCCGCTTT
CCCTGCTGCGTCGTCAGGTGAATGAAGTCGCTTAA (SEQ ID N° 20)

Figure 18 – cont

> Cas 10.
CCCGTCTTACTGTCGGGAATTCGCGTTGGCCGATTCATTTAACCGATAAGCTTCTTGACATGTT
TAGGGTGTTATGATATAATCACCCAATTAGGGCCCAAGTTCACTTAAAAAGGAGATCAACAATG
AAAGCAATTTTCGTACTGAAACATCTTAATCATGCGTAGGATTTTTCTATGTACTATTTAAAA
AACACAAACTTTTGGATGTTCGGTTTATTCTTTTTCTTTTACTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCTGCTGCGTC
GTCAGGTGAATGAAGTCGCTTAA (SEQ ID N° 21)

Figure 18 – cont

> Cas 11.
GGCACCTGAGTCGCTGTCTTTTTCGTGACATTCAGTTCGCTGCGCTCACGGCTCTGGCAGTGAA
TGGGGGTAAATGGCACTACAGGCGCCTTTTATGGATTCATGCAAGGAAACTACCCATAATACAA
GAAAAGCCCGTCACGGGCTTCTCAGGGCGTTTTATGGCGGGTCTGCTATGTGGTGCTATCTGAC
TTTTTGCTGTTCAGCAGTTCCTGCCCTCTGATTTTCCAGTCTGACCACTTCGGATTATCCCGTG
ACAGGTCATTCAGACTGGCTAATGCACCCAGTAAGGCAGCGGTATCATCAACAGGCTTACCCGT
CTTACTGTCGGGAATTCGCGTTGGCCGATTAAAGGAGATCAACA*ATGAAAGC*ACTGTCGGGAAT
TCGCGTTGGCCGATTCATTAATGGTATAAGGTTCTTGACATCTTACAATCAATATGGTATAATA
ATTTAGTTAGGGCCCAAGTTCACTTAAAAAGGAGATCAACAATGAAAGCAAGCGGTATCATCAA
CAGGCTTACCCGTCTTACTGTCGGGAATTCGCGTTGGCCGATTCATTAATGGTATAAGGTTCTT
GACATCTTACAATCAATATGGTATAATAATTTAGTTAGGGCCCAAGTTCACTTAAAAAGGAGAT
CAACAATGAAAGCAATTTTCGTACTGAAACATCTTAATCATGCTAGGATTTTTCTATGTACT
ATTTAAAAAACACAAACTTTTGGATGTTCGGTTTATTCTTTTTCTTTTACTTTTTATCATGGG
AGCCTACTTCCCGTTTTCCCGATTTGGCTACATGACATCAACCATATCAGCAAAAGTGATACG
GGTATTATTTTGCCGCTATTTCTCTGTTCTCGCTATTATTCCAACCGCTGTTTGGTCTGCTTT
CTGACAAACTCGGGCTGCGCAAATACCTGCTGTGGATTATTACCGGCATGTTAGTGATGTTTGC
GCCGTTCTTTATTTTATCTTCGGGCCACTGTTACAATACAACATTTAGTAGGATCGATTGTT
GGTGGTATTTATCTAGGCTTTTGTTTAACGCCGGTGCGCCAGCAGTAGAGGCATTTATTGAGA
AAGTCAGCCGTCGCAGTAATTTCGAATTTGGTCGCGCGCGGATGTTTGGCTGTGTTGGCTGGGC
GCTGTGTGCCTCGATTGTCGGCATCATGTTCACCATCAATAATCAGTTTGTTTCTGGCTGGGC
TCTGGCTGTGCACTCATCCTCGCCGTTTTACTCTTTTCGCCAAAACGGATGCGCCCTCTTCTG
CCACGGTTGCCAATGCGGTAGGTGCCAACCATTCGGCATTTAGCCTTAAGCTGGCACTGGAACT
GTTCAGACAGCCAAAACTGTGGTTTTTGTCACTGTATGTTATTGGCGTTTCCTGCACCTACGAT
GTTTTTGACCAACAGTTTGCTAATTTCTTTACTTCGTTCTTTGCTACCGGTGAACAGGGTACGC
GGGTATTTGGCTACGTAACGACAATGGGCGAATTACTTAACGCCTCGATTATGTTCTTTGCGCC
ACTGATCATTAATCGCATCGGTGGGAAAAACGCCCTGCTGCTGGCTGGCACTATTATGTCTGTA
CGTATTATTGGCTCATCGTTCGCCACCTCAGCGCTGGAAGTGGTTATTCTGAAAACGCTGCATA
TGTTTGAAGTACCGTTCCTGCTGGTGGGCTGCTTTAAATATATTACCAGCCAGTTTGAAGTGCG
TTTTTCAGCGACGATTTATCTGGTCTGTTTCTGCTTCTTTAAGCAACTGGCGATGATTTTATG
TCTGTACTGGCGGGCAATATGTATGAAAGCATCGGTTCCAGGGCGCTTATCTGGTGCTGGGTC
TGGTGGCGCTGGGCTTCACCTTAATTTCCGTGTTCACGCTTAGCGGCCCCGGCCCGCTTTCCCT
GCTGCGTCGTCAGGTGAATGAAGTCGCTTAA (SEQ ID N° 22)

Figure 18 – cont

> Cas 12.
CCCGTCTTACTGTCGGGAATTCGCGTTGGCCGATTCGAATTCGCGTTGGCCGATTCGAATTCGC
GTTGGCCGATTCGAATTCGCGTTGGCCGATTCGAATTCGCGTTGGCCGATTCGAATTCGCGTTG
GCCGATTCGAATTCGCGTTGGCCGATTAAAGGAGATCAACAATGAAAGCTTACTGTCGGGAATT
CGCGTTGGCCGATTCGAATTCGCGTTGGCCGATTCATTAATGGTATAAGGTTCTTGACATCTTA
CAATCAATATGGTATAATAATTTAGTTAGGGCCCAAGTTCACTTAAAAGGAGATCAACAATGA
AAGCTTACTGTCGGGAATTCGCGTTGGCCGATTCATTAATGGTATAAGGTTCTTGACATCTTAC
AATCAATATGGTATAATAATTTAGTTAGGGCCCAAGTTCACTTAAAAGGAGATCAACAATGAA
AGCAATTTTCGTACTGAAACATCTTAATCATGCGTAGGATTTTTCTATGTACTATTTAAAAAA
CACAAACTTTTGGATGTTCGGTTTATTCTTTTCTTTTACTTTTTTATCATGGGAGCCTACTTC
CCGTTTTTCCCGATTTGGCTACATGACATCAACCATATCAGCAAAAGTGATACGGGTATTATTT
TTGCCGCTATTTCTCTGTTCTCGCTATTATTCCAACCGCTGTTTGGTCTGCTTTCTGACAAACT
CGGGCTGCGCAAATACCTGCTGTGGATTATTACCGGCATGTTAGTGATGTTTGCGCCGTTCTTT
ATTTTTATCTTCGGGCCACTGTTACAATACAACATTTTAGTAGGATCGATTGTTGGTGGTATTT
ATCTAGGCTTTTGTTTTAACGCCGGTGCGCCAGCAGTAGAGGCATTTATTGAGAAAGTCAGCCG
TCGCAGTAATTTCGAATTTGGTCGCGCGCGGATGTTTGGCTGTGTTGGCTGGGCGCTGTGTGCC
TCGATTGTCGGCATCATGTTCACCATCAATAATCAGTTTGTTTCTGGCTGGGCTCTGGCTGTG
CACTCATCCTCGCCGTTTACTCTTTTCGCCAAAACGGATGCGCCCTCTTCTGCCACGGTTGC
CAATGCGGTAGGTGCCAACCATTCGGCATTTAGCCTTAAGCTGGCACTGGAACTGTTCAGACAG
CCAAAACTGTGGTTTTTGTCACTGTATGTTATTGGCGTTTCCTGCACCTACGATGTTTTTGACC
AACAGTTTGCTAATTTCTTTACTTCGTTCTTTGCTACCGGTGAACAGGGTACGCGGGTATTTGG
CTACGTAACGACAATGGGCGAATTACTTAACGCCTCGATTATGTTCTTTGCGCCACTGATCATT
AATCGCATCGGTGGGAAAAACGCCCTGCTGCTGGCTGGCACTATTATGTCTGTACGTATTATTG
GCTCATCGTTCGCCACCTCAGCGCTGGAAGTGGTTATTCTGAAAACGCTGCATATGTTTGAAGT
ACCGTTCCTGCTGGTGGGCTGCTTTAAATATATTACCAGCCAGTTTGAAGTGCGTTTTTCAGCG
ACGATTTATCTGGTCTGTTTCTGCTTCTTTAAGCAACTGGCGATGATTTTATGTCTGTACTGG
CGGGCAATATGTATGAAAGCATCGGTTTCCAGGGCGCTTATCTGGTGCTGGGTCTGGTGGCGCT
GGGCTTCACCTTAATTTCCGTGTTCACGCTTAGCGGCCCCGGCCCGCTTTCCCTGCTGCGTCGT
CAGGTGAATGAAGTCGCTTAA (SEQ ID N° 23)

Figure 18 – cont

> Cas 13.
CCCGTCTTACTGTCGGGAATTCGCGTTGGCCGATTCATACTAAGCATTATATTCTTGACATCTT
ACAATCAATATGGTATAATAATTTAGTTAGGGCCCAAGTTCACTTAAAAAGGAGATCAACAATG
AAAGCACTGTCGGGAATTCGCGTTGGCCAATTAATTAATGGTATAAGGTTCTTGACATCTTACA
ATCAATATGGTATAATAATTTAGTTAGGGCCCAAGTTCACTTAAAAAGGAGATCAACAATGAAA
GCAATTTTCGTACTGAAACATCTTAATCATGCGTAGGATTTTTCTATGTACTATTTAAAAAAC
ACAAACTTTTGGATGTTCGGTTTATTCTTTTTCTTTTACTTTTTTATCATGGGAGCCTACTTCC
CGTTTTTCCCGATTTGGCTACATGACATCAACCATATCAGCAAAAGTGATACGGGTATTATTTT
TGCCGCTATTTCTCTGTTCTCGCTATTATTCCAACCGCTGTTTGGTCTGCTTTCTGACAAACTC
GGGCTGCGCAAATACCTGCTGTGGATTATTACCGGCATGTTAGTGATGTTTGCGCCGTTCTTTA
TTTTTATCTTCGGGCCACTGTTACAATACAACATTTTAGTAGGATCGATTGTTGGTGGTATTTA
TCTAGGCTTTTGTTTAACGCCGGTGCGCCAGCAGTAGAGGCATTTATTGAGAAAGTCAGCCGT
CGCAGTAATTTCGAATTTGGTCGCGCGCGGATGTTTGGCTGTGTTGGCTGGGCGCTGTGTGCCT
CGATTGTCGGCATCATGTTCACCATCAATAATCAGTTTGTTTCTGGCTGGGCTCTGGCTGTGC
ACTCATCCTCGCCGTTTTACTCTTTTTCGCCAAAACGGATGCGCCCTCTTCTGCCACGGTTGCC
AATGCGGTAGGTGCCAACCATTCGGCATTTAGCCTTAAGCTGGCACTGGAACTGTTCAGACAGC
CAAAACTGTGGTTTTTGTCACTGTATGTTATTGGCGTTTCCTGCACCTACGATGTTTTGACCA
ACAGTTTGCTAATTTCTTTACTTCGTTCTTTGCTACCGGTGAACAGGGTACGCGGGTATTTGGC
TACGTAACGACAATGGGCGAATTACTTAACGCCTCGATTATGTTCTTTGCGCCACTGATCATTA
ATCGCATCGGTGGGAAAAACGCCCTGCTGCTGGCTGGCACTATTATGTCTGTACGTATTATTGG
CTCATCGTTCGCCACCTCAGCGCTGGAAGTGGTTATTCTGAAAACGCTGCATATGTTTGAAGTA
CCGTTCCTGCTGGTGGGCTGCTTTAAATATATTACCAGCCAGTTTGAAGTGCGTTTTTCAGCGA
CGATTTATCTGGTCTGTTTCTGCTTCTTTAAGCAACTGGCGATGATTTTATGTCTGTACTGGC
GGGCAATATGTATGAAAGCATCGGTTTCCAGGGCGCTTATCTGGTGCTGGGTCTGGTGGCGCTG
GGCTTCACCTTAATTTCCGTGTTCACGCTTAGCGGCCCCGGCCCGCTTTCCTGCTGCGTCGTC
AGGTGAATGAAGTCGCTTAA (SEQ ID N° 24)

Figure 18 – cont

\> Cas 14.
CCCGTCTTACTGTCGGGAATTCGCGTTGGCCGATTCGAATTCGCGTTGGCCGATTCGAATTCGC
GTTGGCCGATTCGAATTCGCGTTGGCCGATTAAAGGAGATCAACAATGAAAGCTTACTGTCGGG
AATTCGCGTTGGCCGATTCATTAATGGTATAAGGTTCTTGACATCTTACAATCAATATGGTATA
ATAATTTAGTTAGGGCCCAAGTTCACTTAAAAAGGAGATCAACACTTACTGTCGGGAATTCGCG
TTGGCCAATTAATTAATGGTATAAGGTTCTTGACATCTTACAATCAATATGGTATAATAATTTA
GTTAGGGCCCAAGTTCACTTAAAAAGGAGATCAACAATGAAAGCAGGCTTACCCGTCTTACTGT
CGGGAATTCGCGTTGGCCGATTCATTAATGGTATAAGGTTCTTGACATCTTACAATCAATATGG
TATAATAATTTAGTTAGGGCCCAAGTTCACTTAAAAAGGAGATCAACAATGAAAGCAATTTTCG
TACTGAAACATCTTAATCATGCGTAGGATTTTTCTATGTACTATTTAAAAAACACAAACTTTT
GGATGTTCGGTTTATTCTTTTCTTTTACTTTTTATCATGGGAGCCTACTTCCCGTTTTTCCC
GATTTGGCTACATGACATCAACCATATCAGCAAAAGTGATACGGGTATTATTTTGCCGCTATT
TCTCTGTTCTCGCTATTATTCCAACCGCTGTTTGGTCTGCTTTCTGACAAACTCGGGCTGCGCA
AATACCTGCTGTGGATTATTACCGGCATGTTAGTGATGTTTGCGCCGTTCTTTATTTTATCTT
CGGGCCACTGTTACAATACAACATTTTAGTAGGATCGATTGTTGGTGGTATTTATCTAGGCTTT
TGTTTTAACGCCGGTGCGCCAGCAGTAGAGGCATTTATTGAGAAAGTCAGCCGTCGCAGTAATT
TCGAATTTGGTCGCGCGCGGATGTTTGGCTGTGTTGGCTGGGCGCTGTGTGCCTCGATTGTCGG
CATCATGTTCACCATCAATAATCAGTTTGTTTCTGGCTGGGCTCTGGCTGTGCACTCATCCTC
GCCGTTTTACTCTTTTCGCCAAAACGGATGCGCCCTCTTCTGCCACGGTTGCCAATGCGGTAG
GTGCCAACCATTCGGCATTTAGCCTTAAGCTGGCACTGGAACTGTTCAGACAGCCAAAACTGTG
GTTTTGTCACTGTATGTTATTGGCGTTTCCTGCACCTACGATGTTTTTGACCAACAGTTTGCT
AATTTCTTTACTTCGTTCTTTGCTACCGGTGAACAGGGTACGCGGGTATTTGGCTACGTAACGA
CAATGGGCGAATTACTTAACGCCTCGATTATGTTCTTTGCGCCACTGATCATTAATCGCATCGG
TGGGAAAAACGCCCTGCTGCTGGCTGGCACTATTATGTCTGTACGTATTATTGGCTCATCGTTC
GCCACCTCAGCGCTGGAAGTGGTTATTCTGAAAACGCTGCATATGTTTGAAGTACCGTTCCTGC
TGGTGGGCTGCTTTAAATATATTACCAGCCAGTTTGAAGTGCGTTTTTCAGCGACGATTTATCT
GGTCTGTTTCTGCTTCTTTAAGCAACTGGCGATGATTTTATGTCTGTACTGGCGGGCAATATG
TATGAAAGCATCGGTTTCCAGGGCGCTTATCTGGTGCTGGGTCTGGTGGCGCTGGGCTTCACCT
TAATTTCCGTGTTCACGCTTAGCGGCCCCGGCCCGCTTTCCCTGCTGCGTCGTCAGGTGAATGA
AGTCGCTTAA (SEQ ID N° 25)

Figure 18 – cont

> Cas 15.
CCTGAGTCGCTGTCTTTTTCGTGACATTCAGTTCGCTGCGCTCACGGCTCTGGCAGTGAATGGG
GGTAAATGGCACTACAGGCGCCTTTTATGGATTCATGCAAGGAAACTACCCATAATACAAGAAA
AGCCCGTCACGGGCTTCTCAGGGCGTTTTATGGCGGGTCTGCTATGTGGTGCTATCTGACTTTT
TGCTGTTCAGCAGTTCCTGCCCTCTGATTTTCCAGTCTGACCACTTCGGATTATCCCGTGACAG
GTCATTCAGACTGGCTAATGCACCCAGTAAGGCAGCGGTATCATCAACAGGCTTACCCGTCTTA
CTGTCGGGAATTCGCGTTGGCCGATTAAAGGAGAT*CAACAATGAAAGC*ACTGTCGGGAATTCGC
GTTGGCCGATTCATTAATGGTATAAGGTTCTTGACATCTTACAATCAATATGGTATAATAATTT
AGTTAGGGCCCAAGTTCACTTAAAAAGGAGATCAACAATGAAAGCAAGCGGTATCATCAACAGG
CTTACCCGTCTTACTGTCGGGAATTCGCGTTGGCCGATTCATTAATGGTATAAGGTTCTTGACA
TCTTACAATCAATATGGCATAATAATTTAGTTAGGGCCCAAGTTCACTTAAAAGGAGATCAAC
AATGAAAGCAATTTTCGTACTGAAACATCTTAATCATGCGTAGGATTTTTCTATGTACTATTT
AAAAAACACAAACTTTTGGATGTTCGGTTTATTCTTTTTCTTTTACTTTTTATCATGGGAGCC
TACTTCCCGTTTTTCCCGATTTGGCTACATGACATCAACCATATCAGCAAAAGTGATACGGGTA
TTATTTTGCCGCTATTTCTCTGTTCTCGCTATTATTCCAACCGCTGTTTGGTCTGCTTTCTGA
CAAACTCGGGCTGCGCAAATACCTGCTGTGGATTATTACCGGCATGTTAGTGATGTTTGCGCCG
TTCTTTATTTTTATCTTCGGGCCACTGTTACAATACAACATTTTAGTAGGATCGATTGTTGGTG
GTATTTATCTAGGCTTTTGTTTTAACGCCGGTGCGCCAGCAGTAGAGGCATTTATTGAGAAAGT
CAGCCGTCGCAGTAATTCGAATTTGGTCGCGCGCGGATGTTTGGCTGTGTTGGCTGGGCGCTG
TGTGCCTCGATTGTCGGCATCATGTTCACCATCAATAATCAGTTTGTTTCTGGCTGGGCTCTG
GCTGTGCACTCATCCTCGCCGTTTTACTCTTTTTCGCCAAAACGGATGCGCCCTCTTCTGCCAC
GGTTGCCAATGCGGTAGGTGCCAACCATTCGGCATTTAGCCTTAAGCTGGCACTGGAACTGTTC
AGACAGCCAAAACTGTGGTTTTGTCACTGTATGTTATTGGCGTTTCCTGCACCTACGATGTTT
TTGACCAACAGTTTGCTAATTTCTTTACTTCGTTCTTTGCTACCGGTGAACAGGGTACGCGGGT
ATTTGGCTACGTAACGACAATGGGCGAATTACTTAACGCCTCGATTATGTTCTTTGCGCCACTG
ATCATTAATCGCATCGGTGGGAAAAACGCCCTGCTGCTGGCTGGCACTATTATGTCTGTACGTA
TTATTGGCTCATCGTTCGCCACCTCAGCGCTGGAAGTGGTTATTCTGAAAACGCTGCATATGTT
TGAAGTACCGTTCCTGCTGGTGGGCTGCTTTAAATATATTACCAGCCAGTTTGAAGTGCGTTTT
TCAGCGACGATTTATCTGGTCTGTTTCTGCTTCTTTAAGCAACTGGCGATGATTTTATGTCTG
TACTGGCGGGCAATATGTATGAAAGCATCGGTTTCCAGGGCGCTTATCTGGTGCTGGGTCTGGT
GGCGCTGGGCTTCACCTTAATTTCCGTGTTCACGCTTAGCGGCCCCGGCCCGCTTTCCCTGCTG
CGTCGTCAGGTGAATGAAGTCGCTTAA (SEQ ID N° 26)

Figure 18 – cont

> Cas 16.
CCCGTCTTACTGTCGGGAATTCGCGTTGGCCGATTCGAATTCGCGTTGGCCGATTCGAATT
CGCGTTGGCCGATTCGAATTCGCGTTGGCCGATTCGAATTCGCGTTGGCCAATTAATTAAT
GGTATAAGGTTCTTGACATCTTACAATCAATATGGTATAATAATTTAGTTAGGGCCCAAGT
TCACTTAAAAAGGAGATCAACAATGAAAGCAATTTTCGTACTGAAACATCTTAATCATGCG
TAGGATTTTTTCTATGTACTATTTAAAAAACACAAACTTTTGGATGTTCGGTTTATTCTTT
TTCTTTTACTTTTTTATCATGGGAGCCTACTTCCCGTTTTCCCGATTTGGCTACATGACA
TCAACCATATCAGCAAAAGTGATACGGGTATTATTTTTGCCGCTATTTCTCTGTTCTCGCT
ATTATTCCAACCGCTGTTTGGTCTGCTTTCTGACAAACTCGGGCTGCGCAAATACCTGCTG
TGGATTATTACCGGCATGTTAGTGATGTTTGCGCCGTTCTTTATTTTATCTTCGGGCCAC
TGTTACAATACAACATTTTAGTAGGATCGATTGTTGGTGGTATTTATCTAGGCTTTTGTTT
TAACGCCGGTGCGCCAGCAGTAGAGGCATTTATTGAGAAAGTCAGCCGTCGCAGTAATTTC
GAATTTGGTCGCGCGCGGATGTTTGGCTGTGTTGGCTGGGCGCTGTGTGCCTCGATTGTCG
GCATCATGTTCACCATCAATAATCAGTTTGTTTTCTGGCTGGGCTCTGGCTGTGCACTCAT
CCTCGCCGTTTTACTCTTTTTCGCCAAAACGGATGCGCCCTCTTCTGCCACGGTTGCCAAT
GCGGTAGGTGCCAACCATTCGGCATTTAGCCTTAAGCTGGCACTGGAACTGTTCAGACAGC
CAAAACTGTGGTTTTGTCACTGTATGTTATTGGCGTTTCCTGCACCTACGATGTTTTTGA
CCAACAGTTTGCTAATTTCTTTACTTCGTTCTTTGCTACCGGTGAACAGGGTACGCGGGTA
TTTGGCTACGTAACGACAATGGGCGAATTACTTAACGCCTCGATTATGTTCTTTGCGCCAC
TGATCATTAATCGCATCGGTGGGAAAAACGCCCTGCTGCTGGCTGGCACTATTATGTCTGT
ACGTATTATTGGCTCATCGTTCGCCACCTCAGCGCTGGAAGTGGTTATTCTGAAAACGCTG
CATATGTTTGAAGTACCGTTCCTGCTGGTGGGCTGCTTTAAATATATTACCAGCCAGTTTG
AAGTGCGTTTTTCAGCGACGATTTATCTGGTCTGTTTCTGCTTCTTTAAGCAACTGGCGAT
GATTTTATGTCTGTACTGGCGGGCAATATGTATGAAAGCATCGGTTTCCAGGGCGCTTAT
CTGGTGCTGGGTCTGGTGGCGCTGGGCTTCACCTTAATTTCCGTGTTCACGCTTAGCGGCC
CCGGCCCGCTTTCCCTGCTGCGTCGTCAGGTGAATGAAGTCGCTTAA (SEQ ID N° 27)

Figure 18 – cont

> Cas 17.
CCTGAGTCGCTGTCTTTTTCGTGACATTCAGTTCGCTGCGCTCACGGCTCTGGCAGTGAATGGG
GGTAAATGGCACTACAGGCGCCTTTTATGGATTCATGCAAGGAAACTACCCATAATACAAGAAA
AGCCCGTCACGGGCTTCTCAGGGCGTTTTATGGCGGGTCTGCTATGTGGTGCTATCTGACTTTT
TGCTGTTCAGCAGTTCCTGCCCTCTGATTTTCCAGTCTGACCACTTCGGATTATCCCGTGACAG
GTCATTCAGACTGGCTAATGCACCCAGTAAGGCAGCGGTATCATCAACAGGCTTACCCGTCTTA
CTGTCGGGAATTCGCGTTGGCCGATTAAAGGAGAT*CAACAATGAAAGC*ACTGTCGGGAATTCGC
GTTGGCCGATTCATTAATGGTATAAGGTTCTTGACATCTTACAATCAATATGGTATAATAATTT
AGTTAGGGCCCAAGTTCACTTAAAAAGGAGATCAACAATGAAAGCAAGCGGTATCATCAACAGG
CTTACCCGTCTTACTGTCGGGAATTCGCGTTGGCCGATTCATTAATGGTATAAGGTTCTTTGAC
ATCTTACAATCAATATGGTATAATAATTTAGTTA*GGGCCCAAGTTCACTTAAAAAGGAGATCA
ACAATGAAAGCAATTTTCGTACTGAAACATCTTAATCATGCGTAGGATTTTTTT*CTATGTACTA
TTTAAAAAACACAAACTTTTGGATGTTCGGTTTATTCTTTTTCTTTTACTTTTTTATCATGGGA
GCCTACTTCCCGTTTTTCCCGATTTGGCTACATGACATCAACCATATCAGCAAAAGTGATACGG
GTATTATTTTGCCGCTATTTCTCTGTTCTCGCTATTATTCCAACCGCTGTTTGGTCTGCTTTC
TGACAAACTCGGGCTGCGCAAATACCTGCTGTGGATTATTACCGGCATGTTAGTGATGTTTGCG
CCGTTCTTTATTTTTATCTTCGGGCCACTGTTACAATACAACATTTTAGTAGGATCGATTGTTG
GTGGTATTTATCTAGGCTTTTGTTTAACGCCGGTGCGCCAGCAGTAGAGGCATTTATTGAGAA
AGTCAGCCGTCGCAGTAATTTCGAATTTGGTCGCGCGCGGATGTTTGGCTGTGTTGGCTGGGCG
CTGTGTGCCTCGATTGTCGGCATCATGTTCACCATCAATAATCAGTTTGTTTCTGGCTGGGCT
CTGGCTGTGCACTCATCCTCGCCGTTTTACTCTTTTCGCCAAAACGGATGCGCCCTCTTCTGC
CACGGTTGCCAATGCGGTAGGTGCCAACCATTCGGCATTTAGCCTTAAGCTGGCACTGGAACTG
TTCAGACAGCCAAAACTGTGGTTTTGTCACTGTATGTTATTGGCGTTTCCTGCACCTACGATG
TTTTTGACCAACAGTTTGCTAATTTCTTTACTTCGTTCTTTGCTACCGGTGAACAGGGTACGCG
GGTATTTGGCTACGTAACGACAATGGGCGAATTACTTAACGCCTCGATTATGTTCTTTGCGCCA
CTGATCATTAATCGCATCGGTGGGAAAAACGCCCTGCTGCTGGCTGGCACTATTATGTCTGTAC
GTATTATTGGCTCATCGTTCGCCACCTCAGCGCTGGAAGTGGTTATTCTGAAAACGCTGCATAT
GTTTGAAGTACCGTTCCTGCTGGTGGGCTGCTTTAAATATATTACCAGCCAGTTTGAAGTGCGT
TTTTCAGCGACGATTTATCTGGTCTGTTTCTGCTTCTTTAAGCAACTGGCGATGATTTTATGT
CTGTACTGGCGGGCAATATGTATGAAAGCATCGGTTTCCAGGGCGCTTATCTGGTGCTGGGTCT
GGTGGCGCTGGGCTTCACCTTAATTTCCGTGTTCACGCTTAGCGGCCCCGGCCCGCTTTCCCTG
CTGCGTCGTCAGGTGAATGAAGTCGCTTAA (SEQ ID N° 28)

Figure 18 – cont

> Cas 18.
CCCGTCTTACTGTCGGGAATTCGCGTTGGCCGATTCATTAATGGCATAAGGTTCTTGACATCTT
ACAATCAATATGGTATAATAATTTAGTTAGGGCCCAAGTTCACTTAAAAAGGAGATCAACACTT
ACTGTCGGGAATTCGCGTTGGCCAATTAATTAATGGTATAAGGTTCTTGACATCTTACAATCAA
TATGGTATAATAATTTAGTTAGGGCCCAAGTTCACTTAAAAAGGAGATCAACAATGAAAGCAAT
TTTCGTACTGAAACATCTTAATCATGCGTATGATTTTTCTATGTACTATTTAAAAAACACAAA
CTTTTGGATGTTCGGTTTATTCTTTTTCTTTTACTTTTTTATCATGGGAGCCTACTTCCCGTTT
TTCCCGATTTGGCTACATGACATCAACCATATCAGCAAAAGTGATACGGGTATTATTTTTGCCG
CTATTTCTCTGTTCTCGCTATTATTCCAACCGCTGTTTGGTCTGCTTTCTGACAAACTCGGGCT
GCGCAAATACCTGCTGTGGATTATTACCGGCATGTTAGTGATGTTTGCGCCGTTCTTTATTTTT
ATCTTCGGGCCACTGTTACAATACAACATTTTAGTAGGATCGATTGTTGGTGGTATTTATCTAG
GCTTTTGTTTTAACGCCGGTGCGCCAGCAGTAGAGGCATTTATTGAGAAAGTCAGCCGTCGCAG
TAATTTCGAATTTGGTCGCGCGCGGATGTTTGGCTGTGTTGGCTGGGCGCTGTGTGCCTCGATT
GTCGGCATCATGTTCACCATCAATAATCAGTTTGTTTCTGGCTGGGCTCTGGCTGTGCACTCA
TCCTCGCCGTTTTACTCTTTTTCGCCAAAACGGATGCGCCCTCTTCTGCCACGGTTGCCAATGC
GGTAGGTGCCAACCATTCGGCATTTAGCCTTAAGCTGGCACTGGAACTGTTCAGACAGCCAAAA
CTGTGGTTTTTGTCACTGTATGTTATTGGCGTTTCCTGCACCTACGATGTTTTGACCAACAGT
TTGCTAATTTCTTTACTTCGTTCTTTGCTACCGGTGAACAGGGTACGCGGGTATTGGCTACGT
AACGACAATGGGCGAATTACTTAACGCCTCGATTATGTTCTTTGCGCCACTGATCATTAATCGC
ATCGGTGGGAAAAACGCCCTGCTGCTGGCTGGCACTATTATGTCTGTACGTATTATTGGCTCAT
CGTTCGCCACCTCAGCGCTGGAAGTGGTTATTCTGAAAACGCTGCATATGTTTGAAGTACCGTT
CCTGCTGGTGGGCTGCTTTAAATATATTACCAGCCAGTTTGAAGTGCGTTTTTCAGCGACGATT
TATCTGGTCTGTTTCTGCTTCTTTAAGCAACTGGCGATGATTTTTATGTCTGTACTGGCGGGCA
ATATGTATGAAAGCATCGGTTTCCAGGGCGCTTATCTGGTGCTGGGTCTGGTGGCGCTGGGCTT
CACCTTAATTTCCGTGTTCACGCTTAGCGGCCCCGGCCCGCTTTCCTGCTGCGTCGTCAGGTG
AATGAAGTCGCTTAA (SEQ ID N° 29)

Figure 18 – cont

> Cas 19.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCAATTTTCGTACTGAAACATCTTAATCATGCGTAGGATTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCTGCTGCGTC
GTCAGGTGAATGAAGTCGCTTAA (SEQ ID N° 30)

Figure 18 – cont

> Cas 20.
CCCGTCTTACTGTCGGGAATTCGCGTTGGCCGATTCATTCAATCCAATAGGTTCTTGACATCTT
ACAATCAATATGGTATAATAATTTAGTTAGGGCCCAAGTTCACTTAAAAAGGAGATCAACACTT
ACTGTCGGGAATTCGCGTTGGCCAATTAATTAATGGTATAAGGTTCTTGACATCTTACAATCAA
TATGGTATAATAATTTAGTTAGGGCCCAAGTTCACTTAAAAAGGAGATCAACAATGAAAGCAAT
TTTCGTACTGAAACATCTTAATCATGCGTAGGATTTTTCTATGTACTATTTAAAAAACACAAA
CTTTTGGATGTTCGGTTTATTCTTTTCTTTTACTTTTTTATCATGGGAGCCTACTTCCCGTTT
TTCCCGATTTGGCTACATGACATCAACCATATCAGCAAAAGTGATACGGGTATTATTTTGCCG
CTATTTCTCTGTTCTCGCTATTATTCCAACCGCTGTTTGGTCTGCTTTCTGACAAACTCGGGCT
GCGCAAATACCTGCTGTGGATTATTACCGGCATGTTAGTGATGTTTGCGCCGTTCTTTATTTTT
ATCTTCGGGCCACTGTTACAATACAACATTTAGTAGGATCGATTGTTGGTGGTATTTATCTAG
GCTTTTGTTTTAACGCCGGTGCGCCAGCAGTAGAGGCATTTATTGAGAAAGTCAGCCGTCGCAG
TAATTTCGAATTTGGTCGCGCGCGGATGTTTGGCTGTGTTGGCTGGCGCTGTGTGCCTCGATT
GTCGGCATCATGTTCACCATCAATAATCAGTTTGTTTTCTGGCTGGGCTCTGGCTGTGCACTCA
TCCTCGCCGTTTTACTCTTTTTCGCCAAAACGGATGCGCCCTCTTCTGCCACGGTTGCCAATGC
GGTAGGTGCCAACCATTCGGCATTTAGCCTTAAGCTGGCACTGGAACTGTTCAGACAGCCAAAA
CTGTGGTTTTTGTCACTGTATGTTATTGGCGTTTCCTGCACCTACGATGTTTTGACCAACAGT
TTGCTAATTTCTTTACTTCGTTCTTTGCTACCGGTGAACAGGGTACGCGGGTATTTGGCTACGT
AACGACAATGGGCGAATTACTTAACGCCTCGATTATGTTCTTTGCGCCACTGATCATTAATCGC
ATCGGTGGGAAAAACGCCCTGCTGCTGGCTGGCACTATTATGTCTGTACGTATTATTGGCTCAT
CGTTCGCCACCTCAGCGCTGGAAGTGGTTATTCTGAAAACGCTGCATATGTTTGAAGTACCGTT
CCTGCTGGTGGCTGCTTTAAATATATTACCAGCCAGTTTGAAGTGCGTTTTTCAGCGACGATT
TATCTGGTCTGTTTCTGCTTCTTTAAGCAACTGGCGATGATTTTATGTCTGTACTGGCGGGCA
ATATGTATGAAAGCATCGGTTTCCAGGGCGCTTATCTGGTGCTGGGTCTGGTGGCGCTGGGCTT
CACCTTAATTTCCGTGTTCACGCTTAGCGGCCCCGGCCCGCTTTCCTGCTGCGTCGTCAGGTG
AATGAAGTCGCTTAA (SEQ ID N° 31)

Figure 18 – cont

> Cas 21.
CCCGTCTTACTGTCGGGAATTCGCGTTGGCCGATTCATTAATGGTATAAGGTTCTTGACAT
CTTACAATCAATATGGGATAATAATTTAGTTAGGGCCCAAGTTCACTTAAAAAGGAGATCA
ACAATGAAAGCTTACTGTCGGGAATTCGCGTTGGCCGATTCTTATAAATCATTATCTTCTT
GACATTTTAGAAACAATATGGTATAATATAACGATAAGGGCCCAAGTTCACTTAAAAAGGA
GATCAACAATGAAAGCAATTTTCGTACTGAAACATCTTAATCATGCGTAGGATTTTTTCTA
TGTACTATTTAAAAAACACAAACTTTTGGATGTTCGGTTTATTCTTTTTCTTTTACTTTTT
TATCATGGGAGCCTACTTCCCGTTTTTCCCGATTTGGCTACATGACATCAACCATATCAGC
AAAAGTGATACGGGTATTATTTTGCCGCTATTTCTCTGTTCTCGCTATTATTCCAACCGC
TGTTTGGTCTGCTTTCTGACAAACTCGGGCTGCGCAAATACCTGCTGTGGATTATTACCGG
CATGTTAGTGATGTTTGCGCCGTTCTTTATTTTATCTTCGGGCCACTGTTACAATACAAC
ATTTTAGTAGGATCGATTGTTGGTGGTATTTATCTAGGCTTTTGTTTAACGCCGGTGCGC
CAGCAGTAGAGGCATTTATTGAGAAAGTCAGCCGTCGCAGTAATTTCGAATTTGGTCGCGC
GCGGATGTTTGGCTGTGTTGGCTGGGCGCTGTGTGCCTCGATTGTCGGCATCATGTTCACC
ATCAATAATCAGTTTGTTTTCTGGCTGGGCTCTGGCTGTGCACTCATCCTCGCCGTTTTAC
TCTTTTTCGCCAAAACGGATGCGCCCTCTTCTGCCACGGTTGCCAATGCGGTAGGTGCCAA
CCATTCGGCATTTAGCCTTAAGCTGGCACTGGAACTGTTCAGACAGCCAAAACTGTGGTTT
TTGTCACTGTATGTTATTGGCGTTTCCTGCACCTACGATGTTTTTGACCAACAGTTTGCTA
ATTTCTTTACTTCGTTCTTTGCTACCGGTGAACAGGGTACGCGGGTATTTGGCTACGTAAC
GACAATGGGCGAATTACTTAACGCCTCGATTATGTTCTTTGCGCCACTGATCATTAATCGC
ATCGGTGGGAAAAACGCCCTGCTGCTGGCTGGCACTATTATGTCTGTACGTATTATTGGCT
CATCGTTCGCCACCTCAGCGCTGGAAGTGGTTATTCTGAAAACGCTGCATATGTTTGAAGT
ACCGTTCCTGCTGGTGGGCTGCTTTAAATATATTACCAGCCAGTTTGAAGTGCGTTTTTCA
GCGACGATTTATCTGGTCTGTTTCTGCTTCTTTAAGCAACTGGCGATGATTTTTATGTCTG
TACTGGCGGGCAATATGTATGAAAGCATCGGTTTCCAGGGCGCTTATCTGGTGCTGGGTCT
GGTGGCGCTGGGCTTCACCTTAATTTCCGTGTTCACGCTTAGCGGCCCCGGCCCGCTTTCC
CTGCTGCGTCGTCAGGTGAATGAAGTCGCTTAA (SEQ ID N° 32)

Figure 18 – cont

\> Cas 22.
CCCGTCTTACTGTCGGGAATTCGCGTTGGCCGATTCGAATTCGCGTTGGCCGATTCGAATTCGC
GCTGGCCGATTCGAATTCGCGTTGGCCGATTAAAGGAGATCAACTATGAAAGCTTACTGTCGGG
AATTCGCGTTGGCCGATTCATTAATGGTATAAGGCTCTTGACATCTTACAATCAATATGGTATA
ATAATTTAGTTAGGGCCCAAGTTCACTTAAAAAGGAGATCAACAATGAAAGCAATTTTCGTACT
GAAACATCTTAATCATGCGTAGGATTTTTCTATGTACTATTTAAAAAACACAAACTTTTGGAT
GTTCGGTTTATTCTTTTTCTTTTACTTTTTTATCATGGGAGCCTACTTCCCGTTTTTCCCGATT
TGGCTACATGACATCAACCATATCAGCAAAAGTGATACGGGTATTATTTTGCCGCTATTTCTC
TGTTCTCGCTATTATTCCAACCGCTGTTTGGTCTGCTTTCTGACAAACTCGGGCTGCGCAAATA
CCTGCTGTGGATTATTACCGGCATGTTAGTGATGTTTGCGCCGTTCTTTATTTTATCTTCGGG
CCACTGTTACAATACAACATTTTAGTAGGATCGATTGTTGGTGGTATTTATCTAGGCTTTTGTT
TTAACGCCGGTGCGCCAGCAGTAGAGGCATTTATTGAGAAAGTCAGCCGTCGCAGTAATTTCGA
ATTTGGTCGCGCGCGGATGTTTGGCTGTGTTGGCTGGGCGCTGTGTGCCTCGATTGTCGGCATC
ATGTTCACCATCAATAATCAGTTTGTTTCTGGCTGGGCTCTGGCTGTGCACTCATCCTCGCCG
TTTTACTCTTTTTCGCCAAAACGGATGCGCCCTCTTCTGCCACGGTTGCCAATGCGGTAGGTGC
CAACCATTCGGCATTTAGCCTTAAGCTGGCACTGGAACTGTTCAGACAGCCAAAACTGTGGTTT
TTGTCACTGTATGTTATTGGCGTTTCCTGCACCTACGATGTTTTGACCAACAGTTTGCTAATT
TCTTTACTTCGTTCTTTGCTACCGGTGAACAGGGTACGCGGGTATTTGGCTACGTAACGACAAT
GGGCGAATTACTTAACGCCTCGATTATGTTCTTTGCGCCACTGATCATTAATCGCATCGGTGGG
AAAAACGCCCTGCTGCTGGCTGGCACTATTATGTCTGTACGTATTATTGGCTCATCGTTCGCCA
CCTCAGCGCTGGAAGTGGTTATTCTGAAAACGCTGCATATGTTTGAAGTACCGTTCCTGCTGGT
GGGCTGCTTTAAATATATTACCAGCCAGTTTGAAGTGCGTTTTTCAGCGACGATTTATCTGGTC
TGTTTCTGCTTCTTTAAGCAACTGGCGATGATTTTATGTCTGTACTGGCGGGCAATATGTATG
AAAGCATCGGTTTCCAGGGCGCTTATCTGGTGCTGGGTCTGGTGGCGCTGGGCTTCACCTTAAT
TTCCGTGTTCACGCTTAGCGGCCCCGGCCCGCTTTCCCTGCTGCGTCGTCAGGTGAATGAAGTC
GCTTAA (SEQ ID N° 33)

Figure 18 – cont

> Cas 23.
CCCGTCTTACTGTCGGGAATTCGCGTTGGCCGATTCATACTACCCATAATGTTCTTGACATCTT
ACAATCAATATGGTATAATAATTTAGTTAGGGCCCAAGTTCACTTAAAAAGGAGATCAACAATG
AAAGCAATTTTCGTACTGAAACATCTTAATCATGCGTAGGATTTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCCTGCTGCGTC
GTCAGGTGAATGAAGTCGCTTAA (SEQ ID N° 34)

Figure 18 – cont

> Cas 24.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACACTT
ACTGTCGGGAATTCGCGTTGGCCAATTAATTAATGGTATAAGGTTCTTGACATCTTACAATCAA
TATGGTATAATAATTTAGTTAGGGCCCAAGTTCACTTAAAAAGGAGATCAACAATGAAAGCAAT
TTTCGTACTGAAACATCTTAATCATGCGTAGGATTTTTCTATGTACTATTTAAAAAACACAAA
CTTTTGGATGTTCGGTTTATTCTTTTTCTTTTACTTTTTTATCATGGGAGCCTACTTCCCGTTT
TTCCCGATTTGGCTACATGACATCAACCATATCAGCAAAAGTGATACGGGTATTATTTTTGCCG
CTATTTCTCTGTTCTCGCTATTATTCCAACCGCTGTTTGGTCTGCTTTCTGACAAACTCGGGCT
GCGCAAATACCTGCTGTGGATTATTACCGGCATGTTAGTGATGTTTGCGCCGTTCTTTATTTTT
ATCTTCGGGCCACTGTTACAATACAACATTTTAGTAGGATCGATTGTTGGTGGTATTTATCTAG
GCTTTTGTTTTAACGCCGGTGCGCCAGCAGTAGAGGCATTTATTGAGAAAGTCAGCCGTCGCAG
TAATTTCGAATTTGGTCGCGCGCGGATGTTTGGCTGTGTTGGCTGGGCGCTGTGTGCCTCGATT
GTCGGCATCATGTTCACCATCAATAATCAGTTTGTTTCTGGCTGGGCTCTGGCTGTGCACTCA
TCCTCGCCGTTTTACTCTTTTTCGCCAAAACGGATGCGCCCTCTTCTGCCACGGTTGCCAATGC
GGTAGGTGCCAACCATTCGGCATTTAGCCTTAAGCTGGCACTGGAACTGTTCAGACAGCCAAAA
CTGTGGTTTTTGTCACTGTATGTTATTGGCGTTTCCTGCACCTACGATGTTTTGACCAACAGT
TTGCTAATTTCTTTACTTCGTTCTTTGCTACCGGTGAACAGGGTACGCGGGTATTGGCTACGT
AACGACAATGGGCGAATTACTTAACGCCTCGATTATGTTCTTTGCGCCACTGATCATTAATCGC
ATCGGTGGGAAAAACGCCCTGCTGCTGGCTGGCACTATTATGTCTGTACGTATTATTGGCTCAT
CGTTCGCCACCTCAGCGCTGGAAGTGGTTATTCTGAAAACGCTGCATATGTTTGAAGTACCGTT
CCTGCTGGTGGCTGCTTTAAATATATTACCAGCCAGTTTGAAGTGCGTTTTTCAGCGACGATT
TATCTGGTCTGTTTCTGCTTCTTTAAGCAACTGGCGATGATTTTATGTCTGTACTGGCGGGCA
ATATGTATGAAAGCATCGGTTTCCAGGGCGCTTATCTGGTGCTGGGTCTGGTGGCGCTGGGCTT
CACCTTAATTTCCGTGTTCACGCTTAGCGGCCCCGGCCCGCTTTCCTGCTGCGTCGTCAGGTG
AATGAAGTCGCTTAA (SEQ ID N° 35)

Figure 18 – cont

> Cas 25.
CCCGTCTTACTGTCGGGAATTCGCGTTGGCCGATTCGAATTCGCGATGGCCGATTCGAATT
CGCGTTGGCCGATTCGAATTCGCGTTGGCCGATTCTTACACGATATATACTTCTTGACATT
TTGCGGGAATTATGGTATAATCACAAGGTTAGGGCCCAAGTTCACTTAAAAAGGAGATCAA
CAATGAAAGCAATTTTCGTACTGAAACATCTTAATCATGCGTAGGATTTTTTCTATGTACT
ATTTAAAAAACACAAACTTTTGGATGTTCGGTTTATTCTTTTCTTTTACTTTTTATCAT
GGGAGCCTACTTCCCGTTTTTCCCGATTTGGCTACATGACATCAACCATATCAGCAAAAGT
GATACGGGTATTATTTTTGCCGCTATTTCTCTGTTCTCGCTATTATTCCAACCGCTGTTTG
GTCTGCTTTCTGACAAACTCGGGCTGCGCAAATACCTGCTGTGGATTATTACCGGCATGTT
AGTGATGTTTGCGCCGTTCTTTATTTTATCTTCGGGCCACTGTTACAATACAACATTTTA
GTAGGATCGATTGTTGGTGGTATTTATCTAGGCTTTTGTTTAACGCCGGTGCGCCAGCAG
TAGAGGCATTTATTGAGAAAGTCAGCCGTCGCAGTAATTTCGAATTTGGTCGCGCGCGGAT
GTTTGGCTGTGTTGGCTGGGCGCTGTGTGCCTCGATTGTCGGCATCATGTTCACCATCAAT
AATCAGTTTGTTTCTGGCTGGGCTCTGGCTGTGCACTCATCCTCGCCGTTTTACTCTTTT
TCGCCAAAACGGATGCGCCCTCTTCTGCCACGGTTGCCAATGCGGTAGGTGCCAACCATTC
GGCATTTAGCCTTAAGCTGGCACTGGAACTGTTCAGACAGCCAAAACTGTGGTTTTTGTCA
CTGTATGTTATTGGCGTTTCCTGCACCTACGATGTTTTGACCAACAGTTTGCTAATTTCT
TTACTTCGTTCTTTGCTACCGGTGAACAGGGTACGCGGGTATTGGCTACGTAACGACAAT
GGGCGAATTACTTAACGCCTCGATTATGTTCTTTGCGCCACTGATCATTAATCGCATCGGT
GGGAAAAACGCCCTGCTGCTGGCTGGCACTATTATGTCTGTACGTATTATTGGCTCATCGT
TCGCCACCTCAGCGCTGGAAGTGGTTATTCTGAAAACGCTGCATATGTTTGAAGTACCGTT
CCTGCTGGTGGGCTGCTTTAAATATATTACCAGCCAGTTTGAAGTGCGTTTTTCAGCGACG
ATTTATCTGGTCTGTTTCTGCTTCTTTAAGCAACTGGCGATGATTTTATGTCTGTACTGG
CGGGCAATATGTATGAAAGCATCGGTTTCCAGGGCGCTTATCTGGTGCTGGGTCTGGTGGC
GCTGGGCTTCACCTTAATTTCCGTGTTCACGCTTAGCGGCCCCGGCCCGCTTTCCCTGCTG
CGTCGTCAGGTGAATGAAGTCGCTTAA (SEQ ID N° 36)

Figure 18 – cont

> Cas 26.
CCCGTCTTACTGTCGGGAATTCGCGTTGGCCAATTAATTAATGGTATAAGGTTCTTGACATCTT
ACAGGGCCCAAGTTCACTTAAAAAGGAGATCAACAATGAAAGCAATTTTCGTACTGAAACATCT
TAATCATGCGTAGGATTTTTCTATGTACTATTTAAAAAACACAAACTTTTGGATGTTCGGTTT
ATTCTTTTTCTTTTACTTTTTTATCATGGGAGCCTACTTCCCGTTTTTCCCGATTTGGCTACAT
GACATCAACCATATCAGCAAAAGTGATACGGGTATTATTTTTGCCGCTATTTCTCTGTTCTCGC
TATTATTCCAACCGCTGTTTGGTCTGCTTTCTGACAAACTCGGGCTGCGCAAATACCTGCTGTG
GATTATTACCGGCATGTTAGTGATGTTTGCGCCGTTCTTTATTTTTATCTTCGGGCCACTGTTA
CAATACAACATTTTAGTAGGATCGATTGTTGGTGGTATTTATCTAGGCTTTTGTTTTAACGCCG
GTGCGCCAGCAGTAGAGGCATTTATTGAGAAAGTCAGCCGTCGCAGTAATTTCGAATTTGGTCG
CGCGCGGATGTTTGGCTGTGTTGGCTGGGCGCTGTGTGCCTCGATTGTCGGCATCATGTTCACC
ATCAATAATCAGTTTGTTTTCTGGCTGGGCTCTGGCTGTGCACTCATCCTCGCCGTTTTACTCT
TTTTCGCCAAAACGGATGCGCCCTCTTCTGCCACGGTTGCCAATGCGGTAGGTGCCAACCATTC
GGCATTTAGCCTTAAGCTGGCACTGGAACTGTTCAGACAGCCAAAACTGTGGTTTTTGTCACTG
TATGTTATTGGCGTTTCCTGCACCTACGATGTTTTGACCAACAGTTTGCTAATTTCTTTACTT
CGTTCTTTGCTACCGGTGAACAGGGTACGCGGGTATTTGGCTACGTAACGACAATGGGCGAATT
ACTTAACGCCTCGATTATGTTCTTTGCGCCACTGATCATTAATCGCATCGGTGGGAAAAACGCC
CTGCTGCTGGCTGGCACTATTATGTCTGTACGTATTATTGGCTCATCGTTCGCCACCTCAGCGC
TGGAAGTGGTTATTCTGAAAACGCTGCATATGTTTGAAGTACCGTTCCTGCTGGTGGGCTGCTT
TAAATATATTACCAGCCAGTTTGAAGTGCGTTTTTCAGCGACGATTTATCTGGTCTGTTTCTGC
TTCTTTAAGCAACTGGCGATGATTTTATGTCTGTACTGGCGGGCAATATGTATGAAAGCATCG
GTTTCCAGGGCGCTTATCTGGTGCTGGGTCTGGTGGCGCTGGGCTTCACCTTAATTTCCGTGTT
CACGCTTAGCGGCCCCGGCCCGCTTTCCTGCTGCGTCGTCAGGTGAATGAAGTCGCTTAA
(SEQ ID N° 37)

Figure 18 – cont

> Cas 27.
CCCGTCTTACTGTCGGGAATTCGCGTTGGCCGATTCGAATTCGCGTTGGCCGATTCGAATTCGC
GTTGGCCGATTCGAATTCGCGTTGGCCGATTCTTACACGATATATACTTCTTGACATTTTGCGG
GAATTATGGTATAATCACAAGGTTAGGGCCCAAGTTCACTTAAAAAGGAGATCAACAATGAAAG
CAATTTTCGTACTGAAACATCTTAATCATGCGTAGGATTTTTCTATGTACTATTTAAAAAACA
CAAACTTTTGGATGTTCGGTTTATTCTTTTCTTTTACTTTTTTATCATGGGAGCCTACTTCCC
GTTTTTCCCGATTTGGCTACATGACATCAACCATATCAGCAAAAGTGATACGGGTATTATTTTT
GCCGCTATTTCTCTGTTCTCGCTATTATTCCAACCGCTGTTTGGTCTGCTTTCTGACAAACTCG
GGCTGCGCAAATACCTGCTGTGGATTATTACCGGCATGTTAGTGATGTTTGCGCCGTTCTTTAT
TTTTATCTTCGGGCCACTGTTACAATACAACATTTTAGTAGGATCGATTGTTGGTGGTATTTAT
CTAGGCTTTTGTTTTAACGCCGGTGCGCCAGCAGTAGAGGCATTTATTGAGAAAGTCAGCCGTC
GCAGTAATTTCGAATTTGGTCGCGCGCGGATGTTTGGCTGTGTTGGCTGGGCGCTGTGTGCCTC
GATTGTCGGCATCATGTTCACCATCAATAATCAGTTTGTTTTCTGGCTGGGCTCTGGCTGTGCA
CTCATCCTCGCCGTTTTACTCTTTTTCGCCAAAACGGATGCGCCCTCTTCTGCCACGGTTGCCA
ATGCGGTAGGTGCCAACCATTCGGCATTTAGCCTTAAGCTGGCACTGGAACTGTTCAGACAGCC
AAAACTGTGGTTTTTGTCACTGTATGTTATTGGCGTTTCCTGCACCTACGATGTTTTGACCAA
CAGTTGCTAATTTCTTTACTTCGTTCTTTGCTACCGGTGAACAGGGTACGCGGGTATTTGGCT
ACGTAACGACAATGGGCGAATTACTTAACGCCTCGATTATGTTCTTTGCGCCACTGATCATTAA
TCGCATCGGTGGGAAAAACGCCCTGCTGCTGGCTGGCACTATTATGTCTGTACGTATTATTGGC
TCATCGTTCGCCACCTCAGCGCTGGAAGTGGTTATTCTGAAAACGCTGCATATGTTTGAAGTAC
CGTTCCTGCTGGTGGGCTGCTTTAAATATATTACCAGCCAGTTTGAAGTGCGTTTTTCAGCGAC
GATTTATCTGGTCTGTTTCTGCTTCTTTAAGCAACTGGCGATGATTTTTATGTCTGTACTGGCG
GGCAATATGTATGAAAGCATCGGTTTCCAGGGCGCTTATCTGGTGCTGGGTCTGGTGGCGCTGG
GCTTCACCTTAATTTCCGTGTTCACGCTTAGCGGCCCCGGCCCGCTTTCCCTGCTGCGTCGTCA
GGTGAATGAAGTCGCTTAA (SEQ ID N° 38)

Figure 18 – cont

> Cas 28.
CCTGAGTCGCTGTCTTTTTCGTGACATTCAGTTCGCTGCGCTCACGGCTCTGGCAGTGAATGGG
GGTAAATGGCACTACAGGCGCCTTTTATGGATTCATGCAAGGAAACTACCCATAATACAAGAAA
AGCCCGTCACGGGCTTCTCAGGGCGTTTTATGGCGGGTCTGCTATGTGGTGCTATCTGACTTTT
TGCTGTTCAGCAGTTCCTGCCCTCTGATTTTCCAGTCTGACCACTTCGGATTATCCCGTGACAG
GTCATTCAGACTGGCTAATGCACCCAGTAAGGCAGCGGTATCATCAACAGGCTTACCCGTCTTA
CTGTCGGGAATTCGCGTTGGCCGATTCATTAATGGTATAAGGTTCTTGACATCTTACAATCAAT
ATGGTATAATAATTTAGTTAGGGCCCAAGTTCACTTAAAAAGGAGATCAACAATGAAAGCTTAC
TGTCGGGAATTCGCGTTGGCCGATTCATTAATGGTATAAGGTTCTTGACATCTTACAATCAATA
TGGTATAATAATTTAGTTAGGGCCCAAGTTCACTTAAAAAGGAGATCAACAATGAAAGCTTACT
GTCGGGAATTCGCGTTGGCCGATTCATTAATGGTATAAGGTTCTTGACATCTTACAATCAATAT
GGTATAATAATTTAGTTAGGGCCCAAGTTCACTTAAAAAGGAGATCAACACTTACTGTCGGGAA
TTCGCGTTGGCCAATTAATTAATGGTATAAGGTTCTTGACATCTTACAATCAATATGGTATAAT
AATTTAGTTAGGGCCCAAGTTCACTTAAAAAGGAGATCAACAATGAAAGCAATTTCGTACTGA
AACATCTTAATCATGCGTAGGATTTTTTCTATGTACTATTTAAAAAACACAAACTTTTGGATGT
TCGGTTTATTCTTTTTCTTTTACTTTTTTATCATGGGAGCCTACTTCCCGTTTTTCCCGATTTG
GCTACATGACATCAACCATATCAGCAAAAGTGATACGGGTATTATTTTGCCGCTATTTCTCTG
TTCTCGCTATTATTCCAACCGCTGTTTGGTCTGCTTTCTGACAAACTCGGGCTGCGCAAATACC
TGCTGTGGATTATTACCGGCATGTTAGTGATGTTTGCGCCGTTCTTTATTTTATCTTCGGGCC
ACTGTTACAATACAACATTTTAGTAGGATCGATTGTTGGTGGTATTTATCTAGGCTTTTGTTTT
AACGCCGGTGCGCCAGCAGTAGAGGCATTTATTGAGAAAGTCAGCCGTCGCAGTAATTTCGAAT
TTGGTCGCGCGGATGTTTGGCTGTGTTGGCTGGGCGCTGTGTGCCTCGATTGTCGGCATCAT
GTTCACCATCAATAATCAGTTTGTTTTCTGGCTGGGCTCTGGCTGTGCACTCATCCTCGCCGTT
TTACTCTTTTTCGCCAAAACGGATGCGCCCTCTTCTGCCACGGTTGCCAATGCGGTAGGTGCCA
ACCATTCGGCATTTAGCCTTAAGCTGGCACTGGAACTGTTCAGACAGCCAAAACTGTGGTTTTT
GTCACTGTATGTTATTGGCGTTTCCTGCACCTACGATGTTTTTGACCAACAGTTTGCTAATTTC
TTTACTTCGTTCTTTGCTACCGGTGAACAGGGTACGCGGGTATTTGGCTACGTAACGACAATGG
GCGAATTACTTAACGCCTCGATTATGTTCTTTGCGCCACTGATCATTAATCGCATCGGTGGGAA
AAACGCCCTGCTGCTGGCTGGCACTATTATGTCTGTACGTATTATTGGCTCATCGTTCGCCACC
TCAGCGCTGGAAGTGGTTATTCTGAAAACGCTGCATATGTTTGAAGTACCGTTCCTGCTGGTGG
GCTGCTTTAAATATATTACCAGCCAGTTTGAAGTGCGTTTTTCAGCGACGATTTATCTGGTCTG
TTTCTGCTTCTTTAAGCAACTGGCGATGATTTTATGTCTGTACTGGCGGGCAATATGTATGAA
AGCATCGGTTTCCAGGGCGCTTATCTGGTGCTGGGTCTGGTGGCGCTGGGCTTCACCTTAATTT
CCGTGTTCACGCTTAGCGGCCCCGGCCCGCTTTCCCTGCTGCGTCGTCAGGTGAATGAAGTCGC
TTAA (SEQ ID N° 39)

Figure 18 – cont

> Cas 29.
TGTCTTTTTCGTGACATTCAGTTCGCTGCGCTCACGGCTCTGGCAGTGAATGGGGGTAAATGGC
ACTACAGGCGCCTTTTATGGATTCATGCAAGGAAACTACCCATAATACAAGAAAAGCCCGTCAC
GGGCTTCTCAGGGCGTTTTATGGCGGGTCTGCTATGTGGTGCTATCTGACTTTTTGCTGTTCAG
CAGTTCCTGCCCTCTGATTTTCCAGTCTGACCACTTCGGATTATCCCGTGACAGGTCATTCAGA
CTGGCTAATGCACCCAGTAAGGCAGCGGTATCATCAACAGGCTTACCCGTCTTACTGTCGGGAA
TTCGCGTTGGCCGATTCATTAATGGTATAAGGTTCTTGACATCTTACAATCAATATGGTATAAT
AATTTAGTTAGGGCCCAAGTTCACTTAAAAAGGAGATCAACAATGAAAGCTTACTGTCGGGAAT
TCGCGTTGGCCGATTCATTAATGGTATAAGGTTCTTGACATCTTACAATCAATATGGTATAATA
ATTTAGTTAGGGCCCAAGTTCACTTAAAAAGGAGATCAACAATGAAAGCACTGTCGGGAATTCG
CGTTGGCCGATTCATTAATGGTATAAGGTTCTTGACATCTTACAATCAATATGGTATAATAATT
TAGTTAGGGCCCAAGTTCACTTAAAAAGGAGATCAACAATGAAAGCTTACTGTCGGGAATTCGC
GTTGGCCGATTCATTAATGGTATAAGGTTCTTGACATCTTACAATCAATATGGTATAATAATTT
AGTTAGGGCCCAAGTTCACTTAAAAAGGAGATCAACACTTTACTGTCGGGGAATTCGCCGTTGG
GCCAATTTAATTAATGGGTATAAGGGTTCCTTGACAATGTACTATTTAAAAAACACAAACTTTT
GGATGTTCGGTTTATTCTTTTCTTTTACTTTTTATCATGGGAGCCTACTTCCCGTTTTTCCC
GATTTGGCTACATGACATCAACCATATCAGCAAAAGTGATACGGGTATTATTTTGCCGCTATT
TCTCTGTTCTCGCTATTATTCCAACCGCTGTTTGGTCTGCTTTCTGACAAACTCGGGCTGCGCA
AATACCTGCTGTGGATTATTACCGGCATGTTAGTGATGTTTGCGCCGTTCTTTATTTTATCTT
CGGGCCACTGTTACAATACAACATTTTAGTAGGATCGATTGTTGGTGGTATTTATCTAGGCTTT
TGTTTTAACGCCGGTGCGCCAGCAGTAGAGGCATTTATTGAGAAAGTCAGCCGTCGCAGTAATT
TCGAATTTGGTCGCGCGCGGATGTTTGGCTGTGTTGGCTGGGCGCTGTGTGCCTCGATTGTCGG
CATCATGTTCACCATCAATAATCAGTTTGTTTTCTGGCTGGGCTCTGGCTGTGCACTCATCCTC
GCCGTTTTACTCTTTTTCGCCAAAACGGATGCGCCCTCTTCTGCCACGGTTGCCAATGCGGTAG
GTGCCAACCATTCGGCATTTAGCCTTAAGCTGGCACTGGAACTGTTCAGACAGCCAAAACTGTG
GTTTTTGTCACTGTATGTTATTGGCGTTTCCTGCACCTACGATGTTTTTGACCAACAGTTTGCT
AATTTCTTTACTTCGTTCTTTGCTACCGGTGAACAGGGTACGCGGGTATTTGGCTACGTAACGA
CAATGGGCGAATTACTTAACGCCTCGATTATGTTCTTTGCGCCACTGATCATTAATCGCATCGG
TGGGAAAAACGCCCTGCTGCTGGCTGGCACTATTATGTCTGTACGTATTATTGGCTCATCGTTC
GCCACCTCAGCGCTGGAAGTGGTTATTCTGAAAACGCTGCATATGTTTGAAGTACCGTTCCTGC
TGGTGGGCTGCTTTAAATATATTACCAGCCAGTTTGAAGTGCGTTTTTCAGCGACGATTTATCT
GGTCTGTTTCTGCTTCTTTAAGCAACTGGCGATGATTTTTATGTCTGTACTGGCGGGCAATATG
TATGAAAGCATCGGTTTCCAGGGCGCTTATCTGGTGCTGGGTCTGGTGGCGCTGGGCTTCACCT
TAATTTCCGTGTTCACGCTTAGCGGCCCCGGCCCGCTTTCCCTGCTGCGTCGTCAGGTGAATGA
AGTCGCTTAA (SEQ ID N° 40)

Figure 18 – cont

> Cas 30.
TCGCTGTCTTTTTCGTGACATTCAGTTCGCTGCGCTCACGGCTCTGGCAGTGAATGGGGGT
AAATGGCACTACAGGCGCCTTTTATGGATTCATGCAAGGAAACTACCCATAATACAAGAAA
AGCCCGTCACGGGCTTCTCAGGGCGTTTTATGGCGGGTCTGCTATGTGGTGCTATCTGACT
TTTTGCTGTTCAGCAGTTCCTGCCCTCTGATTTTCCAGTCTGACCACTTCGGATTATCCCG
TGACAGGTCATTCAGACTGGCTAATGCACCCAGTAAGGCAGCGGTATCATCAACAGGCTTA
CCCGTCTTACTGTCGGGAATTCGCGTTGGCCGATTCATTAATGGTATAAGGTTCTTGACAT
CTTACAATCAATATGGTATAATAATTTAGTTAGGGCCCAAGTTCACTTAAAAAGGAGATCA
ACAATGAAAGCTTACTGTCGGGAATTCGCGTTGGCCGATTCATTAATGGTATAAGGTTCTT
GACATCTTACAATCAATATGGTATAATAATTTAGTTAGGGCCCAAGTTCACTTAAAAAGGA
GATCAACAATGAAAGCACTGTCGGGAATTCGCGTTGGCCGATTCATTAATGGTATAAGGGT
CTTGACATCTTACAATCAATATGGTATAATAATTTAGGTAGGGGCCAAGTTCACTTAGAAA
GGAGATCAACAATGAAAGCTTACTGTCGGGAATTCGCGTTGGCCGATTCATTAATGGTATA
AGGTTCTTGACATCTTACAATCTATATGGTATCATAATATACTTAGGGCCCAAGTTCACTT
AAAAAGGAGATCAACACTTACTGTCGCGAATTCGCGTTGGCCAATTAATTCATGGTATAAG
GTTCTTGACATCTTACAATCAAATGTACTATTTAAAAAACACAAACTTTTGGATGTTCGGT
TTATTCTTTTCTTTTACTTTTTATCATGGGAGCCTACTTCCCGTTTTTCCCGATTTGGC
TACATGACATCAACCATATCAGCAAAAGTGATACGGGTATTATTTTGCCGCTATTTCTCT
GTTCTCGCTATTATTCCAACCGCTGTTTGGTCTGCTTTCTGACAAACTCGGGCTGCGCAAA
TACCTGCTGTGGATTATTACCGGCATGTTAGTGATGTTTGCGCCGTTCTTTATTTTTATCT
TCGGGCCACTGTTACAATACAACATTTTAGTAGGATCGATTGTTGGTGGTATTTATCTAGG
CTTTTGTTTTAACGCCGGTGCGCCAGCAGTAGAGGCATTTATTGAGAAAGTCAGCCGTCGC
AGTAATTTCGAATTTGGTCGCGCGCGGATGTTTGGCTGTGTTGGCTGGCGCTGTGTGCCT
CGATTGTCGGCATCATGTTCACCATCAATAATCAGTTTGTTTTCTGGCTGGGCTCTGGCTG
TGCACTCATCCTCGCCGTTTTACTCTTTTTCGCCAAAACGGATGCGCCCTCTTCTGCCACG
GTTGCCAATGCGGTAGGTGCCAACCATTCGGCATTTAGCCTTAAGCTGGCACTGGAACTGT
TCAGACAGCCAAAACTGTGGTTTTTGTCACTGTATGTTATTGGCGTTTCCTGCACCTACGA
TGTTTTTGACCAACAGTTTGCTAATTTCTTTACTTCGTTCTTTGCTACCGGTGAACAGGGT
ACGCGGGTATTTGGCTACGTAACGACAATGGGCGAATTACTTAACGCCTCGATTATGTTCT
TTGCGCCACTGATCATTAATCGCATCGGTGGGAAAAACGCCCTGCTGCTGGCTGGCACTAT
TATGTCTGTACGTATTATTGGCTCATCGTTCGCCACCTCAGCGCTGGAAGTGGTTATTCTG
AAAACGCTGCATATGTTTGAAGTACCGTTCCTGCTGGTGGGCTGCTTTAAATATATTACCA
GCCAGTTTGAAGTGCGTTTTTCAGCGACGATTTATCTGGTCTGTTTCTGCTTCTTTAAGCA
ACTGGCGATGATTTTATGTCTGTACTGGCGGGCAATATGTATGAAAGCATCGGTTTCCAG
GGCGCTTATCTGGTGCTGGGTCTGGTGGCGCTGGGCTTCACCTTAATTTCCGTGTTCACGC
TTAGCGGCCCCGGCCCGCTTTCCCTGCTGCGTCGTCAGGTGAATGAAGTCGCTTAA
(SEQ ID N° 41)

Figure 18 – cont

> Cas 31.
GCCCGTCACGGGCTTCTCAGGGCGTTTTATGGCGGGTCTGCTATGTGGTGCTATCTGACTTTTT
GCTGTTCAGCAGTTCCTGCCCTCTGATTTTCCAGTCTGACCACTTCGGATTATCCCGTGACAGG
TCATTCAGACTGGCTAATGCACCCAGTAAGGCAGCGGTATCATCAACAGGCTTACCCGTCTTAC
TGTCGGGAATTCGCGTTGGCCGATTCATTAATGGTATAAGGTTCTTGACATCTTACAATCAATA
TGGTATAATAATTTAGTTAGGGCCCAAGTTCACTTAAAAAGGAGATCAACAATGAAAGCTTACT
GTCGGGAATTCGCGTTGGCCGATTCATTAATGGTATAAGGTTCTTGACATCTTACAATCAATAT
GGTATAATAATTTAGTTAGGGCCCAAGTTCACTTAAAAAGGAGATCAACAATGAAAGCACTGTC
GGGAATTCGCGTTGGCCAATTAATTAATGGTATAAGGTTCTTGACATCTTACAATCAATATGGT
ATAATAATTTAGTTAGGGCCCAAGTTCACTTAAAAAGGAGATCAACAATGAAAGCAATTTTCGT
ACTGAAACATCTTAATCATGCGTAGGATTTTTTCTATGTACTATTTAAAAAACACAAACTTTTG
GATGTTCGGTTTATTCTTTTTCTTTTACTTTTTTATCATGGGAGCCTACTTCCCGTTTTTCCCG
ATTTGGCTACATGACATCAACCATATCAGCAAAAGTGATACGGGTATTATTTTGCCGCTATTT
CTCTGTTCTCGCTATTATTCCAACCGCTGTTTGGTCTGCTTTCTGACAAACTCGGGCTGCGCAA
ATACCTGCTGTGGATTATTACCGGCATGTTAGTGATGTTTGCGCCGTTCTTTATTTTATCTTC
GGGCCACTGTTACAATACAACATTTTAGTAGGATCGATTGTTGGTGGTATTTATCTAGGCTTTT
GTTTTAACGCCGGTGCGCCAGCAGTAGAGGCATTTATTGAGAAAGTCAGCCGTCGCAGTAATTT
CGAATTTGGTCGCGCGCGGATGTTTGGCTGTGTTGGCTGGGCGCTGTGTGCCTCGATTGTCGGC
ATCATGTTCACCATCAATAATCAGTTTGTTTTCTGGCTGGGCTCTGGCTGTGCACTCATCCTCG
CCGTTTTACTCTTTTTCGCCAAAACGGATGCGCCCTCTTCTGCCACGGTTGCCAATGCGGTAGG
TGCCAACCATTCGGCATTTAGCCTTAAGCTGGCACTGGAACTGTTCAGACAGCCAAAACTGTGG
TTTTTGTCACTGTATGTTATTGGCGTTTCCTGCACCTACGATGTTTTGACCAACAGTTTGCTA
ATTTCTTTACTTCGTTCTTTGCTACCGGTGAACAGGGTACGCGGGTATTTGGCTACGTAACGAC
AATGGGCGAATTACTTAACGCCTCGATTATGTTCTTTGCGCCACTGATCATTAATCGCATCGGT
GGGAAAAACGCCCTGCTGCTGGCTGGCACTATTATGTCTGTACGTATTATTGGCTCATCGTTCG
CCACCTCAGCGCTGGAAGTGGTTATTCTGAAAACGCTGCATATGTTTGAAGTACCGTTCCTGCT
GGTGGGCTGCTTTAAATATATTACCAGCCAGTTTGAAGTGCGTTTTTCAGCGACGATTTATCTG
GTCTGTTTCTGCTTCTTTAAGCAACTGGCGATGATTTTTATGTCTGTACTGGCGGGCAATATGT
ATGAAAGCATCGGTTTCCAGGGCGCTTATCTGGTGCTGGGTCTGGTGGCGCTGGGCTTCACCTT
AATTTCCGTGTTCACGCTTAGCGGCCCCGGCCCGCTTTCCTGCTGCGTCGTCAGGTGAATGAA
GTCGCTTAA (SEQ ID N° 42)

Figure 18 – cont

> Cas 32.
GCTGTTCAGCAGTTCCTGCCCTCTGATTTTCCAGTCTGACCACTTCGGATTATCCCGTGACAGG
TCATTCAGACTGGCTAATGCACCCAGTAAGGCAGCGGTATCATCAACAGGCTTACCCGTCTTAC
TGTCGGGAATTCGCGTTGGCCGATTCATTAATGGTATAAGGTTCTTGACATCTTACAATCAATA
TGGTATAATAATTTAGTTAGGGCCCAAGTTCACTTAAAAAGGAGATCAACAATGAAAGCTTACT
GTCGGGAATTCGCGTTGGCCGATTCATTAATGGTATAAGGTTCTTGACATCTTACAATCAATAT
GGGTATAATAATTTAGTTAGGGCCCAAGTTCACTTAAAAAGGAGATCAACAATGAAAGCACTGT
CGGGAATTCGCGTTGGCCGATTCATTAATGGTATAAGGTTCTTGACATCTTACAATCAATATGG
TATAATAATTTAGTTAGGGCCCAAGTTCACTTAAAAAGGAGATCAACAATGAAAGCAATTTTCG
TACTGAAACATCTTAATCATGCGTAGGATTTTTCTATGTACTATTTAAAAAACACAAACTTTT
GGATGTTCGGTTTATTCTTTTCTTTTACTTTTTTATCATGGGAGCCTACTTCCCGTTTTTCCC
GATTTGGCTACATGACATCAACCATATCAGCAAAAGTGATACGGGTATTATTTTGCCGCTATT
TCTCTGTTCTCGCTATTATTCCAACCGCTGTTTGGTCTGCTTTCTGACAAACTCGGGCTGCGCA
AATACCTGCTGTGGATTATTACCGGCATGTTAGTGATGTTTGCGCCGTTCTTTATTTTATCTT
CGGGCCACTGTTACAATACAACATTTTAGTAGGATCGATTGTTGGTGGTATTTATCTAGGCTTT
TGTTTAACGCCGGTGCGCCAGCAGTAGAGGCATTTATTGAGAAAGTCAGCCGTCGCAGTAATT
TCGAATTTGGTCGCGCGCGGATGTTTGGCTGTGTTGGCTGGGCGCTGTGTGCCTCGATTGTCGG
CATCATGTTCACCATCAATAATCAGTTTGTTTCTGGCTGGGCTCTGGCTGTGCACTCATCCTC
GCCGTTTTACTCTTTTTCGCCAAAACGGATGCGCCCTCTTCTGCCACGGTTGCCAATGCGGTAG
GTGCCAACCATTCGGCATTTAGCCTTAAGCTGGCACTGGAACTGTTCAGACAGCCAAAACTGTG
GTTTTTGTCACTGTATGTTATTGGCGTTTCCTGCACCTACGATGTTTTTGACCAACAGTTTGCT
AATTTCTTTACTTCGTTCTTTGCTACCGGTGAACAGGGTACGCGGGTATTGGCTACGTAACGA
CAATGGGCGAATTACTTAACGCCTCGATTATGTTCTTTGCGCCACTGATCATTAATCGCATCGG
TGGGAAAAACGCCCTGCTGCTGGCTGGCACTATTATGTCTGTACGTATTATTGGCTCATCGTTC
GCCACCTCAGCGCTGGAAGTGGTTATTCTGAAAACGCTGCATATGTTTGAAGTACCGTTCCTGC
TGGTGGGCTGCTTTAAATATATTACCAGCCAGTTTGAAGTGCGTTTTTCAGCGACGATTTATCT
GGTCTGTTTCTGCTTCTTTAAGCAACTGGCGATGATTTTATGTCTGTACTGGCGGGCAATATG
TATGAAAGCATCGGTTTCCAGGGCGCTTATCTGGTGCTGGGTCTGGTGGCGCTGGGCTTCACCT
TAATTTCCGTGTTCACGCTTAGCGGCCCCGGCCCGCTTTCCCTGCTGCGTCGTCAGGTGAATGA
AGTCGCTTAA (SEQ ID N° 43)

Figure 18 – cont

> Cas 33.
GGCACCTGAGTCGCTGTCTTTTTCGTGACATTCAGTTCGCTGCGCTCACGGCTCTGGCAGTGAA
TGGGGGTAAATGGCACTACAGGCGCCTTTTATGGATTCATGCAAGGAAACTACCCATAATACAA
GAAAAGCCCGTCACGGGCTTCTCAGGGCGTTTTATGGCGGGTCTGCTATGTGGTGCTATCTGAC
TTTTTGCTGTTCAGCAGTTCCTGCCCTCTGATTTTCCAGTCTGACCACTTCGGATTATCCCGTG
ACAGGTCATTCAGACTGGCTAATGCACCCAGTAAGGCAGCGGTATCATCAACAGGCTTACCCGT
CTTACTGTCGGGAATTCGCGTTGGCCGATTCATTAATGGTATAAGGTTCTTGACATCTTACAAT
CAATATGGTATAATAATTTAGTTAGGGCCCAAGTTCACTTAAAAAGGAGATCAACAATGAAAGC
TTACTGTCGGGAATTCGCGTTGGCCGATTCATTAATGGTATAAGGTTCTTGACATCTTACAATC
AATATGGTATAATAATTTAGTTAGGGCCCAAGTTCACTTAAAAAGGAGATCAACAATGAAAGCA
CTGTCGGGAATTCGCGTTGGCCGATTCATTAATGGTATAAGGTTCTTGACATCTTACAATCAAT
ATGGTATAATAATTTAGTTAGGGCCCAAGTTCACTTAAAAAGGAGATCAACAATGAAAGCTTAC
TGTCGGGAATTCGCGTTGGCCGATTCATTAATGGTATAAGGTTCTTGACATCTTACAATCAATA
TGGTATAATAATTTAGTTAGGGCCCAAGTTCACTTAAAAAGGAGATCAACACTTACTGTCGGGA
ATTCGCGTTGGCCAATTAATTAATGGTATAAGGTTCTTGACATCTTACAATCAATATGGTATAA
TAATTTAGTTAGGGCCCAAGTTCACTTAAAAAGGAGATCAACAATGAAAGCAATTTCGTACTG
AAACATCTTAATCATGCGTAGGATTTTTCTATGTACTATTTAAAAAACACAAACTTTTGGATG
TTCGGTTTATTCTTTTCTTTTACTTTTTATCATGGGAGCCTACTTCCCGTTTTTCCCGATTT
GGCTACATGACATCAACCATATCAGCAAAAGTGATACGGGTATTATTTTGCCGCTATTTCTCT
GTTCTCGCTATTATTCCAACCGCTGTTTGGTCTGCTTTCTGACAAACTCGGGCTGCGCAAATAC
CTGCTGTGGATTATTACCGGCATGTTAGTGATGTTTGCGCCGTTCTTTATTTTATCTTCGGGC
CACTGTTACAATACAACATTTAGTAGGATCGATTGTTGGTGGTATTTATCTAGGCTTTTGTTT
TAACGCCGGTGCGCCAGCAGTAGAGGCATTTATTGAGAAAGTCAGCCGTCGCAGTAATTTCGAA
TTTGGTCGCGCGCGGATGTTTGGCTGTGTTGGCTGGGCGCTGTGTGCCTCGATTGTCGGCATCA
TGTTCACCATCAATAATCAGTTTGTTTTCTGGCTGGGCTCTGGCTGTGCACTCATCCTCGCCGT
TTTACTCTTTTTCGCCAAAACGGATGCGCCCTCTTCTGCCACGGTTGCCAATGCGGTAGGTGCC
AACCATTCGGCATTTAGCCTTAAGCTGGCACTGGAACTGTTCAGACAGCCAAAACTGTGGTTTT
TGTCACTGTATGTTATTGGCGTTTCCTGCACCTACGATGTTTTTGACCAACAGTTTGCTAATTT
CTTTACTTCGTTCTTTGCTACCGGTGAACAGGGTACGCGGGTATTTGGCTACGTAACGACAATG
GGCGAATTACTTAACGCCTCGATTATGTTCTTTGCGCCACTGATCATTAATCGCATCGGTGGGA
AAAACGCCCTGCTGCTGGCTGGCACTATTATGTCTGTACGTATTATTGGCTCATCGTTCGCCAC
CTCAGCGCTGGAAGTGGTTATTCTGAAAACGCTGCATATGTTTGAAGTACCGTTCCTGCTGGTG
GGCTGCTTTAAATATATTACCAGCCAGTTTGAAGTGCGTTTTTCAGCGACGATTTATCTGGTCT
GTTTCTGCTTCTTTAAGCAACTGGCGATGATTTTTATGTCTGTACTGGCGGGCAATATGTATGA
AAGCATCGGTTTCCAGGGCGCTTATCTGGTGCTGGGTCTGGTGGCGCTGGGCTTCACCTTAATT
TCCGTGTTCACGCTTAGCGGCCCCGGCCCGCTTTCCCTGCTGCGTCGTCAGGTGAATGAAGTCG
CTTAA (SEQ ID N° 44)

Figure 18 – cont

> Cas 34.
GCAAGGAAACTACCCATAATACAAGAAAAGCCCGTCACGGGCTTCTCAGGGCGTTTTATGGCGG
GTCTGCTATGTGGTGCTATCTGACTTTTTGCTGTTCAGCAGTTCCTGCCCTCTGATTTTCCAGT
CTGACCACTTCGGATTATCCCGTGACAGGTCATTCAGACTGGCTAATGCACCCAGTAAGGCAGC
GGTATCATCAACAGGCTTACCCGTCTTACTGTCGGGAATTCGCGTTGGCCGATTAATTAATGGT
ATAAGGTTCTTGACATCTTACAATCAATATGGTATAATAATTTAGTTAGGGCCCAAGTTCACTT
AAAAAGGAGATCAACAATGAAAGCTTACTGTCGGGAATTCGCGTTGGCCGATTCATTAATGGTA
TAAGGTTCTTGACATCTTACAATCAATATGGTATAATAATTTAGTTAGGGCCCAAGTTCACTTA
AAAAGGAGATCAACAATGAAAGCAGGCTTACCCGTCTTACTGTCGGGAATTCGCGTTGGCCGAT
TCATTAATGGTATAAGGTTCTTGACATCTTACAATCAATATGGTATAATAATTTAGTTAGGGCC
CAAGTTCACTTAAAAAGGAGATCAACACTTACTGTCGGGAATTCGCGTTGGCCAATTAATTAAT
GGTATAAGGTTCTTGACATCTTACAATCAATATGGTATAATAATTTAGTTAGGGCCCAAGTTCA
CTTAAAAAGGAGATCAACAATGAAAGCAATTTTCGTACTGAAACATCTTAATCATGCGTAGGAT
TTTTTCTATGTACTATTTAAAAAACACAAACTTTTGGATGTTCGGTTTATTCTTTTTCTTTTAC
TTTTTTATCATGGGAGCCTACTTCCCGTTTTTCCCGATTTGGCTACATGACATCAACCATATCA
GCAAAAGTGATACGGGTATTATTTTTGCCGCTATTTCTCTGTTCTCGCTATTATTCCAACCGCT
GTTTGGTCTGCTTTCTGACAAACTCGGGCTGCGCAAATACCTGCTGTGGATTATTACCGGCATG
TTAGTGATGTTTGCGCCGTTCTTTATTTTATCTTCGGGCCACTGTTACAATACAACATTTTAG
TAGGATCGATTGTTGGTGGTATTTATCTAGGCTTTTGTTTTAACGCCGGTGCGCCAGCAGTAGA
GGCATTTATTGAGAAAGTCAGCCGTCGCAGTAATTTCGAATTTGGTCGCGCGCGGATGTTTGGC
TGTGTTGGCTGGGCGCTGTGTGCCTCGATTGTCGGCATCATGTTCACCATCAATAATCAGTTTG
TTTTCTGGCTGGGCTCTGGCTGTGCACTCATCCTCGCCGTTTTACTCTTTTCGCCAAAACGGA
TGCGCCCTCTTCTGCCACGGTTGCCAATGCGGTAGGTGCCAACCATTCGGCATTTAGCCTTAAG
CTGGCACTGGAACTGTTCAGACAGCCAAAACTGTGGTTTTTGTCACTGTATGTTATTGGCGTTT
CCTGCACCTACGATGTTTTTGACCAACAGTTTGCTAATTTCTTTACTTCGTTCTTTGCTACCGG
TGAACAGGGTACGCGGGTATTTGGCTACGTAACGACAATGGGCGAATTACTTAACGCCTCGATT
ATGTTCTTTGCGCCACTGATCATTAATCGCATCGGTGGGAAAAACGCCCTGCTGCTGGCTGGCA
CTATTATGTCTGTACGTATTATTGGCTCATCGTTCGCCACCTCAGCGCTGGAAGTGGTTATTCT
GAAAACGCTGCATATGTTTGAAGTACCGTTCCTGCTGGTGGGCTGCTTTAAATATATTACCAGC
CAGTTTGAAGTGCGTTTTTCAGCGACGATTTATCTGGTCTGTTTCTGCTTCTTTAAGCAACTGG
CGATGATTTTTATGTCTGTACTGGCGGGCAATATGTATGAAAGCATCGGTTTCCAGGGCGCTTA
TCTGGTGCTGGGTCTGGTGGCGCTGGGCTTCACCTTAATTTCCGTGTTCACGCTTAGCGGCCCC
GGCCCGCTTTCCCTGCTGCGTCGTCAGGTGAATGAAGTCGCTTAA (SEQ ID N° 45)

Figure 18 – cont

\> Cas 35.
TTCAGTTCGCTGCGCTCACGGCTCTGGCAGTGAATGGGGGTAAATGGCACTACAGGCGCCTTTT
ATGGATTCATGCAAGGAAACTACCCATAATACAAGAAAAGCCCGTCACGGGCTTCTCAGGGCGT
TTTATGGCGGGTCTGCTATGTGGTGCTATCTGACTTTTTGCTGTTCAGCAGTTCCTGCCCTCTG
ATTTTCCAGTCTGACCACTTCGGATTATCCCGTGACAGGTCATTCAGACTGGCTAATGCACCCA
GTAAGGCAGCGGTATCATCAACAGGCTTACCCGTCTTACTGTCGGGAATTCGCGTTGGCCGATT
CATTAATGGTATAAGGTTCTTGACATCTTACAATCAATATGGTATAATAATTTAGTTAGGGCCC
AAGTTCACTTAAAAAGGAGATCAACAATGAAAGCTTACTGTCGGGAATTCGCGTTGGCCGATTC
ATTAATGGTATAAGGTTCTTGACATCTTACAATCAATATGGTATAATAATTTAGTTAGGGCCCA
AGTTCACTTAAAAAGGAGATCAACAATGAAAGCACTGTCGGGAATTCGCGTTGGCCGATTCATT
AATGGTATAAGGTTCTTGACATCTTACAATCAATATGGTATAATAATTTAGTTAGGGCCCAAGT
TCACTTAAAAAGGAGATCAACACTTACTGTCGGGAATTCGCGTTGGCCAATTAATTAATGGTAT
AAGGTTCTTGACATCTTACAATCAATATGGTATAATAATTTAGTTAGGGCCCAAGTTCACTTAA
AAAGGAGATCAACAATGAAAGCAATTTCGTACTGAAACATCTTAATCATGCTAGGATTTTTT
CTATGTACTATTTAAAAAACACAAACTTTTGGATGTTCGGTTTATTCTTTTTCTTTTACTTTTT
TATCATGGGAGCCTACTTCCCGTTTTTCCCGATTTGGCTACATGACATCAACCATATCAGCAAA
AGTGATACGGGTATTATTTTGCCGCTATTTCTCTGTTCTCGCTATTATTCCAACCGCTGTTTG
GTCTGCTTTCTGACAAACTCGGGCTGCGCAAATACCTGCTGTGGATTATTACCGGCATGTTAGT
GATGTTTGCGCCGTTCTTTATTTTATCTTCGGGCCACTGTTACAATACAACATTTTAGTAGGA
TCGATTGTTGGTGGTATTTATCTAGGCTTTTGTTTTAACGCCGGTGCGCCAGCAGTAGAGGCAT
TTATTGAGAAAGTCAGCCGTCGCAGTAATTTCGAATTGGTCGCGCGCGGATGTTTGGCTGTGT
TGGCTGGGCGCTGTGTGCCTCGATTGTCGGCATCATGTTCACCATCAATAATCAGTTTGTTTTC
TGGCTGGGCTCTGGCTGTGCACTCATCCTCGCCGTTTACTCTTTTCGCCAAAACGGATGCGC
CCTCTTCTGCCACGGTTGCCAATGCGGTAGGTGCCAACCATTCGGCATTTAGCCTTAAGCTGGC
ACTGGAACTGTTCAGACAGCCAAAACTGTGGTTTTTGTCACTGTATGTTATTGGCGTTTCCTGC
ACCTACGATGTTTTTGACCAACAGTTTGCTAATTTCTTTACTTCGTTCTTTGCTACCGGTGAAC
AGGGTACGCGGGTATTTGGCTACGTAACGACAATGGGCGAATTACTTAACGCCTCGATTATGTT
CTTTGCGCCACTGATCATTAATCGCATCGGTGGGAAAAACGCCCTGCTGCTGGCTGGCACTATT
ATGTCTGTACGTATTATTGGCTCATCGTTCGCCACCTCAGCGCTGGAAGTGGTTATTCTGAAAA
CGCTGCATATGTTTGAAGTACCGTTCCTGCTGGTGGGCTGCTTTAAATATATTACCAGCCAGTT
TGAAGTGCGTTTTTCAGCGACGATTTATCTGGTCTGTTTCTGCTTCTTTAAGCAACTGGCGATG
ATTTTTATGTCTGTACTGGCGGGCAATATGTATGAAAGCATCGGTTCCAGGGCGCTTATCTGG
TGCTGGGTCTGGTGGCGCTGGGCTTCACCTTAATTTCCGTGTTCACGCTTAGCGGCCCCGGCCC
GCTTTCCCTGCTGCGTCGTCAGGTGAATGAAGTCGCTTAA (SEQ ID N° 46)

Figure 18 – cont

> Cas 36.
GCTGCGCTCACGGCTCTGGCAGTGAATGGGGGTAAATGGCACTACAGGCGCCTTTTATGGATTC
ATGCAAGGAAACTACCCATAATACAAGAAAAGCCCGTCACGGGCTTCTCAGGGCGTTTTATGGC
GGGTCTGCTATGTGGTGCTATCTGACTTTTTGCTGTTCAGCAGTTCCTGCCCTCTGATTTTCCA
GTCTGACCACTTCGGATTATCCCGTGACAGGTCATTCAGACTGGCTAATGCACCCAGTAAGGCA
GCGGTATCATCAACAGGCTTACCCGTCTTACTGTCGGGAATTCGCGTTGGCCGATTCGAATTCG
CGTTGGCCGATTCGAATTCGCGTTGGCCGATTCGAATTCGCGTTGGCCGATTCGAATTCGCGTT
GGCCGATTCGAATTCGCGTTGGCCGATTCGAATTCGCGTTGGCCGATTCGAATTCGCGTTGGCC
GATTCATTAATGGTATAAGGTTCTTGACATCTTACAATCAATATGGTATAATAATTTAGTTAGG
GCCCAAGTTCACTTAAAAAGGAGATCAACAATGAAAGCTTACTGTCGGGAATTCGCGTTGGCCG
ATTCATTAATGGTATAAGGTTCTTGACATCTTACAATCAATATGGTATAATAATTTAGTTAGGG
CCCAAGTTCACTTAAAAAGGAGATCAACAATGAAAGCTTACTGTCGGGAATTCGCGTTGGCCGA
TTCATTAATGGTATAAGGTTCTTGACATCTTACAATCAATATGGTATAATAATTTAGTTAGGGC
CCAAGTTCACTTAAAAAGGAGATCAACAATGAAAGCAATTTTCGTACTGAAACATCTTAATCAT
GCGTAGGATTTTTTCTATGTACTATTTAAAAAACACAAACTTTTGGATGTTCGGTTTATTCTTT
TTCTTTTACTTTTTTATCATGGGAGCCTACTTCCCGTTTTTCCCGATTTGGCTACATGACATCA
ACCATATCAGCAAAAGTGATACGGGTATTATTTTTGCCGCTATTTCTCTGTTCTCGCTATTATT
CCAACCGCTGTTTGGTCTGCTTTCTGACAAACTCGGGCTGCGCAAATACCTGCTGTGGATTATT
ACCGGCATGTTAGTGATGTTTGCGCCGTTCTTTATTTTTATCTTCGGGCCACTGTTACAATACA
ACATTTTAGTAGGATCGATTGTTGGTGGTATTTATCTAGGCTTTTGTTTAACGCCGGTGCGCC
AGCAGTAGAGGCATTTATTGAGAAAGTCAGCCGTCGCAGTAATTTCGAATTGGTCGCGCGCGG
ATGTTTGGCTGTGTTGGCTGGGCGCTGTGTGCCTCGATTGTCGGCATCATGTTCACCATCAATA
ATCAGTTTGTTTTCTGGCTGGGCTCTGGCTGTGCACTCATCCTCGCCGTTTTACTCTTTTCGC
CAAAACGGATGCGCCCTCTTCTGCCACGGTTGCCAATGCGGTAGGTGCCAACCATTCGGCATTT
AGCCTTAAGCTGGCACTGGAACTGTTCAGACAGCCAAAACTGTGGTTTTTGTCACTGTATGTTA
TTGGCGTTTCCTGCACCTACGATGTTTTTGACCAACAGTTTGCTAATTTCTTTACTTCGTTCTT
TGCTACCGGTGAACAGGGTACGCGGGTATTTGGCTACGTAACGACAATGGGCGAATTACTTAAC
GCCTCGATTATGTTCTTTGCGCCACTGATCATTAATCGCATCGGTGGGAAAAACGCCCTGCTGC
TGGCTGGCACTATTATGTCTGTACGTATTATTGGCTCATCGTTCGCCACCTCAGCGCTGGAAGT
GGTTATTCTGAAAACGCTGCATATGTTTGAAGTACCGTTCCTGCTGGTGGGCTGCTTTAAATAT
ATTACCAGCCAGTTTGAAGTGCGTTTTTCAGCGACGATTTATCTGGTCTGTTTCTGCTTCTTTA
AGCAACTGGCGATGATTTTTATGTCTGTACTGGCGGGCAATATGTATGAAAGCATCGGTTTCCA
GGGCGCTTATCTGGTGCTGGGTCTGGTGGCGCTGGGCTTCACCTTAATTTCCGTGTTCACGCTT
AGCGGCCCCGGCCCGCTTTCCCTGCTGCGTCGTCAGGTGAATGAAGTCGCTTAA (SEQ ID
N° 47)

Figure 18 – cont

> Cas 37.
GCTGTTCAGCAGTTCCTGCCCTCTGATTTTCCAGTCTGACCACTTCGGATTATCCCGTGACAGG
TCATTCAGACTGGCTAATGCACCCAGTAAGGCAGCGGTATCATCAACAGGCTTACCCGTCTTAC
TGTCGGGAATTCGCGTTGGCCGATTAATTAATGGTATAAGGTTCTTGACATCTTACAATCAATA
TGGTATAATAATTTAGTTAGGGCCCAAGTTCACTTAAAAAGGAGATCAACAATGAAAGCTTACT
GTCGGGAATTCGCGTTGGCCGATTCATTAATGGTATAAGGTTCTTGACATCTTACAATCAATAT
GGTATAATAATTTAGTTAGGGCCCAAGTTCACTTAAAAAGGAGATCAACAATGAAAGCAGGCTT
ACCCGTCTTACTGTCGGGAATTCGCGTTGGCCGATTCATTAATGGTATAAGGTTCTTGACATCT
TACAATCAATATGGTATAATAATTTAGTTAGGGCCCAAGTTCACTTAAAAGGAGATCAACACT
TACTGTCGGGAATTCGCGTTGGCCAATTAATTAATGGTATAAGGTTCTTGACATCTTACAATCA
ATATGGTATAATAATTTAGTTAGGGCCCAAGTTCACTTANAAAGGAGATCAACACTTACTGTCG
GGAATTCGCGTTGGCNCATTAATTAATGGTATANAGTTCTTGACATCTTACCAATCATATGGTA
TAATAATTTAGTTAGGGCCCAAGTTCACTTAAAAAGGAGATCAACAATGAAAGCAATTTTCGTA
CTGAAACATCTTAATCATGCGTAGGATTTTTTCTATGTACTATTTAAAAAACACAAACTTTTGG
ATGTTCGGTTTATTCTTTTTCTTTTACTTTTTATCATGGGAGCCTACTTCCCGTTTTTCCCGA
TTTGGCTACATGACATCAACCATATCAGCAAAAGTGATACGGGTATTATTTTGCCGCTATTTC
TCTGTTCTCGCTATTATTCCAACCGCTGTTTGGTCTGCTTTCTGACAAACTCGGGCTGCGCAAA
TACCTGCTGTGGATTATTACCGGCATGTTAGTGATGTTTGCGCCGTTCTTTATTTTATCTTCG
GGCCACTGTTACAATACAACATTTTAGTAGGATCGATTGTTGGTGGTATTTATCTAGGCTTTTG
TTTTAACGCCGGTGCGCCAGCAGTAGAGGCATTTATTGAGAAAGTCAGCCGTCGCAGTAATTTC
GAATTTGGTCGCGCGGATGTTTGGCTGTGTTGGCTGGGCGCTGTGTGCCTCGATTGTCGGCA
TCATGTTCACCATCAATAATCAGTTTGTTTTCTGGCTGGGCTCTGGCTGTGCACTCATCCTCGC
CGTTTTACTCTTTTTCGCCAAAACGGATGCGCCCTCTTCTGCCACGGTTGCCAATGCGGTAGGT
GCCAACCATTCGGCATTTAGCCTTAAGCTGGCACTGGAACTGTTCAGACAGCCAAAACTGTGGT
TTTTGTCACTGTATGTTATTGGCGTTTCCTGCACCTACGATGTTTTTGACCAACAGTTTGCTAA
TTTCTTTACTTCGTTCTTTGCTACCGGTGAACAGGGTACGCGGGTATTTGGCTACGTAACGACA
ATGGGCGAATTACTTAACGCCTCGATTATGTTCTTTGCGCCACTGATCATTAATCGCATCGGTG
GGAAAAACGCCCTGCTGCTGGCTGGCACTATTATGTCTGTACGTATTATTGGCTCATCGTTCGC
CACCTCAGCGCTGGAAGTGGTTATTCTGAAAACGCTGCATATGTTTGAAGTACCGTTCCTGCTG
GTGGGCTGCTTTAAATATATTACCAGCCAGTTTGAAGTGCGTTTTTCAGCGACGATTTATCTGG
TCTGTTTCTGCTTCTTTAAGCAACTGGCGATGATTTTATGTCTGTACTGGCGGGCAATATGTA
TGAAAGCATCGGTTTCCAGGGCGCTTATCTGGTGCTGGGTCTGGTGGCGCTGGGCTTCACCTTA
ATTTCCGTGTTCACGCTTAGCGGCCCCGGCCCGCTTTCCCTGCTGCGTCGTCAGGTGAATGAAG
TCGCTTAA (SEQ ID N° 48)

Figure 18 – cont

\> Cas 38.
CCCGTCTTACTGTCGGGAATTCGCGTTGGCCGATTCATTAATGGTATAAGGTTCTTGACATCTT
ACAATCAATATGGTATAATAATTTAGTTA*GGGCCCAAGTTCACTTAAAAAGGAGATCAACAATG*
*AAAGC*TTACTGTCGGGAATTCGCGTTGGCCGATTCTTATAAATCATTATCTTCTTGACATTTTA
GAAACAATATGGTATAATATAACGATAAGGGCCCAAGTTCACTTAAAAAGGAGATCAACAATGA
AAGCAATTTTCGTACTGAAACATCTTAATCATGCGTAGGATTTTTCTATGTACTATTTAAAAA
ACACAAACTTTTGGATGTTCGGTTTATTCTTTTTCTTTTACTTTTTTATCATGGGAGCCTACTT
CCCGTTTTTCCCGATTTGGCTACATGACATCAACCATATCAGCAAAAGTGATACGGGTATTATT
TTTGCCGCTATTTCTCTGTTCTCGCTATTATTCCAACCGCTGTTTGGTCTGCTTTCTGACAAAC
TCGGGCTGCGCAAATACCTGCTGTGGATTATTACCGGCATGTTAGTGATGTTTGCGCCGTTCTT
TATTTTATCTTCGGGCCACTGTTACAATACAACATTTTAGTAGGATCGATTGTTGGTGGTATT
TATCTAGGCTTTTGTTTTAACGCCGGTGCGCCAGCAGTAGAGGCATTTATTGAGAAAGTCAGCC
GTCGCAGTAATTTCGAATTTGGTCGCGCGCGGATGTTTGGCTGTGTTGGCTGGGCGCTGTGTGC
CTCGATTGTCGGCATCATGTTCACCATCAATAATCAGTTTGTTTTCTGGCTGGGCTCTGGCTGT
GCACTCATCCTCGCCGTTTTACTCTTTTTCGCCAAAACGGATGCGCCCTCTTCTGCCACGGTTG
CCAATGCGGTAGGTGCCAACCATTCGGCATTTAGCCTTAAGCTGGCACTGGAACTGTTCAGACA
GCCAAAACTGTGGTTTTGTCACTGTATGTTATTGGCGTTTCCTGCACCTACGATGTTTTGAC
CAACAGTTTGCTAATTTCTTTACTTCGTTCTTTGCTACCGGTGAACAGGGTACGCGGGTATTTG
GCTACGTAACGACAATGGGCGAATTACTTAACGCCTCGATTATGTTCTTTGCGCCACTGATCAT
TAATCGCATCGGTGGGAAAAACGCCCTGCTGCTGGCTGGCACTATTATGTCTGTACGTATTATT
GGCTCATCGTTCGCCACCTCAGCGCTGGAAGTGGTTATTCTGAAAACGCTGCATATGTTTGAAG
TACCGTTCCTGCTGGTGGGCTGCTTTAAATATATTACCAGCCAGTTTGAAGTGCGTTTTTCAGC
GACGATTTATCTGGTCTGTTTCTGCTTCTTTAAGCAACTGGCGATGATTTTTATGTCTGTACTG
GCGGGCAATATGTATGAAAGCATCGGTTTCCAGGGCGCTTATCTGGTGCTGGGTCTGGTGGCGC
TGGGCTTCACCTTAATTTCCGTGTTCACGCTTAGCGGCCCCGGCCCGCTTTCCTGCTGCGTCG
TCAGGTGAATGAAGTCGCTTAA (SEQ ID N° 49)

Figure 18 – cont

> Cas 39.
CCCGTCTTACTGTCGGGAATTCGCGTTGGCCGATTCATTTAACCGATAAGCTTCTTGACATGTT
TAGGGTGTTATGATATAATCACCCAATTAGGGCCCAAGTTCACTTAAAAAGGAGATCAACAATG
AAAGCAATTTTCGTACTGAAACATCTTAATCATGCGTAGGATTTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCCTGCTGCGTC
GTCAGGTGAATGAAGTCGCTTAA (SEQ ID N° 50)

Figure 18 – cont

> Cas 40.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCAATTTTCGTACTGAAACATCTTAATCATGCGTAGGATTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCCTGCTGCGTC
GTCAGGTGAATGAAGTCGCTTAA (SEQ ID N° 51)

Figure 18 – cont

> Cas 41.
CCCGTCTTACTGTCGGGAATTCGCGTTGGCCGATTCTTAAATTCAATAACTTTCTTGACATGTT
ATTAGATTTATGGTATAATGACCCGATATGGGCCCAAGTTCACTTAAAAAGGAGATCAACAATG
AAAGCAATTTTCGTACTGAAACATCTTAATCATGCGTAGGATTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCCTGCTGCGTC
GTCAGGTGAATGAAGTCGCTTAA (SEQ ID N° 52)

Figure 18 – cont

> Cas 42.
*CCCGTCTTACTGTCGGGAATTCGCGTTGGCCGATTAATTAATGGTATAAGGTTCTTGACATCTT*
*ACAATCAATATGGTATAATAATTTAGTTAGGGCCCAAGTTCACTTAAAAAGGAGATCAACAATG*
*AAAGCAGGCTTACCCGTCTTACTGTCGGGAATTCGCGTTGGCCAATTAATTAATGGTATAAGGT*
TCTTGACATCTTACAATCAATATGGTATAATAATTTAGTTAGGGCCCAAGTTCACTTAAAAAGG
AGATCAACAATGAAAGCAATTTTCGTACTGAAACATCTTAATCATGCGTAGGATTTTTCTATG
TACTATTTAAAAAACACAAACTTTTGGATGTTCGGTTTATTCTTTTTCTTTTACTTTTTTATCA
TGGGAGCCTACTTCCCGTTTTTCCCGATTTGGCTACATGACATCAACCATATCAGCAAAAGTGA
TACGGGTATTATTTTTGCCGCTATTTCTCTGTTCTCGCTATTATTCCAACCGCTGTTTGGTCTG
CTTTCTGACAAACTCGGGCTGCGCAAATACCTGCTGTGGATTATTACCGGCATGTTAGTGATGT
TGCGCCGTTCTTTATTTTTATCTTCGGGCCACTGTTACAATACAACATTTTAGTAGGATCGAT
TGTTGGTGGTATTTATCTAGGCTTTTGTTTTAACGCCGGTGCGCCAGCAGTAGAGGCATTTATT
GAGAAAGTCAGCCGTCGCAGTAATTTCGAATTTGGTCGCGCGCGGATGTTTGGCTGTGTTGGCT
GGGCGCTGTGTGCCTCGATTGTCGGCATCATGTTCACCATCAATAATCAGTTTGTTTCTGGCT
GGGCTCTGGCTGTGCACTCATCCTCGCCGTTTACTCTTTTTCGCCAAAACGGATGCGCCCTCT
TCTGCCACGGTTGCCAATGCGGTAGGTGCCAACCATTCGGCATTTAGCCTTAAGCTGGCACTGG
AACTGTTCAGACAGCCAAAACTGTGGTTTTGTCACTGTATGTTATTGGCGTTTCCTGCACCTA
CGATGTTTTTGACCAACAGTTTGCTAATTTCTTTACTTCGTTCTTTGCTACCGGTGAACAGGGT
ACGCGGGTATTTGGCTACGTAACGACAATGGGCGAATTACTTAACGCCTCGATTATGTTCTTTG
CGCCACTGATCATTAATCGCATCGGTGGGAAAAACGCCCTGCTGCTGGCTGGCACTATTATGTC
TGTACGTATTATTGGCTCATCGTTCGCCACCTCAGCGCTGGAAGTGGTTATTCTGAAAACGCTG
CATATGTTTGAAGTACCGTTCCTGCTGGTGGGCTGCTTTAAATATATTACCAGCCAGTTTGAAG
TGCGTTTTTCAGCGACGATTTATCTGGTCTGTTTCTGCTTCTTTAAGCAACTGGCGATGATTTT
TATGTCTGTACTGGCGGGCAATATGTATGAAAGCATCGGTTTCCAGGGCGCTTATCTGGTGCTG
GGTCTGGTGGCGCTGGGCTTCACCTTAATTTCCGTGTTCACGCTTAGCGGCCCCGGCCCGCTTT
CCCTGCTGCGTCGTCAGGTGAATGAAGTCGCTTAA (SEQ ID N° 53)

Figure 18 – cont

> Cas 43.
CCCGTCTTACTGTCGGGAATTCGCGTTGGCCGATTCATTAATGGTATAAGGTTCTTGACATCTT
ACAATCAATATGGTATAATAATTTAGTTAGGGCCCAAGTTCACTTAAAAAGGAGATCAACAATG
AAAGCAATTTTCGTACTGAAACATCTTAATCATGCGTAGGATTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCTGCTGCGTC
GTCAGGTGAATGAAGTCGCTTAA (SEQ ID N° 54)

Figure 18 – cont

> Cas 44.
CCCGTCTTACTGTCGGGAATTCGCGTTGGCCGATTCGAATTCGCGTTGGCCGATTCGAATTCGC
GTTGGCCGATTCGAATTCGCGTTGGCCGATTCATTAATGGTATAAGGTTCTTGACATCTTACAA
TCAATATGGTATAATAATTTAGTTA*GGGCCCAAGTTCACTTAAAAAGGAGATCAAC*ACTTACTG
TCGGGAATTCGCGTTGGCCGATTCATTAATGGTATAAGGTTCTTGACATCTTACAATCAATATG
GTATAATAATTTAGTTA*GGGCCCAAGTTCACTTAAAAGGAGATCAACAATGAAAGC*TTACTGT
CGGGAATTCGCGTTGGCCGATTCATTAATGGTATAAGGTTCTTGACATCTTACAATCAATATGG
TATAATAATTTAGTTA*GGGCCCAAGTTCACTTAAAAGGAGATCAACAATGAAAGC*TTACTGTC
GGGAATTCGCGTTGGCCGATTCATTAATGGTATAAGGTTCTTGACATCTTACAATCAATATGGT
ATAATAATTTAGTTAGGGCCCAAGTTCACTTAAAAGGAGATCAACACTTACTGTCGGGAATTC
GCGTTGGCCAATTAATTAATGGTATAAGGTTCTTGACATCTTACCATCAATATGGGGCCCAAGT
TCACTTAAAAGGAGATCAACAATGAAAGCAATTTCGTACTGAAACATCTTAATCATGCGTAG
GATTTTTCTATGTACTATTTAAAAAACACAAACTTTTGGATGTTCGGTTTATTCTTTTTCTTT
TACTTTTTATCATGGGAGCCTACTTCCCGTTTTCCCGATTTGGCTACATGACATCAACCATA
TCAGCAAAAGTGATACGGGTATTATTTTTGCCGCTATTTCTCTGTTCTCGCTATTATTCCAACC
GCTGTTTGGTCTGCTTTCTGACAAACTCGGGCTGCGCAAATACCTGCTGTGGATTATTACCGGC
ATGTTAGTGATGTTTGCGCCGTTCTTTATTTTATCTTCGGGCCACTGTTACAATACAACATTT
TAGTAGGATCGATTGTTGGTGGTATTTATCTAGGCTTTTGTTTTAACGCCGGTGCGCCAGCAGT
AGAGGCATTTATTGAGAAAGTCAGCCGTCGCAGTAATTTCGAATTTGGTCGCGCGCGGATGTTT
GGCTGTGTTGGCTGGGCGCTGTGTGCCTCGATTGTCGGCATCATGTTCACCATCAATAATCAGT
TTGTTTTCTGGCTGGGCTCTGGCTGTGCACTCATCCTCGCCGTTTTACTCTTTTCGCCAAAAC
GGATGCGCCCTCTTCTGCCACGGTTGCCAATGCGGTAGGTGCCAACCATTCGGCATTTAGCCTT
AAGCTGGCACTGGAACTGTTCAGACAGCCAAAACTGTGGTTTTTGTCACTGTATGTTATTGGCG
TTTCCTGCACCTACGATGTTTTTGACCAACAGTTTGCTAATTTCTTTACTTCGTTCTTTGCTAC
CGGTGAACAGGGTACGCGGGTATTTGGCTACGTAACGACAATGGGCGAATTACTTAACGCCTCG
ATTATGTTCTTTGCGCCACTGATCATTAATCGCATCGGTGGGAAAAACGCCCTGCTGCTGGCTG
GCACTATTATGTCTGTACGTATTATTGGCTCATCGTTCGCCACCTCAGCGCTGGAAGTGGTTAT
TCTGAAAACGCTGCATATGTTTGAAGTACCGTTCCTGCTGGTGGGCTGCTTTAAATATATTACC
AGCCAGTTTGAAGTGCGTTTTTCAGCGACGATTTATCTGGTCTGTTTCTGCTTCTTTAAGCAAC
TGGCGATGATTTTATGTCTGTACTGGCGGGCAATATGTATGAAAGCATCGGTTTCCAGGGCGC
TTATCTGGTGCTGGGTCTGGTGGCGCTGGGCTTCACCTTAATTTCCGTGTTCACGCTTAGCGGC
CCCGGCCCGCTTTCCCTGCTGCGTCGTCAGGTGAATGAAGTCGCTTAA (SEQ ID N° 55)

Figure 18 – cont

> Cas 45.
CCCGTCTTACTGTCGGGAATTCGCGTTGGCCGATTCATTAATGGGATAAGGTTCTTGACATCTT
ACAATCAATATGGTATAATAATTTAGTTAGGGCCCAAGTTCACTTAAAAAGGAGATCAACAATG
AAAGCAATTTTCGTACTGAAACATCTTAATCATGCGTAGGATTTTTTCTATGTACTATTTAAAA
AACACAAACTTTTGGATGTTCGGTTTATTCTTTTTCTTTTACTTTTTTATCATGGGAGCCTACT
TCCCGTTTTTCCCGATTTGGCTACATGACATCAACCATATCAGCAAAAGTGATACGGGTATTAT
TTTTGCCGCTATTTCTCTGTTCTCGCTATTATTCCAACCGCTGTTTGGTCTGCTTTCTGACAAA
CTCGGGCTGCGCAAATACCTGCTGTGGATTATTACCGGCATGTTAGTGATGTTTGCGCCGTTCT
TTATTTTATCTTCGGGCCACTGTTACAATACAACATTTTAGTAGGATCGATTGTTGGTGGTAT
TTATCTAGGCTTTTGTTTTAACGCCGGTGCGCCAGCAGTAGAGGCATTTATTGAGAAAGTCAGC
CGTCGCAGTAATTTCGAATTTGGTCGCGCGGATGTTTGGCTGTGTTGGCTGGGCGCTGTGTG
CCTCGATTGTCGGCATCATGTTCACCATCAATAATCAGTTTGTTTCTGGCTGGGCTCTGGCTG
TGCACTCATCCTCGCCGTTTACTCTTTTCGCCAAAACGGATGCGCCCTCTTCTGCCACGGTT
GCCAATGCGGTAGGTGCCAACCATTCGGCATTTAGCCTTAAGCTGGCACTGGAACTGTTCAGAC
AGCCAAAACTGTGGTTTTTGTCACTGTATGTTATTGGCGTTTCCTGCACCTACGATGTTTTGA
CCAACAGTTTGCTAATTTCTTTACTTCGTTCTTTGCTACCGGTGAACAGGGTACGCGGGTATTT
GGCTACGTAACGACAATGGGCGAATTACTTAACGCCTCGATTATGTTCTTTGCGCCACTGATCA
TTAATCGCATCGGTGGGAAAAACGCCCTGCTGCTGGCTGGCACTATTATGTCTGTACGTATTAT
TGGCTCATCGTTCGCCACCTCAGCGCTGGAAGTGGTTATTCTGAAAACGCTGCATATGTTTGAA
GTACCGTTCCTGCTGGTGGGCTGCTTTAAATATATTACCAGCCAGTTTGAAGTGCGTTTTTCAG
CGACGATTTATCTGGTCTGTTTCTGCTTCTTTAAGCAACTGGCGATGATTTTATGTCTGTACT
GGCGGGCAATATGTATGAAAGCATCGGTTTCCAGGGCGCTTATCTGGTGCTGGGTCTGGTGGCG
CTGGGCTTCACCTTAATTTCCGTGTTCACGCTTAGCGGCCCCGGCCCGCTTTCCCTGCTGCGTC
GTCAGGTGAATGAAGTCGCTTAA (SEQ ID N° 56)

Figure 18 – cont

> Cas 46.
GGCACCTGAGTCGCTGTCTTTTCGTGACATTCAGTTCGCTGCGCTCACGGCTCTGGCAGTGAA
TGGGGGTAAATGGCACTACAGGCGCCTTTTATGGATTCATGCAAGGAAACTACCCATAATACAA
GAAAAGCCCGTCACGGGCTTCTCAGGGCGTTTTATGGCGGGTCTGCTATGTGGTGCTATCTGAC
TTTTTGCTGTTCAGCAGTTCCTGCCCTCTGATTTTCCAGTCTGACCACTTCGGATTATCCCGTG
ACAGGTCATTCAGACTGGCTAATGCACCCAGTAAGGCAGCGGTATCATCAACAGGCTTACCCGT
CTTACTGTCGGGAATTCGCGTTGGCCGATTCGAATTCGCGTTGGCCGATTCTTAGAGATAAAAA
ATTTCTTGACATGTTCTATGTTTTGTGATATAATCGTGAGATAAGGGCCCAAGTTCACTTAAAA
AGGAGATCAACAATGAAAGCAAGCGGTATCATCAACAGGCTTACCCGTCTTACTGTCGGGAATT
CGCGTTGGCCGATTCATTAATGGTATAAGGTTCTTGACATCTTACAATCAATATGGTATAATAA
TTTAGTTAGGGCCCAAGTTCACTTAAAAGGAGATCAACAATGAAAGCTTACTGTCGGGAATTC
GCGTTGGCCGATTCATTAATGGTATAAGGTTCTTGACATCTTACAATCAATATGGTATAATAAT
TTAGTTAGGGCCCAAGTTCACTTAAAAGGAGATCAACAATGAAAGCTTACTGTCGGGAATTCG
CGTTGGCCGATTCATTAATGGTATAAGGTTCTTGACATCTTACAATCAATATGGTATAATAATT
TAGTTAGGGCCCAAGTTCACTTAAAAGGAGATCAACACTTACTGTCGGGAATTCGCGTTGGCC
AATTAATTAATGGTATAAGGTTCTTGACATCTTACAATCAATATTGTATAATAATTTAGTTAGG
GCCCAAGTTCACTTAAAAGGAGATCAACAATGAAAGCAATTTTCGTACTGAAACATCTTAATC
ATGCGTAGGATTTTTTCTATGTACTATTTAAAAAACACAAACTTTTGGATGTTCGGTTTATTCT
TTTTCTTTTACTTTTTTATCATGGGAGCCTACTTCCCGTTTTTCCCGATTTGGCTACATGACAT
CAACCATATCAGCAAAAGTGATACGGGTATTATTTTGCCGCTATTTCTCTGTTCTCGCTATTA
TTCCAACCGCTGTTTGGTCTGCTTTCTGACAAACTCGGGCTGCGCAAATACCTGCTGTGGATTA
TTACCGGCATGTTAGTGATGTTTGCGCCGTTCTTTATTTTATCTTCGGGCCACTGTTACAATA
CAACATTTAGTAGGATCGATTGTTGGTGGTATTTATCTAGGCTTTTGTTTAACGCCGGTGCG
CCAGCAGTAGAGGCATTTATTGAGAAAGTCAGCCGTCGCAGTAATTTCGAATTTGGTCGCGCGC
GGATGTTTGGCTGTGTTGGCTGGCGCTGTGTGCCTCGATTGTCGGCATCATGTTCACCATCAA
TAATCAGTTTGTTTTCTGGCTGGGCTCTGGCTGTGCACTCATCCTCGCCGTTTTACTCTTTTTC
GCCAAAACGGATGCGCCCTCTTCTGCCACGGTTGCCAATGCGGTAGGTGCCAACCATTCGGCAT
TTAGCCTTAAGCTGGCACTGGAACTGTTCAGACAGCCAAAACTGTGGTTTTTGTCACTGTATGT
TATTGGCGTTTCCTGCACCTACGATGTTTTGACCAACAGTTTGCTAATTTCTTTACTTCGTTC
TTTGCTACCGGTGAACAGGGTACGCGGGTATTTGGCTACGTAACGACAATGGGCGAATTACTTA
ACGCCTCGATTATGTTCTTTGCGCCACTGATCATTAATCGCATCGGTGGGAAAAACGCCCTGCT
GCTGGCTGGCACTATTATGTCTGTACGTATTATTGGCTCATCGTTCGCCACCTCAGCGCTGGAA
GTGGTTATTCTGAAAACGCTGCATATGTTTGAAGTACCGTTCCTGCTGGTGGGCTGCTTTAAAT
ATATTACCAGCCAGTTTGAAGTGCGTTTTTCAGCGACGATTTATCTGGTCTGTTTCTGCTTCTT
TAAGCAACTGGCGATGATTTTTATGTCTGTACTGGCGGGCAATATGTATGAAAGCATCGGTTTC
CAGGGCGCTTATCTGGTGCTGGGTCTGGTGGCGCTGGCTTCACCTTAATTTCCGTGTTCACGC
TTAGCGGCCCCGGCCCGCTTTCCCTGCTGCGTCGTCAGGTGAATGAAGTCGCTTAA (SEQ ID
N° 57)

Figure 18 – cont

Sequence of the placIQ_lacY_terminator construct

```
TCGCGTTGGCCGATTCGGAATAGGACACCATCGAATGGTGCAAAACCTTTCGCGGTATGGCATG
ATAGCGCCCGGAAGAGAGTCAATTCAGGGTGGTGAATATGTACTATTTAAAAAACACAAACTTT
TGGATGTTCGGTTTATTCTTTTTCTTTTACTTTTTATCATGGGAGCCTACTTCCCGTTTTCC
CGATTTGGCTACATGACATCAACCATATCAGCAAAAGTGATACGGGTATTATTTTGCCGCTAT
TTCTCTGTTCTCGCTATTATTCCAACCGCTGTTTGGTCTGCTTTCTGACAAACTCGGGCTGCGC
AAATACCTGCTGTGGATTATTACCGGCATGTTAGTGATGTTTGCGCCGTTCTTTATTTTATCT
TCGGGCCACTGTTACAATACAACATTTTAGTAGGATCGATTGTTGGTGGTATTTATCTAGGCTT
TTGTTTTAACGCCGGTGCGCCAGCAGTAGAGGCATTTATTGAGAAAGTCAGCCGTCGCAGTAAT
TTCGAATTTGGTCGCGCGCGGATGTTTGGCTGTGTTGGCTGGGCGCTGTGTGCCTCGATTGTCG
GCATCATGTTCACCATCAATAATCAGTTTGTTTTCTGGCTGGGCTCTGGCTGTGCACTCATCCT
CGCCGTTTTACTCTTTTCGCCAAAACGGATGCGCCCTCTTCTGCCACGGTTGCCAATGCGGTA
GGTGCCAACCATTCGGCATTTAGCCTTAAGCTGGCACTGGAACTGTTCAGACAGCCAAAACTGT
GGTTTTTGTCACTGTATGTTATTGGCGTTTCCTGCACCTACGATGTTTTGACCAACAGTTTGC
TAATTTCTTTACTTCGTTCTTTGCTACCGGTGAACAGGGTACGCGGGTATTTGGCTACGTAACG
ACAATGGGCGAATTACTTAACGCCTCGATTATGTTCTTTGCGCCACTGATCATTAATCGCATCG
GTGGGAAAAACGCCCTGCTGCTGGCTGGCACTATTATGTCTGTACGTATTATTGGCTCATCGTT
CGCCACCTCAGCGCTGGAAGTGGTTATTCTGAAAACGCTGCATATGTTTGAAGTACCGTTCCTG
CTGGTGGGCTGCTTTAAATATATTACCAGCCAGTTTGAAGTGCGTTTTCAGCGACGATTTATC
TGGTCTGTTTCTGCTTCTTTAAGCAACTGGCGATGATTTTATGTCTGTACTGGCGGGCAATAT
GTATGAAAGCATCGGTTTCCAGGGCGCTTATCTGGTGCTGGGTCTGGTGGCGCTGGGCTTCACC
TTAATTTCCGTGTTCACGCTTAGCGGCCCCGGCCCGCTTTCCCTGCTGCGTCGTCAGGTGAATG
AAGTCGCTCATCATCACCACCATCATTAGGATGGTGGTGATGATAATGGAGAAAAAAATCACTG
GATATACCACCGTTGATATATCCCAATGGCATCGTAAAGAACATTTTGAGGCATTTCAGTCAGT
TGCTCAATGTACCTATAACCAGACCGTTCAGCTGGATATTACGGCCTTTTTAAAGACCGTAAAG
AAAAATAAGCACAAGTTTTATCCGGCCTTTATTCACATTCTTGCCCGCCTGATGAATGCTCATC
CGGAGTTCCGTATGGCAATGAAAGACGGTGAGCTGGTGATATGGGATAGTGTTCACCCTTGTTA
CACCGTTTTCCATGAGCAAACTGAAACGTTTTCATCGCTCTGGAGTGAATACCACGACGATTTC
CGGCAGTTTCTACACATATATTCGCAAGATGTGGCGTGTTACGGTGAAAACCTGGCCTATTTCC
CTAAAGGGTTTATTGAGAATATGTTTTCGTCAGCGCCAATCCCTGGGTGAGTTTCACCAGTTT
TGATTTAAACGTGGCCAATATGGACAACTTCTTCGCCCCGTTTTCACTATGGGCAAATATTAT
ACGCAAGGCGACAAGGTGCTGATGCCGCTGGCGATTCAGGTTCATCATGCCGTTTGTGATGGCT
TCCATGTCGGCAGAATGCTTAATGAATTACAACAGTACTGCGATGAGTGGCAGGGCGGGGCGTA
AGGATCCAAAGGTACCTCTAGAGTCGACCTGCAGGCCTTCGTAAATCTGGCGAGTGGGGAACTG
CCAGACATCAAATAAAACAAAAGGCTCAGTCGGAAGACTGGGCCTTTTGTTTTATCTGTTGTTT
GTCGGTGAACACTCTCCCGTGTAGGCTGGAGCTG (SEQ ID N° 58)
```

Figure 20

ID No 2).

SEQUENCE LISTING

```
<160> NUMBER OF SEQ ID NOS: 58

<210> SEQ ID NO 1
<211> LENGTH: 1460
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 1
agcgcaacgc aattaatgtg agttagctca ctcattaggc accccaggct tgtgtaggct      60
ggagctgctt cgaagttcct atactttcta gagaatagga acttcggaat aggaactaag    120
gaggatattc atatggaccg atatcccggg cggccgctct agaagaagct tgggatccgt    180
cgacctcgaa ttcggaggaa acaaagatgt actatttaaa aaacacaaac ttttggatgt    240
tcggtttatt cttttttcttt tactttttta tcatgggagc ctacttcccg ttttttcccga    300 tttggctaca tgacatcaac catatcagca aaagtgatac gggtattatt tttgccgcta    360
tttctctgtt ctcgctatta ttccaaccgc tgtttggtct gctttctgac aaactcgggc    420
tgcgcaaata cctgctgtgg attattaccg gcatgttagt gatgtttgcg ccgttctta    480 tttttatctt cgggccactg ttacaataca acatttttagt aggatcgatt gttggtggta    540
tttatctagg cttttgtttt aacgccggtg cgccagcagt agaggcattt attgagaaag    600
tcagccgtcg cagtaatttc gaatttggtc gcgcgcggat gtttggctgt gttggctggg    660
cgctgtgtgc ctcgattgtc ggcatcatgt tcaccatcaa taatcagttt gttttctggc    720
tgggctctgg ctgtgcactc atcctcgccg tttttactctt tttcgccaaa acggatgcgc    780
cctcttctgc cacggttgcc aatgcggtag gtgccaacca ttcggcattt agccttaagc    840
tggcactgga actgttcaga cagccaaaac tgtggttttt gtcactgtat gttattggcg    900
tttcctgcac ctacgatgtt tttgaccaac agtttgctaa tttctttact tcgttctttg    960
ctaccggtga acagggtacg cgggtatttg gctacgtaac gacaatgggc gaattactta   1020
acgcctcgat tatgttcttt gcgccactga tcattaatcg catcggtggg aaaaacgccc   1080
tgctgctggc tggcactatt atgtctgtac gtattattgg ctcatcgttc gccacctcag   1140
cgctggaagt ggttattctg aaaacgctgc atatgtttga agtaccgttc ctgctggtgg   1200
gctgctttaa atatattacc agccagtttg aagtgcgttt tcagcgacg atttatctgg   1260 tctgtttctg cttctttaag caactggcga tgatttttat gtctgtactg gcgggcaata   1320
tgtatgaaag catcggtttc cagggcgctt atctggtgct gggtctggtg gcgctgggct   1380
tcaccttaat ttccgtgttc acgcttagcg gccccgccc gctttccctg ctgcgtcgtc   1440
aggtgaatga agtcgcttaa                                                1460
```

<210> SEQ ID NO 2
<211> LENGTH: 4432
<212> TYPE: DNA
<213> ORGANISM: Artificial sequence
<220> FEATURE:
<223> OTHER INFORMATION: Genetic constructs detecting expressed lactose
      transporters

<400> SEQUENCE: 2

| | | | | | |
|---|---|---|---|---|---|
| atgtactatt | taaaaaacac | aaacttttgg | atgttcggtt | tattcttttt | cttttacttt | 60 |
| tttatcatgg | gagcctactt | cccgtttttc | ccgatttggc | tacatgacat | caaccatatc | 120 |
| agcaaaagtg | atacgggtat | tattttttgcc | gctatttctc | tgttctcgct | attattccaa | 180 |
| ccgctgtttg | gtctgctttc | tgacaaactc | gggctgcgca | aatacctgct | gtggattatt | 240 |
| accggcatgt | tagtgatgtt | tgcgccgttc | tttattttta | tcttcgggcc | actgttacaa | 300 |
| tacaacattt | tagtaggatc | gattgttggt | ggtatttatc | taggcttttg | ttttaacgcc | 360 |
| ggtgcgccag | cagtagaggc | atttattgag | aaagtcagcc | gtcgcagtaa | tttcgaattt | 420 |
| ggtcgcgcgc | ggatgtttgg | ctgtgttggc | tgggcgctgt | gtgcctcgat | tgtcggcatc | 480 |
| atgttcacca | tcaataatca | gtttgttttc | tggctgggct | ctggctgtgc | actcatcctc | 540 |
| gccgttttac | tcttttttcgc | caaaacggat | gcgccctctt | ctgccacggt | tgccaatgcg | 600 |
| gtaggtgcca | accattcggc | atttagcctt | aagctggcac | tggaactgtt | cagacagcca | 660 |
| aaactgtggt | ttttgtcact | gtatgttatt | ggcgtttcct | gcacctacga | tgttttttgac | 720 |
| caacagtttg | ctaatttctt | tacttcgttc | tttgctaccg | gtgaacaggg | tacgcgggta | 780 |
| tttggctacg | taacgacaat | gggcgaatta | cttaacgcct | cgattatgtt | ctttgcgcca | 840 |
| ctgatcatta | atcgcatcgg | tgggaaaaac | gccctgctgc | tggctggcac | tattatgtct | 900 |
| gtacgtatta | ttggctcatc | gttcgccacc | tcagcgctgg | aagtggttat | tctgaaaacg | 960 |
| ctgcatatgt | ttgaagtacc | gttcctgctg | gtgggctgct | taaatatat | taccagccag | 1020 |
| tttgaagtgc | gtttttcagc | gacgatttat | ctggtctgtt | tctgcttctt | taagcaactg | 1080 |
| gcgatgattt | ttatgtctgt | actggcgggc | aatatgtatg | aaagcatcgg | tttccagggc | 1140 |
| gcttatctgg | tgctgggtct | ggtggcgctg | gcttcacct | taatttccgt | gttcacgctt | 1200 |
| agcggccccg | gcccgcttttc | cctgctgcgt | cgtcaggtga | atgaagtcgc | tgataaaaac | 1260 |
| tggaggcgtc | atagggggatc | ccgtcgtttt | acaacgtcgt | gactgggaaa | accctggcgt | 1320 |
| tacccaactt | aatcgccttg | cagcacatcc | ccctttcgcc | agctggcgta | atagcgaaga | 1380 |
| ggcccgcacc | gatcgccctt | cccaacagtt | gcgcagcctg | aatggcgaat | ggcgctttgc | 1440 |
| ctggtttccg | gcaccagaag | cggtgccgga | aagctggctg | gagtgcgatc | ttcctgaggc | 1500 |
| cgatactgtc | gtcgtcccct | caaactggca | gatgcacggt | tacgatgcgc | ccatctacac | 1560 |
| caacgtgacc | tatcccatta | cggtcaatcc | gccgtttgtt | cccacggaga | atccgacggg | 1620 |
| ttgttactcg | ctcacattta | atgttgatga | aagctggcta | caggaaggcc | agacgcgaat | 1680 |
| tattttttgat | ggcgttaact | cggcgtttca | tctgtggtgc | aacgggcgct | gggtcggtta | 1740 |
| cggccaggac | agtcgtttgc | cgtctgaatt | tgacctgagc | gcatttttac | gcgcggaga | 1800 |
| aaaccgcctc | gcggtgatgg | tgctgcgctg | gagtgacggc | agttatctgg | aagatcagga | 1860 |
| tatgtggcgg | atgagcggca | ttttccgtga | cgtctcgttg | ctgcataaac | cgactacaca | 1920 |
| aatcagcgat | ttccatgttg | ccactcgctt | taatgatgat | ttcagccgcg | ctgtactgga | 1980 |
| ggctgaagtt | cagatgtgcg | gcgagttgcg | tgactaccta | cgggtaacag | tttcttttatg | 2040 |

```
gcagggtgaa acgcaggtcg ccagcggcac cgcgcctttc ggcggtgaaa ttatcgatga    2100
gcgtggtggt tatgccgatc gcgtcacact acgtctgaac gtcgaaaacc cgaaactgtg    2160
gagcgccgaa atcccgaatc tctatcgtgc ggtggttgaa ctgcacaccg ccgacggcac    2220
gctgattgaa gcagaagcct gcgatgtcgg tttccgcgag gtgcggattg aaaatggtct    2280
gctgctgctg aacggcaagc cgttgctgat tcgaggcgtt aaccgtcacg agcatcatcc    2340
tctgcatggt caggtcatgg atgagcagac gatggtgcag atatcctgc tgatgaagca     2400
gaacaacttt aacgccgtgc gctgttcgca ttatccgaac catccgctgt ggtacacgct    2460
gtgcgaccgc tacggcctgt atgtggtgga tgaagccaat attgaaaccc acggcatggt    2520
gccaatgaat cgtctgaccg atgatccgcg ctggctaccg gcgatgagcg aacgcgtaac    2580
gcgaatggtg cagcgcgatc gtaatcaccc gagtgtgatc atctggtcgc tggggaatga    2640
atcaggccac ggcgctaatc acgacgcgct gtatcgctgg atcaaatctg tcgatccttc    2700
ccgcccggtg cagtatgaag gcggcggagc cgacaccacg ccaccgata ttatttgccc     2760
gatgtacgcg cgcgtggatg aagaccagcc cttcccggct gtgccgaaat ggtccatcaa    2820
aaaatggctt tcgctacctg gagagacgcg cccgctgatc cttgtcgaat acgcccacgc    2880
gatgggtaac agtcttggcg gtttcgctaa atactggcag gcgtttcgtc agtatccccg    2940
tttacagggc ggcttcgtct gggactgggt ggatcagtcg ctgattaaat atgatgaaaa    3000
cggcaacccg tggtcggctt acggcggtga ttttggcgat acgccgaacg atcgccagtt    3060
ctgtatgaac ggtctggtct ttgccgaccg cacgccgcat ccagcgctga cggaagcaaa    3120
acaccagcag cagttttcc agttccgttt atccgggcaa accatcgaag tgaccagcga     3180
ataccgtttc cgtcatagcg ataacgagct cctgcactgg atggtggcgc tggatggtaa    3240
gccgctggca agcggtgaag tgcctctgga tgtcgctcca caaggtaaac agttgattga    3300
actgcctgaa ctaccgcagc cggagagcgc cgggcaactc tggctcacag tacgcgtagt    3360
gcaaccgaac gcgaccgcat ggtcagaagc cgggcacatc agcgcctggc agcagtggcg    3420
tctggcggaa aacctcagtg tgacgctccc cgccgcgtcc cacgccatcc cgcatctgac    3480
caccagcgaa atggatttt gcatcgagct gggtaataag cgttggcaat taaccgcca     3540
gtcaggctt ctttcacaga tgtggattgg cgataaaaaa caactgctga cgccgctgcg     3600
cgatcagttc acccgtgcac cgctggataa cgacattggc gtaagtgaag cgacccgcat    3660
tgaccctaac gcctgggtcg aacgctggaa ggcggcgggc cattaccagg ccgaagcagc    3720
gttgttgcag tgcacggcag atacacttgc tgatgcggtg ctgattacga ccgctcacgc    3780
gtggcagcat caggggaaaa ccttatttat cagccggaaa acctaccgga ttgatggtag    3840
tggtcaaatg gcgattaccg ttgatgttga agtggcgagc gatacaccgc atccggcgcg    3900
gattggcctg aactgccagc tggcgcaggt agcagagcgg gtaaactggc tcggattagg    3960
gccgcaagaa aactatcccg accgccttac tgccgcctgt tttgaccgct gggatctgcc    4020
attgtcagac atgtataccc cgtacgtctt cccgagcgaa aacggtctgc gctgcgggac    4080
gcgcgaattg aattatggcc cacaccagtg gcgcggcgac ttccagttca acatcagccg    4140
ctacagtcaa cagcaactga tggaaaccag ccatcgccat ctgctgcacg cggaagaagg    4200
cacatggctg aatatcgacg gtttccatat ggggattggt ggcgacgact cctggagccc    4260
gtcagtatcg gcggaattcc agctgagcgc cggtcgctac cattaccagt ggtctggtg     4320
tcaaaaataa gctggtttga agggtattgg tcggtcagtt tcacctgatt tacgtaaaaa    4380
```
cccgcttcgg cgggtttttg cttttggagg ggcagaaaga tgaatgactg tc    4432

<210> SEQ ID NO 3
<211> LENGTH: 2093
<212> TYPE: DNA
<213> ORGANISM: Artificial sequence
<220> FEATURE:
<223> OTHER INFORMATION: Genetic constructs detecting expressed lactose
      transporters <400> SEQUENCE: 3

```
atgtactatt taaaaaacac aaacttttgg atgttcggtt tattcttttt cttttacttt      60
tttatcatgg gagcctactt cccgtttttc ccgatttggc tacatgacat caaccatatc     120
agcaaaagtg atacgggtat tattttgcc gctatttctc tgttctcgct attattccaa      180
ccgctgtttg gtctgctttc tgacaaactc gggctgcgca aatacctgct gtggattatt     240
accggcatgt tagtgatgtt tgcgccgttc tttatttta tcttcgggcc actgttacaa      300
tacaacattt tagtaggatc gattgttggt ggtatttatc taggcttttg ttttaacgcc     360
ggtgcgccag cagtagaggc atttattgag aaagtcagcc gtcgcagtaa tttcgaattt     420
ggtcgcgcgc ggatgtttgg ctgtgttggc tgggcgctgt gtgcctcgat tgtcggcatc     480
atgttcacca tcaataatca gtttgttttc tggctgggct ctggctgtgc actcatcctc     540
gccgttttac tcttttttcgc caaaacggat gcgccctctt ctgccacggt tgccaatgcg    600
gtaggtgcca accattcggc atttagcctt aagctggcac tggaactgtt cagacagcca    660
aaactgtggt ttttgtcact gtatgttatt ggcgtttcct gcacctacga tgtttttgac    720
caacagtttg ctaatttctt tacttcgttc tttgctaccg gtgaacaggg tacgcgggta    780
tttggctacg taacgacaat gggcgaatta cttaacgcct cgattatgtt ctttgcgcca    840
ctgatcatta atcgcatcgg tgggaaaaac gccctgctgc tggctggcac tattatgtct    900
gtacgtatta ttggctcatc gttcgccacc tcagcgctgg aagtggttat tctgaaaacg    960
ctgcatatgt ttgaagtacc gttcctgctg gtgggctgct ttaaatatat taccagccag   1020
tttgaagtgc gtttttcagc gacgattat ctggtctgtt tctgcttctt taagcaactg    1080
gcgatgattt ttatgtctgt actggcgggc aatatgtatg aaagcatcgg tttccagggc   1140
gcttatctgg tgctgggtct ggtggcgctg gcttcacct taatttccgt gttcacgctt    1200
agcggccccg gccgctttc cctgctgcgt cgtcaggtga tgaagtcgc tcatcatcac    1260
caccatcatt aggatggtgg tgatgataat ggagaaaaaa atcactggat ataccaccgt    1320
tgatatatcc caatggcatc gtaaagaaca ttttgaggca tttcagtcag ttgctcaatg   1380
tacctataac cagaccgttc agctggatat tacggccttt ttaaagaccg taagaaaaa    1440
taagcacaag ttttatccgg cctttattca cattcttgcc cgcctgatga atgctcatcc   1500
ggagttccgt atggcaatga agacggtga gctggtgata tgggatagtg ttcacccttg    1560
ttacaccgtt ttccatgagc aaactgaaac gttttcatcg ctctggagtg aataccacga   1620
cgatttccgg cagtttctac acatatattc gcaagatgtg gcgtgttacg gtgaaaacct   1680
ggcctatttc cctaaagggt ttattgagaa tatgttttc gtcagcgcca atccctgggt    1740
gagtttcacc agttttgatt taaacgtggc caatatggac aacttcttcg ccccgttt    1800
cactatgggc aaatattata cgcaaggcga caaggtgctg atgccgctgg cgattcaggt    1860
tcatcatgcc gttgtgatg cttccatgt cggcagaatg cttaatgaat tacaacagta    1920
ctgcgatgag tggcagggcg gggcgtaagg atccaaaggt acctctagag tcgacctgca   1980
```

| | | |
|---|---|---|
| ggccttcgta aatctggcga gtggggaact gccagacatc aaataaaaca aaaggctcag | 2040 |
| tcggaagact gggccttttg ttttatctgt tgtttgtcgg tgaacactct ccc | 2093 |

<210> SEQ ID NO 4
<211> LENGTH: 2628
<212> TYPE: DNA
<213> ORGANISM: Artificial sequence
<220> FEATURE:
<223> OTHER INFORMATION: Genetic constructs detecting expressed lactose transporters

<400> SEQUENCE: 4

| | |
|---|---|
| atggcagatc attcgagcag ctcatcttcg ctgcagaaga agccaattaa tactatcgag | 60 |
| cataaagaca ctttgggcaa tgatcgggat cacaaggaag ccttgaacag tgataatgat | 120 |
| aatacttctg gattgaaaat caatggtgtc cccatcgagg acgctagaga ggaagtgctc | 180 |
| ttaccaggtt acttgtcgaa gcaatattac aaattgtacg gtttatgttt tataacatat | 240 |
| ctgtgtgcta ctatgcaagg ttatgatggg gctttaatgg gttctatcta taccgaagat | 300 |
| gcatatttga aatactacca tttggatatt aactcatcct ctggtactgg tctagtgttc | 360 |
| tctatttttca acgttggtca aatttgcggt gcattctttg ttcctcttat ggattggaaa | 420 |
| ggtagaaaac ctgctatttt aattgggtgt ctgggtgttg ttattggtgc tattatttcg | 480 |
| tctttaacaa caacaaagag tgcattaatt ggtggtagat ggtcgtggc cttttttcgct | 540 |
| acaatcgcta atgcagcagc tccaacatac tgtgcagaag tggctccagc tcacttaaga | 600 |
| ggtaaggttg caggtctttta taacacccct tggtctgtcg gttccattgt tgctgccttt | 660 |
| agcacttacg gtaccaacaa aaacttccct aactcctcca aggcttttaa gattccatta | 720 |
| tacttacaaa tgatgttccc aggtcttgtg tgtatatttg gttggttaat cccagaatct | 780 |
| ccaagatggt tggttggtgt tggccgtgag gaagaagctc gtgaattcat tatcaaatac | 840 |
| cacttaaatg gcgatagaac tcatccatta ttggatatgg agatggcaga ataatagaa | 900 |
| tctttccatg gtacagattt atcaaaccct ctagaaatgt tagatgtaag gagcttattc | 960 |
| agaacgagat cggataggta cagagcaatg ttggttatac ttatggcttg gttcggtcaa | 1020 |
| ttttccggta acaatgtgtg ttcgtactat ttgcctacca tgttgagaaa tgttggtatg | 1080 |
| aagagtgtct cattgaatgt gttaatgaat ggtgtttatt ccatcgtcac ttggatttct | 1140 |
| tcaatttgcg gtgcattctt tattgataag attggtagaa gggaaggttt ccttggttct | 1200 |
| atctcaggtg ctgcattagc attgacaggt ctatctatct gtactgctcg ttatgagaag | 1260 |
| actaagaaga gagtgcttc caatggtgca ttggtgttca tttatctctt tggtggtatc | 1320 |
| ttttcttttg ctttcactcc aatgcaatcc atgtactcaa cagaagtgtc tacaaacttg | 1380 |
| acgagatcta aggcccaact cctcaacttt gtggtttctg tgttgcccca atttgttaat | 1440 |
| caatttgcta ctccaaaggc aatgaagaat atcaaatatt ggttctatgt gttctacgtt | 1500 |
| ttcttcgata ttttcgaatt tattgttatc tacttcttct tcgttgaaac taagggtaga | 1560 |
| agcttagaag aattagaagt tgtctttgaa gctccaaacc caagaaaggc atccgttgat | 1620 |
| caagcattct tggctcaagt cagggcaact ttggtccaac gaaatgacgt tagagttgca | 1680 |
| aatgctcaaa atttgaaaga gcaagagcct ctaaagagcg atgctgatca tgtcgaaaag | 1740 |
| ctttcagagg cagaatctgt tagagcagaa ggaaggggtt cttttgttgac ttgtggagat | 1800 |
| gttgaggaga atccaggacc aggtaaggaa aagactcacg tttcgaggcc gcgattaaat | 1860 |
| tccaacatgg atgctgattt atatgggtat aaatgggctc gcgataatgt cgggcaatca | 1920 |

| | |
|---|---|
| ggtgcgacaa tctatcgatt gtatgggaag cccgatgcgc cagagttgtt tctgaaacat | 1980 |
| ggcaaaggta gcgttgccaa tgatgttaca gatgagatgg tcagactaaa ctggctgacg | 2040 |
| gaatttatgc ctcttccgac catcaagcat tttatccgta ctcctgatga tgcatggtta | 2100 |
| ctcaccactg cgatccccgg caaaacagca ttccaggtat tagaagaata tcctgattca | 2160 |
| ggtgaaaata ttgttgatgc gctggcagtg ttcctgcgcc ggttgcattc gattcctgtt | 2220 |
| tgtaattgtc cttttaacag cgatcgcgta tttcgtctcg ctcaggcgca atcacgaatg | 2280 |
| aataacggtt tggttgatgc gagtgatttt gatgacgagc gtaatggctg gcctgttgaa | 2340 |
| caagtctgga agaaaatgca taagcttttg ccattctcac cggattcagt cgtcactcat | 2400 |
| ggtgatttct cacttgataa ccttattttt gacgagggga aattaatagg ttgtattgat | 2460 |
| gttggacgag tcggaatcgc agaccgatac caggatcttg ccatcctatg gaactgcctc | 2520 |
| ggtgagtttt ctccttcatt acagaaacgg cttttcaaa atatggtat tgataatcct | 2580 |
| gatatgaata aattgcagtt tcatttgatg ctcgatgagt ttttctaa | 2628 |

<210> SEQ ID NO 5
<211> LENGTH: 1457
<212> TYPE: DNA
<213> ORGANISM: Artificial sequence
<220> FEATURE:
<223> OTHER INFORMATION: Genetic constructs detecting expressed lactose transporters

<400> SEQUENCE: 5

| | |
|---|---|
| atgtactatt taaaaaacac aaacttttgg atgttcggtt tattcttttt cttttacttt | 60 |
| tttatcatgg gagcctactt cccgttttc ccgatttggc tacatgacat caaccatatc | 120 |
| agcaaaagtg atacgggtat tattttttgcc gctatttctc tgttctcgct attattccaa | 180 |
| ccgctgtttg gtctgctttc tgacaaactc gggctgcgca atacctgct gtggattatt | 240 |
| accggcatgt tagtgatgtt tgcgccgttc tttatttttta tcttcgggcc actgttacaa | 300 |
| tacaacattt tagtaggatc gattgttggt ggtatttatc taggcttttg ttttaacgcc | 360 |
| ggtgcgccag cagtagaggc atttattgag aaagtcagcc gtcgcagtaa tttcgaattt | 420 |
| ggtcgcgcgc ggatgtttgg ctgtgttggc tgggcgctgt gtgcctcgat tgtcggcatc | 480 |
| atgttcacca tcaataatca gtttgttttc tggctgggct ctggctgtgc actcatcctc | 540 |
| gccgttttac tcttttttcgc caaaacggat gcgccctctt ctgccacggt tgccaatgcg | 600 |
| gtaggtgcca accattcggc atttagcctt aagctggcac tggaactgtt cagacagcca | 660 |
| aaactgtggt tttgtcact gtatgttatt ggcgtttcct gcacctacga tgttttttgac | 720 |
| caacagtttg ctaatttctt tacttcgttc tttgctaccg gtgaacaggg tacgcgggta | 780 |
| tttggctacg taacgacaat gggcgaatta cttaacgcct cgattatgtt ctttgcgcca | 840 |
| ctgatcatta atcgcatcgg tgggaaaaac gccctgctgc tggctggcac tattatgtct | 900 |
| gtacgtatta ttggctcatc gttcgccacc tcagcgctgg aagtggttat tctgaaaacg | 960 |
| ctgcatatgt ttgaagtacc gttcctgctg gtgggctgct taaatatat taccagccag | 1020 |
| tttgaagtgc gtttttcagc gacgatttat ctggtctgtt tctgcttctt taagcaactg | 1080 |
| gcgatgattt ttatgtctgt actggcgggc aatatgtatg aaagcatcgg tttccagggc | 1140 |
| gcttatctgg tgctgggtct ggtggcgctg gcttcacct taatttccgt gttcacgctt | 1200 |
| agcggccccg gccgctttc cctgctgcgt cgtcaggtga atgaagtcgc tgataactct | 1260 |
| acgacaacct cttcacagcc aatctcgccc ggatagctca gtcggtagag cagcggccgg | 1320 |

| | |
|---|---:|
| acgcaactga atgaaatggt gaaggacggg tccaggtgtg gctgcttcgg cagtgcagct | 1380 |
| tgttgagtag agtgtgagct ccgtaactag tcgcgtccgg ccgcgggtcc agggttcaag | 1440 |
| tccctgttcg ggcgcca | 1457 |

<210> SEQ ID NO 6
<211> LENGTH: 3638
<212> TYPE: DNA
<213> ORGANISM: Artificial sequence
<220> FEATURE:
<223> OTHER INFORMATION: Vector

<400> SEQUENCE: 6

| | |
|---|---:|
| cgcgttggat gcaggcatgc aagcttggct gttttggcgg atgagagaag attttcagcc | 60 |
| tgatacagat taaatcagaa cgcagaagcg gtctgataaa acagaatttg cctggcggca | 120 |
| gtagcgcggt ggtcccacct gacccccatgc cgaactcaga agtgaaacgc cgtagcgccg | 180 |
| atggtagtgt ggggtctccc catgcgagag tagggaactg ccaggcatca aataaaacga | 240 |
| aaggctcagt cgaaagactg ggcctttcgt tttatctgtt gtttgtcggt gaacgctctc | 300 |
| ctgagtagga caaatccgcc gggagcggat ttgaacgttg cgaagcaacg gcccggaggg | 360 |
| tggcgggcag gacgcccgcc ataaactgcc aggcatcaaa ttaagcagaa ggccatcctg | 420 |
| acggatggcc tttttgcgtt tctacaaact cttttgttt attttctaa atacattcaa | 480 |
| atatgtatcc gctcatgaga caataaccct gataaatgct tcaataatat tgaaaaagga | 540 |
| agagtatgag tattcaacat ttccgtgtcg cccttattcc cttttttgcg cattttgcc | 600 |
| ttcctgtttt tgctcaccca gaaacgctgg tgaaagtaaa agatgctgaa gatcagttgg | 660 |
| gtgcacgagt gggttacatc gaactggatc tcaacagcgg taagatcctt gagagttttc | 720 |
| gccccgaaga acgttttcca atgatgagca cttttaaagt tctgctatgt ggcgcggtat | 780 |
| tatcccgtgt tgacgccggg caagagcaac tcggtcgccg catacactat tctcagaatg | 840 |
| acttggttga gtactcacca gtcacagaaa agcatcttac ggatggcatg acagtaagag | 900 |
| aattatgcag tgctgccata accatgagtg ataacactgc ggccaactta cttctgacaa | 960 |
| cgatcggagg accgaaggag ctaaccgctt ttttgcacaa catgggggat catgtaactc | 1020 |
| gccttgatcg ttgggaaccg gagctgaatg aagccatacc aaacgacgag cgtgacacca | 1080 |
| cgatgcctac agcaatggca acaacgttgc gcaaactatt aactggcgaa ctacttactc | 1140 |
| tagcttcccg gcaacaatta atagactgga tggaggcgga taaagttgca ggaccacttc | 1200 |
| tgcgctcggc ccttccggct ggctggttta ttgctgataa atctggagcc ggtgagcgtg | 1260 |
| ggtctcgcgg tatcattgca gcactggggc cagatggtaa gccctcccgt atcgtagtta | 1320 |
| tctacacgac ggggagtcag gcaactatgg atgaacgaaa tagacagatc gctgagatag | 1380 |
| gtgcctcact gattaagcat tggtaactgt cagaccaagt ttactcatat atactttaga | 1440 |
| ttgatttaaa acttcatttt taatttaaaa ggatctaggt gaagatcctt tttgataatc | 1500 |
| tcatgaccaa aatcccttaa cgtgagtttt cgttccactg agcgtcagac cccgtagaaa | 1560 |
| agatcaaagg atcttcttga gatccttttt ttctgcgcgt aatctgctgc ttgcaaacaa | 1620 |
| aaaaaccacc gctaccagcg gtggtttgtt tgccggatca agagctacca actctttttc | 1680 |
| cgaaggtaac tggcttcagc agagcgcaga taccaaatac tgtccttcta gtgtagccgt | 1740 |
| agttaggcca ccacttcaag aactctgtag caccgcctac atacctcgct ctgctaatcc | 1800 |
| tgttaccagt ggctgctgcc agtggcgata agtcgtgtct taccgggttg gactcaagac | 1860 |
| gatagttacc ggataaggcg cagcggtcgg gctgaacggg gggttcgtgc acacagccca | 1920 |

```
gcttggagcg aacgacctac accgaactga gatacctaca gcgtgagcta tgagaaagcg   1980
ccacgcttcc cgaagggaga aaggcggaca ggtatccggt aagcggcagg gtcggaacag   2040
gagagcgcac gagggagctt ccagggggaa acgcctggta tctttatagt cctgtcgggt   2100
ttcgccacct ctgacttgag cgtcgatttt tgtgatgctc gtcagggggg cggagcctat   2160
ggaaaaacgc cagcaacgcg gcctttttac ggttcctggc cttttgctgg ccttttgctc   2220
acatgttctt tcctgcgtta tcccctgatt ctgtggataa ccgtattacc gcctttgagt   2280
gagctgatac cgctcgccgc agccgaacga ccgagcgcag cgagtcagtg agcgaggaag   2340
cggaagagcg cctgatgcgg tattttctcc ttacgcatct gtgcggtatt tcacaccgca   2400
tatggtgcac tctcagtaca atctgctctg atgccgcata gttaagccag tatacactcc   2460
gctatcgcta cgtgactggg tcatggctgc gccccgacac cgccaacac ccgctgacgc    2520 gccctgacgg gcttgtctgc tcccggcatc cgcttacaga caagctgtga ccgtctccgg   2580
gagagctcga tatcccgggc ggccgccttc attctataag tttcttgaca tcttggccgg   2640
catatggtat aatagggaaa tttccatggc ggccgctcta aagaagcttg ggatccgtc    2700 gacctcgaat tcggaggaaa caaagatggc ctttaaagtt gttcagattt gtggtggtct   2760
gggcaatcag atgtttcagt atgcatttgc aaaaagcctg cagaaacata gcaatacacc   2820
ggttctgctg gatattacca gctttgattg gagcaatcgt aaaatgcagc tggaactgtt   2880
tccgattgat ctgccgtatg caagcgaaaa agaaattgca attgccaaaa tgcagcatct   2940
gccgaaactg gttcgtaatg ttctgaaatg catgggtttt gatcgtgtga gccaagaaat   3000
cgtgtttgaa tatgaaccga actgctgaa accagccgt ctgacctatt tttatggcta     3060
ttttcaggat ccgcgttatt ttgatgcaat tagtccgctg atcaaacaga cctttaccct   3120
gcctccgcct ccggaaaatg gtaataacaa aaaaaaagaa gaagagtatc atcgtaaact   3180
ggcactgatt ctggcagcaa aaaatagcgt gtttgtgcat attcgtcgcg gtgattatgt   3240
tggtattggt tgtcagctgg gcatcgatta tcagaaaaaa gcactggaat acatggcaaa   3300
acgtgttccg aatatggaac tgtttgtgtt ttgcgaggac ctggaattta cccagaatct   3360
ggatctgggc tatccgttta tggatatgac cacccgtgat aaagaggaag aggcatattg   3420
ggatatgctg ctgatgcaga gctgtaaaca tggtattatt gccaacagca cctatagttg   3480
gtgggcagca tatctgatta ataacccgga aaaatcatt attggtccga acattggct    3540 gtttggccat gaaaacatcc tgtgtaaaga atgggtgaaa atcgaaagcc actttgaagt   3600
gaaaagccag aaatataatg cctaataaga gctcccaa                           3638
```

<210> SEQ ID NO 7
<211> LENGTH: 2660
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 7

```
tattttagat tcctgacttc aactcaagac gcacagatat tataacatct gcagaatagg     60
catttgcaag aattactcgt gagtaaggaa agagtgagga actatcgcat acctgcattt    120
aaagatgccg atttgggcgc gaatccttta ttttggcttc accctcatac tattatcagg    180
gccagaaaaa ggaagtgttt ccctccttct tgaattgatg ttaccctcat aaagcacgtg    240
gcctcttatc gagaaagaaa ttaccgtcgc tcgtgatttg tttgcaaaaa gaacaaaact    300
```

```
gaaaaaaccc agacacgctc gacttcctct cttcctattg attgcagctt ccaatttcgt    360
cacacaacaa ggtcctagcg acggctcaca ggttttgtaa caagcaatcg aaggttctgg    420
aatggcggga aagggtttag taccacatgc tatgatgccc actgtgatca ccagagcaaa    480
gttcgttcga tcgtactgtt actctctctc tttcaaacag aattgtccga atcgtgtgac    540
aacaacagcc tgttctcaca cactcttttc ttctaaccaa gggggtggtt tagtttagta    600
gaacctcgtg aaacttacat ttacatatat ataaacttgc ataaattggt caatgcaaga    660
aatacatatt tggtctttc taattcgtag tttttcaag ttcttagatg ctttctttt       720 ctctttttt acagatcatc aaggaagtaa ttatctactt tttacaacaa atataaaaaa     780
aatggcagat cattcgagca gctcatcttc gctgcagaag aagccaatta atactatcga    840
gcataaagac actttgggca ttgatctgga tcacaaggaa gccttgaaca gtgataatga    900
taatacttct ggattgaaaa tcaatggtgt ccccatcgag gacgctagag aggaagtgct    960
cttaccaggt tacttgtcga agcaatatta caaattgtac agtttatgtt ttgtaacata    1020
tctgtgtgct actatgcaag gttatgatgg ggctttaatg ggttctatct ataccgaaaa    1080
tgcatatttg gaatactacc atttggatat taactcatcc agtggtactg gtctagtgtt    1140 ctctatttc aacgttggtc aaatttgcgg tgcattcttt gttcctctta tggattggaa     1200
aggtagaaaa cctgctattt taattgggtg tctgggtgtt gttattggtg gtattattac    1260
gtctgtaaca acaacaaaga gtgcattaat tggtggtaga tggttcatgg ccttttcgc    1320 tacaatcgct aattcagcag ctccagcata ctgtgcagaa gtggctccag ctcacttaag    1380
aggtaaggtt gcaggtcttt ataacaccct ttggtctgtc ggttccattg ttgctgcctt    1440
taccactctc ggtaccaaca aaaacttccc taactcctcc aaggctttta agattccatt    1500
atacttacaa atgatgttcc caggtcttgt gtgtatattt ggttggttaa tcccagaatc    1560
tccaagatgg ttggttggtg ttggccgtga ggaagaagct cgtgaattca ttatcaaata    1620
ccacttaaat ggcgatagaa ctcatccatt attggatatg gagatggcag aaataataga    1680
atctttccat ggtacagatt tatcaaaccc tctagaaatg ttagatgtaa ggatcttatt    1740
cagaacgaga tcggataggt acagagcaat gttggttata cttatggctt ggttcggtca    1800
attttccggt aacaatgtgt gttcgtacta tttgcctacc atgttgagaa atgttggtat    1860
gaagagtgtc tcattgaatg tgttaatgaa tggtgtttat tccatcgtct cttggatttc    1920
ttcaatttgc ggtgcattct ttattgataa gattggtaga agggaaggtt tccttggttc    1980
tatctcaggt gctgcattag cattgacagg tctatctatc tgtactgctc gttatgagaa    2040
gactaagaag aagagtgctt ccaatggtgc attggtgttc atttatctct ttggtgttat    2100
cttttctttt gctttcactc caatgcaatc catgtactca acagaagtgt ctacaaactt    2160
gacgagatct aaggcccaac tcctcaacgg tgtggtttct ggtgttgccc aatttgttaa    2220
tcaatttgct actccaaagg caatgaagaa tatcaaatat tggttctatg tgttctacgt    2280
tttcttcgat attttcgaat ttattgttat ctacttcttc ttcgttgaaa ctaagggtag    2340
aagcttagaa gaattagaag ctgtctttga agctccaaac ccaagaaagg catccgttga    2400
tcaagcattc ttggctcaag ccagggcaac tttggtccaa caaaatgacg ttagagttgc    2460
aaatgctcaa aatttgaaag agcaagagct tctaaagagc gatgctgatc atgtcgaaaa    2520
gctttcagag gcagaatctg tttaaagagt cttttgtaac gacccgtct ccaccaactt    2580 ggtatgcttg aaatctcaag gccattacac attcagttat gtgaacgaaa ggtctttatt    2640
```
taacgtagca taaactaaat					2660

<210> SEQ ID NO 8
<211> LENGTH: 2554
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 8

```
aggaataagg atacttcaag actagattcc ccctgcatt cccatcagaa ccgtaaacct      60
tggcgctttc cttgggaagt attcaagaag tgccttgtcc ggtttctgtg gctcacaaac    120
cagcgcgccc gatatggctt tcttttcact tatgaatgta ccagtacggg acaattagaa    180
cgctcctgta acaatctctt tgcaaatgtg gggttacatt ctaaccatgt cacactgctg    240
acgaaattca agtaaaaaaa aaatgggacc acgtcttgag aacgatagat tttctttatt    300
ttacattgaa cagtcgttgt ctcagcgcgc tttatgtttt cattcatact tcatattata    360
aaataacaaa agaagaattt catattcacg cccaagaaat caggctgctt ccaaatgca     420
attgacactt cattagccat cacacaaaac tctttcttgc tggagcttct tttaaaaaag    480
acctcagtac accaaacacg ttacccgacc tcgttatttt acgacaacta tgataaaatt    540
ctgaagaaaa aataaaaaaa ttttcatact tcttgctttt atttaaacca ttgaatgatt    600
tcttttgaac aaaactacct gtttcaccaa aggaaataga agaaaaaat caattagaag     660
aaaacaaaaa acaaaatggc agatcattcg agcagctcat cttcgctgca gaagaagcca    720
attaatacta tcgagcataa agacactttg ggcattgatc tggatcacaa ggaagccttg    780
aacagtgata atgataatac ttctggattg aaaatcaatg gtgtccccat cgaggacgct    840
agagaggaag tgctcttacc aggttacttg tcgaagcaat attacaaatt gtacagttta    900
tgttttgtaa catatctgtg tgctactatg caaggttatg atggggcttt aatgggttct    960
atctataccg aaaatgcata tttggaatac taccatttgg atattaactc atccagtggt   1020
actggtctag tgttctctat tttcaacgtt ggtcaaattt gcggtgcatt ctttgttcct   1080
cttatggatt ggaaaggtag aaaacctgct attttaattg ggtgtctggg tgttgttatt   1140
ggtggtatta ttacgtctgt aacaacaaca aagagtgcat taattggtgg tagatggttc   1200
atggccttt tcgctacaat cgctaattca gcagctccag catactgtgc agaagtggct   1260
ccagctcact taagaggtaa ggttgcaggt ctttataaca ccctttggtc tgtcggttcc   1320
attgttgctg cctttaccac tctcggtacc aacaaaaact tccctaactc ctccaaggct   1380
tttaagattc cattatactt acaaatgatg ttcccaggtc ttgtgtgtat atttggttgg   1440
ttaatcccag aatctccaag atggttggtt ggtgttggcc gtgaggaaga agctcgtgaa   1500
ttcattatca ataccactt aaatggcgat agaactcatc cattattgga tatggagatg   1560
gcagaaataa tagaatcttt ccatggtaca gatttatcaa accctctaga atgttagat    1620
gtaaggatct tattcagaac gagatcggat aggtacagag caatgttggt tatacttatg   1680
gcttggttcg gtcaattttc cggtaacaat gtgtgttcgt actatttgcc taccatgttg   1740
agaaatgttg gtatgaagag tgtctcattg aatgtgttaa tgaatggtgt ttattccatc   1800
gtctcttgga tttcttcaat ttgcggtgca ttctttattg ataagattgg tagaagggaa   1860
ggtttccttg gttctatctc aggtgctgca ttagcattga caggtctatc tatctgtact   1920
gctcgttatg agaagactaa gaagaagagt gcttccaatg gtgcattggt gttcattat    1980
```

```
ctctttggtg ttatctttc ttttgctttc actccaatgc aatccatgta ctcaacagaa    2040
gtgtctacaa acttgacgag atctaaggcc caactcctca acggtgtggt ttctggtgtt    2100
gcccaatttg ttaatcaatt tgctactcca aaggcaatga agaatatcaa atattggttc    2160
tatgtgttct acgttttctt cgatattttc gaatttattg ttatctactt cttcttcgtt    2220
gaaactaagg gtagaagctt agaagaatta gaagctgtct ttgaagctcc aaacccaaga    2280
aaggcatccg ttgatcaagc attcttggct caagccaggg caactttggt ccaacaaaat    2340
gacgttagag ttgcaaatgc tcaaaatttg aaagagcaag agcttctaaa gagcgatgct    2400
gatcatgtcg aaaagctttc agaggcagaa tctgtttaaa gagtcttttg taacgacccc    2460
gtctccacca acttggtatg cttgaaatct caaggccatt acacattcag ttatgtgaac    2520
gaaaggtctt tatttaacgt agcataaact aaat                               2554
```

<210> SEQ ID NO 9
<211> LENGTH: 4141
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 9

```
tattttagat tcctgacttc aactcaagac gcacagatat tataacatct gcagaatagg     60
catttgcaag aattactcgt gagtaaggaa agagtgagga actatcgcat acctgcattt    120
aaagatgccg atttgggcgc gaatccttta ttttggcttc accctcatac tattatcagg    180
gccagaaaaa ggaagtgttt ccctccttct tgaattgatg ttaccctcat aaagcacgtg    240
gcctcttatc gagaaagaaa ttaccgtcgc tcgtgatttg tttgcaaaaa gaacaaaact    300
gaaaaaaccc agacacgctc gacttcctct cttcctattg attgcagctt ccaatttcgt    360
cacacaacaa ggtcctagcg acggctcaca ggttttgtaa caagcaatcg aaggttctgg    420
aatggcggga aagggtttag taccacatgc tatgatgccc actgtgatca ccagagcaaa    480
gttcgttcga tcgtactgtt actctctctc tttcaaacag aattgtccga atcgtgtgac    540
aacaacagcc tgttctcaca cactcttttc ttctaaccaa gggggtggtt tagtttagta    600
gaacctcgtg aaacttacat ttacatatat ataaacttgc ataaattggt caatgcaaga    660
aatacatatt tggtctttc taattcgtag tttttttcaag ttcttagatg ctttcttttt    720 ctctttttt acagatcatc aaggaagtaa ttatctactt tttacaacaa atataaaaaa    780
aatgtcttgc cttattcctg agaatttaag gaaccccaaa aaggttcacg aaaatagatt    840
gcctactagg gcttactact atgatcagga tattttcgaa tctctcaatg ggccttgggc    900
ttttgcgttt tttgatgcac ctcttgacgc tccggatgct aagaatttag actgggaaac    960
ggcaaagaaa tggagcacca tttctgtgcc atcccattgg gaacttcagg aagactggaa   1020
gtacggtaaa ccaatttaca cgaacgtaca gtacccatc ccaatcgaca tcccaaatcc   1080
tcccactgta atcctactg gtgtttatgc tagaactttt gaattagatt cgaaatcgat   1140
tgagtcgttc gagcacagat tgagatttga gggtgtggac aattgttacg agctttatgt   1200
taatggtcaa tatgtgggtt tcaataaggg gtcccgtaac ggggctgaat tgatatcca   1260 aaagtacgtt tctgagggcg aaaacttagt ggtcgtcaag gttttcaagt ggtccgattc   1320
cacttatatc gaggaccaag atcaatggtg gctctctggt atttacagag acgtttcttt   1380
actaaaattg cctaagaagg cccatattga agacgttagg gtcactacaa cttttgtgga   1440
```

```
ctctcagtat caggatgcag agctttctgt gaaagttgat gtccagggtt cttcttatga    1500
tcacatcaat ttcacacttt acgaacctga agatggatct aaagtttacg atgcaagctc    1560
tttgttgaac gaggagaatg ggaacacgac tttttcaact aaagaattta tttccttctc    1620
caccaaaaag aacgaagaaa cagctttcaa gatcaacgtc aaggcccag aacattggac     1680 cgcagaaaat cctactttgt acaagtacca gttggattta attggatctg atggcagtgt    1740
gattcaatct attaagcacc atgttggttt cagacaagtg gagttgaagg acggtaacat    1800
tactgttaat ggcaaagaca ttctctttag aggtgtcaac agacatgatc accatccaag    1860
gttcggtaga gctgtgccat tagattttgt tgttagggac ttgattctaa tgaagaagtt    1920
taacatcaat gctgttcgta actcgcatta tccaaaccat cctaaggtgt atgacctctt    1980
cgataagctg ggcttctggg tcattgacga ggcagatctt gaaactcatg gtgttcaaga    2040
gccatttaat cgtcatacga acttggaggc tgaatatcca gatactaaaa ataaactcta    2100
cgatgttaat gcccattact tatcagataa tccagagtac gaggtcgcgt acttagacag    2160
agcttcccaa cttgtcctaa gagatgtcaa tcatccttcg attattatct ggtccttggg    2220
taacgaagct tgttatggca gaaaccacaa agccatgtac aagttaatta acaattgga    2280 tcctaccaga cttgtgcatt atgagggtga cttgaacgct ttgagtgcag atatctttag    2340
tttcatgtac ccaacatttg aaattatgga aggtggagg aagaaccaca ctgatgaaaa     2400
tggtaagttt gaaaagcctt tgatcttgtg tgagtacgc catgcaatgg gtaacggtcc     2460
tggctctttg aaagaatatc aagagttgtt ctacaaggag agttttacc aaggtggctt     2520 tatctgggaa tgggcaaatc acggtattga attcgaagat gttagtactg cagatggtaa    2580
gttgcataaa gcttatgctt atggtggtga ctttaaggaa gaggttcatg acggagtgtt    2640
catcatggat ggtttgtgta acagtgagca taatcctact ccgggccttg tagagtataa    2700
gaaggttatt gaacccgttc atattaaaat tgcgcacgga tctgtaacaa tcacaaataa    2760
gcacgacttc attacgacag accacttatt gtttatcgac aaggacacgg gaaagacaat    2820
cgacgttcca tctttaaagc cagaagaatc tgttactatt ccttctgata caacttatgt    2880
tgttgccgtg ttgaaagatg atgctggtgt tctaaaggca ggtcatgaaa ttgcctgggg    2940
ccaagctgaa cttccattga aggtaccga ttttgttaca gagacagcag aaaaagctgc     3000
gaagatcaac gacggtaaac gttatgtctc agttgaatcc agtggattgc attttatctt    3060
ggacaaattg ttgggtaaaa ttgaaagcct aaaggtcaag ggtaaggaaa tttccagcaa    3120
gtttgagggt tcttcaatca cttttctgga gacctccaacg aataatgatg aacctaggga   3180
ctttaagaac tggaagaagt acaatattga tttaatgaag caaaacatcc atggagtgag    3240
tgtcgaaaaa ggttctaatg gttctctagc tgtagtcacg gttaactctc gtatatcccc    3300
agttgtattt tactatgggt ttgagactgt tcagaagtac acgatctttg ctaacaaaat    3360
aaacttgaac acttctatga agcttactgg cgaatatcag cctcctgatt tcccaagagt    3420
tgggtacgaa ttctggctag gagatagtta tgaatcattt gaatggttag tcgcgggcc     3480 cggcgaatca tatccggata agaaggaatc tcaagattc ggtctttacg attccaaaga    3540
tgtagaggaa ttcgtatatg actatcctca agaaaatgga aatcatacag atacccactt    3600
tttgaacatc aaatttgaag gtgcaggaaa actatcgatc ttccaaaagg agaagccatt    3660
taacttcaag atttcagacg aatacggggt tgatgaagct gcccacgctt gtgacgttaa    3720
aagatacggc agacactatc taaggttgga ccatgcaatc catggtgttg gtagcgaagc    3780
atgcggacct gctgttctgg accagtacag attgaaagct caagatttca actttgagtt    3840
```

```
tgatctcgct tttgaataag ccggccattg aattgaattg aaatcgatag atcaattttt    3900 ttctttctc tttccccatc ctttacgcta aataatagt ttattttatt ttttgaatat     3960
tttttattta tatacgtata tatagactat tatttatctt ttaatgatta ttaagatttt    4020
tattaaaaaa aaattcgcac ctcttttaat gcctttatgc agttttttt tcccattcga     4080 tatttctatg ttcgggttca gcgtatttta agtttaataa ctcgaaaatt ctgcgtttcg    4140
a                                                                     4141

<210> SEQ ID NO 10
<211> LENGTH: 1187
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 10
ttaatctcag cagatcgtaa caacaaggct actctactgc ttacaatacc ccgttgtaca      60
tctaagtcgt atacaaatga tttatcccca cgcaaaatga cattgcaatt cgccagcaag    120
cacccaaggc ctttccgcca agtgcaccgt tgctagcctg ctatggttca gcgacgccac    180
aaggacgcct tattcgtatc catctatatt gtgtggagca agaaatcac cgcgttctag     240 catggattct gacttagagg cgttcagcca taatccagcg gatggtagct tcgcggcaat    300
gcctgatcag acagccgcaa aaaccaatta tccgaatgaa ctgttcctct cgtactaagt    360
tcaattacta ttgcggtaac attcatcagt agggtaaaac taacctgtct cacgacggtc    420
taaacccagc tcacgttccc tattagtggg tgaacaatcc aacgcttacc gaattctgct    480
tcggtatgat aggaagagcc gacatcgaag aatcaaaaag caatgtcgct atgaacgctt    540
gactgccaca agccagttat ccctgtggta acttttctgg cacctctagc ctcaaattcc    600
gagggactaa aggatcgata ggccacactt tcatggtttg tattcacact gaaaatcaaa    660
atcaaggggg cttttaccct tttgttctac tggagatttc tgttctccat gagccccct     720 taggacatct gcgttatcgt ttaacagatg tgccgcccca gccaaactcc ccacctgaca    780
atgtcttcaa cccggatcag ccccgaatgg gaccttgaat gctagaacgt ggaaaatgaa    840
ttccagctcc gcttcattga ataagtaaag aaactataaa ggtagtggta tttcactggc    900
gccgaagctc ccacttattc tacaccctct atgtctcttc acaatgtcaa actagagtca    960
agctcaacag ggtcttcttt ccccgctgat tctgccaagc ccgttccctt ggctgtggtt   1020
tcgctagata gtagataggg acagtgggaa tctcgttaat ccattcatgc gcgtcactaa   1080
ttagatgacg aggcatttgg ctaccttaag agagtcatag ttactcccgc cgtttacccg   1140
cgcttggttg aatttcttca ctttgacatt cagagcactg ggcagaa                 1187

<210> SEQ ID NO 11
<211> LENGTH: 2010
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 11
agtagtccgc ctagcagagc aagccccacc aagcagtcca caagcacgcc cgctgcgtct     60
gaccaaggcc ctcactaccc gacccttaga gccaatcctt atcccgaagt tacggatcta    120
```

```
ttttgccgac ttcccttatc tacattattc tatcaactag aggctgttca ccttggagac      180
ctgctgcggt tatcagtacg acctggcatg aaaactattc cttcctgtgg attttcacgg      240
gccgtcacaa gcgcaccgga gccagcaaag gtgctggcct cttccagcca taagacccca      300
tctccggata aaccaattcc ggggtgataa gctgttaaga agaaaagata actcctccca      360
gggctcgcgc cgacgtctcc acattcagtt acgttaccgt gaagaatcca tatccaggtt      420
ccggaatctt aaccggattc cctttcgatg gtggcctgca taaaatcagg cctttgaaac      480
ggagcttccc catctcttag gatcgactaa cccacgtcca actgctgttg acgtggaacc      540
tttccccact tcagtcttca aagttctcat ttgaatattt gctactacca ccaagatctg      600
cactagaggc cgttcgaccc gaccttacgg tctaggcttc gtcactgacc tccacgcctg      660
cctactcgtc agggcatcat atcaaccctg acggtagagt ataggtaaca cgcttgagcg      720
ccatccattt tcagggctag ttcattcggc cggtgagttg ttacacactc cttagcggat      780
tccgacttcc atggccaccg tccggctgtc tagatgaact aacacctttt gtggtgtctg      840
atgagcgtgt attccggcac cttaactcta cgttcggttc atcccgcatc gccagttctg      900
cttaccaaaa atggcccact aaaagctctt cattcaaatg tccacgttca attaagtaac      960
aaggacttct tacatattta aagtttgaga ataggtcaag gtcatttcga ccccggaacc     1020
tctaatcatt cgctttacct cataaaactg atacgagctt ctgctatcct gagggaaact     1080
tcggcaggaa ccagctacta gatggttcga ttagtctttc gccctatac ccaaattcga     1140 cgatcgattt gcacgtcaga accgctacga gcctccacca gagtttcctc tggcttcacc     1200
ctattcaggc atagttcacc atctttcggg tcccaacagc tatgctctta ctcaaatcca     1260
tccgaagaca tcaggatcgg tcgattgtgc acctcttgcg aggccccaac ctacgttcac     1320
tttcattacg cgtatgggtt ttacacccaa acactcgcat agacgttaga ctccttggtc     1380
cgtgtttcaa gacgggcggc atataaccat tatgccagca tccttgactt acgtcgcagt     1440
cctcagtccc agctggcagt attcccacag gctataatac ttaccgaggc aagctacatt     1500
cctatggatt tatcctgcca ccaaaactga tgctggccca gtgaaatgcg agattcccct     1560
acccacaagg agcagagggc acaaaacacc atgtctgatc aaatgccctt ccctttcaac     1620
aatttcacgt acttttttcac tctctttttca aagttctttt catctttcca tcactgtact     1680
tgttcgctat cggtctctcg ccaatatttta gctttagatg gaatttacca cccacttaga     1740
gctgcattcc caaacaactc gactcttcga aggcacttta caaagaaccg cactcctcgc     1800
cacacgggat tctcaccctc tatgacgtcc tgttccaagg aacatagaca aggaacggcc     1860
ccaaagttgc cctctccaaa ttacaactcg ggcaccgaag gtaccagatt tcaaatttga     1920
gcttttgccg cttcactcgc cgttactaag gcaatcccgg ttggtttctt ttcctccgct     1980
tattgatatg cttaagttca gcgggtactc                                      2010
```

<210> SEQ ID NO 12
<211> LENGTH: 1558
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 12

```
cccgtcttac tgtcgggaat tcgcgttggc cgattcatta atggtataag gttcttgaca        60
tcttacaatc aatatggtat aataatttag ttagggccca agttcactta aaaaggagat       120
```

```
caacaatgaa agcttactgt cgggaattcg cgttggccaa ttcattaatg gtataaggtt      180
cttgacatct tacaatcaat atggtataat aatttagtta gggcccaagt tcacttaaaa      240
aggagatcaa caatgaaagc aattttcgta ctgaaacatc ttaatcatgc gtaggatttt      300
ttctatgtac tatttaaaaa acacaaactt tggatgttc ggtttattct tttcttta       360 cttttttatc atgggagcct acttcccgtt tttcccgatt tggctacatg acatcaacca      420
tatcagcaaa agtgatacgg gtattatttt tgccgctatt tctctgttct cgctattatt      480
ccaaccgctg tttggtctgc tttctgacaa actcgggctg cgcaaatacc tgctgtggat      540
tattaccggc atgttagtga tgtttgcgcc gttctttatt tttatcttcg ggccactgtt      600
acaatacaac attttagtag gatcgattgt tggtggtatt tatctaggct tttgttttaa      660
cgccggtgcg ccagcagtag aggcattat tgagaaagtc agccgtcgca gtaatttcga      720
atttggtcgc gcgcggatgt ttggctgtgt tggctgggcg ctgtgtgcct cgattgtcgg      780
catcatgttc accatcaata atcagtttgt tttctggctg ggctctggct gtgcactcat      840
cctcgccgtt ttactctttt tcgccaaaac ggatgcgccc tcttctgcca cggttgccaa      900
tgcggtaggt gccaaccatt cggcatttag ccttaagctg gcactggaac tgttcagaca      960
gccaaaactg tggttttgt cactgtatgt tattggcgtt tcctgcacct acgatgtttt     1020
tgaccaacag tttgctaatt tctttacttc gttctttgct accggtgaac agggtacgcg     1080
ggtatttggc tacgtaacga caatgggcga attacttaac gcctcgatta tgttcttgc      1140 gccactgatc attaatcgca tcggtgggaa aaacgccctg ctgctggctg cactattat      1200 gtctgtacgt attattggct catcgttcgc cacctcagcg ctggaagtgg ttattctgaa     1260
aacgctgcat atgtttgaag taccgttcct gctggtgggc tgctttaaat atattaccag     1320
ccagtttgaa gtgcgttttt cagcgacgat ttatctggtc tgtttctgct tctttaagca     1380
actggcgatg atttttatgt ctgtactggc gggcaatatg tatgaaagca tcggtttcca     1440
gggcgcttat ctggtgctgg gtctggtggc gctgggcttc accttaattt ccgtgttcac     1500
gcttagcggc cccggcccgc tttccctgct gcgtcgtcag gtgaatgaag tcgcttaa      1558
```

<210> SEQ ID NO 13
<211> LENGTH: 1551
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 13

```
cccgtcttac tgtcgggaat tcgcgttggc cgattcatta atggtataag gttcttgaca       60
tcttacaatc aatatggtat aataatttag ttagggccca agttcactta aaaggagat       120 caacacttac tgtcgggaat tcgcgttggc caattaatta atggtataag gttcttgaca      180
tcttacaatc aatatggtat aataatttag ttagggccca agttcactta aaaggagat       240 caacaatgaa agcaattttc gtactgaaac atcttaatca tgcgtaggat ttttttctatg     300 tactatttaa aaacacaaa cttttggatg ttcggtttat tcttttttctt ttactttttt      360 atcatgggag cctacttccc gttttttccg atttggctac atgacatcaa ccatatcagc     420
aaaagtgata cggtattatt tttgccgct atttctctgt tctcgctatt attccaaccg      480
ctgtttggtc tgctttctga caaactcggg ctgcgcaaat acctgctgtg gattattacc     540
ggcatgttag tgatgtttgc gccgttcttt atttttatct tcgggccact gttacaatac    600
```

| | |
|---|---|
| aacattttag taggatcgat tgttggtggt atttatctag gcttttgttt taacgccggt | 660 |
| gcgccagcag tagaggcatt tattgagaaa gtcagccgtc gcagtaattt cgaatttggt | 720 |
| cgcgcgcgga tgtttggctg tgttggctgg gcgctgtgtg cctcgattgt cggcatcatg | 780 |
| ttcaccatca ataatcagtt tgttttctgg ctgggctctg gctgtgcact catcctcgcc | 840 |
| gttttactct ttttcgccaa aacggatgcg ccctcttctg ccacggttgc caatgcggta | 900 |
| ggtgccaacc attcggcatt tagccttaag ctggcactgg aactgttcag acagccaaaa | 960 |
| ctgtggtttt tgtcactgta tgttattggc gtttcctgca cctacgatgt ttttgaccaa | 1020 |
| cagtttgcta atttctttac ttcgttcttt gctaccggtg aacagggtac gcgggtattt | 1080 |
| ggctacgtaa cgacaatggg cgaattactt aacgcctcga ttatgttctt tgcgccactg | 1140 |
| atcattaatc gcatcggtgg gaaaaacgcc ctgctgctgg ctggcactat tatgtctgta | 1200 |
| cgtattattg gctcatcgtt cgccacctca gcgctggaag tggttattct gaaaacgctg | 1260 |
| catatgtttg aagtaccgtt cctgctggtg ggctgcttta aatatattac cagccagttt | 1320 |
| gaagtgcgtt tttcagcgac gatttatctg gtctgtttct gcttctttaa gcaactggcg | 1380 |
| atgattttta tgtctgtact ggcgggcaat atgtatgaaa gcatcggttt ccagggcgct | 1440 |
| tatctggtgc tgggtctggt ggcgctgggc ttcaccttaa ttttccgtgtt cacgcttagc | 1500 |
| ggccccggcc cgctttccct gctgcgtcgt caggtgaatg aagtcgctta a | 1551 |

<210> SEQ ID NO 14
<211> LENGTH: 1398
<212> TYPE: DNA
<213> ORGANISM: Artificial sequence
<220> FEATURE:
<223> OTHER INFORMATION: Heterologous sequences in front of a lactose transporter gene

<400> SEQUENCE: 14

| | |
|---|---|
| cccgtcttac tgtcgggaat tcgcgttggc cgattcatta atggtataag gttcttgaca | 60 |
| tcttacaatc aaatatggtat aataatttag ttagggccca agttcactta aaaaggagat | 120 |
| caacaatgaa agcaattttc gtacatgtac tatttaaaaa acacaaactt ttggatgttc | 180 |
| ggtttattct ttttcttttta cttttttatc atgggagcct acttcccgtt tttcccgatt | 240 |
| tgctacatg acatcaacca tatcagcaaa agtgatacgg gtattatttt tgccgctatt | 300 |
| tctctgttct cgctattatt ccaaccgctg tttggtctgc tttctgacaa actcgggctg | 360 |
| cgcaaatacc tgctgtggat tattaccggc atgttagtga tgtttgcgcc gttctttatt | 420 |
| tttatcttcg ggccactgtt acaatacaac attttagtag gatcgattgt tggtggtatt | 480 |
| tatctaggct tttgttttaa cgccggtgcg ccagcagtag aggcatttat tgagaaagtc | 540 |
| agccgtcgca gtaatttcga atttggtcgc gcgcggatgt ttggctgtgt tggctgggcg | 600 |
| ctgtgtgcct cgattgtcgg catcatgttc accatcaata atcagtttgt tttctggctg | 660 |
| ggctctggct gtgcactcat cctcgccgtt ttactctttt tcgccaaaac ggatgcgccc | 720 |
| tcttctgcca cggttgccaa tgcggtaggt gccaaccatt cggcatttag ccttaagctg | 780 |
| gcactggaac tgttcagaca gccaaaactg tggttttgt cactgtatgt tattggcgtt | 840 |
| tcctgcacct acgatgtttt tgaccaacag tttgctaatt tctttacttc gttctttgct | 900 |
| accggtgaac agggtacgcg ggtatttggc tacgtaacga caatgggcga attacttaac | 960 |
| gcctcgatta tgttctttgc gccactgatc attaatcgca tcggtgggaa aaacgccctg | 1020 |
| ctgctggctg gcactattat gtctgtacgt attattggct catcgttcgc cacctcagcg | 1080 |

```
ctggaagtgg ttattctgaa aacgctgcat atgtttgaag taccgttcct gctggtgggc    1140
tgctttaaat atattaccag ccagtttgaa gtgcgttttt cagcgacgat ttatctggtc    1200
tgtttctgct tctttaagca actggcgatg attttatgt ctgtactggc gggcaatatg     1260
tatgaaagca tcggtttcca gggcgcttat ctggtgctgg gtctggtggc gctgggcttc    1320
accttaattt ccgtgttcac gcttagcggc cccggcccgc tttccctgct gcgtcgtcag    1380
gtgaatgaag tcgcttaa                                                  1398
```

```
<210> SEQ ID NO 15
<211> LENGTH: 1558
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 15
cccgtcttac tgtcgggaat tcgcgttggc caattaatta atggtataag gttcttgaca     60
tcttacaatc aatatggtat aataatttag ttagggccca agttcactta aaaaggagat    120
caacaatgaa agcttactgt cgggaattcg cgttggccga ttcattaatg gtataaggtt    180
cttgacatct tacaatcaat atggtataat aatttagtta gggcccaagt tcacttaaaa    240
aggagatcaa caatgaaagc aatttttcgta ctgaaacatc ttaatcatgc gtaggatttt    300
ttctatgtac tatttaaaaa acacaaactt ttggatgttc ggtttattct ttttctttta    360 ctttttatc atgggagcct acttcccgtt ttcccgatt tggctacatg acatcaacca     420
tatcagcaaa agtgatacgg gtattatttt tgccgctatt tctctgttct cgctatatt    480 ccaaccgctg tttggtctgc tttctgacaa actcggctg cgcaaatacc tgctgtggat    540
tattaccggc atgttagtga tgtttgcgcc gttctttatt tttatcttcg ggccactgtt    600
acaatacaac attttagtag gatcgattgt tggtggtatt tatctaggct ttgttttaa    660 cgccggtgcg ccagcagtag aggcatttat tgagaaagtc agccgtcgca gtaatttcga    720
atttggtcgc gcgcggatgt ttggctgtgt tggctgggcg ctgtgtgcct cgattgtcgg    780
catcatgttc accatcaata atcagtttgt ttctggctg ggctctggct gtgcactcat    840
cctcgccgtt ttactctttt cgccaaaaac ggatgcgccc tcttctgcca cggttgccaa    900
tgcggtaggt gccaaccatt cggcatttag ccttaagctg gcactggaac tgttcagaca    960
gccaaaactg tggttttgt cactgtatgt tattggcgtt tcctgcacct acgatgtttt    1020
tgaccaacag ttttgctaatt tctttacttc gttctttgct accggtgaac agggtacgcg    1080
ggtatttggc tacgtaacga caatgggcga attacttaac gcctcgatta tgttctttgc    1140
gccactgatc attaatcgca tcggtgggaa aaacgccctg ctgctggctg gcactattat    1200
gtctgtacgt attattggct catcgttcgc cacctcagcg ctggaagtgg ttattctgaa    1260
aacgctgcat atgtttgaag taccgttcct gctggtgggc tgctttaaat atattaccag    1320
ccagtttgaa gtgcgttttt cagcgacgat ttatctggtc tgtttctgct tctttaagca    1380
actggcgatg attttatgt ctgtactggc gggcaatatg tatgaaagca tcggtttcca    1440
gggcgcttat ctggtgctgg gtctggtggc gctgggcttc accttaattt ccgtgttcac    1500
gcttagcggc cccggcccgc tttccctgct gcgtcgtcag gtgaatgaag tcgcttaa     1558
```

```
<210> SEQ ID NO 16
<211> LENGTH: 1558
<212> TYPE: DNA
```

<213> ORGANISM: Artificial sequence
<220> FEATURE:
<223> OTHER INFORMATION: Heterologous sequences in front of a lactose
      transporter gene

<400> SEQUENCE: 16

| | | | | | | |
|---|---|---|---|---|---|---|
| cccgtcttac | tgtcgggaat | tcgcgttggc | cgattcatta | atggtataag | gttcttgaca | 60 |
| tcttacaatc | aatatggtat | aataatttag | ttagggccca | agttcactta | aaaaggagat | 120 |
| caacaatgaa | agcttactgt | cgggaattcg | cgttggccga | ttcttataaa | tcattatctt | 180 |
| cttgacattt | tagaaacaat | atggtataat | ataacgataa | gggcccaagt | tcacttaaaa | 240 |
| aggagatcaa | caatgaaagc | aattttcgta | ctgaaacatc | ttaatcatgc | gtaggatttt | 300 |
| ttctatgtac | tatttaaaaa | acacaaactt | ttggatgttc | ggtttattct | tttctttta | 360 |
| cttttttatc | atgggagcct | acttcccgtt | tttcccgatt | tggctacatg | acatcaacca | 420 |
| tatcagcaaa | agtgatacgg | gtattatttt | tgccgctatt | tctctgttct | cgctattatt | 480 |
| ccaaccgctg | tttggtctgc | tttctgacaa | actcgggctg | cgcaaatacc | tgctgtggat | 540 |
| tattaccggc | atgttagtga | tgtttgcgcc | gttctttatt | tttatcttcg | ggccactgtt | 600 |
| acaatacaac | attttagtag | gatcgattgt | tggtggtatt | tatctaggct | tttgttttaa | 660 |
| cgccggtgcg | ccagcagtag | aggcatttat | tgagaaagtc | agccgtcgca | gtaatttcga | 720 |
| atttggtcgc | gcgcggatgt | ttggctgtgt | tggctgggcg | ctgtgtgcct | cgattgtcgg | 780 |
| catcatgttc | accatcaata | atcagtttgt | tttctggctg | ggctctggct | gtgcactcat | 840 |
| cctcgccgtt | ttactctttt | tcgccaaaac | ggatgcgccc | tcttctgcca | cggttgccaa | 900 |
| tgcggtaggt | gccaaccatt | cggcatttag | ccttaagctg | gcactggaac | tgttcagaca | 960 |
| gccaaaactg | tggttttttgt | cactgtatgt | tattggcgtt | tcctgcacct | acgatgtttt | 1020 |
| tgaccaacag | tttgctaatt | tctttacttc | gttctttgct | accggtgaac | agggtacgcg | 1080 |
| ggtatttggc | tacgtaacga | caatgggcga | attacttaac | gcctcgatta | tgttctttgc | 1140 |
| gccactgatc | attaatcgca | tcggtgggaa | aaacgccctg | ctgctggctg | gcactattat | 1200 |
| gtctgtacgt | attattggct | catcgttcgc | cacctcagcg | ctggaagtgg | ttattctgaa | 1260 |
| aacgctgcat | atgtttgaag | taccgttcct | gctggtgggc | tgctttaaat | atattaccag | 1320 |
| ccagtttgaa | gtgcgttttt | cagcgacgat | ttatctggtc | tgtttctgct | tctttaagca | 1380 |
| actggcgatg | atttttatgt | ctgtactggc | gggcaatatg | tatgaaagca | tcggtttcca | 1440 |
| gggcgcttat | ctggtgctgg | gtctggtggc | gctgggcttc | accttaattt | ccgtgttcac | 1500 |
| gcttagcggc | cccggcccgc | tttccctgct | gcgtcgtcag | gtgaatgaag | tcgcttaa | 1558 |

<210> SEQ ID NO 17
<211> LENGTH: 1471
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 17

| | | | | | | |
|---|---|---|---|---|---|---|
| cccgtcttac | tgtcgggaat | tcgcgttggc | cgattcgaat | tcgcgttggc | cgattcgaat | 60 |
| tcgcgttggc | cgattcttat | taacaatatc | cttcttgaca | ttttgcaggg | attgtgatat | 120 |
| aatcaataag | tatgggccca | agttcactta | aaaaggagat | caacaatgaa | agcaattttc | 180 |
| gtactgaaac | atcttaatca | tgcgtaggat | tttttctatg | tactatttaa | aaacacaaa | 240 |
| cttttggatg | ttcggtttat | tcttttttctt | ttactttttt | atcatgggag | cctacttccc | 300 |

```
gtttttcccg atttggctac atgacatcaa ccatatcagc aaaagtgata cgggtattat        360
ttttgccgct atttctctgt tctcgctatt attccaaccg ctgtttggtc tgctttctga        420
caaactcggg ctgcgcaaat acctgctgtg gattattacc ggcatgttag tgatgtttgc        480
gccgttcttt attttatct tcgggccact gttacaatac aacattttag taggatcgat        540
tgttggtggt atttatctag cttttgtttt aacgccggt gcgccagcag tagaggcatt        600
tattgagaaa gtcagccgtc gcagtaattt cgaatttggt cgcgcgcgga tgtttggctg        660
tgttggctgg gcgctgtgtg cctcgattgt cggcatcatg ttcaccatca ataatcagtt        720
tgttttctgg ctgggctctg gctgtgcact catcctcgcc gttttactct ttttcgccaa        780
aacggatgcg ccctcttctg ccacggttgc caatgcggta ggtgccaacc attcggcatt        840
tagccttaag ctggcactgg aactgttcag acagccaaaa ctgtggtttt tgtcactgta        900
tgttattggc gtttcctgca cctacgatgt ttttgaccaa cagtttgcta atttctttac        960
ttcgttcttt gctaccggtg aacagggtac gcgggtattt ggctacgtaa cgacaatggg       1020
cgaattactt aacgcctcga ttatgttctt tgcgccactg atcattaatc gcatcggtgg       1080
gaaaaacgcc ctgctgctgg ctggcactat tatgtctgta cgtattattg gctcatcgtt       1140
cgccacctca gcgctggaag tggttattct gaaaacgctg catatgtttg aagtaccgtt       1200
cctgctggtg ggctgcttta aatatattac cagccagttt gaagtgcgtt tttcagcgac       1260
gatttatctg gtctgtttct gcttctttaa gcaactggcg atgatttta tgtctgtact       1320 ggcgggcaat atgtatgaaa gcatcggttt ccagggcgct tatctggtgc tgggtctggt       1380
ggcgctgggc ttcaccttaa tttccgtgtt cacgcttagc ggccccggcc cgctttccct       1440
gctgcgtcgt caggtgaatg aagtcgctta a                                     1471
```

<210> SEQ ID NO 18
<211> LENGTH: 1632
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 18

```
cccgtcttac tgtcgggaat tcgcgttggc cgattcgaat tcgcgttggc cgattcgaat         60
tcgcgttggc cgattcgaat tcgcgttggc cgattcgaat tcgcgttggc caattaatta        120
atggtataag gttcttgaca tcttacaatc aatatggtat aataatttag ttagggccca        180
agttcactta aaaggagat caacacttac tgtcgggaat tcgcgttggc caattaatta        240
atggtataag gttcttgaca tcttacaatc aatatggtat aaataattta gttagggccc        300
aagttcactt aaaaggaga tcaacaatga agcaattttt cgtactgaaa catcttaatc        360
atgcgtagga ttttttctat gtactattta aaaaacacaa actttggat gttcggttta        420 ttcttttttct tttacttttt tatcatggga gcctacttcc cgttttttccc gatttggcta        480 catgacatca accatatcag caaaagtgat acgggtatta ttttgccgc tatttctctg        540 ttctcgctat tattccaacc gctgtttggt ctgcttctg acaaactcgg ctgcgcaaa        600 tacctgctgt ggattattac cggcatgtta gtgatgtttg cgccgttctt tatttttatc        660
ttcgggccac tgttacaata caacatttta gtaggatcga ttgttggtgg tatttatcta        720
ggcttttgtt ttaacgccgg tgcgccagca gtagaggcat ttattgagaa agtcagccgt        780
cgcagtaatt tcgaatttgg tcgcgcgcgg atgtttggct gtgttggctg ggcgctgtgt        840
```

```
gcctcgattg tcggcatcat gttcaccatc aataatcagt ttgttttctg gctgggctct    900
ggctgtgcac tcatcctcgc cgttttactc tttttcgcca aaacggatgc gccctcttct    960
gccacggttg ccaatgcggt aggtgccaac cattcggcat ttagccttaa gctggcactg   1020
gaactgttca gacagccaaa actgtggttt ttgtcactgt atgttattgg cgtttcctgc   1080
acctacgatg ttttgacca acagtttgct aatttcttta cttcgttctt tgctaccggt    1140
gaacagggta cgcgggtatt tggctacgta acgacaatgg cgaattact taacgcctcg    1200
attatgttct ttgcgccact gatcattaat cgcatcggtg ggaaaaacgc cctgctgctg   1260
gctggcacta ttatgtctgt acgtattatt ggctcatcgt tcgccacctc agcgctggaa   1320
gtggttattc tgaaaacgct gcatatgttt gaagtaccgt tcctgctggt gggctgcttt   1380
aaatatatta ccagccagtt tgaagtgcgt ttttcagcga cgatttatct ggtctgtttc   1440
tgcttcttta agcaactggc gatgattttt atgtctgtac tggcgggcaa tatgtatgaa   1500
agcatcggtt tccagggcgc ttatctggtg ctgggtctgg tggcgctggg cttcaccta    1560
atttccgtgt tcacgcttag cggccccggc ccgctttccc tgctgcgtcg tcaggtgaat   1620
gaagtcgctt aa                                                      1632

<210> SEQ ID NO 19
<211> LENGTH: 1558
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 19
cccgtcttac tgtcgggaat tcgcgttggc cgattcatta atggtataag gttcttgaca     60
tcttacaatc aatatggtat aataatttag ttagggccca agttcactta aaaggagat    120
caacaatgaa agcttactgt cgggaattcg cgttggccga ttcattaatg gtataaggtt   180
cttgacatct tacaatcaat atggtataat aatttagtta gggcccaagt tcacttaaaa   240
aggagatcaa caatgaaagc aattttcgta ctgaaacatc ttaatcatgc gtaggatttt   300
ttctatgtac tatttaaaaa acacaaactt ttggatgttc ggtttattct ttttctttta   360
cttttttatc atgggagcct acttcccgtt tttcccgatt tggctacatg acatcaacca   420
tatcagcaaa agtgatacgg gtattatttt tgccgctatt tctctgttct cgctatatt    480
ccaaccgctg tttggtctgc tttctgacaa actcgggctg cgcaaatacc tgctgtggat   540
tattaccggc atgttagtga tgtttgcgcc gttctttatt tttatcttcg ggccactgtt   600
acaatacaac atttttagtag gatcgattgt tggtggtatt tatctaggct tttgttttaa   660
cgccggtgcg ccagcagtag aggcatttat tgagaaagtc agccgtcgca gtaatttcga   720
atttggtcgc gcgcggatgt ttggctgtgt tggctgggcg ctgtgtgcct cgattgtcgg   780
catcatgttc accatcaata atcagtttgt tttctggctg gctctggct gtgcactcat    840
cctcgccgtt ttactctttt cgccaaaaac ggatgcgccc tcttctgcca cggttgccaa   900
tgcggtaggt gccaaccatt cggcatttag ccttaagctg gcactggaac tgttcagaca   960
gccaaaactg tggttttgt cactgtatgt tattggcgtt tcctgcacct acgatgtttt   1020
tgaccaacag tttgctaatt tctttactc gttctttgct accggtgaac agggtacgcg   1080
ggtatttggc tacgtaacga caatgggcga attacttaac gcctcgatta tgttctttgc   1140
gccactgatc attaatcgca tcggtgggaa aaacgccctg ctgctggctg gcactattat   1200
```

```
gtctgtacgt attattggct catcgttcgc cacctcagcg ctggaagtgg ttattctgaa    1260
aacgctgcat atgtttgaag taccgttcct gctggtgggc tgctttaaat atattaccag    1320
ccagtttgaa gtgcgttttt cagcgacgat ttatctggtc tgtttctgct tctttaagca    1380
actggcgatg atttttatgt ctgtactggc gggcaatatg tatgaaagca tcggtttcca    1440
gggcgcttat ctggtgctgg gtctggtggc gctgggcttc accttaattt ccgtgttcac    1500
gcttagcggc cccggcccgc tttccctgct gcgtcgtcag gtgaatgaag tcgcttaa     1558
```

<210> SEQ ID NO 20
<211> LENGTH: 1571
<212> TYPE: DNA
<213> ORGANISM: Artificial sequence
<220> FEATURE:
<223> OTHER INFORMATION: Heterologous sequences in front of a lactose
    transporter gene

<400> SEQUENCE: 20

```
cccgtcttac tgtcgggaat tcgcgttggc cgattcatta atggtataag gttcttgaca      60
tcttacaatc aatatggtat aataatttag ttagggccca agttcactta aaaaggagat     120
caacaatgaa agcaggctta cccgtcttac tgtcgggaat tcgcgttggc cgattcatta    180
atggtataag gttcttgaca tcttacaatc aatatggtat aataatttag ttagggccca    240
agttcactta aaaaggagat caacaatgaa agcaatttc gtactgaaac atcttaatca     300
tgcgtaggat ttttctatg tactatttaa aaaacacaaa cttttggatg ttcggtttat      360 tcttttctt ttacttttt atcatgggag cctacttccc gttttcccg atttggctac        420 atgacatcaa ccatatcagc aaaagtgata cgggtattat ttttgccgct atttctctgt    480
tctcgctatt attccaaccg ctgtttggtc tgctttctga caaactcggg ctgcgcaaat    540
acctgctgtg gattattacc ggcatgttag tgatgtttgc gccgttcttt attttatct     600 tcgggccact gttacaatac aacattttag taggatcgat tgttggtggt atttatctag    660
gcttttgttt taacgccggt gcgccagcag tagaggcatt tattgagaaa gtcagccgtc    720
gcagtaattt cgaatttggt cgcgcgcgga tgtttggctg tgttggctgg gcgctgtgtg    780
cctcgattgt cggcatcatg ttaccatca ataatcagtt tgttttctgg ctgggctctg      840
gctgtgcact catcctcgcc gttttactct ttttcgccaa aacggatgcg ccctcttctg    900
ccacggttgc caatgcggta ggtgccaacc attcggcatt tagccttaag ctggcactgg    960
aactgttcag acagccaaaa ctgtggtttt tgtcactgta tgttattggc gtttcctgca   1020
cctacgatgt ttttgaccaa cagtttgcta atttctttac ttcgttcttt gctaccggtg   1080
aacagggtac gcgggtattt ggctacgtaa cgacaatggg cgaattactt aacgcctcga   1140
ttatgttctt tgcgccactg atcattaatc gcatcggtgg aaaaacgcc ctgctgctgg   1200 ctggcactat tatgtctgta cgtattattg gctcatcgtt cgccacctca gcgctggaag   1260
tggttattct gaaaacgctg catatgtttg aagtaccgtt cctgctggtg gctgctttta   1320
aatatattac cagccagttt gaagtgcgtt tttcagcgac gatttatctg gtctgtttct   1380
gcttctttaa gcaactggcg atgatttta tgtctgtact ggcgggcaat atgtatgaaa    1440
gcatcggttt ccagggcgct tatctggtgc tgggtctggt ggcgctgggc ttcaccttaa   1500
tttccgtgtt cacgcttagc ggccccggcc cgctttccct gctgcgtcgt caggtgaatg   1560
aagtcgctta a                                                       1571
```

<210> SEQ ID NO 21
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 21

| | | | | | |
|---|---|---|---|---|---|
| cccgtcttac | tgtcgggaat | tcgcgttggc | cgattcattt | aaccgataag | cttcttgaca | 60 |
| tgtttagggt | gttatgatat | aatcacccaa | ttagggccca | agttcactta | aaaaggagat | 120 |
| caacaatgaa | agcaattttc | gtactgaaac | atcttaatca | tgcgtaggat | tttttctatg | 180 |
| tactatttaa | aaaacacaaa | cttttggatg | ttcggtttat | tctttttctt | ttacttttt | 240 |
| atcatgggag | cctacttccc | gttttttccg | atttggctac | atgacatcaa | ccatatcagc | 300 |
| aaaagtgata | cgggtattat | ttttgccgct | atttctctgt | tctcgctatt | attccaaccg | 360 |
| ctgtttggtc | tgcttctga | caaactcggg | ctgcgcaaat | acctgctgtg | gattattacc | 420 |
| ggcatgttag | tgatgtttgc | gccgttcttt | attttatct | tcgggccact | gttacaatac | 480 |
| aacatttag | taggatcgat | tgttggtggt | atttatctag | gcttttgttt | taacgccggt | 540 |
| gcgccagcag | tagaggcatt | tattgagaaa | gtcagccgtc | gcagtaattt | cgaatttggt | 600 |
| cgcgcgcgga | tgtttggctg | tgttggctgg | gcgctgtgtg | cctcgattgt | cggcatcatg | 660 |
| ttcaccatca | ataatcagtt | tgttttctgg | ctgggctctg | gctgtgcact | catcctcgcc | 720 |
| gttttactct | ttttcgccaa | aacggatgcg | ccctcttctg | ccacggttgc | caatgcggta | 780 |
| ggtgccaacc | attcggcatt | tagccttaag | ctggcactgg | aactgttcag | acagccaaaa | 840 |
| ctgtggtttt | tgtcactgta | tgttattggc | gtttcctgca | cctacgatgt | ttttgaccaa | 900 |
| cagtttgcta | atttctttac | ttcgttcttt | gctaccggtg | aacagggtac | gcgggtattt | 960 |
| ggctacgtaa | cgacaatggg | cgaattactt | aacgcctcga | ttatgttctt | tgcgccactg | 1020 |
| atcattaatc | gcatcggtgg | gaaaaacgcc | ctgctgctgg | ctggcactat | tatgtctgta | 1080 |
| cgtattattg | gctcatcgtt | cgccacctca | gcgctggaag | tggttattct | gaaaacgctg | 1140 |
| catatgtttg | aagtaccgtt | cctgctggtg | ggctgcttta | aatatattac | cagccagttt | 1200 |
| gaagtgcgtt | tttcagcgac | gatttatctg | gtctgtttct | gcttctttaa | gcaactggcg | 1260 |
| atgattttta | tgtctgtact | ggcgggcaat | atgtatgaaa | gcatcggttt | ccagggcgct | 1320 |
| tatctggtgc | tgggtctggt | ggcgctgggc | ttcaccttaa | tttccgtgtt | cacgcttagc | 1380 |
| ggccccggcc | cgctttccct | gctgcgtcgt | caggtgaatg | aagtcgctta | a | 1431 |

<210> SEQ ID NO 22
<211> LENGTH: 1951
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 22

| | | | | | |
|---|---|---|---|---|---|
| ggcacctgag | tcgctgtctt | tttcgtgaca | ttcagttcgc | tgcgctcacg | gctctggcag | 60 |
| tgaatggggg | taaatggcac | tacaggcgcc | ttttatggat | tcatgcaagg | aaactaccca | 120 |
| taatacaaga | aaagcccgtc | acgggcttct | cagggcgttt | tatggcgggt | ctgctatgtg | 180 |
| gtgctatctg | acttttttgct | gttcagcagt | tcctgccctc | tgattttcca | gtctgaccac | 240 |
| ttcggattat | cccgtgacag | gtcattcaga | ctggctaatg | cacccagtaa | ggcagcggta | 300 |

```
tcatcaacag gcttacccgt cttactgtcg ggaattcgcg ttggccgatt aaaggagatc      360
aacaatgaaa gcactgtcgg gaattcgcgt tggccgattc attaatggta taaggttctt      420
gacatcttac aatcaatatg gtataataat ttagttaggg cccaagttca cttaaaaagg      480
agatcaacaa tgaaagcaag cggtatcatc aacaggctta cccgtcttac tgtcgggaat      540
tcgcgttggc cgattcatta atggtataag gttcttgaca tcttacaatc aatatggtat      600
aataatttag ttagggccca agttcactta aaaaggagat caacaatgaa agcaattttc      660
gtactgaaac atcttaatca tgcgtaggat tttttctatg tactatttaa aaaacacaaa      720
cttttggatg ttcggtttat tcttttttctt ttacttttttt atcatgggag cctacttccc      780 gttttttcccg atttggctac atgacatcaa ccatatcagc aaaagtgata cgggtattat      840
ttttgccgct atttctctgt tctcgctatt attccaaccg ctgtttggtc tgctttctga      900
caaactcggg ctgcgcaaat acctgctgtg gattattacc ggcatgttag tgatgtttgc      960
gccgttcttt atttttatct tcgggccact gttacaatac aacatttttag taggatcgat     1020 tgttggtggt atttatctag ctttttgttt taacgccggt gcgccagcag tagaggcatt     1080
tattgagaaa gtcagccgtc gcagtaattt cgaatttggt cgcgcgcgga tgtttggctg     1140
tgttggctgg gcgctgtgtg cctcgattgt cggcatcatg ttcaccatca ataatcagtt     1200
tgttttctgg ctgggctctg gctgtgcact catcctcgcc gttttactct ttttcgccaa     1260
aacggatgcg ccctcttctg ccacggttgc caatgcggta ggtgccaacc attcggcatt     1320
tagccttaag ctggcactgg aactgttcag acagccaaaa ctgtggtttt tgtcactgta     1380
tgttattggc gtttcctgca cctacgatgt ttttgaccaa cagtttgcta atttctttac     1440
ttcgttcttt gctaccggtg aacagggtac gcgggtattt ggctacgtaa cgacaatggg     1500
cgaattactt aacgcctcga ttatgttctt tgcgccactg atcattaatc gcatcggtgg     1560
gaaaaacgcc ctgctgctgg ctggcactat tatgtctgta cgtattattg gctcatcgtt     1620
cgccacctca gcgctggaag tggttattct gaaaacgctg catatgtttg aagtaccgtt     1680
cctgctggtg ggctgcttta aatatattac cagccagttt gaagtgcgtt tttcagcgac     1740
gatttatctg gtctgtttct gcttctttaa gcaactggcg atgattttta tgtctgtact     1800
ggcgggcaat atgtatgaaa gcatcggttt ccagggcgct tatctggtgc tgggtctggt     1860
ggcgctgggc ttcaccttaa ttttccgtgtt cacgcttagc ggccccggcc cgctttccct     1920
gctgcgtcgt caggtgaatg aagtcgctta a                                   1951
```

<210> SEQ ID NO 23
<211> LENGTH: 1749
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 23

```
cccgtcttac tgtcgggaat tcgcgttggc cgattcgaat tcgcgttggc cgattcgaat       60
tcgcgttggc cgattcgaat tcgcgttggc cgattcgaat tcgcgttggc cgattcgaat      120
tcgcgttggc cgattcgaat tcgcgttggc cgattaaagg agatcaacaa tgaaagctta     180
ctgtcgggaa ttcgcgttgg ccgattcgaa ttcgcgttgg ccgattcatt aatggtataa     240
ggttcttgac atcttacaat caatatggta taataattta gttagggccc aagttcactt     300
aaaaaggaga tcaacaatga agcttactg tcgggaattc gcgttggccg attcattaat      360
```

```
ggtataaggt tcttgacatc ttacaatcaa tatggtataa taatttagtt agggcccaag    420
ttcacttaaa aaggagatca acaatgaaag caattttcgt actgaaacat cttaatcatg    480
cgtaggattt tttctatgta ctatttaaaa aacacaaact tttggatgtt cggtttattc    540
tttttctttt acttttttat catgggagcc tacttcccgt ttttcccgat ttggctacat    600
gacatcaacc atatcagcaa aagtgatacg ggtattattt ttgccgctat ttctctgttc    660
tcgctattat tccaaccgct gtttggtctg ctttctgaca aactcgggct gcgcaaatac    720
ctgctgtgga ttattaccgg catgttagtg atgtttgcgc cgttctttat ttttatcttc    780
gggccactgt tacaatacaa cattttagta ggatcgattg ttggtggtat ttatctaggc    840
ttttgtttta acgccggtgc gccagcagta gaggcattta ttgagaaagt cagccgtcgc    900
agtaatttcg aatttggtcg cgcgcggatg tttggctgtg ttggctgggc gctgtgtgcc    960
tcgattgtcg gcatcatgtt caccatcaat aatcagtttg ttttctggct gggctctggc   1020
tgtgcactca tcctcgccgt tttactcttt ttcgccaaaa cggatgcgcc ctcttctgcc   1080
acggttgcca atgcggtagg tgccaaccat tcggcattta gccttaagct ggcactggaa   1140
ctgttcagac agccaaaact gtggttttg tcactgtatg ttattggcgt ttcctgcacc   1200
tacgatgttt tgaccaaca gtttgctaat ttctttactt cgttctttgc taccggtgaa   1260
cagggtacgc gggtatttgg ctacgtaacg acaatgggcg aattacttaa cgcctcgatt   1320
atgttctttg cgccactgat cattaatcgc atcggtggga aaaacgccct gctgctggct   1380
ggcactatta tgtctgtacg tattattggc tcatcgttcg ccacctcagc gctggaagtg   1440
gttattctga aaacgctgca tatgtttgaa gtaccgttcc tgctggtggg ctgctttaaa   1500
tatattacca gccagtttga agtgcgtttt tcagcgacga tttatctggt ctgtttctgc   1560
ttctttaagc aactggcgat gatttttatg tctgtactgg cggcaatat gtatgaaagc   1620 atcggtttcc agggcgctta tctggtgctg gtctggtgg cgctgggctt caccttaatt   1680
tccgtgttca cgcttagcgg ccccggcccg ctttccctgc tgcgtcgtca ggtgaatgaa   1740
gtcgcttaa                                                           1749
```

<210> SEQ ID NO 24
<211> LENGTH: 1556
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 24

```
cccgtcttac tgtcgggaat tcgcgttggc cgattcatac taagcattat attcttgaca     60
tcttacaatc aatatggtat aataatttag ttagggccca agttcactta aaaaggagat    120
caacaatgaa agcactgtcg ggaattcgcg ttggccaatt aattaatggt ataaggttct    180
tgacatctta caatcaatat ggtataataa tttagttagg gcccaagttc acttaaaaag    240
gagatcaaca atgaaagcaa ttttcgtact gaaacatctt aatcatgcgt aggatttttt    300
ctatgtacta tttaaaaaac acaaactttt ggatgttcgg tttattcttt ttcttttact    360
tttttatcat gggagcctac ttcccgtttt tcccgatttg ctacatgac atcaaccata    420 tcagcaaaag tgatacgggt attatttttg ccgctatttc tctgttctcg ctattattcc    480
aaccgctgtt tggtctgctt tctgacaaac tcgggctgcg caaatacctg ctgtggatta    540
ttaccggcat gttagtgatg tttgcgccgt tctttatttt tatcttcggg ccactgttac    600
```

| | |
|---|---|
| aatacaacat tttagtagga tcgattgttg gtggtattta tctaggcttt tgttttaacg | 660 |
| ccggtgcgcc agcagtagag gcatttattg agaaagtcag ccgtcgcagt aatttcgaat | 720 |
| ttggtcgcgc gcggatgttt ggctgtgttg gctgggcgct gtgtgcctcg attgtcggca | 780 |
| tcatgttcac catcaataat cagtttgttt tctggctggg ctctggctgt gcactcatcc | 840 |
| tcgccgtttt actcttttc gccaaaacgg atgcgccctc ttctgccacg gttgccaatg | 900 |
| cggtaggtgc caaccattcg gcatttagcc ttaagctggc actggaactg ttcagacagc | 960 |
| caaaactgtg gttttgtca ctgtatgtta ttggcgtttc ctgcacctac gatgttttg | 1020 |
| accaacagtt tgctaatttc tttacttcgt tctttgctac cggtgaacag ggtacgcggg | 1080 |
| tatttggcta cgtaacgaca atgggcgaat tacttaacgc ctcgattatg ttctttgcgc | 1140 |
| cactgatcat taatcgcatc ggtgggaaaa acgccctgct gctggctggc actattatgt | 1200 |
| ctgtacgtat tattggctca tcgttcgcca cctcagcgct ggaagtggtt attctgaaaa | 1260 |
| cgctgcatat gtttgaagta ccgttcctgc tggtgggctg ctttaaatat attaccagcc | 1320 |
| agtttgaagt gcgttttca gcgacgattt atctggtctg tttctgcttc tttaagcaac | 1380 |
| tggcgatgat ttttatgtct gtactggcgg gcaatatgta tgaaagcatc ggtttccagg | 1440 |
| gcgcttatct ggtgctgggt ctggtggcgc tgggcttcac cttaatttcc gtgttcacgc | 1500 |
| ttagcggccc cggcccgctt tccctgctgc gtcgtcaggt gaatgaagtc gcttaa | 1556 |

<210> SEQ ID NO 25
<211> LENGTH: 1802
<212> TYPE: DNA
<213> ORGANISM: Artificial sequence
<220> FEATURE:
<223> OTHER INFORMATION: Heterologous sequences in front of a lactose
   transporter gene

<400> SEQUENCE: 25

| | |
|---|---|
| cccgtcttac tgtcgggaat tcgcgttggc cgattcgaat tcgcgttggc cgattcgaat | 60 |
| tcgcgttggc cgattcgaat tcgcgttggc cgattaaagg agatcaacaa tgaaagctta | 120 |
| ctgtcgggaa ttcgcgttgg ccgattcatt aatggtataa ggttcttgac atcttacaat | 180 |
| caatatggta taataattta gttagggccc aagttcactt aaaaaggaga tcaacactta | 240 |
| ctgtcgggaa ttcgcgttgg ccaattaatt aatggtataa ggttcttgac atcttacaat | 300 |
| caatatggta taataattta gttagggccc aagttcactt aaaaaggaga tcaacaatga | 360 |
| aagcaggctt acccgtctta ctgtcgggaa ttcgcgttgg ccgattcatt aatggtataa | 420 |
| ggttcttgac atcttacaat caatatggta taataattta gttagggccc aagttcactt | 480 |
| aaaaaggaga tcaacaatga aagcaatttt cgtactgaaa catcttaatc atgcgtagga | 540 |
| ttttttctat gtactatttta aaaaacacaa acttttggat gttcggttta ttcttttct | 600 |
| tttactttt tatcatggga gcctacttcc cgttttcc gatttggcta catgacatca | 660 |
| accatatcag caaaagtgat acgggtatta ttttgccgc tatttctctg ttctcgctat | 720 |
| tattccaacc gctgtttggt ctgctttctg acaaactcgg gctgcgcaaa tacctgctgt | 780 |
| ggattattac cggcatgtta gtgatgtttg cgccgttctt tatttttatc ttcgggccac | 840 |
| tgttacaata caacatttta gtaggatcga ttgttggtgg tatttatcta ggcttttgtt | 900 |
| ttaacgccgg tgcgccagca gtagaggcat ttattgagaa agtcagccgt cgcagtaatt | 960 |
| tcgaatttgg tcgcgcgcgg atgtttggct gtgttggctg ggcgctgtgt gcctcgattg | 1020 |
| tcggcatcat gttcaccatc aataatcagt ttgttttctg gctgggctct ggctgtgcac | 1080 |

```
tcatcctcgc cgtttttactc tttttcgcca aaacggatgc gccctcttct gccacggttg     1140
ccaatgcggt aggtgccaac cattcggcat ttagccttaa gctggcactg gaactgttca     1200
gacagccaaa actgtggttt ttgtcactgt atgttattgg cgtttcctgc acctacgatg     1260
tttttgacca acagtttgct aatttcttta cttcgttctt tgctaccggt gaacagggta     1320
cgcgggtatt tggctacgta acgacaatgg gcgaattact taacgcctcg attatgttct     1380
ttgcgccact gatcattaat cgcatcggtg ggaaaaacgc cctgctgctg ctggcacta     1440 ttatgtctgt acgtattatt ggctcatcgt tcgccaccct agcgctggaa gtggttattc     1500
tgaaaacgct gcatatgttt gaagtaccgt tcctgctggt gggctgcttt aaatatatta     1560
ccagccagtt tgaagtgcgt ttttcagcga cgatttatct ggtctgtttc tgcttcttta     1620
agcaactggc gatgatttttt atgtctgtac tggcgggcaa tatgtatgaa agcatcggtt     1680
tccagggcgc ttatctggtg ctgggtctgg tggcgctggg cttcaccttaa atttccgtgt     1740 tcacgcttag cggccccggc ccgctttccc tgctgcgtcg tcaggtgaat gaagtcgctt     1800
aa                                                                      1802
```

<210> SEQ ID NO 26
<211> LENGTH: 1947
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 26

```
cctgagtcgc tgtcttttc gtgacattca gttcgctgcg ctcacggctc tggcagtgaa       60
tgggggtaaa tggcactaca ggcgcctttt atggattcat gcaaggaaac tacccataat     120
acaagaaaag cccgtcacgg gcttctcagg gcgttttatg gcgggtctgc tatgtggtgc     180
tatctgactt tttgctgttc agcagttcct gccctctgat tttccagtct gaccacttcg     240
gattatcccg tgacaggtca ttcagactgg ctaatgcacc cagtaaggca gcggtatcat     300
caacaggctt acccgtctta ctgtcgggaa ttcgcgttgg ccgattaaag gagatcaaca     360
atgaaagcac tgtcgggaat cgcgttggc cgattcatta atggtataag gttcttgaca     420
tcttacaatc aatatggtat aataattag ttagggccca agttcactta aaaaggagat      480
caacaatgaa agcaagcgt atcatcaaca ggcttaccc tcttactgtc gggaattcgc      540
gttggccgat tcattaatgg tataaggttc ttgacatctt acaatcaata tggcataata     600
atttagttag ggcccaagtt cacttaaaaa ggagatcaac aatgaaagca attttcgtac     660
tgaaacatct taatcatgcg taggattttt tctatgtact atttaaaaaa cacaaacttt     720
tggatgttcg gtttattctt tttcttttac tttttttca tgggagccta cttcccgttt     780
ttcccgattt ggctacatga catcaaccat atcagcaaaa gtgatacggg tattattttt     840
gccgctattt ctctgttctc gctattattc caaccgctgt ttggtctgct ttctgacaaa     900
ctcgggctgc gcaaatacct gctgtggatt attaccggca tgttagtgat gtttgcgccg     960
ttctttattt ttatcttcgg gccactgtta caatacaaca ttttagtagg atcgattgtt    1020
ggtggtattt atctaggctt tgttttaac gccggtgcgc cagcagtaga ggcatttatt     1080
gagaaagtca gccgtcgcag taatttcgaa tttggtcgcg cgcggatgtt ggctgtgtt     1140 ggctgggcgc tgtgtgcctc gattgtcggc atcatgttca ccatcaataa tcagtttgtt     1200
ttctggctgg gctctggctg tgcactcatc ctcgccgttt tactcttttt cgccaaaacg    1260
```

| | |
|---|---|
| gatgcgccct cttctgccac ggttgccaat gcggtaggtg ccaaccattc ggcatttagc | 1320 |
| cttaagctgg cactggaact gttcagacag ccaaaactgt ggtttttgtc actgtatgtt | 1380 |
| attggcgttt cctgcaccta cgatgttttt gaccaacagt ttgctaattt ctttacttcg | 1440 |
| ttctttgcta ccggtgaaca gggtacgcgg gtatttggct acgtaacgac aatgggcgaa | 1500 |
| ttacttaacg cctcgattat gttctttgcg ccactgatca ttaatcgcat cggtgggaaa | 1560 |
| aacgccctgc tgctggctgg cactattatg tctgtacgta ttattggctc atcgttcgcc | 1620 |
| acctcagcgc tggaagtggt tattctgaaa acgctgcata tgtttgaagt accgttcctg | 1680 |
| ctggtgggct gctttaaata tattaccagc cagtttgaag tgcgtttttc agcgacgatt | 1740 |
| tatctggtct gtttctgctt ctttaagcaa ctggcgatga ttttatgtc tgtactggcg | 1800 |
| ggcaatatgt atgaaagcat cggttttcag ggcgcttatc tggtgctggg tctggtggcg | 1860 |
| ctgggcttca ccttaatttc cgtgttcacg cttagcggcc ccggcccgct ttccctgctg | 1920 |
| cgtcgtcagg tgaatgaagt cgcttaa | 1947 |

<210> SEQ ID NO 27
<211> LENGTH: 1511
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 27

| | |
|---|---|
| cccgtcttac tgtcgggaat tcgcgttggc cgattcgaat tcgcgttggc cgattcgaat | 60 |
| tcgcgttggc cgattcgaat tcgcgttggc cgattcgaat tcgcgttggc caattaatta | 120 |
| atggtataag gttcttgaca tcttacaatc aatatggtat aataatttag ttagggccca | 180 |
| agttcactta aaaaggagat caacaatgaa agcaattttc gtactgaaac atcttaatca | 240 |
| tgcgtaggat ttttctatg tactatttaa aaaacacaaa cttttggatg ttcggtttat | 300 |
| tcttttctt ttactttttt atcatgggag cctacttccc gttttccccg atttggctac | 360 |
| atgacatcaa ccatatcagc aaaagtgata cgggtattat ttttgccgct atttctctgt | 420 |
| tctcgctatt attccaaccg ctgtttggtc tgctttctga caaactcggg ctgcgcaaat | 480 |
| acctgctgtg gattattacc ggcatgttag tgatgtttgc gccgttcttt attttatct | 540 |
| tcgggccact gttacaatac aacatttag taggatcgat tgttggtggt atttatctag | 600 |
| gcttttgttt taacgccggt gcgccagcag tagaggcatt tattgagaaa gtcagccgtc | 660 |
| gcagtaattt cgaatttggt cgcgcgcgga tgtttggctg tgttggctgg gcgctgtgtg | 720 |
| cctcgattgt cggcatcatg ttcaccatca ataatcagtt tgttttctgg ctgggctctg | 780 |
| gctgtgcact catcctcgcc gttttactct ttttcgccaa aacggatgcg ccctcttctg | 840 |
| ccacggttgc caatgcggta ggtgccaacc attcggcatt tagccttaag ctggcactgg | 900 |
| aactgttcag acagccaaaa ctgtggtttt tgtcactgta tgttattggc gtttcctgca | 960 |
| cctacgatgt ttttgaccaa cagtttgcta atttctttac ttcgttcttt gctaccggtg | 1020 |
| aacagggtac gcgggtattt ggctacgtaa cgacaatggg cgaattactt aacgcctcga | 1080 |
| ttatgttctt tgcgccactg atcattaatc gcatcggtgg gaaaaacgcc ctgctgctgg | 1140 |
| ctggcactat tatgtctgta cgtattattg gctcatcgtt cgccacctca gcgctggaag | 1200 |
| tggttattct gaaaacgctg catatgtttg aagtaccgtt cctgctggtg ggctgcttta | 1260 |
| aatatattac cagccagttt gaagtgcgtt tttcagcgac gatttatctg gtctgtttct | 1320 |

```
gcttctttaa gcaactggcg atgattttta tgtctgtact ggcgggcaat atgtatgaaa    1380
gcatcggttt ccagggcgct tatctggtgc tgggtctggt ggcgctgggc ttcaccttaa    1440
tttccgtgtt cacgcttagc ggccccggcc cgctttccct gctgcgtcgt caggtgaatg    1500
aagtcgctta a                                                        1511

<210> SEQ ID NO 28
<211> LENGTH: 1950
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 28
cctgagtcgc tgtctttttc gtgacattca gttcgctgcg ctcacggctc tggcagtgaa      60
tgggggtaaa tggcactaca ggcgcctttt atggattcat gcaaggaaac tacccataat     120
acaagaaaag cccgtcacgg gcttctcagg gcgttttatg gcgggtctgc tatgtggtgc     180
tatctgactt tttgctgttc agcagttcct gccctctgat tttccagtct gaccacttcg     240
gattatcccg tgacaggtca ttcagactgg ctaatgcacc cagtaaggca gcggtatcat     300
caacaggctt acccgtctta ctgtcgggaa ttcgcgttgg ccgattaaag gagatcaaca     360
atgaaagcac tgtcgggaat tcgcgttggc cgattcatta atggtataag gttcttgaca     420
tcttacaatc aatatggtat aataatttag ttagggccca agttcactta aaaaggagat     480
caacaatgaa agcaagcggt atcatcaaca ggcttacccg tcttactgtc gggaattcgc     540
gttggccgat tcattaatgg tataaggttc tttgacatct acaatcaat atggtataat      600 aatttagtta gggcccaagt tcacttaaaa aaggagatca acaatgaaag cattttcgt     660 actgaaacat cttaatcatg cgtaggattt ttttctatgt actatttaaa aaacacaaac     720
ttttggatgt tcggtttatt cttttttctt tactttttta tcatgggagc ctacttcccg     780 ttttttcccga tttggctaca tgacatcaac catatcagca aaagtgatac gggtattatt     840
tttgccgcta tttctctgtt ctcgctatta ttccaaccgc tgtttggtct gctttctgac     900
aaactcgggc tgcgcaaata cctgctgtgg attattaccg gcatgttagt gatgtttgcg     960
ccgttcttta tttttatctt cgggccactg ttacaataca acattttagt aggatcgatt    1020
gttggtggta tttatctagg ctttttgttt aacgccggtg cgccagcagt agaggcattt    1080
attgagaaag tcagccgtcg cagtaatttc gaatttggtc gcgcgcggat gtttggctgt    1140
gttggctggg cgctgtgtgc ctcgattgtc ggcatcatgt tcaccatcaa taatcagttt    1200
gttttctggc tgggctctgg ctgtgcactc atcctcgccg ttttactctt tttcgccaaa    1260
acggatgcgc cctcttctgc cacggttgcc aatgcggtag tgccaaccca tcggcatttt    1320
agccttaagc tggcactgga actgttcaga cagccaaaac tgtggttttt gtcactgtat    1380
gttattggcg tttcctgcac ctacgatgtt tttgaccaac agtttgctaa tttcttttact    1440 tcgttctttg ctaccggtga acagggtacg cgggtatttg gctacgtaac gacaatgggc    1500
gaattactta acgcctcgat tatgttcttt gcgccactga tcattaatcg catcggtggg    1560
aaaaacgccc tgctgctggc tggcactatt atgtctgtac gtattattgg ctcatcgttc    1620
gccacctcag cgctggaagt ggttattctg aaaacgctgc atatgtttga agtaccgttc    1680
ctgctggtgg gctgctttaa atatattacc agccagtttg aagtgcgttt tcagcgacg    1740 atttatctgg tctgtttctg cttctttaag caactggcga tgatttttat gtctgtactg    1800
```

```
gcgggcaata tgtatgaaag catcggtttc cagggcgctt atctggtgct gggtctggtg    1860
gcgctgggct tcaccttaat ttccgtgttc acgcttagcg ccccggccc gctttccctg     1920 ctgcgtcgtc aggtgaatga agtcgcttaa                                     1950

<210> SEQ ID NO 29
<211> LENGTH: 1551
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 29
cccgtcttac tgtcgggaat tcgcgttggc cgattcatta atggcataag gttcttgaca     60
tcttacaatc aatatggtat aataatttag ttagggccca agttcactta aaaaggagat    120
caacacttac tgtcgggaat tcgcgttggc caattaatta atggtataag gttcttgaca    180
tcttacaatc aatatggtat aataatttag ttagggccca agttcactta aaaaggagat    240
caacaatgaa agcaattttc gtactgaaac atcttaatca tgcgtatgat ttttctatg     300 tactatttaa aaaacacaaa cttttggatg ttcggtttat tcttttctct ttactttttt    360
atcatgggag cctacttccc gttttcccg atttggctac atgacatcaa ccatatcagc     420
aaaagtgata cgggtattat ttttgccgct atttctctgt tctcgctatt attccaaccg    480
ctgtttggtc tgctttctga caaactcggg ctgcgcaaat acctgctgtg gattattacc    540
ggcatgttag tgatgtttgc gccgttcttt atttttatct tcgggccact gttacaatac    600 aacatttag taggatcgat tgttggtggt atttatctag gcttttgttt taacgccggt    660
gcgccagcag tagaggcatt tattgagaaa gtcagccgtc gcagtaattt cgaatttggt    720
cgcgcgcgga tgtttggctg tgttggctgg gcgctgtgtg cctcgattgt cggcatcatg    780
ttcaccatca ataatcagtt tgttttctgg ctgggctctg gctgtgcact catcctcgcc    840
gttttactct ttttcgccaa aacggatgcg ccctcttctg ccacggttgc caatgcggta    900
ggtgccaacc attcggcatt tagccttaag ctggcactgg aactgttcag acagccaaaa    960
ctgtggtttt tgtcactgta tgttattggc gtttcctgca cctacgatgt ttttgaccaa    1020
cagtttgcta atttctttac ttcgttcttt gctaccggtg aacagggtac gcgggtattt    1080
ggctacgtaa cgacaatggg cgaattactt aacgcctcga ttatgttctt tgcgccactg    1140
atcattaatc gcatcggtgg gaaaaacgcc ctgctgctgg ctggcactat tatgtctgta    1200
cgtattattg gctcatcgtt cgccacctca gcgctggaag tggttattct gaaaacgctg    1260
catatgtttg aagtaccgtt cctgctggtg ggctgcttta aatatattac cagccagttt    1320
gaagtgcgtt tttcagcgac gatttatctg gtctgtttct gcttctttaa gcaactggcg    1380 atgatttta tgtctgtact ggcgggcaat atgtatgaaa gcatcggttt ccagggcgct    1440
tatctggtgc tgggtctggt ggcgctgggc ttcaccttaa tttccgtgtt cacgcttagc    1500
ggccccggcc cgctttccct gctgcgtcgt caggtgaatg aagtcgctta a              1551

<210> SEQ ID NO 30
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 30
```

```
cccgtcttac tgtcgggaat tcgcgttggc cgattcatta atggtataag gttcttgaca      60
tcttacaatc aatatggtat aataatttag ttagggccca agttcactta aaaaggagat    120
caacaatgaa agcaattttc gtactgaaac atcttaatca tgcgtaggat tttttctatg    180
tactatttaa aaaacacaaa cttttggatg ttcggtttat tcttttttctt ttacttttttt   240 atcatgggag cctacttccc gttttttcccg atttggctac atgacatcaa ccatatcagc   300
aaaagtgata cgggtattat ttttgccgct atttctctgt tctcgctatt attccaaccg    360
ctgtttggtc tgctttctga caaactcggg ctgcgcaaat acctgctgtg gattattacc   420
ggcatgttag tgatgtttgc gccgttcttt attttttatct tcgggccact gttacaatac   480 aacatttag taggatcgat tgttggtggt atttatctag gcttttgttt taacgccggt    540
gcgccagcag tagaggcatt tattgagaaa gtcagccgtc gcagtaattt cgaatttggt   600
cgcgcgcgga tgtttggctg tgttggctgg gcgctgtgtg cctcgattgt cggcatcatg    660
ttcaccatca ataatcagtt tgtttttctgg ctgggtctg gctgtgcact catcctcgcc    720
gttttactct ttttcgccaa acggatgcg ccctcttctg ccacggttgc caatgcggta    780
ggtgccaacc attcggcatt tagccttaag ctggcactgg aactgttcag acagccaaaa   840
ctgtggtttt tgtcactgta tgttattggc gtttcctgca cctacgatgt ttttgaccaa   900
cagtttgcta atttctttac ttcgttcttt gctaccggtg aacagggtac gcgggtattt    960
ggctacgtaa cgacaatggg cgaattactt aacgcctcga ttatgttctt tgcgccactg   1020
atcattaatc gcatcggtgg gaaaaacgcc ctgctgctgg ctggcactat tatgtctgta   1080
cgtattattg gctcatcgtt cgccaacctca gcgctggaag tggttattct gaaaacgctg   1140
catatgtttg aagtaccgtt cctgctggtg gctgctttta aatatattac cagccagttt   1200
gaagtgcgtt tttcagcgac gatttatctg gtctgtttct gcttctttaa gcaactggcg   1260 atgatttta tgtctgtact ggcgggcaat atgtatgaaa gcatcggttt ccagggcgct   1320
tatctggtgc tgggtctggt ggcgctgggc ttcaccttaa tttccgtgtt cacgcttagc   1380
ggccccggcc cgctttccct gctgcgtcgt caggtgaatg aagtcgctta a           1431
```

<210> SEQ ID NO 31
<211> LENGTH: 1551
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 31

```
cccgtcttac tgtcgggaat tcgcgttggc cgattcattc aatccaatag gttcttgaca     60
tcttacaatc aatatggtat aataatttag ttagggccca agttcactta aaaaggagat    120
caacacttac tgtcgggaat tcgcgttggc caattaatta atggtataag gttcttgaca    180
tcttacaatc aatatggtat aataatttag ttagggccca agttcactta aaaaggagat    240
caacaatgaa agcaattttc gtactgaaac atcttaatca tgcgtaggat tttttctatg    300
tactatttaa aaaacacaaa cttttggatg ttcggtttat tcttttttctt ttacttttttt   360 atcatgggag cctacttccc gttttttcccg atttggctac atgacatcaa ccatatcagc   420
aaaagtgata cgggtattat ttttgccgct atttctctgt tctcgctatt attccaaccg    480
ctgtttggtc tgctttctga caaactcggg ctgcgcaaat acctgctgtg gattattacc   540
ggcatgttag tgatgtttgc gccgttcttt attttttatct tcgggccact gttacaatac   600
```

```
aacattttag taggatcgat tgttggtggt atttatctag gcttttgttt taacgccggt      660
gcgccagcag tagaggcatt tattgagaaa gtcagccgtc gcagtaattt cgaatttggt      720
cgcgcgcgga tgtttggctg tgttggctgg gcgctgtgtg cctcgattgt cggcatcatg      780
ttcaccatca ataatcagtt tgttttctgg ctgggtctg gctgtgcact catcctcgcc       840
gttttactct ttttcgccaa aacggatgcg ccctcttctg ccacggttgc caatgcggta      900
ggtgccaacc attcggcatt tagccttaag ctggcactgg aactgttcag acagccaaaa      960
ctgtggtttt tgtcactgta tgttattggc gtttcctgca cctacgatgt ttttgaccaa     1020
cagtttgcta atttctttac ttcgttcttt gctaccggtg aacagggtac gcgggtattt     1080
ggctacgtaa cgacaatggg cgaattactt aacgcctcga ttatgttctt gcgccactg      1140 atcattaatc gcatcggtgg gaaaaacgcc ctgctgctgg ctggcactat tatgtctgta     1200
cgtattattg gctcatcgtt cgccacctca gcgctggaag tggttattct gaaaacgctg     1260
catatgtttg aagtaccgtt cctgctggtg ggctgcttta aatatattac cagccagttt     1320
gaagtgcgtt tttcagcgac gatttatctg gtctgtttct gcttctttaa gcaactggcg     1380
atgattttta tgtctgtact ggcgggcaat atgtatgaaa gcatcggttt ccagggcgct     1440
tatctggtgc tgggtctggt ggcgctgggc ttcaccttaa tttccgtgtt cacgcttagc     1500
ggccccggcc cgctttccct gctgcgtcgt caggtgaatg aagtcgctta a              1551
```

<210> SEQ ID NO 32
<211> LENGTH: 1558
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 32

```
cccgtcttac tgtcgggaat tcgcgttggc cgattcatta atggtataag gttcttgaca       60
tcttacaatc aatatgggat aataatttag ttagggccca agttcactta aaaaggagat      120
caacaatgaa agcttactgt cgggaattcg cgttggccga ttcttataaa tcattatctt      180
cttgacattt tagaaacaat atggtataat ataacgataa gggcccaagt tcacttaaaa      240
aggagatcaa caatgaaagc aatttttcgta ctgaaacatc ttaatcatgc gtaggatttt     300
ttctatgtac tatttaaaaa acacaaactt ttggatgttc ggtttattct ttttctttta      360 ctttttttatc atgggagcct acttcccgtt tttcccgatt tggctacatg acatcaacca     420
tatcagcaaa agtgatacgg gtattatttt tgccgctatt tctctgttct cgctattatt      480
ccaaccgctg tttggtctgc tttctgacaa actcgggctg cgcaaatacc tgctgtggat     540
tattaccggc atgttagtga tgtttgcgcc gttctttatt tttatcttcg ggccactgtt     600
acaatacaac attttagtag gatcgattgt tggtggtatt tatctaggct tttgttttaa      660
cgccggtgcg ccagcagtag aggcatttat tgagaaagtc agccgtcgca gtaatttcga     720
atttggtcgc gcgcggatgt ttggctgtgt tggctgggcg ctgtgtgcct cgattgtcgg     780
catcatgttc accatcaata tcagttttgt tttctggctg gctctggct gtgcactcat       840 cctcgccgtt ttactctttt tcgccaaaac ggatgcgccc tcttctgcca cggttgccaa     900
tgcggtaggt gccaaccatt cggcatttag ccttaagctg gcactggaac tgttcagaca      960
gccaaaactg tggttttttgt cactgtatgt tattggcgtt tcctgcacct acgatgtttt    1020
tgaccaacag tttgctaatt tctttacttc gttctttgct accggtgaac agggtacgcg     1080
```

```
ggtatttggc tacgtaacga caatgggcga attacttaac gcctcgatta tgttctttgc    1140
gccactgatc attaatcgca tcggtgggaa aaacgccctg ctgctggctg cactattat    1200 gtctgtacgt attattggct catcgttcgc cacctcagcg ctggaagtgg ttattctgaa    1260
aacgctgcat atgtttgaag taccgttcct gctggtgggc tgctttaaat atattaccag    1320
ccagtttgaa gtgcgttttt cagcgacgat ttatctggtc tgtttctgct tctttaagca    1380
actggcgatg attttatgt ctgtactggc gggcaatatg tatgaaagca tcggtttcca    1440
gggcgcttat ctggtgctgg gtctggtggc gctgggcttc accttaatttt ccgtgttcac    1500 gcttagcggc cccggcccgc tttccctgct gcgtcgtcag gtgaatgaag tcgcttaa    1558

<210> SEQ ID NO 33
<211> LENGTH: 1542
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 33
cccgtcttac tgtcgggaat tcgcgttggc cgattcgaat tcgcgttggc cgattcgaat      60
tcgcgctggc cgattcgaat tcgcgttggc cgattaaagg agatcaacta tgaaagctta    120
ctgtcgggaa ttcgcgttgg ccgattcatt aatggtataa ggctcttgac atcttacaat    180
caatatggta taataattta gtttagggcc aagttcactt aaaaaggaga tcaacaatga    240
aagcaatttt cgtactgaaa catcttaatc atgcgtagga ttttttctat gtactattta    300
aaaaacacaa acttttggat gttcggttta ttcttttttct tttacttttt tatcatggga    360
gcctacttcc cgttttttccc gatttggcta catgacatca accatatcag caaaagtgat    420
acgggtatta ttttgccgc tatttctctg ttctcgctat tattccaacc gctgtttggt    480
ctgctttctg acaaactcgg gctgcgcaaa tacctgctgt ggattattac cggcatgtta    540
gtgatgtttg cgccgttctt tatttttatc ttcgggccac tgttacaata caacatttta    600
gtaggatcga ttgttggtgg tatttatcta ggcttttgtt ttaacgccgg tgcgccagca    660
gtagaggcat ttattgagaa agtcagccgt cgcagtaatt tcgaatttgg tcgcgcgcgg    720
atgtttggct gtgttggctg ggcgctgtgt gcctcgattg tcggcatcat gttcaccatc    780
aataatcagt ttgttttctg gctgggctct ggctgtgcac tcatcctcgc cgttttactc    840 ttttttcgcca aaacggatgc gccctcttct gccacggttg ccaatgcggt aggtgccaac    900
cattcggcat ttagccttaa gctggcactg gaactgttca gacagccaaa actgtggttt    960
ttgtcactgt atgttattgg cgtttcctgc acctacgatg ttttttgacca acagtttgct    1020 aatttctttta cttcgttctt tgctaccggt gaacagggta cgcgggtatt tggctacgta    1080
acgacaatgg gcgaattact taacgcctcg attatgttct ttgcgccact gatcattaat    1140
cgcatcggtg gaaaaacgc cctgctgctg ctggcactta tatgtctgt acgtattatt    1200 ggctcatcgt tcgccaccctc agcgctggaa gtggttattc tgaaaacgct gcatatgttt    1260
gaagtaccgt tcctgctggt gggctgcttt aaatatatta ccagccagtt tgaagtgcgt    1320
ttttcagcga cgatttatct ggtctgtttc tgcttcttta agcaactggc gatgattttt    1380
atgtctgtac tggcgggcaa tatgtatgaa agcatcggtt ccagggcgc ttatctggtg    1440 ctgggtctgg tggcgctggg cttcacctta atttccgtgt tcacgcttag cggccccggc    1500
ccgctttccc tgctgcgtcg tcaggtgaat gaagtcgctt aa    1542
```

<210> SEQ ID NO 34
<211> LENGTH: 1431
<212> TYPE: DNA
<213> ORGANISM: Artificial sequence
<220> FEATURE:
<223> OTHER INFORMATION: Heterologous sequences in front of a lactose transporter gene

<400> SEQUENCE: 34

```
cccgtcttac tgtcgggaat tcgcgttggc cgattcatac tacccataat gttcttgaca      60
tcttacaatc aatatggtat aataatttag ttagggccca agttcactta aaaaggagat     120
caacaatgaa agcaatttc gtactgaaac atcttaatca tgcgtaggat ttttctatg      180 tactatttaa aaacacaaa cttttggatg ttcggtttat tcttttttctt ttacttttt     240 atcatgggag cctacttccc gttttccccg atttggctac atgacatcaa ccatatcagc    300
aaaagtgata cgggtattat ttttgccgct atttctctgt tctcgctatt attccaaccg    360
ctgtttggtc tgctttctga caaactcggg ctgcgcaaat acctgctgtg gattattacc    420
ggcatgttag tgatgtttgc gccgttcttt attttatct tcgggccact gttacaatac    480
aacattttag taggatcgat tgttggtggt atttatctag gcttttgttt taacgccggt    540
gcgccagcag tagaggcatt tattgagaaa gtcagccgtc gcagtaattt cgaatttggt    600
cgcgcgcgga tgtttggctg tgttggctgg gcgctgtgtg cctcgattgt cggcatcatg    660
ttcaccatca ataatcagtt tgtttctgg ctgggctctg gctgtgcact catcctcgcc    720
gttttactct ttttcgccaa aacggatgcg ccctcttctg ccacggttgc caatgcggta    780
ggtgccaacc attcggcatt tagccttaag ctggcactgg aactgttcag acagccaaaa    840
ctgtggtttt tgtcactgta tgttattggc gtttcctgca cctacgatgt ttttgaccaa    900
cagtttgcta atttctttac ttcgttcttt gctaccggtg aacagggtac gcgggtattt    960
ggctacgtaa cgacaatggg cgaattactt aacgcctcga ttatgttctt tgcgccactg   1020
atcattaatc gcatcggtgg gaaaaacgcc ctgctgctgg ctggcactat tatgtctgta   1080
cgtattattg gctcatcgtt cgccacctca gcgctggaag tggttattct gaaaacgctg   1140
catatgtttg aagtaccgtt cctgctggtg ggctgcttta atatattac cagccagttt   1200 gaagtgcgtt tttcagcgac gatttatctg gtctgttttct gcttctttaa gcaactggcg   1260 atgatttta tgtctgtact ggcgggcaat atgtatgaaa gcatcggttt ccagggcgct   1320
tatctggtgc tgggtctggt ggcgctgggc ttcaccttaa tttccgtgtt cacgcttagc   1380
ggccccggcc cgctttccct gctgcgtcgt caggtgaatg aagtcgctta a           1431
```

<210> SEQ ID NO 35
<211> LENGTH: 1551
<212> TYPE: DNA
<213> ORGANISM: Artificial sequence
<220> FEATURE:
<223> OTHER INFORMATION: Heterologous sequences in front of a lactose transporter gene

<400> SEQUENCE: 35

```
cccgtcttac tgtcgggaat tcgcgttggc cgattcatta atggtataag gttcttgaca      60
tcttacaatc aatatggtat aataatttag ttagggccca agttcactta aaaaggagat     120
caacacttac tgtcgggaat tcgcgttggc caattaatta atggtataag gttcttgaca     180
tcttacaatc aatatggtat aataatttag ttagggccca agttcactta aaaaggagat     240
```

```
caacaatgaa agcaattttc gtactgaaac atcttaatca tgcgtaggat tttttctatg      300
tactatttaa aaaacacaaa cttttggatg ttcggtttat tcttttttct ttactttttt      360
atcatgggag cctacttccc gttttttccg atttggctac atgacatcaa ccatatcagc      420
aaaagtgata cgggtattat ttttgccgct atttctctgt tctcgctatt attccaaccg      480
ctgtttggtc tgcttttctga caaactcggg ctgcgcaaat acctgctgtg gattattacc      540
ggcatgttag tgatgtttgc gccgttcttt attttatct tcgggccact gttacaatac       600
aacattttag taggatcgat tgttggtggt atttatctag gcttttgttt taacgccggt       660
gcgccagcag tagaggcatt tattgagaaa gtcagccgtc gcagtaattt cgaatttggt       720
cgcgcgcgga tgtttggctg tgttggctgg gcgctgtgtg cctcgattgt cggcatcatg       780
ttcaccatca ataatcagtt tgttttctgg ctgggctctg gctgtgcact catcctcgcc       840
gttttactct ttttcgccaa aacgatgcg ccctcttctg ccacggttgc caatgcggta       900
ggtgccaacc attcggcatt tagccttaag ctggcactgg aactgttcag acagccaaaa       960
ctgtggtttt tgtcactgta tgttattggc gtttcctgca cctacgatgt ttttgaccaa      1020
cagtttgcta atttctttac ttcgttcttt gctaccggtg aacagggtac gcgggtatttt      1080 ggctacgtaa cgacaatggg cgaattactt aacgcctcga ttatgttctt tgcgccactg      1140
atcattaatc gcatcggtgg gaaaacgcc ctgctgctgg ctggcactat tatgtctgta       1200
cgtattattg gctcatcgtt cgccacctca gcgctggaag tggttattct gaaaacgctg      1260
catatgtttg aagtaccgtt cctgctggtg ggctgcttta aatatattac cagccagttt     1320
gaagtgcgtt tttcagcgac gatttatctg gtctgtttct gcttctttaa gcaactggcg     1380
atgattttta tgtctgtact ggcgggcaat atgtatgaaa gcatcggttt ccagggcgct      1440
tatctggtgc tgggtctggt ggcgctgggc ttcaccttaa tttccgtgtt cacgcttagc      1500
ggccccggcc cgctttccct gctgcgtcgt caggtgaatg aagtcgctta a              1551
```

<210> SEQ ID NO 36
<211> LENGTH: 1491
<212> TYPE: DNA
<213> ORGANISM: Artificial sequence
<220> FEATURE:
<223> OTHER INFORMATION: Heterologous sequences in front of a lactose
    transporter gene

<400> SEQUENCE: 36

```
cccgtcttac tgtcgggaat tcgcgttggc cgattcgaat tcgcgatggc cgattcgaat      60
tcgcgttggc cgattcgaat tcgcgttggc cgattcttac acgatatata cttcttgaca     120
ttttgcggga attatggtat aatcacaagg ttagggccca agttcactta aaaaggagat     180
caacaatgaa agcaattttc gtactgaaac atcttaatca tgcgtaggat tttttctatg     240
tactatttaa aaaacacaaa cttttggatg ttcggtttat tcttttttct ttactttttt     300
atcatgggag cctacttccc gttttttccg atttggctac atgacatcaa ccatatcagc     360
aaaagtgata cgggtattat ttttgccgct atttctctgt tctcgctatt attccaaccg     420
ctgtttggtc tgcttttctga caaactcggg ctgcgcaaat acctgctgtg gattattacc     480
ggcatgttag tgatgtttgc gccgttcttt attttatct tcgggccact gttacaatac      540
aacattttag taggatcgat tgttggtggt atttatctag gcttttgttt taacgccggt      600
gcgccagcag tagaggcatt tattgagaaa gtcagccgtc gcagtaattt cgaatttggt      660
cgcgcgcgga tgtttggctg tgttggctgg gcgctgtgtg cctcgattgt cggcatcatg      720
```

-continued

```
ttcaccatca ataatcagtt tgttttctgg ctgggctctg gctgtgcact catcctcgcc      780
gttttactct ttttcgccaa aacggatgcg ccctcttctg ccacggttgc caatgcggta      840
ggtgccaacc attcggcatt tagccttaag ctggcactgg aactgttcag acagccaaaa     900
ctgtggtttt tgtcactgta tgttattggc gtttcctgca cctacgatgt ttttgaccaa      960
cagtttgcta atttctttac ttcgttcttt gctaccggtg aacagggtac gcgggtattt     1020
ggctacgtaa cgacaatggg cgaattactt aacgcctcga ttatgttctt tgcgccactg     1080
atcattaatc gcatcggtgg gaaaaacgcc ctgctgctgg ctggcactat tatgtctgta     1140
cgtattattg gctcatcgtt cgccacctca gcgctggaag tggttattct gaaaacgctg     1200
catatgtttg aagtaccgtt cctgctggtg ggctgcttta aatatattac cagccagttt     1260
gaagtgcgtt tttcagcgac gatttatctg gtctgtttct gcttcttaa gcaactggcg      1320 atgattttta tgtctgtact ggcgggcaat atgtatgaaa gcatcggttt ccagggcgct     1380
tatctggtgc tgggtctggt ggcgctgggc ttcaccttaa tttccgtgtt cacgcttagc     1440
ggccccggcc cgcttccct gctgcgtcgt caggtgaatg aagtcgctta a               1491
```

<210> SEQ ID NO 37
<211> LENGTH: 1405
<212> TYPE: DNA
<213> ORGANISM: Artificial sequence
<220> FEATURE:
<223> OTHER INFORMATION: Heterologous sequences in front of a lactose transporter gene

<400> SEQUENCE: 37

```
cccgtcttac tgtcgggaat tcgcgttggc caattaatta atggtataag gttcttgaca       60
tcttacaggg cccaagttca cttaaaaagg agatcaacaa tgaaagcaat tttcgtactg      120
aaacatctta atcatgcgta ggattttttc tatgtactat ttaaaaaaca caaacttttg      180
gatgttcggt ttattctttt tcttttactt tttatcatg ggagcctact tcccgttttt       240
cccgatttgg ctacatgaca tcaaccatat cagcaaaagt gatacgggta ttattttgc       300 cgctatttct ctgttctcgc tattattcca accgctgttt ggtctgcttt ctgacaaact      360
cgggctgcgc aaatacctgc tgtggattat taccggcatg ttagtgatgt ttgcgccgtt      420
ctttattttt atcttcgggc cactgttaca atacaacatt ttagtaggat cgattgttgg     480
tggtatttat ctaggcttt gttttaacgc cggtgcgcca gcagtagagg catttattga      540
gaaagtcagc cgtcgcagta atttcgaatt tggtcgcgcg cggatgtttg gctgtgttgg      600
ctgggcgctg tgtgcctcga ttgtcggcat catgttcacc atcaataatc agtttgtttt      660
ctggctgggc tctggctgtg cactcatcct cgccgtttta ctcttttcg ccaaaacgga      720 tgcgccctct tctgccacgg ttgccaatgc ggtaggtgcc aaccattcgg catttagcct     780
taagctggca ctggaactgt tcagacagcc aaaactgtgg ttttgtcac tgtatgttat      840 tggcgtttcc tgcacctacg atgttttga ccaacagttt gctaatttct ttacttcgtt     900
ctttgctacc ggtgaacagg gtacgcgggt atttggctac gtaacgacaa tgggcgaatt     960
acttaacgcc tcgattatgt tctttgcgcc actgatcatt aatcgcatcg gtgggaaaaa     1020
cgccctgctg ctggctggca ctattatgtc tgtacgtatt attggctcat cgttcgccac     1080
ctcagcgctg gaagtggtta ttctgaaaac gctgcatatg tttgaagtac cgttcctgct     1140
ggtgggctgc tttaaatata ttaccagcca gtttgaagtg cgttttcag cgacgattta      1200 tctggtctgt ttctgcttct ttaagcaact ggcgatgatt tttatgtctg tactggcggg     1260
```

```
caatatgtat gaaagcatcg gtttccaggg cgcttatctg gtgctgggtc tggtggcgct    1320
gggcttcacc ttaatttccg tgttcacgct tagcggcccc ggcccgcttt ccctgctgcg    1380
tcgtcaggtg aatgaagtcg cttaa                                          1405
```

<210> SEQ ID NO 38
<211> LENGTH: 1491
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 38

```
cccgtcttac tgtcgggaat tcgcgttggc cgattcgaat tcgcgttggc cgattcgaat      60
tcgcgttggc cgattcgaat tcgcgttggc cgattcttac acgatatata cttcttgaca     120
ttttgcggga attatggtat aatcacaagg ttagggccca agttcactta aaaaggagat     180
caacaatgaa agcaattttc gtactgaaac atcttaatca tgcgtaggat ttttctatg     240 tactatttaa aaacacaaa cttttggatg ttcggtttat tctttttctt ttactttttt     300
atcatgggag cctacttccc gttttccccg atttggctac atgacatcaa ccatatcagc     360
aaaagtgata cgggtattat ttttgccgct atttctctgt tctcgctatt attccaaccg     420
ctgtttggtc tgctttctga caaactcggg ctgcgcaaat acctgctgtg gattattacc     480
ggcatgttag tgatgtttgc gccgttcttt atttttatct tcgggccact gttacaatac     540
aacattttag taggatcgat tgttggtggt atttatctag gcttttgttt taacgccggt     600
gcgccagcag tagaggcatt tattgagaaa gtcagccgtc gcagtaattt cgaatttggt     660
cgcgcgcgga tgtttggctg tgttggctgg gcgctgtgtg cctcgattgt cggcatcatg     720
ttcaccatca ataatcagtt tgtttctgg ctgggctctg gctgtgcact catcctcgcc     780
gttttactct ttttcgccaa aacggatgcg ccctcttctg ccacggttgc caatgcggta     840
ggtgccaacc attcggcatt tagccttaag ctggcactgg aactgttcag acagccaaaa     900
ctgtggtttt tgtcactgta tgttattggc gtttcctgca cctacgatgt ttttgaccaa     960
cagtttgcta atttctttac ttcgttcttt gctaccggtg aacagggtac gcgggtattt    1020
ggctacgtaa cgacaatggg cgaattactt aacgcctcga ttatgttctt gcgccactg    1080 atcattaatc gcatcggtgg gaaaaacgcc ctgctgctgg ctggcactat tatgtctgta    1140
cgtattattg gctcatcgtt cgccacctca gcgctggaag tggttattct gaaaacgctg    1200
catatgtttg aagtaccgtt cctgctggtg ggctgcttta atatattac cagccagttt    1260 gaagtgcgtt tttcagcgac gatttatctg gtctgtttct gcttctttaa gcaactggcg    1320 atgatttta tgtctgtact ggcgggcaat atgtatgaaa gcatcggttt ccagggcgct    1380
tatctggtgc tgggtctggt ggcgctgggc ttcaccttaa tttccgtgtt cacgcttagc    1440
ggccccggcc cgctttcccct gctgcgtcgt caggtgaatg aagtcgctta a            1491
```

<210> SEQ ID NO 39
<211> LENGTH: 2116
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 39

```
cctgagtcgc tgtcttttc gtgacattca gttcgctgcg ctcacggctc tggcagtgaa      60
```

```
tgggggtaaa tggcactaca ggcgccttt  atggattcat gcaaggaaac tacccataat    120
acaagaaaag cccgtcacgg gcttctcagg gcgttttatg gcgggtctgc tatgtggtgc    180
tatctgactt tttgctgttc agcagttcct gccctctgat tttccagtct gaccacttcg    240
gattatcccg tgacaggtca ttcagactgg ctaatgcacc cagtaaggca gcggtatcat    300
caacaggctt acccgtctta ctgtcgggaa ttcgcgttgg ccgattcatt aatggtataa    360
ggttcttgac atcttacaat caatatggta taataattta gttagggccc aagttcactt    420
aaaaaggaga tcaacaatga aagcttactg tcgggaattc gcgttggccg attcattaat    480
ggtataaggt tcttgacatc ttacaatcaa tatggtataa taatttagtt agggcccaag    540
ttcacttaaa aaggagatca acaatgaaag cttactgtcg ggaattcgcg ttggccgatt    600
cattaatggt ataaggttct tgacatctta caatcaatat ggtataataa tttagttagg    660
gcccaagttc acttaaaaag gagatcaaca cttactgtcg ggaattcgcg ttggccaatt    720
aattaatggt ataaggttct tgacatctta caatcaatat ggtataataa tttagttagg    780
gcccaagttc acttaaaaag gagatcaaca atgaaagcaa ttttcgtact gaaacatctt    840
aatcatgcgt aggatttttt ctatgtacta tttaaaaaac acaaactttt ggatgttcgg    900
tttattcttt ttctttttact ttttatcat gggagcctac ttcccgtttt tcccgatttg    960
gctacatgac atcaaccata tcagcaaaag tgatacgggt attattttg ccgctatttc   1020 tctgttctcg ctattattcc aaccgctgtt tggtctgctt tctgacaaac tcgggctgcg   1080
caaatacctg ctgtggatta ttaccggcat gttagtgatg tttgcgccgt tctttatttt   1140
tatcttcggg ccactgttac aatacaacat tttagtagga tcgattgttg gtggtattta   1200
tctaggcttt tgttttaacg ccggtgcgcc agcagtagag gcatttattg agaaagtcag   1260
ccgtcgcagt aatttcgaat tggtcgcgc gcggatgttt ggctgtgttg gctgggcgct   1320
gtgtgcctcg attgtcggca tcatgttcac catcaataat cagtttgttt ctggctggg   1380 ctctggctgt gcactcatcc tcgccgtttt actctttttc gccaaaacgg atgcgccctc   1440
ttctgccacg gttgccaatg cggtaggtgc caaccattcg gcatttagcc ttaagctggc   1500
actggaactg ttcagacagc caaaactgtg gttttgtca ctgtatgtta ttggcgtttc   1560
ctgcacctac gatgttttg accaacagtt tgctaatttc tttacttcgt tctttgctac   1620
cggtgaacag ggtacgcggg tatttggcta cgtaacgaca atgggcgaat acttaacgc   1680 ctcgattatg ttctttgcgc cactgatcat taatcgcatc ggtgggaaaa acgccctgct   1740
gctggctggc actattatgt ctgtacgtat tattggctca tcgttcgcca cctcagcgct   1800
ggaagtggtt attctgaaaa cgctgcatat gtttgaagta ccgttcctgc tggtgggctg   1860
ctttaaatat attaccagcc agtttgaagt gcgttttca gcgacgattt atctggtctg   1920
tttctgcttc tttaagcaac tggcgatgat ttttatgtct gtactggcgg gcaatatgta   1980
tgaaagcatc ggtttccagg gcgcttatct ggtgctgggt ctggtggcgc tgggcttcac   2040
cttaatttcc gtgttcacgc ttagcggccc cggcccgctt tccctgctgc gtcgtcaggt   2100
gaatgaagtc gcttaa                                                  2116
```

<210> SEQ ID NO 40
<211> LENGTH: 2122
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 40

```
tgtctttttc gtgacattca gttcgctgcg ctcacggctc tggcagtgaa tgggggtaaa    60
tggcactaca ggcgcctttt atggattcat gcaaggaaac tacccataat acaagaaaag   120
cccgtcacgg gcttctcagg gcgttttatg gcgggtctgc tatgtggtgc tatctgactt   180
tttgctgttc agcagttcct gccctctgat tttccagtct gaccacttcg gattatcccg   240
tgacaggtca ttcagactgg ctaatgcacc cagtaaggca gcggtatcat caacaggctt   300
acccgtctta ctgtcgggaa ttcgcgttgg ccgattcatt aatggtataa ggttcttgac   360
atcttacaat caatatggta taataattta gttagggccc aagttcactt aaaaaggaga   420
tcaacaatga agcttactg tcgggaattc gcgttggccg attcattaat ggtataaggt   480
tcttgacatc ttacaatcaa tatggtataa taatttagtt agggcccaag ttcacttaaa   540
aaggagatca acaatgaaag cactgtcggg aattcgcgtt ggccgattca ttaatggtat   600
aaggttcttg acatcttaca atcaatatgg tataataatt tagttagggc ccaagttcac   660
ttaaaaagga gatcaacaat gaaagcttac tgtcgggaat tcgcgttggc cgattcatta   720
atggtataag gttcttgaca tcttacaatc aatatggtat aataatttag ttagggccca   780
agttcactta aaaaggagat caacacttta ctgtcgggga attcgccgtt gggccaattt   840
aattaatggg tataagggtt ccttgacaat gtactattta aaaacacaa acttttggat   900
gttcggttta ttctttttct tttacttttt tatcatggga gcctacttcc gttttttccc   960
gatttggcta catgacatca accatatcag caaaagtgat acgggtatta ttttttgccgc  1020
tatttctctg ttctcgctat tattccaacc gctgtttggt ctgctttctg acaaactcgg  1080
gctgcgcaaa tacctgctgt ggattattac cggcatgtta gtgatgtttg cgccgttctt  1140
tattttatc ttcgggccac tgttacaata caacatttta gtaggatcga ttgttggtgg  1200
tatttatcta ggcttttgtt ttaacgccgg tgcgccagca gtagaggcat ttattgagaa  1260
agtcagccgt cgcagtaatt tcgaatttgg tcgcgcgcgg atgtttggct gtgttggctg  1320
ggcgctgtgt gcctcgattg tcggcatcat gttcaccatc aataatcagt ttgttttctg  1380
gctgggctct ggctgtgcac tcatcctcgc cgttttactc ttttttcgcca aaacggatgc  1440
gccctcttct gccacggttg ccaatgcggt aggtgccaac cattcggcat ttagccttaa  1500
gctggcactg gaactgttca gacagccaaa actgtggttt ttgtcactgt atgttattgg  1560
cgtttcctgc acctacgatg ttttttgacca acagtttgct aatttcttta cttcgttctt  1620
tgctaccggt gaacagggta cgcgggtatt tggctacgta acgacaatgg gcgaattact  1680
taacgcctcg attatgttct ttgcgccact gatcattaat cgcatcggtg ggaaaaacgc  1740
cctgctgctg gctggcacta ttatgtctgt acgtattatt ggctcatcgt tcgccacctc  1800
agcgctggaa gtggttattc tgaaaacgct gcatatgttt gaagtaccgt tcctgctggt  1860
gggctgcttt aaatatatta ccagccagtt tgaagtgcgt ttttcagcga cgatttatct  1920
ggtctgtttc tgcttctttta agcaactggc gatgattttt atgtctgtac tggcgggcaa  1980
tatgtatgaa agcatcggtt tccagggcgc ttatctggtg ctgggtctgg tggcgctggg  2040
cttcaccta atttccgtgt tcacgcttag cggccccggc ccgctttccc tgctgcgtcg  2100
tcaggtgaat gaagtcgctt aa                                            2122
```

<210> SEQ ID NO 41
<211> LENGTH: 2130
<212> TYPE: DNA

<213> ORGANISM: Artificial sequence
<220> FEATURE:
<223> OTHER INFORMATION: Heterologous sequences in front of a lactose
      transporter gene

<400> SEQUENCE: 41

| | | | | | |
|---|---|---|---|---|---|
| tcgctgtctt | tttcgtgaca | ttcagttcgc | tgcgctcacg | gctctggcag | tgaatggggg | 60 |
| taaatggcac | tacaggcgcc | ttttatggat | tcatgcaagg | aaactaccca | taatacaaga | 120 |
| aaagcccgtc | acgggcttct | cagggcgttt | tatggcgggt | ctgctatgtg | gtgctatctg | 180 |
| acttttgct | gttcagcagt | tcctgccctc | tgattttcca | gtctgaccac | ttcggattat | 240 |
| cccgtgacag | gtcattcaga | ctggctaatg | cacccagtaa | ggcagcggta | tcatcaacag | 300 |
| gcttacccgt | cttactgtcg | ggaattcgcg | ttggccgatt | cattaatggt | ataaggttct | 360 |
| tgacatctta | caatcaatat | ggtataataa | tttagttagg | gcccaagttc | acttaaaaag | 420 |
| gagatcaaca | atgaaagctt | actgtcggga | attcgcgttg | gccgattcat | taatggtata | 480 |
| aggttcttga | catcttacaa | tcaatatggt | ataataattt | agttagggcc | caagttcact | 540 |
| taaaaggag | atcaacaatg | aaagcactgt | cgggaattcg | cgttggccga | ttcattaatg | 600 |
| gtataagggt | cttgacatct | tacaatcaat | atggtataat | aatttaggta | ggggccaagt | 660 |
| tcacttagaa | aggagatcaa | caatgaaagc | ttactgtcgg | gaattcgcgt | tggccgattc | 720 |
| attaatggta | taaggttctt | gacatcttac | aatctatatg | gtatcataat | atacttaggg | 780 |
| cccaagttca | cttaaaaagg | agatcaacac | ttactgtcgc | gaattcgcgt | tggccaatta | 840 |
| attcatggta | taaggttctt | gacatcttac | aatcaaatgt | actatttaaa | aaacacaaac | 900 |
| ttttggatgt | tcggtttatt | cttttctt | tactttttta | tcatgggagc | ctacttcccg | 960 |
| tttttcccga | tttggctaca | tgacatcaac | catatcagca | aaagtgatac | gggtattatt | 1020 |
| tttgccgcta | tttctctgtt | ctcgctatta | ttccaaccgc | tgtttggtct | gctttctgac | 1080 |
| aaactcgggc | tgcgcaaata | cctgctgtgg | attattaccg | gcatgttagt | gatgtttgcg | 1140 |
| ccgttcttta | ttttatctt | cgggccactg | ttacaataca | acatttttagt | aggatcgatt | 1200 |
| gttggtggta | tttatctagg | cttttgtttt | aacgccggtg | cgccagcagt | agaggcattt | 1260 |
| attgagaaag | tcagccgtcg | cagtaatttc | gaatttggtc | gcgcgcggat | gtttggctgt | 1320 |
| gttggctggg | cgctgtgtgc | ctcgattgtc | ggcatcatgt | tcaccatcaa | taatcagttt | 1380 |
| gttttctggc | tgggctctgg | ctgtgcactc | atcctcgccg | ttttactctt | tttcgccaaa | 1440 |
| acggatgcgc | cctcttctgc | cacggttgcc | aatgcggtag | gtgccaacca | ttcggcattt | 1500 |
| agccttaagc | tggcactgga | actgttcaga | cagccaaaac | tgtggttttt | gtcactgtat | 1560 |
| gttattggcg | tttcctgcac | ctacgatgtt | tttgaccaac | agtttgctaa | tttctttact | 1620 |
| tcgttctttg | ctaccggtga | acagggtacg | cgggtatttg | gctacgtaac | gacaatgggc | 1680 |
| gaattactta | acgcctcgat | tatgttcttt | gcgccactga | tcattaatcg | catcggtggg | 1740 |
| aaaaacgccc | tgctgctggc | tggcactatt | atgtctgtac | gtattattgg | ctcatcgttc | 1800 |
| gccacctcag | cgctggaagt | ggttattctg | aaaacgctgc | atatgtttga | agtaccgttc | 1860 |
| ctgctggtgg | gctgctttaa | atatattacc | agccagtttg | aagtgcgttt | ttcagcgacg | 1920 |
| atttatctgg | tctgtttctg | cttcttaag | caactggcga | tgattttat | gtctgtactg | 1980 |
| gcgggcaata | tgtatgaaag | catcggtttc | cagggcgctt | atctggtgct | gggtctggtg | 2040 |
| gcgctgggct | tcaccttaat | ttccgtgttc | acgcttagcg | gccccggccc | gctttccctg | 2100 |
| ctgcgtcgtc | aggtgaatga | agtcgcttaa | | | | 2130 |

<210> SEQ ID NO 42
<211> LENGTH: 1865
<212> TYPE: DNA
<213> ORGANISM: Artificial sequence
<220> FEATURE:
<223> OTHER INFORMATION: Heterologous sequences in front of a lactose transporter gene

<400> SEQUENCE: 42

| | | | | | |
|---|---|---|---|---|---|
| gcccgtcacg | ggcttctcag | ggcgttttat | ggcgggtctg | ctatgtggtg | ctatctgact | 60 |
| ttttgctgtt | cagcagttcc | tgccctctga | ttttccagtc | tgaccacttc | ggattatccc | 120 |
| gtgacaggtc | attcagactg | gctaatgcac | ccagtaaggc | agcggtatca | tcaacaggct | 180 |
| tacccgtctt | actgtcggga | attcgcgttg | gccgattcat | taatggtata | aggttcttga | 240 |
| catcttacaa | tcaatatggt | ataataattt | agtagggcc | caagttcact | taaaaaggag | 300 |
| atcaacaatg | aaagcttact | gtcgggaatt | cgcgttggcc | gattcattaa | tggtataagg | 360 |
| ttcttgacat | cttacaatca | atatggtata | ataatttagt | tagggcccaa | gttcacttaa | 420 |
| aaaggagatc | aacaatgaaa | gcactgtcgg | gaattcgcgt | tggccaatta | ttaatggta | 480 |
| taaggttctt | gacatcttac | aatcaatatg | gtataataat | ttagttaggg | cccaagttca | 540 |
| cttaaaaagg | agatcaacaa | tgaaagcaat | tttcgtactg | aaacatctta | atcatgcgta | 600 |
| ggatttttc | tatgtactat | ttaaaaaaca | caaacttttg | gatgttcggt | ttattctttt | 660 |
| tcttttactt | ttttatcatg | ggagcctact | tcccgttttt | cccgatttgg | ctacatgaca | 720 |
| tcaaccatat | cagcaaaagt | gatacgggta | tttttttgc | cgctatttct | ctgttctcgc | 780 |
| tattattcca | accgctgttt | ggtctgcttt | ctgacaaact | cgggctgcgc | aaatacctgc | 840 |
| tgtggattat | taccggcatg | ttagtgatgt | ttgcgccgtt | cttatttt | atcttcgggc | 900 |
| cactgttaca | atacaacatt | ttagtaggat | cgattgttgg | tggtatttat | ctaggcttt | 960 |
| gttttaacgc | cggtgcgcca | gcagtagagg | catttattga | aaagtcagc | cgtcgcagta | 1020 |
| atttcgaatt | tggtcgcgcg | cggatgtttg | gctgtgttgg | ctgggcgctg | tgtgcctcga | 1080 |
| ttgtcggcat | catgttcacc | atcaataatc | agtttgtttt | ctggctgggc | tctggctgtg | 1140 |
| cactcatcct | cgccgtttta | ctcttttcg | ccaaaacgga | tgcgccctct | tctgccacgg | 1200 |
| ttgccaatgc | ggtaggtgcc | aaccattcgg | catttagcct | taagctggca | ctggaactgt | 1260 |
| tcagacagcc | aaaactgtgg | ttttttgtcac | tgtatgttat | tggcgtttcc | tgcacctacg | 1320 |
| atgttttga | ccaacagttt | gctaatttct | ttacttcgtt | ctttgctacc | ggtgaacagg | 1380 |
| gtacgcgggt | atttggctac | gtaacgacaa | tgggcgaatt | acttaacgcc | tcgattatgt | 1440 |
| tctttgcgcc | actgatcatt | aatcgcatcg | gtgggaaaaa | cgccctgctg | ctggctggca | 1500 |
| ctattatgtc | tgtacgtatt | attggctcat | cgttcgccac | ctcagcgctg | gaagtggtta | 1560 |
| ttctgaaaac | gctgcatatg | tttgaagtac | cgttcctgct | ggtgggctgc | tttaaatata | 1620 |
| ttaccagcca | gtttgaagtg | cgttttcag | cgacgattta | tctggtctgt | ttctgcttct | 1680 |
| ttaagcaact | ggcgatgatt | tttatgtctg | tactggcggg | caatatgtat | gaaagcatcg | 1740 |
| gtttccaggg | cgcttatctg | gtgctgggtc | tggtggcgct | gggcttcacc | ttaatttccg | 1800 |
| tgttcacgct | tagcggcccc | ggcccgcttt | ccctgctgcg | tcgtcaggtg | aatgaagtcg | 1860 |
| cttaa | | | | | 1865 |

<210> SEQ ID NO 43
<211> LENGTH: 1802
<212> TYPE: DNA

<213> ORGANISM: Artificial sequence
<220> FEATURE:
<223> OTHER INFORMATION: Heterologous sequences in front of a lactose transporter gene

<400> SEQUENCE: 43

```
gctgttcagc agttcctgcc ctctgatttt ccagtctgac cacttcggat tatcccgtga    60
caggtcattc agactggcta atgcacccag taaggcagcg gtatcatcaa caggcttacc   120
cgtcttactg tcgggaattc gcgttggccg attcattaat ggtataaggt tcttgacatc   180
ttacaatcaa tatggtataa taatttagtt agggcccaag ttcacttaaa aaggagatca   240
acaatgaaag cttactgtcg ggaattcgcg ttggccgatt cattaatggt ataaggttct   300
tgacatctta caatcaatat gggtataata atttagttag ggcccaagtt cacttaaaaa   360
ggagatcaac aatgaaagca ctgtcgggaa ttcgcgttgg ccgattcatt aatggtataa   420
ggttcttgac atcttacaat caatatggta taataattta gttagggccc aagttcactt   480
aaaaaggaga tcaacaatga agcaattttc gtactgaaa catcttaatc atgcgtagga   540
tttttctat gtactattta aaaacacaa acttttggat gttcggttta ttcttttct   600
tttactttt tatcatggga gcctacttcc cgttttccc gatttggcta catgacatca   660
accatatcag caaaagtgat acgggtatta ttttgccgc tatttctctg ttctcgctat   720
tattccaacc gctgtttggt ctgctttctg acaaactcgg gctgcgcaaa tacctgctgt   780
ggattattac cggcatgtta gtgatgtttg cgccgttctt tattttatc ttcgggccac   840
tgttacaata caacatttta gtaggatcga ttgttggtgg tatttatcta ggcttttgtt   900
ttaacgccgg tgcgccagca gtagaggcat ttattgagaa agtcagccgt cgcagtaatt   960
tcgaatttgg tcgcgcgcgg atgtttggct gtgttggctg ggcgctgtgt gcctcgattg  1020
tcggcatcat gttcaccatc aataatcagt ttgttttctg gctgggctct ggctgtgcac  1080
tcatcctcgc cgttttactc tttttcgcca aaacggatgc gccctcttct gccacggttg  1140
ccaatgcggt aggtgccaac cattcggcat ttagccttaa gctggcactg gaactgttca  1200
gacagccaaa actgtggttt ttgtcactgt atgttattgg cgtttcctgc acctacgatg  1260
tttttgacca acagtttgct aatttcttta cttcgttctt tgctaccggt gaacagggta  1320
cgcgggtatt tggctacgta acgacaatgg gcgaattact taacgcctcg attatgttct  1380
ttgcgccact gatcattaat cgcatcggtg ggaaaaacgc cctgctgctg ctggcacta  1440
ttatgtctgt acgtattatt ggctcatcgt tcgccacctc agcgctggaa gtggttattc  1500
tgaaaacgct gcatatgttt gaagtaccgt tcctgctggt gggctgcttt aaatatatta  1560
ccagccagtt tgaagtgcgt ttttcagcga cgatttatct ggtctgtttc tgcttcttta  1620
agcaactggc gatgattttt atgtctgtac tggcgggcaa tatgtatgaa agcatcggtt  1680
tccagggcgc ttatctggtg ctgggtctgg tggcgctggg cttcaccta atttccgtgt  1740
tcacgcttag cggccccggc ccgctttccc tgctgcgtcg tcaggtgaat gaagtcgctt  1800
aa                                                                 1802
```

<210> SEQ ID NO 44
<211> LENGTH: 2245
<212> TYPE: DNA
<213> ORGANISM: Artificial sequence
<220> FEATURE:
<223> OTHER INFORMATION: Heterologous sequences in front of a lactose transporter gene

<400> SEQUENCE: 44

```
ggcacctgag tcgctgtctt tttcgtgaca ttcagttcgc tgcgctcacg gctctggcag      60
tgaatggggg taaatggcac tacaggcgcc ttttatggat tcatgcaagg aaactaccca     120
taatacaaga aaagcccgtc acgggcttct cagggcgttt tatggcgggt ctgctatgtg     180
gtgctatctg acttttttgct gttcagcagt tcctgccctc tgattttcca gtctgaccac    240
ttcggattat cccgtgacag gtcattcaga ctggctaatg cacccagtaa ggcagcggta     300
tcatcaacag gcttacccgt cttactgtcg ggaattcgcg ttggccgatt cattaatggt     360
ataaggttct tgacatctta caatcaatat ggtataataa tttagttagg gcccaagttc     420
acttaaaaag gagatcaaca atgaaagctt actgtcggga attcgcgttg ccgattcat      480 taatggtata aggttcttga catcttacaa tcaatatggt ataataattt agttagggcc     540
caagttcact aaaaaggag atcaacaatg aaagcactgt cgggaattcg cgttggccga      600
ttcattaatg gtataaggtt cttgacatct acaatcaat atggtataat aatttagtta      660
gggcccaagt tcacttaaaa aggagatcaa caatgaaagc ttactgtcgg gaattcgcgt     720
tggccgattc attaatggta aaggttcttt gacatcttac aatcaatatg gtataataat     780
ttagttaggg cccaagttca cttaaaaagg agatcaacac ttactgtcgg gaattcgcgt     840
tggccaatta attaatggta aaggttcttt gacatcttac aatcaatatg gtataataat     900
ttagttaggg cccaagttca cttaaaaagg agatcaacaa tgaaagcaat tttcgtactg     960
aaacatctta atcatgcgta ggattttttc tatgtactat ttaaaaaaca caaacttttg    1020
gatgttcggt ttattcttt tctttactt ttttatcatg ggagcctact tcccgttttt     1080
cccgatttgg ctacatgaca tcaaccatat cagcaaaagt gatacgggta ttattttgc     1140 cgctatttct ctgttctcgc tattattcca accgctgttt ggtctgcttt ctgacaaact    1200
cgggctgcgc aaatacctgc tgtggattat taccggcatg ttagtgatgt ttgcgccgtt    1260
ctttattttt atcttcgggc cactgttaca atacaacatt ttagtaggat cgattgttgg    1320
tggtatttat ctaggctttt gttttaacgc cggtgcgcca gcagtagagg catttattga    1380
gaaagtcagc cgtcgcagta atttcgaatt tggtcgcgcg cggatgtttg gctgtgttgg    1440
ctgggcgctg tgtgcctcga ttgtcggcat catgttcacc atcaataatc agtttgtttt    1500
ctggctgggc tctggctgtg cactcatcct cgccgtttta ctcttttcg ccaaaacgga     1560 tgcgccctct tctgccacgg ttgccaatgc ggtaggtgcc aaccattcgg catttagcct    1620
taagctggca ctggaactgt tcagacagcc aaaactgtgg ttttgtcac tgtatgttat     1680 tggcgtttcc tgcacctacg atgttttga ccaacagttt gctaatttct ttacttcgtt      1740
ctttgctacc ggtgaacagg gtacgcgggt atttggctac gtaacgacaa tgggcgaatt    1800
acttaacgcc tcgattatgt tctttgcgcc actgatcatt aatcgcatcg gtgggaaaaa    1860
cgccctgctg ctggctggca ctattatgtc tgtacgtatt attggctcat cgttcgccac    1920
ctcagcgctg gaagtggtta ttctgaaaac gctgcatatg tttgaagtac cgttcctgct    1980
ggtgggctgc tttaaatata ttaccagcca gtttgaagtg cgttttcag cgacgattta     2040 tctggtctgt ttctgcttct taagcaact ggcgatgatt tttatgtctg tactggcggg     2100
caatatgtat gaaagcatcg gtttccaggg cgcttatctg gtgctgggtc tggtggcgct    2160
gggcttcacc ttaatttccg tgttcacgct tagcggcccc ggcccgcttt cctgctgcg     2220 tcgtcaggtg aatgaagtcg cttaa                                           2245
```

<210> SEQ ID NO 45

<211> LENGTH: 2029
<212> TYPE: DNA
<213> ORGANISM: Artificial sequence
<220> FEATURE:
<223> OTHER INFORMATION: Heterologous sequences in front of a lactose transporter gene

<400> SEQUENCE: 45

| | | | | | |
|---|---|---|---|---|---|
| gcaaggaaac | tacccataat | acaagaaaag | cccgtcacgg | gcttctcagg | gcgttttatg | 60 |
| gcgggtctgc | tatgtggtgc | tatctgactt | tttgctgttc | agcagttcct | gccctctgat | 120 |
| tttccagtct | gaccacttcg | gattatcccg | tgacaggtca | ttcagactgg | ctaatgcacc | 180 |
| cagtaaggca | gcggtatcat | caacaggctt | acccgtctta | ctgtcgggaa | ttcgcgttgg | 240 |
| ccgattaatt | aatggtataa | ggttcttgac | atcttacaat | caatatggta | taataattta | 300 |
| gttagggccc | aagttcactt | aaaaaggaga | tcaacaatga | aagcttactg | tcgggaattc | 360 |
| gcgttggccg | attcattaat | ggtataaggt | tcttgacatc | ttacaatcaa | tatggtataa | 420 |
| taatttagtt | agggcccaag | ttcacttaaa | aaggagatca | acaatgaaag | caggcttacc | 480 |
| cgtcttactg | tcgggaattc | gcgttggccg | attcattaat | ggtataaggt | tcttgacatc | 540 |
| ttacaatcaa | tatggtataa | taatttagtt | agggcccaag | ttcacttaaa | aaggagatca | 600 |
| acacttactg | tcgggaattc | gcgttggcca | attaattaat | ggtataaggt | tcttgacatc | 660 |
| ttacaatcaa | tatggtataa | taatttagtt | agggcccaag | ttcacttaaa | aaggagatca | 720 |
| acaatgaaag | caattttcgt | actgaaacat | cttaatcatg | cgtaggattt | tttctatgta | 780 |
| ctatttaaaa | aacacaaact | tttggatgtt | cggtttattc | tttttctttt | acttttttat | 840 |
| catgggagcc | tacttcccgt | ttttcccgat | ttggctacat | gacatcaacc | atatcagcaa | 900 |
| aagtgatacg | gtattatttt | tgccgctat | ttctctgttc | tcgctattat | tccaaccgct | 960 |
| gtttggtctg | ctttctgaca | aactcgggct | gcgcaaatac | ctgctgtgga | ttattaccgg | 1020 |
| catgttagtg | atgtttgcgc | cgttctttat | ttttatcttc | gggccactgt | tacaatacaa | 1080 |
| cattttagta | ggatcgattg | ttggtggtat | ttatctaggc | ttttgttta | acgccggtgc | 1140 |
| gccagcagta | gaggcattta | ttgagaaagt | cagccgtcgc | agtaatttcg | aatttggtcg | 1200 |
| cgcgcggatg | tttggctgtg | ttggctgggc | gctgtgtgcc | tcgattgtcg | gcatcatgtt | 1260 |
| caccatcaat | aatcagtttg | ttttctggct | gggctctggc | tgtgcactca | tcctcgccgt | 1320 |
| tttactcttt | ttcgccaaaa | cggatgcgcc | ctcttctgcc | acggttgcca | atgcggtagg | 1380 |
| tgccaaccat | tcggcattta | gccttaagct | ggcactggaa | ctgttcagac | agccaaaact | 1440 |
| gtggttttg | tcactgtatg | ttattggcgt | tcctgcacc | tacgatgttt | ttgaccaaca | 1500 |
| gtttgctaat | ttctttactt | cgttctttgc | taccggtgaa | cagggtacgc | gggtatttgg | 1560 |
| ctacgtaacg | acaatgggcg | aattacttaa | cgcctcgatt | atgttctttg | cgccactgat | 1620 |
| cattaatcgc | atcggtggga | aaaacgccct | gctgctggct | ggcactatta | tgtctgtacg | 1680 |
| tattattggc | tcatcgttcg | ccacctcagc | gctggaagtg | gttattctga | aaacgctgca | 1740 |
| tatgtttgaa | gtaccgttcc | tgctggtggg | ctgctttaaa | tatattacca | gccagtttga | 1800 |
| agtgcgtttt | tcagcgacga | tttatctggt | ctgtttctgc | ttctttaagc | aactggcgat | 1860 |
| gattttatg | tctgtactgg | cgggcaatat | gtatgaaagc | atcggtttcc | agggcgctta | 1920 |
| tctggtgctg | ggtctggtgg | cgctgggctt | caccttaatt | tccgtgttca | cgcttagcgg | 1980 |
| ccccggcccg | ctttccctgc | tgcgtcgtca | ggtgaatgaa | gtcgcttaa | | 2029 |

<210> SEQ ID NO 46

<211> LENGTH: 2088
<212> TYPE: DNA
<213> ORGANISM: Artificial sequence
<220> FEATURE:
<223> OTHER INFORMATION: Heterologous sequences in front of a lactose transporter gene

<400> SEQUENCE: 46

```
ttcagttcgc tgcgctcacg gctctggcag tgaatggggg taaatggcac tacaggcgcc      60
ttttatggat tcatgcaagg aaactaccca taatacaaga aaagcccgtc acgggcttct     120
cagggcgttt tatggcgggt ctgctatgtg gtgctatctg acttttgct gttcagcagt      180
tcctgccctc tgattttcca gtctgaccac ttcggattat cccgtgacag gtcattcaga     240
ctggctaatg cacccagtaa ggcagcggta tcatcaacag gcttacccgt cttactgtcg     300
ggaattcgcg ttggccgatt cattaatggt ataaggttct tgacatctta caatcaatat     360
ggtataataa tttagttagg gcccaagttc acttaaaaag gagatcaaca atgaaagctt     420
actgtcggga attcgcgttg gccgattcat taatggtata aggttcttga catcttacaa     480
tcaatatggt ataataattt agttagggcc caagttcact aaaaaggag atcaacaatg     540
aaagcactgt cggaattcg cgttggccga ttcattaatg gtataaggtt cttgacatct     600
tacaatcaat atggtataat aatttagtta gggcccaagt tcacttaaaa aggagatcaa     660
cacttactgt cggaattcg cgttggccaa ttaattaatg gtataaggtt cttgacatct     720
tacaatcaat atggtataat aatttagtta gggcccaagt tcacttaaaa aggagatcaa     780
caatgaaagc aattttcgta ctgaaacatc ttaatcatgc gtaggatttt ttctatgtac     840
tatttaaaaa acacaaactt tggatgttc ggtttattct ttttctttta cttttttatc      900
atgggagcct acttcccgtt tttcccgatt tggctacatg acatcaacca tatcagcaaa     960
agtgatacgg gtattatttt tgccgctatt tctctgttct cgctattatt ccaaccgctg    1020
tttggtctgc tttctgacaa actcgggctg cgcaaatacc tgctgtggat tattaccggc    1080
atgttagtga tgtttgcgcc gttctttatt tttatcttcg ggccactgtt acaatacaac    1140
attttagtag gatcgattgt tggtggtatt tatctaggct tttgttttaa cgccggtgcg    1200
ccagcagtag aggcatttat tgagaaagtc agccgtcgca gtaatttcga atttggtcgc    1260
gcgcggatgt ttggctgtgt tggctgggcg ctgtgtgcct cgattgtcgg catcatgttc    1320
accatcaata atcagtttgt tttctggctg gctctggct gtgcactcat cctcgccgtt    1380
ttactctttt tcgccaaaac ggatgcgccc tcttctgcca cggttgccaa tgcggtaggt    1440
gccaaccatt cggcatttag ccttaagctg gcactggaac tgttcagaca gccaaaactg    1500
tggttttttgt cactgtatgt tattggcgtt tcctgcacct acgatgtttt tgaccaacag    1560
tttgctaatt tctttacttc gttctttgct accggtgaac agggtacgcg ggtatttggc    1620
tacgtaacga caatgggcga attacttaac gcctcgatta tgttctttgc gccactgatc    1680
attaatcgca tcggtgggaa aaacgccctg ctgctggctg gcactattat gtctgtacgt    1740
attattggct catcgttcgc cacctcagcg ctggaagtgg ttattctgaa aacgctgcat    1800
atgtttgaag taccgttcct gctggtgggc tgctttaaat atattaccag ccagtttgaa    1860
gtgcgtttt cagcgacgat ttatctggtc tgttctgct tctttaagca actggcgatg    1920
atttttatgt ctgtactggc gggcaatatg tatgaaagca tcggtttcca gggcgcttat    1980
ctggtgctgg gtctggtggc gctgggcttc accttaattt ccgtgttcac gcttagcggc    2040
cccggcccgc tttccctgct gcgtcgtcag gtgaatgaag tcgcttaa                 2088
```

<210> SEQ ID NO 47
<211> LENGTH: 2102
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 47

| | | | | | |
|---|---|---|---|---|---|
| gctgcgctca | cggctctggc | agtgaatggg | ggtaaatggc | actacaggcg | ccttttatgg | 60 |
| attcatgcaa | ggaaactacc | cataatacaa | gaaaagcccg | tcacgggctt | ctcagggcgt | 120 |
| tttatggcgg | gtctgctatg | tggtgctatc | tgacttttg | ctgttcagca | gttcctgccc | 180 |
| tctgattttc | cagtctgacc | acttcggatt | atcccgtgac | aggtcattca | gactggctaa | 240 |
| tgcacccagt | aaggcagcgg | tatcatcaac | aggcttaccc | gtcttactgt | cgggaattcg | 300 |
| cgttggccga | ttcgaattcg | cgttggccga | ttcgaattcg | cgttggccga | ttcgaattcg | 360 |
| cgttggccga | ttcgaattcg | cgttggccga | ttcgaattcg | cgttggccga | ttcgaattcg | 420 |
| cgttggccga | ttcgaattcg | cgttggccga | ttcattaatg | gtataaggtt | cttgacatct | 480 |
| tacaatcaat | atggtataat | aatttagtta | gggcccaagt | tcacttaaaa | aggagatcaa | 540 |
| caatgaaagc | ttactgtcgg | gaattcgcgt | tggccgattc | attaatggta | taaggttctt | 600 |
| gacatcttac | aatcaatatg | gtataataat | ttagttaggg | cccaagttca | cttaaaaagg | 660 |
| agatcaacaa | tgaaagctta | ctgtcgggaa | ttcgcgttgg | ccgattcatt | aatggtataa | 720 |
| ggttcttgac | atcttacaat | caatatggta | ataatttta | gttagggccc | aagttcactt | 780 |
| aaaaaggaga | tcaacaatga | aagcaatttt | cgtactgaaa | catcttaatc | atgcgtagga | 840 |
| ttttttctat | gtactattta | aaaaacacaa | acttttggat | gttcggttta | ttctttttct | 900 |
| tttacttttt | tatcatggga | gcctacttcc | cgttttccc | gatttggcta | catgacatca | 960 |
| accatatcag | caaagtgat | acgggtatta | tttttgccgc | tatttctctg | ttctcgctat | 1020 |
| tattccaacc | gctgtttggt | ctgctttctg | acaaactcgg | gctgcgcaaa | tacctgctgt | 1080 |
| ggattattac | cggcatgtta | gtgatgtttg | cgccgttctt | tattttttatc | ttcgggccac | 1140 |
| tgttacaata | caacatttta | gtaggatcga | ttgttggtgg | tatttatcta | ggcttttgtt | 1200 |
| ttaacgccgg | tgcgccagca | gtagaggcat | ttattgagaa | agtcagccgt | cgcagtaatt | 1260 |
| tcgaatttgg | tcgcgcgcgg | atgtttggct | gtgttggctg | ggcgctgtgt | gcctcgattg | 1320 |
| tcggcatcat | gttcaccatc | aataatcagt | ttgttttctg | gctgggctct | ggctgtgcac | 1380 |
| tcatcctcgc | cgttttactc | ttttttcgcca | aaacggatgc | gccctcttct | gccacggttg | 1440 |
| ccaatgcggt | aggtgccaac | cattcggcat | ttagccttaa | gctggcactg | gaactgttca | 1500 |
| gacagccaaa | actgtggttt | ttgtcactgt | atgttattgg | cgtttcctgc | acctacgatg | 1560 |
| tttttgacca | acagtttgct | aatttcttta | cttcgttctt | tgctaccggt | gaacagggta | 1620 |
| cgcgggtatt | tggctacgta | acgacaatgg | gcgaattact | taacgcctcg | attatgttct | 1680 |
| ttgcgccact | gatcattaat | cgcatcggtg | gaaaaacgc | cctgctgctg | gctggcacta | 1740 |
| ttatgtctgt | acgtattatt | ggctcatcgt | tcgccacctc | agcgctggaa | gtggttattc | 1800 |
| tgaaaacgct | gcatatgttt | gaagtaccgt | tcctgctggt | gggctgcttt | aaatatatta | 1860 |
| ccagccagtt | tgaagtgcgt | ttttcagcga | cgatttatct | ggtctgtttc | tgcttcttta | 1920 |
| agcaactggc | gatgatttt | atgtctgtac | tggcgggcaa | tatgtatgaa | agcatcggtt | 1980 |
| tccagggcgc | ttatctggtg | ctgggtctgg | tggcgctggg | cttcaccta | atttccgtgt | 2040 |

```
tcacgcttag cggccccggc ccgctttccc tgctgcgtcg tcaggtgaat gaagtcgctt   2100
aa                                                                  2102

<210> SEQ ID NO 48
<211> LENGTH: 2056
<212> TYPE: DNA
<213> ORGANISM: Artificial sequence
<220> FEATURE:
<223> OTHER INFORMATION: Heterologous sequences in front of a lactose
      transporter gene
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t

<400> SEQUENCE: 48
gctgttcagc agttcctgcc ctctgatttt ccagtctgac cacttcggat tatcccgtga     60
caggtcattc agactggcta atgcacccag taaggcagcg gtatcatcaa caggcttacc    120
cgtcttactg tcgggaattc gcgttggccg attaattaat ggtataaggt tcttgacatc    180
ttacaatcaa tatggtataa taatttagtt agggcccaag ttcacttaaa aaggagatca    240
acaatgaaag cttactgtcg ggaattcgcg ttggccgatt cattaatggt ataaggttct    300
tgacatctta caatcaatat ggtataataa tttagttagg gcccaagttc acttaaaaag    360
gagatcaaca atgaaagcag gcttacccgt cttactgtcg ggaattcgcg ttggccgatt    420
cattaatggt ataaggttct tgacatctta caatcaatat ggtataataa tttagttagg    480
gcccaagttc acttaaaaag gagatcaaca cttactgtcg ggaattcgcg ttggccaatt    540
aattaatggt ataaggttct tgacatctta caatcaatat ggtataataa tttagttagg    600
gcccaagttc acttanaaag gagatcaaca cttactgtcg ggaattcgcg ttggcncatt    660
aattaatggt atanagttct tgacatctta ccaatcatat ggtataataa tttagttagg    720
gcccaagttc acttaaaaag gagatcaaca atgaaagcaa ttttcgtact gaaacatctt    780
aatcatgcgt aggattttt ctatgtacta tttaaaaaac acaaacttt ggatgttcgg    840 tttattcttt ttcttttact tttttatcat gggagcctac ttcccgtttt tcccgatttg    900
gctacatgac atcaaccata tcagcaaaag tgatacgggt attattttg ccgctatttc    960 tctgttctcg ctattattcc aaccgctgtt tggtctgctt tctgacaaac tcgggctgcg   1020
caaatacctg ctgtggatta ttaccggcat gttagtgatg tttgcgccgt tctttatttt   1080
tatcttcggg ccactgttac aatacaacat tttagtagga tcgattgttg gtggtatta   1140 tctaggcttt tgttttaacg ccggtgcgcc agcagtagag gcatttattg agaaagtcag   1200
ccgtcgcagt aatttcgaat tggtcgcgc gcggatgttt ggctgtgttg gctgggcgct   1260
gtgtgcctcg attgtcggca tcatgttcac catcaataat cagtttgttt ctggctggg   1320 ctctggctgt gcactcatcc tcgccgtttt actctttttc gccaaaacgg atgcgccctc   1380
ttctgccacg gttgccaatg cggtaggtgc caaccattcg gcatttagcc ttaagctggc   1440
actggaactg ttcagacagc caaaactgtg gttttgtca ctgtatgtta ttggcgtttc   1500
ctgcacctac gatgttttg accaacagtt tgctaatttc tttacttcgt tctttgctac   1560
```

```
cggtgaacag ggtacgcggg tatttggcta cgtaacgaca atgggcgaat tacttaacgc    1620
ctcgattatg ttctttgcgc cactgatcat taatcgcatc ggtgggaaaa acgccctgct    1680
gctggctggc actattatgt ctgtacgtat tattggctca tcgttcgcca cctcagcgct    1740
ggaagtggtt attctgaaaa cgctgcatat gtttgaagta ccgttcctgc tggtgggctg    1800
ctttaaatat attaccagcc agtttgaagt gcgttttca gcgacgattt atctggtctg     1860
tttctgcttc tttaagcaac tggcgatgat ttttatgtct gtactggcgg gcaatatgta    1920
tgaaagcatc ggtttccagg cgcttatct ggtgctgggt ctggtggcgc tgggcttcac     1980
cttaatttcc gtgttcacgc ttagcggccc cggcccgctt tccctgctgc gtcgtcaggt    2040
gaatgaagtc gcttaa                                                    2056

<210> SEQ ID NO 49
<211> LENGTH: 1558
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 49
cccgtcttac tgtcgggaat cgcgttggc cgattcatta atggtataag gttcttgaca      60
tcttacaatc aatatggtat aataatttag ttagggccca agttcactta aaaaggagat    120
caacaatgaa agcttactgt cgggaattcg cgttggccga ttcttataaa tcattatctt    180
cttgacattt tagaaacaat atggtataat ataacgataa gggcccaagt tcacttaaaa    240
aggagatcaa caatgaaagc aattttcgta ctgaaacatc ttaatcatgc gtaggatttt    300
ttctatgtac tatttaaaaa acacaaactt ttggatgttc ggtttattct ttttctttta    360
cttttttatc atgggagcct acttcccgtt tttcccgatt tggctacatg acatcaacca    420
tatcagcaaa agtgatacgg gtattatttt tgccgctatt tctctgttct cgctattatt    480
ccaaccgctg tttggtctgc tttctgacaa actcgggctg cgcaaatacc tgctgtggat    540
tattaccggc atgttagtga tgtttgcgcc gttctttatt tttatcttcg ggccactgtt    600
acaatacaac attttagtag gatcgattgt tggtggtatt tatctaggct tttgttttaa    660
cgccggtgcg ccagcagtag aggcattat tgagaaagtc agccgtcgca gtaatttcga     720
atttggtcgc gcgcggatgt ttggctgtgt tggctgggcg ctgtgtgcct cgattgtcgg    780
catcatgttc accatcaata atcagtttgt tttctggctg ggctctggct gtgcactcat    840
cctcgccgtt ttactctttt tcgccaaaac ggatgcgccc tcttctgcca cggttgccaa    900
tgcggtaggt gccaaccatt cggcatttag ccttaagctg gcactggaac tgttcagaca    960
gccaaaactg tggtttttgt cactgtatgt tattggcgtt tcctgcacct acgatgtttt   1020
tgaccaacag tttgctaatt tctttacttc gttctttgct accggtgaac agggtacgcg   1080
ggtatttggc tacgtaacga caatgggcga attacttaac gcctcgatta tgttctttgc   1140
gccactgatc attaatcgca tcggtgggaa aaacgccctg ctgctggctg gcactattat   1200
gtctgtacgt attattggct catcgttcgc cacctcagcg ctggaagtgg ttattctgaa   1260
aacgctgcat atgtttgaag taccgttcct gctggtgggc tgctttaaat atattaccag   1320
ccagtttgaa gtgcgttttt cagcgacgat ttatctggtc tgtttctgct tctttaagca   1380
actggcgatg atttttatgt ctgtactggc gggcaatatg tatgaaagca tcggtttcca   1440
gggcgcttat ctggtgctgg gtctggtggc gctgggcttc accttaattt ccgtgttcac   1500
```

```
gcttagcggc cccggcccgc tttccctgct gcgtcgtcag gtgaatgaag tcgcttaa      1558
```

<210> SEQ ID NO 50
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 50

```
cccgtcttac tgtcgggaat tcgcgttggc cgattcattt aaccgataag cttcttgaca      60
tgtttagggt gttatgatat aatcacccaa ttagggccca agttcactta aaaaggagat     120
caacaatgaa agcaattttc gtactgaaac atcttaatca tgcgtaggat ttttctatg      180
tactatttaa aaaacacaaa cttttggatg ttcggtttat tcttttctt ttactttttt      240
atcatgggag cctacttccc gttttcccg atttggctac atgacatcaa ccatatcagc      300
aaaagtgata cgggtattat ttttgccgct atttctctgt tctcgctatt attccaaccg     360
ctgtttggtc tgctttctga caaactcggg ctgcgcaaat acctgctgtg gattattacc     420
ggcatgttag tgatgtttgc gccgttcttt attttatct tcgggccact gttacaatac     480
aacatttag taggatcgat tgttggtggt atttatctag gcttttgttt taacgccggt     540
gcgccagcag tagaggcatt tattgagaaa gtcagccgtc gcagtaattt cgaatttggt     600
cgcgcgcgga tgtttggctg tgttggctgg gcgctgtgtg cctcgattgt cggcatcatg     660
ttcaccatca ataatcagtt tgtttcgg ctgggctctg gctgtgcact catcctcgcc      720
gttttactct ttttcgccaa aacggatgcg ccctcttctg ccacggttgc caatgcggta     780
ggtgccaacc attcggcatt tagccttaag ctggcactgg aactgttcag acagccaaaa     840
ctgtggtttt tgtcactgta tgttattggc gtttcctgca cctacgatgt ttttgaccaa     900
cagtttgcta atttctttac ttcgttcttt gctaccggtg aacagggtac gcgggtattt     960
ggctacgtaa cgacaatggg cgaattactt aacgcctcga ttatgttctt tgcgccactg    1020
atcattaatc gcatcggtgg gaaaaacgcc ctgctgctgg ctggcactat tatgtctgta    1080
cgtattattg gctcatcgtt cgccacctca gcgctggaag tggttattct gaaaacgctg    1140
catatgtttg aagtaccgtt cctgctggtg ggctgcttta aatatattac cagccagttt    1200
gaagtgcgtt tttcagcgac gatttatctg gtctgtttct gcttctttaa gcaactggcg    1260
atgattttta tgtctgtact ggcgggcaat atgtatgaaa gcatcggttt ccagggcgct    1320
tatctggtgc tgggtctggt ggcgctgggc ttcaccttaa tttccgtgtt cacgcttagc    1380
ggccccggcc cgctttccct gctgcgtcgt caggtgaatg aagtcgctta a              1431
```

<210> SEQ ID NO 51
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 51

```
cccgtcttac tgtcgggaat tcgcgttggc cgattcatta atggtataag gttcttgaca      60
tcttacaatc aatatggtat aataatttag ttagggccca agttcactta aaaaggagat     120
caacaatgaa agcaattttc gtactgaaac atcttaatca tgcgtaggat ttttctatg      180
tactatttaa aaaacacaaa cttttggatg ttcggtttat tcttttctt ttactttttt      240
```

```
atcatgggag cctacttccc gttttttcccg atttggctac atgacatcaa ccatatcagc    300
aaaagtgata cgggtattat ttttgccgct atttctctgt tctcgctatt attccaaccg    360
ctgtttggtc tgcttctga caaactcggg ctgcgcaaat acctgctgtg gattattacc    420
ggcatgttag tgatgtttgc gccgttcttt attttatct tcgggccact gttacaatac    480
aacattttag taggatcgat tgttggtggt atttatctag cttttgttt taacgccggt    540 gcgccagcag tagaggcatt tattgagaaa gtcagccgtc gcagtaattt cgaatttggt    600
cgcgcgcgga tgtttggctg tgttggctgg gcgctgtgtg cctcgattgt cggcatcatg    660
ttcaccatca ataatcagtt tgttttctgg ctgggctctg gctgtgcact catcctcgcc    720
gttttactct ttttcgccaa aacggatgcg ccctcttctg ccacggttgc caatgcggta    780
ggtgccaacc attcggcatt tagccttaag ctggcactgg aactgttcag acagccaaaa    840
ctgtggtttt tgtcactgta tgttattggc gtttcctgca cctacgatgt ttttgaccaa    900
cagtttgcta atttctttac ttcgttcttt gctaccggtg aacagggtac gcgggtattt    960
ggctacgtaa cgacaatggg cgaattactt aacgcctcga ttatgttctt tgcgccactg    1020
atcattaatc gcatcggtgg gaaaaacgcc ctgctgctgg ctggcactat tatgtctgta    1080
cgtattattg gctcatcgtt cgccacctca gcgctggaag tggttattct gaaaacgctg    1140
catatgtttg aagtaccgtt cctgctggtg ggctgcttta aatatattac cagccagttt    1200
gaagtgcgtt tttcagcgac gatttatctg gtctgtttct gcttctttaa gcaactggcg    1260
atgattttta tgtctgtact ggcgggcaat atgtatgaaa gcatcggttt ccagggcgct    1320
tatctggtgc tgggtctggt ggcgctgggc ttcaccttaa ttttccgtgtt cacgcttagc    1380 ggccccggcc cgctttccct gctgcgtcgt caggtgaatg aagtcgctta a             1431

<210> SEQ ID NO 52
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 52
cccgtcttac tgtcgggaat tcgcgttggc cgattcttaa attcaataac tttcttgaca     60
tgttattaga tttatggtat aatgacccga tatgggccca agttcactta aaaaggagat    120
caacaatgaa agcaattttc gtactgaaac atcttaatca tgcgtaggat ttttttctatg   180 tactatttaa aaaacacaaa cttttggatg ttcggtttat tctttttctt ttactttttt    240
atcatgggag cctacttccc gttttttcccg atttggctac atgacatcaa ccatatcagc   300
aaaagtgata cgggtattat ttttgccgct atttctctgt tctcgctatt attccaaccg    360
ctgtttggtc tgcttctga caaactcggg ctgcgcaaat acctgctgtg gattattacc    420
ggcatgttag tgatgtttgc gccgttcttt attttatct tcgggccact gttacaatac    480
aacattttag taggatcgat tgttggtggt atttatctag cttttgttt taacgccggt    540 gcgccagcag tagaggcatt tattgagaaa gtcagccgtc gcagtaattt cgaatttggt    600
cgcgcgcgga tgtttggctg tgttggctgg gcgctgtgtg cctcgattgt cggcatcatg    660
ttcaccatca ataatcagtt tgttttctgg ctgggctctg gctgtgcact catcctcgcc    720
gttttactct ttttcgccaa aacggatgcg ccctcttctg ccacggttgc caatgcggta    780
ggtgccaacc attcggcatt tagccttaag ctggcactgg aactgttcag acagccaaaa    840
```

```
ctgtggtttt tgtcactgta tgttattggc gtttcctgca cctacgatgt ttttgaccaa      900
cagtttgcta atttctttac ttcgttcttt gctaccggtg aacagggtac gcgggtattt      960
ggctacgtaa cgacaatggg cgaattactt aacgcctcga ttatgttctt tgcgccactg     1020
atcattaatc gcatcggtgg gaaaaacgcc ctgctgctgg ctggcactat tatgtctgta     1080
cgtattattg gctcatcgtt cgccacctca gcgctggaag tggttattct gaaaacgctg     1140
catatgtttg aagtaccgtt cctgctggtg ggctgcttta aatatattac cagccagttt     1200
gaagtgcgtt tttcagcgac gatttatctg gtctgtttct gcttctttaa gcaactggcg     1260
atgattttta tgtctgtact ggcgggcaat atgtatgaaa gcatcggttt ccagggcgct     1320
tatctggtgc tgggtctggt ggcgctgggc ttcaccttaa tttccgtgtt cacgcttagc     1380
ggccccggcc cgctttccct gctgcgtcgt caggtgaatg aagtcgctta a              1431
```

<210> SEQ ID NO 53
<211> LENGTH: 1571
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 53

```
cccgtcttac tgtcgggaat tcgcgttggc cgattaatta atggtataag gttcttgaca       60
tcttacaatc aatatggtat aataatttag ttagggccca agttcactta aaaaggagat      120
caacaatgaa agcaggctta cccgtcttac tgtcgggaat tcgcgttggc caattaatta      180
atggtataag gttcttgaca tcttacaatc aatatggtat aataatttag ttagggccca      240
agttcactta aaaaggagat caacaatgaa agcaatttc gtactgaaac atcttaatca      300
tgcgtaggat tttttctatg tactatttaa aaaacacaaa cttttggatg ttcggtttat      360 tcttttttctt ttactttttt atcatgggag cctacttccc gttttttcccg atttggctac      420 atgacatcaa ccatatcagc aaaagtgata cgggtattat ttttgccgct atttctctgt      480
tctcgctatt attccaaccg ctgtttggtc tgctttctga caaactcggg ctgcgcaaat      540
acctgctgtg gattattacc ggcatgttag tgatgtttgc gccgttcttt attttttatct      600 tcgggccact gttacaatac aacatttttag taggatcgat tgttggtggt atttatctag      660
gcttttgttt taacgccggt gcgccagcag tagaggcatt tattgagaaa gtcagccgtc      720
gcagtaattt cgaatttggt cgcgcgcgga tgtttggctg tgttggctgg gcgctgtgtg      780
cctcgattgt cggcatcatg ttcaccatca ataatcagtt tgttttctgg ctgggctctg      840
gctgtgcact catcctcgcc gttttactct ttttcgccaa aacggatgcg ccctcttctg      900
ccacggttgc caatgcggta ggtgccaacc attcggcatt tagccttaag ctggcactgg      960
aactgttcag acagccaaaa ctgtggtttt tgtcactgta tgttattggc gtttcctgca     1020
cctacgatgt ttttgaccaa cagtttgcta atttctttac ttcgttcttt gctaccggtg     1080
aacagggtac gcgggtattt ggctacgtaa cgacaatggg cgaattactt aacgcctcga     1140
ttatgttctt tgcgccactg atcattaatc gcatcggtgg gaaaaacgcc ctgctgctgg     1200
ctggcactat tatgtctgta cgtattattg gctcatcgtt cgccacctca gcgctggaag     1260
tggttattct gaaaacgctg catatgtttg aagtaccgtt cctgctggtg ggctgcttta     1320
aatatattac cagccagttt gaagtgcgtt tttcagcgac gatttatctg gtctgtttct     1380
gcttctttaa gcaactggcg atgattttta tgtctgtact ggcgggcaat atgtatgaaa     1440
```

```
gcatcggttt ccagggcgct tatctggtgc tgggtctggt ggcgctgggc ttcaccttaa    1500
tttccgtgtt cacgcttagc ggccccggcc cgctttccct gctgcgtcgt caggtgaatg    1560
aagtcgctta a                                                        1571
```

<210> SEQ ID NO 54
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 54

```
cccgtcttac tgtcgggaat tcgcgttggc cgattcatta atggtataag gttcttgaca     60
tcttacaatc aatatggtat aataatttag ttagggccca agttcactta aaaaggagat    120
caacaatgaa agcaattttc gtactgaaac atcttaatca tgcgtaggat tttttctatg    180
tactatttaa aaaacacaaa cttttggatg ttcggtttat tctttttctt ttactttttt    240
atcatgggag cctacttccc gttttttcccg atttggctac atgacatcaa ccatatcagc    300
aaaagtgata cgggtattat ttttgccgct atttctctgt tctcgctatt attccaaccg    360
ctgtttggtc tgctttctga caaactcggg ctgcgcaaat acctgctgtg gattattacc    420
ggcatgttag tgatgtttgc gccgttcttt attttatct tcgggccact gttacaatac    480
aacattttag taggatcgat tgttggtggt atttatctag gcttttgttt taacgccggt    540
gcgccagcag tagaggcatt tattgagaaa gtcagccgtc gcagtaattt cgaatttggt    600
cgcgcgcgga tgtttggctg tgttggctgg gcgctgtgtg cctcgattgt cggcatcatg    660
ttcaccatca ataatcagtt tgtttttctgg ctgggctctg gctgtgcact catcctcgcc    720
gttttactct tttttcgccaa aacggatgcg ccctcttctg ccacggttgc caatgcggta    780
ggtgccaacc attcggcatt tagccttaag ctggcactgg aactgttcag acagccaaaa    840
ctgtggtttt tgtcactgta tgttattggc gtttcctgca cctacgatgt ttttgaccaa    900
cagtttgcta atttctttac ttcgttcttt gctaccggtg aacagggtac gcgggtattt    960
ggctacgtaa cgacaatggg cgaattactt aacgcctcga ttatgttctt tgcgccactg   1020
atcattaatc gcatcggtgg gaaaaacgcc ctgctgctgg ctggcactat tatgtctgta   1080
cgtattattg gctcatcgtt cgccacctca gcgctggaag tggttattct gaaaacgctg   1140
catatgtttg aagtaccgtt cctgctggtg ggctgctttta aatatattac cagccagttt   1200
gaagtgcgtt tttcagcgac gatttatctg gtctgtttct gcttctttaa gcaactggcg   1260 atgatttttta tgtctgtact ggcgggcaat atgtatgaaa gcatcggttt ccagggcgct   1320
tatctggtgc tgggtctggt ggcgctgggc ttcaccttaa tttccgtgtt cacgcttagc   1380
ggccccggcc cgctttccct gctgcgtcgt caggtgaatg aagtcgctta a             1431
```

<210> SEQ ID NO 55
<211> LENGTH: 1968
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 55

```
cccgtcttac tgtcgggaat tcgcgttggc cgattcgaat tcgcgttggc cgattcgaat     60
```

```
tcgcgttggc cgattcgaat tcgcgttggc cgattcatta atggtataag gttcttgaca    120
tcttacaatc aatatggtat aataatttag ttagggccca agttcactta aaaaggagat    180
caacacttac tgtcgggaat tcgcgttggc cgattcatta atggtataag gttcttgaca    240
tcttacaatc aatatggtat aataatttag ttagggccca agttcactta aaaaggagat    300
caacaatgaa agcttactgt cgggaattcg cgttggccga ttcattaatg gtataaggtt    360
cttgacatct acaatcaat atggtataat aatttagtta gggcccaagt tcacttaaaa    420
aggagatcaa caatgaaagc ttactgtcgg gaattcgcgt tggccgattc attaatggta    480
taaggttctt gacatcttac aatcaatatg gtataataat ttagtaggg cccaagttca    540
cttaaaaagg agatcaacac ttactgtcgg gaattcgcgt tggccaatta attaatggta    600
taaggttctt gacatcttac catcaatatg gggcccaagt tcacttaaaa aggagatcaa    660
caatgaaagc aattttcgta ctgaaacatc ttaatcatgc gtaggatttt ttctatgtac    720
tatttaaaaa acacaaactt tggatgttc ggtttattct ttttctttta ctttttttatc    780
atgggagcct acttcccgtt tttcccgatt ggctacatg acatcaacca tatcagcaaa    840
agtgatacgg gtattatttt tgccgctatt tctctgttct cgctattatt ccaaccgctg    900
tttggtctgc tttctgacaa actcgggctg cgcaaatacc tgctgtggat tattaccggc    960
atgttagtga tgtttgcgcc gttctttatt tttatcttcg ggccactgtt acaatacaac   1020
attttagtag gatcgattgt tggtggtatt tatctaggct tttgttttaa cgccggtgcg   1080
ccagcagtag aggcatttat tgagaaagtc agccgtcgca gtaatttcga atttggtcgc   1140
gcgcggatgt ttggctgtgt tggctgggcg ctgtgtgcct cgattgtcgg catcatgttc   1200
accatcaata atcagtttgt tttctggctg gctctggct gtgcactcat cctcgccgtt   1260
ttactctttt tcgccaaaac ggatgcgccc tcttctgcca cggttgccaa tgcggtaggt   1320
gccaaccatt cggcatttag ccttaagctg gcactggaac tgttcagaca gccaaaactg   1380
tggttttttgt cactgtatgt tattggcgtt tcctgcacct acgatgtttt tgaccaacag   1440
tttgctaatt tctttacttc gttctttgct accggtgaac agggtacgcg ggtatttggc   1500
tacgtaacga caatgggcga attacttaac gcctcgatta tgttctttgc gccactgatc   1560
attaatcgca tcggtgggaa aaacgccctg ctgctggctg gcactattat gtctgtacgt   1620
attattggct catcgttcgc cacctcagcg ctggaagtgg ttattctgaa acgctgcat   1680
atgtttgaag taccgttcct gctggtgggc tgctttaaat atattaccag ccagtttgaa   1740
gtgcgttttt cagcgacgat ttatctggtc tgtttctgct tctttaagca actggcgatg   1800
attttatgt ctgtactggc gggcaatatg tatgaaagca tcggtttcca gggcgcttat   1860
ctggtgctgg gtctggtggc gctgggcttc accttaattt ccgtgttcac gcttagcggc   1920
cccggcccgc tttccctgct gcgtcgtcag gtgaatgaag tcgcttaa                1968
```

<210> SEQ ID NO 56
<211> LENGTH: 1431
<212> TYPE: DNA
<213> ORGANISM: Artificial sequence
<220> FEATURE:
<223> OTHER INFORMATION: Heterologous sequences in front of a lactose
      transporter gene

<400> SEQUENCE: 56

```
cccgtcttac tgtcgggaat tcgcgttggc cgattcatta atgggataag gttcttgaca     60
tcttacaatc aatatggtat aataatttag ttagggccca agttcactta aaaaggagat    120
```

-continued

| | |
|---|---|
| caacaatgaa agcaatttc gtactgaaac atcttaatca tgcgtaggat ttttctatg | 180 |
| tactatttaa aaaacacaaa cttttggatg ttcggtttat tcttttcctt ttactttttt | 240 |
| atcatgggag cctacttccc gttttcccg atttggctac atgacatcaa ccatatcagc | 300 |
| aaaagtgata cgggtattat ttttgccgct atttctctgt tctcgctatt attccaaccg | 360 |
| ctgtttggtc tgcttctga caaactcggg ctgcgcaaat acctgctgtg gattattacc | 420 |
| ggcatgttag tgatgtttgc gccgttcttt atttttatct cgggccact gttacaatac | 480 |
| aacatttag taggatcgat tgttggtggt atttatctag gcttttgttt taacgccggt | 540 |
| gcgccagcag tagaggcatt tattgagaaa gtcagccgtc gcagtaattt cgaatttggt | 600 |
| cgcgcgcgga tgtttggctg tgttggctgg gcgctgtgtg cctcgattgt cggcatcatg | 660 |
| ttcaccatca ataatcagtt tgttttctgg ctgggctctg gctgtgcact catcctcgcc | 720 |
| gttttactct ttttcgccaa aacgatgcg ccctcttctg ccacggttgc caatgcggta | 780 |
| ggtgccaacc attcggcatt tagccttaag ctggcactgg aactgttcag acagccaaaa | 840 |
| ctgtggtttt tgtcactgta tgttattggc gtttcctgca cctacgatgt ttttgaccaa | 900 |
| cagtttgcta atttctttac ttcgttcttt gctaccggtg aacagggtac gcgggtattt | 960 |
| ggctacgtaa cgacaatggg cgaattactt aacgcctcga ttatgttctt tgcgccactg | 1020 |
| atcattaatc gcatcggtgg gaaaaacgcc ctgctgctgg ctggcactat tatgtctgta | 1080 |
| cgtattattg gctcatcgtt cgccacctca gcgctggaag tggttattct gaaaacgctg | 1140 |
| catatgtttg aagtaccgtt cctgctggtg ggctgcttta aatatattac cagccagttt | 1200 |
| gaagtgcgtt tttcagcgac gatttatctg gtctgtttct gcttcttaaa gcaactggcg | 1260 |
| atgattttta tgtctgtact ggcgggcaat atgtatgaaa gcatcggttt ccagggcgct | 1320 |
| tatctggtgc tgggtctggt ggcgctgggc ttcaccttaa tttccgtgtt cacgcttagc | 1380 |
| ggccccggcc cgctttccct gctgcgtcgt caggtgaatg aagtcgctta a | 1431 |

<210> SEQ ID NO 57
<211> LENGTH: 2296
<212> TYPE: DNA
<213> ORGANISM: Artificial sequence
<220> FEATURE:
<223> OTHER INFORMATION: Heterologous sequences in front of a lactose transporter gene

<400> SEQUENCE: 57

| | |
|---|---|
| ggcacctgag tcgctgtctt tttcgtgaca ttcagttcgc tgcgctcacg gctctggcag | 60 |
| tgaatggggg taaatggcac tacaggcgcc tttatggat tcatgcaagg aaactaccca | 120 |
| taatacaaga aaagcccgtc acgggcttct cagggcgttt tatggcgggt ctgctatgtg | 180 |
| gtgctatctg acttttgct gttcagcagt tcctgccctc tgattttcca gtctgaccac | 240 |
| ttcggattat cccgtgacag gtcattcaga ctggctaatg cacccagtaa ggcagcggta | 300 |
| tcatcaacag gcttacccgt cttactgtcg ggaattcgcg ttggccgatt cgaattcgcg | 360 |
| ttggccgatt cttagagata aaaatttct tgacatgttc tatgttttgt gatataatcg | 420 |
| tgagataagg gcccaagttc acttaaaaag gagatcaaca atgaaagcaa gcggtatcat | 480 |
| caacaggctt acccgtctta ctgtcgggaa ttcgcgttgg ccgattcatt aatggtataa | 540 |
| ggttcttgac atcttacaat caatatggta taataattta gttagggccc aagttcactt | 600 |
| aaaaaggaga tcaacaatga agcttactg tcgggaattc gcgttggccg attcattaat | 660 |
| ggtataaggt tcttgacatc ttacaatcaa tatggtataa taatttagtt agggcccaag | 720 |

```
ttcacttaaa aaggagatca acaatgaaag cttactgtcg ggaattcgcg ttggccgatt      780
cattaatggt ataaggttct tgacatctta caatcaatat ggtataataa tttagttagg      840
gcccaagttc acttaaaaag gagatcaaca cttactgtcg ggaattcgcg ttggccaatt      900
aattaatggt ataaggttct tgacatctta caatcaatat tgtataataa tttagttagg      960
gcccaagttc acttaaaaag gagatcaaca atgaaagcaa ttttcgtact gaaacatctt     1020
aatcatgcgt aggattttt ctatgtacta tttaaaaaac acaaacttt ggatgttcgg      1080 tttattcttt ttctttact tttttatcat gggagcctac ttcccgtttt tcccgatttg      1140
gctacatgac atcaaccata tcagcaaaag tgatacgggt attattttg ccgctatttc      1200 tctgttctcg ctattattcc aaccgctgtt tggtctgctt tctgacaaac tcgggctgcg     1260
caaatacctg ctgtggatta taccggcat gttagtgatg tttgcgccgt tctttatttt       1320
tatcttcggg ccactgttac aatacaacat tttagtagga tcgattgttg gtggtatttta    1380 tctaggcttt tgttttaacg ccggtgcgcc agcagtagag gcatttattg agaaagtcag     1440
ccgtcgcagt aatttcgaat tggtcgcgc gcggatgttt ggctgtgttg gctgggcgct       1500
gtgtgcctcg attgtcggca tcatgttcac catcaataat cagtttgttt ctggctggg       1560 ctctggctgt gcactcatcc tcgccgtttt actctttttc gccaaaacgg atgcgccctc     1620
ttctgccacg gttgccaatg cggtaggtgc caaccattcg gcatttagcc ttaagctggc     1680
actggaactg ttcagacagc caaaactgtg gttttttgtca ctgtatgtta ttggcgtttc    1740
ctgcacctac gatgttttg accaacagtt tgctaatttc tttacttcgt tctttgctac       1800
cggtgaacag ggtacgcggg tatttggcta cgtaacgaca atgggcgaat tacttaacgc     1860
ctcgattatg ttctttgcgc cactgatcat taatcgcatc ggtgggaaaa acgccctgct     1920
gctggctggc actattatgt ctgtacgtat tattggctca tcgttcgcca cctcagcgct     1980
ggaagtggtt attctgaaaa cgctgcatat gtttgaagta ccgttcctgc tggtgggctg    2040 cttttaaatat attaccagcc agtttgaagt gcgttttca gcgacgattt atctggtctg    2100
tttctgcttc tttaagcaac tggcgatgat ttttatgtct gtactggcgg caatatgta     2160 tgaaagcatc ggtttccagg cgcttatct ggtgctgggt ctggtggcgc tgggcttcac     2220 cttaattttcc gtgttcacgc ttagcggccc cggcccgctt tccctgctgc gtcgtcaggt    2280
gaatgaagtc gcttaa                                                     2296
```

<210> SEQ ID NO 58
<211> LENGTH: 2210
<212> TYPE: DNA
<213> ORGANISM: Artificial sequence
<220> FEATURE:
<223> OTHER INFORMATION: Terminator construct

<400> SEQUENCE: 58

```
tcgcgttggc cgattcggaa taggacacca tcgaatggtg caaaaccttt cgcggtatgg       60
catgatagcg cccggaagag agtcaattca gggtggtgaa tatgtactat ttaaaaaaca     120 caaactttg gatgttcggt ttattctttt tctttactt ttttatcatg ggagcctact       180
tcccgttttt cccgatttgg ctacatgaca tcaaccatat cagcaaaagt gatacgggta     240 ttattttgc cgctatttct ctgttctcgc tattattcca accgctgttt ggtctgcttt      300
ctgacaaact cgggctgcgc aaatacctg ctgtggattat taccggcatg ttagtgatgt    360
ttgcgccgtt ctttattttt atcttcggc cactgttaca atacaacatt ttagtaggat     420
cgattgttgg tggtatttat ctaggctttt gttttaacgc cggtgcgcca gcagtagagg    480
```

-continued

```
catttattga gaaagtcagc cgtcgcagta atttcgaatt tggtcgcgcg cggatgtttg    540
gctgtgttgg ctgggcgctg tgtgcctcga ttgtcggcat catgttcacc atcaataatc    600
agtttgtttt ctggctgggc tctggctgtg cactcatcct cgccgtttta ctcttttcg     660
ccaaaacgga tgcgccctct tctgccacgg ttgccaatgc ggtaggtgcc aaccattcgg    720
catttagcct taagctggca ctggaactgt tcagacagcc aaaactgtgg tttttgtcac    780
tgtatgttat tggcgtttcc tgcacctacg atgtttttga ccaacagttt gctaatttct    840
ttacttcgtt ctttgctacc ggtgaacagg gtacgcgggt atttggctac gtaacgacaa    900
tgggcgaatt acttaacgcc tcgattatgt tctttgcgcc actgatcatt aatcgcatcg    960
gtgggaaaaa cgccctgctg ctggctggca ctattatgtc tgtacgtatt attggctcat   1020
cgttcgccac ctcagcgctg gaagtggtta ttctgaaaac gctgcatatg tttgaagtac   1080
cgttcctgct ggtgggctgc tttaaatata ttaccagcca gtttgaagtg cgttttcag    1140
cgacgattta tctggtctgt ttctgcttct ttaagcaact ggcgatgatt tttatgtctg   1200
tactggcggg caatatgtat gaaagcatcg gtttccaggg cgcttatctg gtgctgggtc   1260
tggtggcgct gggcttcacc ttaatttccg tgttcacgct tagcggcccc ggcccgcttt   1320
ccctgctgcg tcgtcaggtg aatgaagtcg ctcatcatca ccaccatcat taggatggtg   1380
gtgatgataa tggagaaaaa aatcactgga tataccaccg ttgatatatc ccaatggcat   1440
cgtaaagaac atttttgaggc atttcagtca gttgctcaat gtacctataa ccagaccgtt   1500
cagctggata ttacggcctt tttaaagacc gtaaagaaaa ataagcacaa gttttatccg   1560
gcctttattc acattcttgc ccgcctgatg aatgctcatc cggagttccg tatggcaatg   1620
aaagacggtg agctggtgat atgggatagt gttcaccctt gttacaccgt tttccatgag   1680
caaactgaaa cgttttcatc gctctggagt gaataccacg acgatttccg gcagtttcta   1740
cacatatatt cgcaagatgt ggcgtgttac ggtgaaaacc tggcctattt ccctaaaggg   1800
tttattgaga atatgtttt cgtcagcgcc aatccctggg tgagtttcac cagttttgat   1860
ttaaacgtgg ccaatatgga caacttcttc gcccccgttt tcactatggg caaatattat   1920
acgcaaggcg acaaggtgct gatgccgctg gcgattcagg ttcatcatgc cgtttgtgat   1980
ggcttccatg tcggcagaat gcttaatgaa ttacaacagt actgcgatga gtggcagggc   2040
ggggcgtaag gatccaaagg tacctctaga gtcgacctgc aggccttcgt aaatctggcg   2100
agtggggaac tgccagacat caaataaaac aaaaggctca gtcggaagac tgggccttt    2160
gttttatctg ttgtttgtcg gtgaacactc tcccgtgtag gctggagctg              2210
```

MUTANT MICROORGANISMS RESISTANT TO LACTOSE KILLING

RELATED APPLICATIONS

This application is a 35 U.S.C. § 371 filing of International Application No. PCT/EP2015/076449, filed Nov. 12, 2015, which claims priority to European Patent Application No. 14193151.9, filed Nov. 14, 2014, each of which is incorporated herein by reference in its entirety.

TECHNICAL FIELD OF INVENTION

The present invention relates to a method to produce mutated microorganisms which resist the phenomenon of lactose killing and to the microorganisms obtainable via said method. Such engineered microorganisms can be applied for the production of specialty products, such as but not limited to specialty carbohydrates, glycolipids and galactosylated compounds.

BACKGROUND ART

Lactose killing is a well-known and well-studied principle that hampers growth of many organisms in the presence of lactose with another carbon source. The exact mechanism behind this phenomenon is however not known, although the features needed to induce the phenomenon are quite clear. Lactose killing occurs when lactose is added to a microbial culture that grows on another carbon source, such as but not limited to glycerol or sucrose. It furthermore occurs when lactose transport gene is either inducible or constitutively expressed (33, 39, 75). Lactose killing was first observed for *E. coli* where the expression of lactose permease was modulated with IPTG and lactose in chemostat conditions (28). Lactose killing was later also observed for *Rhizobium meliloti, Kluyveromyces lactis* and *Zymomonas mobilis* (55, 70, 77). One of the potential reasons for this phenomenon was ascribed to the so-called "cost" of lactose transporter activity for the cell, this "cost" results in a reduction or inhibition of growth and is also related to the extracellular lactose concentration (34), which is mostly kept high in industrial processes to acquire high enough product titers and yields. However, the art states that as long as there is lactose transport under these conditions, lactose killing should occur. To solve the problem of lactose killing the deletion of lactose permease or severe impairment of lactose uptake has been proposed (34). For instance Lodi et al (55) deleted (knocked out) lactose permease in *K. lactis* and found that lactose killing did not occur anymore. Spontaneous mutations during their experiments further showed that the selected lactose killing negative strains are severely impaired in their lactose uptake. However, lactose uptake is essential in order to synthesize specialty products or bioproducts efficiently. Hence a deletion of lactose permease or severe impairment in lactose permease activity is clearly not a solution as the production of such bioproducts requires 1) an efficient lactose uptake and 2) an expression cassette that does not lead to 'the lactose-killing phenotype'. Lactose permease for the production of lactose-based bioproducts has been previously used but without solving 'the lactose-killing phenotype'. In the past this problem was solved by either reducing the uptake of lactose severely (and hence little to none specialty product is produced based on lactose) or by decoupling the growth phase and the production phase in order to obtain first enough biomass. After this growth phase lactose is added in a second phase to produce a specialty product. In this second phase no or strongly reduced growth occurs (59).

Thus, current consensus is that, in order to avoid lactose killing, lactose uptake has to be eliminated or severely impaired as normal lactose uptake would always lead to lactose killing. In contrast, the present invention discloses a screening methodology to find expression cassettes of lactose permease that allow efficient uptake of lactose without undergoing lactose killing!. Lactose is a building block for many bioproducts, more particularly specialty carbohydrates (14), glycolipids, and galactosylated compounds such as galactosyllipids, galactosylceramides, and galactosylated aglycons. In many cases the galactose moiety is used for organ targeting of pharmaceuticals (28). The use of lactose as a substrate in combination with other substrates is however not as evident as it might seem due to the above-described phenomenon of 'lactose-killing'. Mostly multi-phase production systems, non-growing coupled cell systems are needed to avoid lactose killing (32, 48).

The basic structural backbone of many specialty carbohydrates consist of lactose or galactose units. More specifically, human milk oligosaccharides and by extension mothers milk oligosaccharides, a broad group of saccharides and oligosaccharides, are build up from galactose and lactose units (15). These carbohydrates are further modified with sugar moieties such as for example N-acetylglucosamine, N-acetylgalactosamine, sialic acids (such as N-acetylneuraminate, N-glycoylneuraminate, 2-keto-3-deoxy-D-glycero-galacto-nonulosonic acid, . . . ) (21), L-fucose, . . . . The synthesis of these compounds requires then activated carbohydrates such as UDP-N-acetylglucosamine, UDP-N-acetylgalactosamine, CMP-sialic acid, GDP-fucose, . . . , which are very expensive and hard to synthesize molecules and are optimally produced by living, growing cells due to the energy their biosynthesis requires.

The oligosaccharide components of human/mothers milk have anti-inflammatory and prebiotic effects and/or have applications in therapeutics as nutraceutical, anti-inflammatory agent, prebiotic, or, pharmaceutics (15, 24, 68). However, an efficient method to produce the latter high-value compounds is still needed.

The present invention describes synthetic expression systems for lactose transporters that do not result in lactose killing, even at high lactose concentrations. The mutated organisms obtainable via said expression systems are thus useful to produce the above-described bioproducts.

BRIEF DESCRIPTION OF FIGURES

FIG. 3: Example of a promoter, RBS and lactose transporter sequence combination (SEQ ID No 1) that does not result in lactose killing when introduced into an *E. coli* mutant strain.

FIG. 4: Example of a sequence of the lactose permease gene translational coupled to the lacZ gene (SEQ ID No 2).

FIG. 5: Example of a sequence of the lactose permease gene lacY translational coupled to the cat gene (SEQ ID No 3).

FIG. 6: Example of a sequence of the *K. maxianus* lactose permease gene translational coupled to the aph 1 gene (SEQ ID No 4).

FIG. 7: Example of a sequence of the lactose permease gene lacy coupled with an aptamer that binds (Z)-4-(3,5-difluoro-4-hydroxybenzylidene)-1,2-dimethyl-1H-imidazol-5(4H)-one (SEQ ID No 5) and allows the detection of lactose permease expression.

FIG. 10: pCXP14-FT_*H. pylori* (SEQ ID No 6).

FIG. 13: Example of a promoter (p1), Kozak, *K. marxianus* lactose permease coding sequence and terminator combination (SEQ ID No 7) that does not result in lactose killing when introduced into a yeast mutant strain.

FIG. 14: Example of a promoter (p2), Kozak, *K. marxianus* lactose permease coding sequence and terminator combination (SEQ ID No 8) that does not result in lactose killing when introduced into a yeast mutant strain.

FIG. 15: Example of a promoter, Kozak, *K. marxianus* β-galactosidase coding sequence and terminator combination (SEQ ID No 9).

FIG. 16: HR1 rDNA (SEQ ID No 10).

FIG. 17: HR2 rDNA (SEQ ID No 11).

FIG. 18: Examples of selected sequences that originate from the lactose killing screening methodology as describe in the examples (SEQ ID No 12 to 57).

FIG. 20: The sequence of the lacIQ_lacY expression cassette that was tested on lactose killing in example 16 (SEQ ID No 58).

SUMMARY OF THE INVENTION

Figure 1:
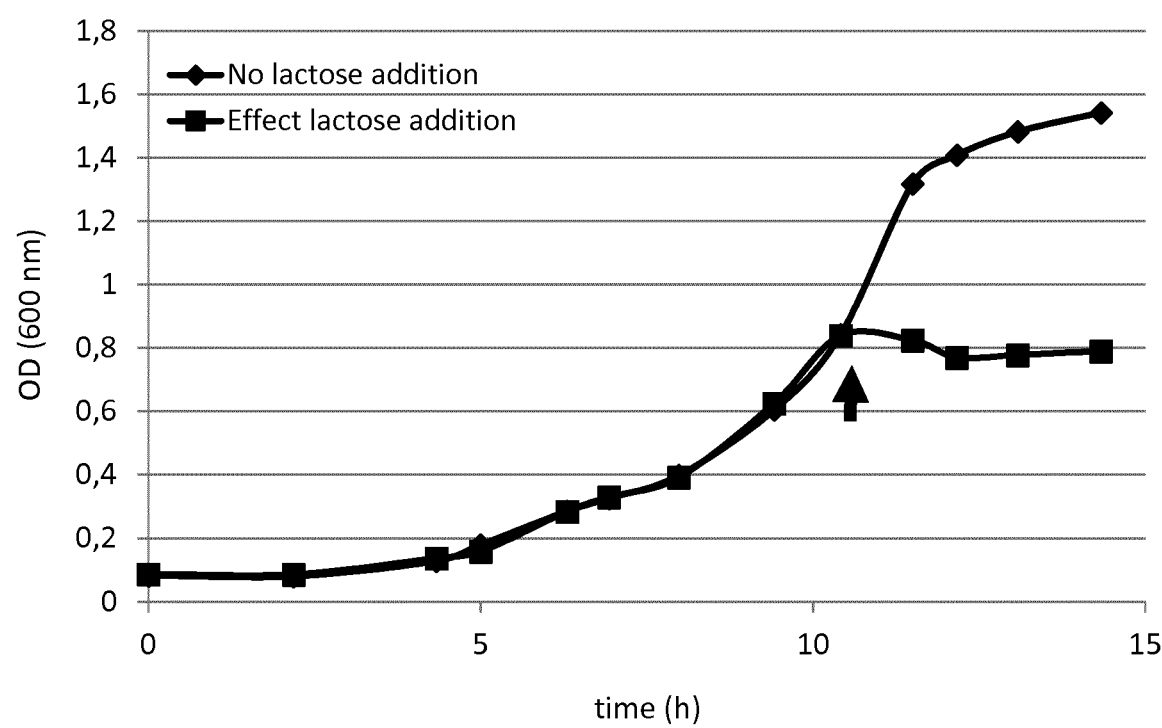
FIG. 1: Effect of lactose on an *E. coli* wild type strain. At the arrow lactose was added to one of the cultures and growth of this culture stopped immediately, while the other strain continued to grow in the other culture.

The present invention relates to a method to produce microorganisms which resist the phenomenon of lactose killing when grown in an environment in which lactose is combined with another carbon source, wherein said method comprises:
a. mutating the expression of lactose transporters within microorganisms, wherein said mutation results in an expressed lactose transporter,
b. growing said mutated microorganisms on a medium comprising a carbon-source which is not lactose,
c. adding lactose to said medium during growth of said mutated microorganisms, and
d. selecting the microorganisms which resist the phenomenon of lactose killing growing on said medium comprising lactose.

More specifically, the present invention relates to a method to produce microorganisms which resist the phenomenon of lactose killing when grown in an environment in which lactose is combined with another carbon source, wherein said method comprises:
a. mutating the expression of lactose transporters within microorganisms, wherein said mutation results in the expression of said lactose transporter
b. growing said mutated microorganisms on a medium comprising a carbon-source which is not lactose,
c. adding lactose to said medium during growth of said mutated microorganisms, and
d. selecting the microorganisms which resist the phenomenon of lactose killing growing on said medium comprising lactose and which retain at least 50% of the lactose influx obtained with the wild type expression cassette of said lactose transporter.

The present invention further relates to a method as indicated above wherein step a) is undertaken by introducing a heterologous promoter in front of an endogenous or exogenous lactose transporter gene, and/or by mutating the untranslated region in front of the coding sequence that contains the ribosome binding or Kozak sequences and/or by modifying the codon usage of the endogenous lactose transporter gene.

The present invention also relates to a method as described wherein said introduction of a heterologous promoter in front of an endogenous or exogenous lactose transporter gene is undertaken by: a) deleting the endogenous lactose transporters from the genome and reintroducing them at another location within the genome of said microorganism, or, b) by introducing a heterologous promoter in front of the endogenous lactose transporters, or, c) by knocking out the endogenous lactose promoter and introducing a heterologous promoter at the same location in the genome of said microorganism.

The present invention further relates to the method described above wherein the expression of lactose permease in step b) is detected by means of translational coupling with a reporter gene and/or via aptamer coupling.

The present invention relates to the method described above wherein the expressed lactose transporter is detected via genetic constructs as given by SEQ ID No 2, 3, 4 and/or 5.

The present invention further relates to a method as described above wherein said lactose transporter is a lactose permease.

The present invention further relates to a method as described above wherein said microorganism is a bacterium, a yeast or a fungus.

The present invention relates also to promoter sequences, untranslated regions in front of the coding sequence that contain ribosome binding sequences or Kozak sequences and/or lactose permease sequences that lead to the expression of a lactose transporter, that does not result into lactose killing phenotype when microorganism containing such sequence is grown in an environment in which lactose is combined with (an)other carbon source(s), and, that is obtainable by the a method as described above.

The present invention also relates to a microorganism which resists the phenomenon of lactose killing when grown in an environment in which lactose is combined with another carbon source, and, is obtainable by a method as described above.

More specifically the present invention relates to a microorganism as described above, and, having a heterologous sequence in front of a lactose transporter gene as given by SEQ ID No 1, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56 or 57.

The present invention relates also to a microorganism which resists the phenomenon of lactose killing in which the genes coding for the enzymes from the lactose and/or galactose degradation pathways are rendered less functional or non-functional.

The present invention further relates to the usage of a microorganism as described above for the production of lactose-based specialty products such as specialty carbohydrates, glycolipids and galactosylated compounds.

The present invention also relates to the usage a microorganism as described above wherein said specialty carbohydrates are 2-fucosyllactose or 2'-fucosyllactose or 3-fucosyllactose or 2',3-difucosyllactose or lactoNtriose or lacto-N-tetraose, or lacto-nN-tetraose or 3'sialyllactose or 6'sialyllactose.

DESCRIPTION OF INVENTION

The present invention describes a novel way to avoid lactose killing by changing the expression of a lactose transporter via genetic engineering in an organism, resulting in a mutant lactose transporter expressing organism. To this end, an exogenous and/or an endogenous lactose transporter gene is expressed by a heterologous promoter that does not lead to a lactose killing phenotype and/or the codon usage of the lactose transporter is modified to create an altered expression of the lactose transporter that does not lead to a lactose killing phenotype. To this end the natural expression control of lactose transporters has to be removed and/or replaced in such a way that lactose killing does not occur. For example, the naturally occurring lactose transporter expression cassette is deleted from the genome and reintroduced at another location, and/or, a heterologous promoter is introduced in front of lactose transporter at its original location, and/or, lactose transporter is knocked out first and reintroduced with a heterologous promoter at the same and/or another location in the genome, and/or, lactose transporter is introduced into an operon that is expressed via a heterologous promoter.

The present invention thus relates to a method to produce microorganisms which resist the phenomenon of lactose killing when grown in an environment in which lactose is combined with another carbon source, wherein said method comprises: 1) mutating the expression of lactose transporters within microorganisms, wherein said mutation results in the expression of said lactose transporter, 2) growing said mutated microorganisms on a medium comprising a carbon-source which is not lactose, 3) adding lactose to said medium during growth of said mutated microorganisms, and 4) selecting the microorganisms which resist the phenomenon of lactose killing growing on said medium comprising lactose and which retain at least 50% of the lactose influx obtained with the wild type expression cassette of said lactose transporter.

The term 'lactose killing' refers to the phenomenon of growth retardation or growth arrest of an organism that is grown in an environment in which lactose or galactoside is combined with (an)other carbon source(s). These carbon sources are, non-limiting, glycerol, maltose, glucose, fructose, sucrose, fucose, mannose, sialic acid, starch, cellulose, polyols (such as mannitol, xylitol, sorbitol), organic acids (lactate, succinate, acetate, . . . ), and/or, pentoses (xylose, arabinose, . . . ).

The present invention describes a method to identify lactose permease expression systems that do not result in lactose killing. This method encompasses a growth analysis of the mutant strain to which lactose is added mid exponential phase. This method can be performed in a high throughput manner in micro-titre plates or with cell sorters, enabling the screening of multiple promoters, ribosome binding sites, codon usage, and other factors that can influence the expression of lactose permease in the mutant micro-organism. The present invention describes a method to detect lactose permease expression via translational coupling and/or aptamer coupling and the selection of sequences that lead to expression via a reporter gene, such as but not limited to an antibiotic resistance gene (for instance but not limited to chloramphenicol, Geneticin G418), a fluorescent protein, a hydrolase (for instance but not limited to galactosidase, xylanase) and, or an aptamer sequence. Sequences that lead to the expression of lactose permease are further selected based on the reporter gene, by growth in a medium with an antibiotic, a colorimetric assay (such as X-gal) and/or by means of a fluorescence-activated cell sorter that sorts out fluorescent cells and/or an aptamer assay for instance, but not limited to, based on (Z)-4-(3,5-difluoro-4-hydroxybenzylidene)-1,2-dimethyl-1H-imidazol-5(4H)-one (37, 64). The present invention further describes a procedure to screen for lactose transporter expressing mutant organisms that do not undergo lactose killing. In addition the present invention describes how libraries of lactose permease expression cassettes can be created via promoter libraries, RBS or Kozak sequence libraries, transcription terminator libraries, and/or codon usages variants of the lactose permease gene. These libraries are further created via methods such as but not limited to Gibson Assembly, Golden Gate assembly, Cliva assembly, LCR or restriction ligation (25, 36, 50, 79).

The term 'which retain at least 50% of the lactose influx obtained with the wild type expression cassette of said lactose transporter' relates to the fact that the mutated microorganisms of the present invention should—although they resist lactose killing—be still capable of retaining at least 50% (i.e. 50, 55, 60, 65, 70, 75, 80, 85, 90, 95, 99%) of the lactose influx which is obtained when using the wild type expression cassette of said lactose transporter.

The term 'expression cassette' relates to any sequence in which a promoter sequence, untranslated region sequence (containing either a ribozyme binding sequence or Kozak sequence), a coding sequence (for instance a lactose permease gene sequence) and optionally a transcription terminator (18) is present.

The term 'lactose transporter' refers to any protein expressed in a microorganism that is capable to translocate (transport) lactose across the cytoplasmic membrane. Such proteins are for instance, lactose permeases (transporters from the superfamily MFS or Major Facilitator Superfamily).

The term 'heterologous promoter' refers to any promoter that does not naturally occur in front of a coding sequence. A "promoter" is the whole of the RNA polymerase binding sequence that is located before the transcription start site and the untranslated region in front of the coding sequence. A "heterologous promoter" sequence is thus: 1) a variant of the naturally occurring promoter sequence containing at least 1 (i.e. 1, 2, 3, 4, . . . ) mutation, and/or 2) a native promoter from the mutant lactose transporter expressing micro-organism that does not naturally occur in front of the coding sequence of said transporter, and/or 3) a sequence that does not occur naturally in the lactose transporter expressing micro-organism, and/or 4) an artificial promoter which is an in silico designed promoter. These promoters can be derived from libraries such as, but not limited to, described by Alper et al. (2005), and/or HXT7p, Hammer et al. (2006), De Mey et al. (2007), Coussement et al (2014) or, Mutalik et al (2013) (3, 25, 29, 41, 60) (66), or Blount et al (2012), promoters such as but not limited to ADH1p, TEF1p, TEF2p, GPDp, PDC1p, FBA1p, PGK1p, PGI1p, TDH2p, PYK1p, ENO2p, GPM1p, TPI1p (13), or designed as described, for example, by Rhodius et al. (2012). The term 'artificial promoter' also refers to promoters with DNA sequences that are combinations of the native (autologous) promoter sequence with parts of different (autologous or heterologous) promoter sequences. Sequences of such 'artificial promoters' can be found in databases such as for example partsregistry.org (19). The heterologous promoters lead either to constitutive expression or regulated expression via a transcription factor.

The term 'constitutive expression' is defined as expression that is not regulated by transcription factors other than the subunits of RNA polymerase (e.g. the bacterial sigma factors) under certain growth conditions. None limiting examples of such transcription factors are CRP, LacI, ArcA, Cra, IclR, . . . in *E. coli*, or, Aft2p, Crz1p, Skn7, . . . in *Saccharomyces cerevisiae*, or, DeoR, GntR, Fur, . . . in *B. subtilis*. These transcription factors bind on a specific sequence and may block or enhance expression in certain growth conditions. RNA polymerase binds a specific sequence to initiate transcription, for instance via a sigma factor in prokaryotic hosts.

The term 'regulated expression' is defined as expression that is regulated by transcription factors other than the subunits of RNA polymerase (e.g. bacterial sigma factors) under certain growth conditions. Examples of such transcription factors are described above.

The term 'untranslated region' in front of the coding sequence that contains the ribosome binding sites or Kozak sequences relates to the sequence between the RNA polymerase binding sequence and the coding sequence. This untranslated region is also the sequence naturally occurring in front of the coding sequence, and/or, a sequence that naturally occurs in the lactose transporter expressing microorganism, and/or, a sequence that is derived from other organisms (either prokaryotes or eukaryotes), and/or, a sequence that is artificially designed, which relates to non-natural or in silico designed ribosome binding sites with known or measurable translation rates, these sequences can be derived from libraries as described by Mutalik et al (2013) (60) or designed via algorithms for example as described by Salis et al (2009) (67) or can be found in databases such as partsregistry.org (19).

The term 'modified codon usage' a relates to the altering of the codons used within a DNA coding sequence, either to codons used more frequently by the organism or used rarely by the organism. Codon usage is defined in databases such as the codon usage database (61) and codon usage is optimized via codon usage design algorithms (73).

The term 'translational coupling' refers to the coupled expression of a gene of interest and a reporter gene such as a green fluorescent proteins, antibiotic resistance genes, toxic genes, (49, 53, 58, 63). The term 'translational sensor' refers to any mechanism that is an indicator for expression and translation of a gene, e.g. fluorescent tags and split tags as described in the following references (17, 72).

The term 'aptamer coupling' refers to the introduction of an aptamer sequence into the messenger RNA of the lactose transporter that can be detected by a fluorophore such as but not limited to (Z)-4-(3,5-difluoro-4-hydroxybenzylidene)-1, 2-dimethyl-1H-imidazol-5(4H)-one (37, 64).

The term 'growth analysis' refers to the analysis of the growth curve of an organism. This organism is cultivated in a growth medium in a growth environment. The term growth environment relates to all environmental parameters such as pH, temperature, dissolved oxygen. The pH is set by means of a pH buffer or by pH control and is for example but not limited to pH 4, 4.5, 5, 5.5, 6, 6.5, 7, 7.5, or 8. The temperature is set at for example but not limited to 25, 28, 30, 32, 34, 37, 40, 42, 45° C. The dissolved oxygen is either anaerobic, micro-aerobic (with dissolved oxygen below 1.5 mg/l) or aerobic conditions.

The term 'medium' or 'growth medium' relates to any solution containing the necessary substrates for an organism to grow. These substrates are, but not limited to, nitrogen sources such as ammonium salts, nitrate salts, yeast extract, pepton, casamino, and/or amino acids, phosphor sources such as but not limited to phosphate salts, sulpher sources such as but not limited to sulphate salts, elements such as but not limited to copper, cobalt, iron, selenium, iodium, molybdate, magnesium, calcium, potassium, sodium, zinc, nickel, manganese, and/or boric acid and/or vitamins such as but not limited to thiamine, pantothenic acid, and/or niacin and/or a carbon source such as but non-limiting, glycerol, maltose, glucose, fructose, sucrose, fucose, mannose, sialic acid, starch, cellulose, polyols (such as mannitol, xylitol, sorbitol), organic acids (lactate, succinate, acetate, . . . ), and/or pentoses (xylose, arabinose, . . . ).

The term 'organism' or 'cell' as indicated above refers to a microorganism chosen from the list consisting of a bacterium, a yeast or a fungus, or, refers to a plant or animal cell.

The latter bacterium preferably belongs to the phylum of the Proteobacteria or the phylum of the Firmicutes or the phylum of the Cyanobactria or the phylum Deinococcus-Thermus. The latter bacterium belonging to the phylum Proteobacteria belongs preferably to the family Enterobacteriaceae, preferably to the species *Escherichia coli*. The latter bacterium preferably relates to any strain belonging to the species *Escherichia coli* such as but not limited to *Escherichia coli* B, *Escherichia coli* C, *Escherichia coli* W, *Escherichia coli* K12, *Escherichia coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1060, MC1061, MC4100, JM101, NZN111 and AA200. Hence, the present invention specifically relates to a mutated and/or transformed *Escherichia coli* strain as indicated above wherein said *E. coli* strain is a K12 strain. More specifically, the present invention relates to a mutated and/or transformed *Escherichia coli* strain as indicated above wherein said K12 strain is *E. coli* MG1655. The latter bacterium belonging to the phylum Firmicutes belongs preferably to the Bacilli, preferably from the species *Bacillus*. The latter yeast preferably belongs to the phylum of the Ascomycota or the phylum of the Basidiomycota or the phylum of the Deuteromycota or the phylum of the Zygomycetes. The latter yeast belongs preferably to the genus *Saccharomyces, Pichia, Hansunella, Kluyveromyces, Yarrowia* or *Starmerella*. The latter fungus belongs preferably to the genus *Rhizopus, Dictyostelium* or *Aspergillus*.

The present invention describes organisms that are able to take up lactose without undergoing lactose killing and are able to convert lactose or its galactose moiety into a specialty product. More particularly said specialty products or bioproducts are specialty carbohydrates, glycolipids, such as but not limited to galactolipids and/or lactolipids, and/or, galactosylated compounds such as galactosyllipids, galactosylceramides and/or galactosylated aglycons.

The present invention describes organisms that are able to take up lactose without undergoing lactose killing and convert of said lactose into a human milk oligosaccharide, such as but not limited to 3-fucosyllactose, 2'-fucosyllactose, 6-fucosyllactose, 2',3-difucosyllactose, 2',2-difucosyllactose, 3,4-difucosyllactose, 6'-sialyllactose, 3'-sialyllactose, 3,6-disialyllactose, 6,6'-disialylactose, 3,6-disialyllacto-N-tetraose, lactodifucotetraose, lacto-N-tetraose, lacto-N-neotetraose, lacto-N-fucopentaose II, lacto-N-fucopentaose I, lacto-N-fucopentaose III, sialyl-lacto-N-tetraose c, sialyllacto-N-tetraose b, sialyllacto-N-tetraose a, lacto-N-difucohexaose I, lacto-N-difucohexaose II, lacto-N-hexaose, lacto-N-neohexaose, para-lacto-N-hexaose, monofucosylmonosialyllacto-N-tetraose c, monofucosyl para-lacto-N-hexaose, monofucosyllacto-N-hexaose III, isomeric fucosylated lacto-N-hexaose III, isomeric fucosylated lacto-N-hexaose I, sialyllacto-N-hexaose, sialyl-lacto-N-neohexaose II, difucosyl-para-lacto-N-hexaose, difucosyllacto-N-hexaose, difucosyllacto-N-hexaose a, difucosyllacto-N-hexaose c, galactosylated chitosan, fucosylalted oligosaccharides, and/or sialylated oligosaccharides . . . .

The present invention further describes organisms that do not undergo lactose killing and that synthesize nucleotide sugars such as but not limited to GDP-L-fucose, GDP-mannose, GDP-glucose, CMP-sialic acid, UDP-glucose, UDP-galactose, UDP-N-acetylglucosamine, UDP-N-acetyl-mannosamine, UDP-N-acetylgalactosamine, UDP-glucuronic acid, UDP-galacturonic acid, UDP-xylose, UDP-arabinose, and/or, dTDP-rhamnose. The term "sialic acid" is the group name for compounds such as, but not limited to neuramic acid, N-acetylneuramic acid, or N-glycoyl-neuramic acid as defined by Varki (1992) (71). The intracellular GDP-fucose concentration or pool is enhanced by upregulation by either the de novo pathway and/or the salvage pathway. The de novo pathway consists of a GDP-4-keto-6-deoxymannose-3,5-epimerase-4-reductase or GDP-fucose synthase, a GDP-mannose 4,6-dehydratase, a GDP-D-mannose pyrophosphorylase, a phosphomannose isomerase and/or a phosphomannomutase, of which the expression is enhanced individually via genetic elements such as but not limited to promoters and/or ribosome binding sites and/or altered codon usage in a mono-cistron or polycistron (operon structure); and/or via the regulators arcA iclR in Enterobacteriaceae and/or via the transcriptional regulator RcsA in Enterobacteriaceae or homologous genes in bacteria, or, Xbp1, Spt20, Sfp1, Rpd3, Rap1, Gcr1, Gcn5, Cst6, Abf1, Hsf1, Reb1, Cad1, Sin4, Ash1, Ixr1, Met32, Pho2, Rgr1, Spt7, Swi4 in *Saccharomyces cerevisiae* or homologous genes in yeasts or fungi. The salvage pathway consists of a L-fucose kinase and/or a GDP-L-fucose pyrophosphorylase. The GDP-mannose pool is enhanced by upregulating genes coding for a GDP-D-mannose pyrophosphorylase, a phosphomannose isomerase and/or a phosphomannomutase; and/or, genes coding for a mannokinase and a GDP-D-mannose pyrophosphorylase. The UDP-galactose pool is enhanced by upregulating the genes coding for a galactokinase and/or galactose 1-phosphate uridyl transferase, and/or, a UDP-galactose-4-epimerase, and/or, a UDP-galactose/glucose pyrophosphorylase, and/or a lactose synthase, and/or a lactose phosphorylase and/or a sucrose phosphorylase. The UDP-glucose pool is enhanced by upregulating the genes coding for a glucokinase, and/or, a UDP-glucose pyrophosphorylase, and/or a sucrose phosphorylase and/or a phosphoglucomutase, and/or a sucrose synthase. The CMP-sialic acid pool is enhanced by upregulating genes coding for L-glutamine:D-fructose-6-phosphate aminotransferase, and/or, phosphoglucosamine mutase, and/or, glucosamine-1-phosphate acetyltransferase and/or N-acetylglucosamine-1-phosphate uridyltransferase, and/or UDP-N-acetylglucosamine 2-epimerase and/or N-acetylneuraminate synthase and/or cytidine 5'-monophosphate N-acetylneuraminate synthetase. The UDP-N-acetylglucosamine pool is enhanced by upregulating genes coding for L-glutamine:D-fructose-6-phosphate aminotransferase, and/or, phosphoglucosamine mutase, and/or, glucosamine-1-phosphate acetyltransferase and/or N-acetylglucosamine-1-phosphate uridyltransferase and/or glucosamine-6-phosphate N-acetyltransferase and/or, phosphoacetylglucosamine mutase, and/or, UDP-N-acetylglucosamine pyrophosphorylase. The UDP-N-acetylmannosamine pool is enhanced by upregulating genes coding for the UDP-N-acetylglucosamine pool enhancement and/or a UDP-N-acetylglucosamine 2-epimerase. The UDP-N-acetylgalactosamine pool is enhanced by upregulating genes coding for the UDP-N-acetylglucosamine pool enhancement and/or a UDP-N-acetylglucosamine C4-epimerase. The UDP-glucuronic acid pool is enhanced by upregulating genes coding for the UDP-glucose pool enhancement and/or UDP-glucose dehydrogenase. The UDP-xylose pool is enhanced by upregulating genes coding for the UDP-glucuronic acid pool enhancement and/or UDP-D-xylose synthase. The UDP-galacturonic acid pool is enhanced by upregulating genes coding for the UDP-glucuronic acid pool enhancement and/or UDP-D-glucuronic acid 4-epimerase. The UDP-arabinose pool is enhanced by upregulating genes coding for the UDP-glucuronic pool enhancement and/or UDP-D-xylose 4-epimerase and/or arabinose kinase and/or UDP-L-arabinose pyrophosphorylase. The dTDP-rhamnose pool is enhanced by upregulating genes coding for a dTDP-glucose pyrophosphorylase and/or dTDP-glucose 4,6-dehydratase and/or dTDP-4-dehydrorhamnose 3,5-epimerase and/or dTDP-4-dehydrorhamnose reductase and or a glucose-1-phosphate thymidylyltransferase and/or a nucleotide rhamnose synthase.

The term "pool" further relates to concentrations of metabolites that naturally occur in the wild type organism, e.g. the concentration of a nucleotide sugar pool. The term "enhanced pool" relates to a significantly increased concentration of said metabolite pool, higher than the metabolite pool in the wild type organism.

The term "upregulating a gene" relates to each genetic modification that leads to the enhanced expression of the gene and/or activity of the product if said gene. Said genetic modification is either a modification in the promoter, untranslated region, ribosome binding site, the coding sequence, the gene location, the intron/exon structure and/or the transcriptional terminator, leading to said increased expression and/or activity.

In addition, the present invention describes genetically modified organisms that can transfer these nucleotide sugars onto a mono-, di- or oligosaccharide, such as, but not limited to, galactose, lactose, lactoNbiose, lactoNtriose, lactoNtetraose, lacto-N-neotetraose, globotriose, 2'fucosyllactose, 3-fucosylactose, 3-sialyllactose, 6-sialyllactose, human milk oligosaccharides, heparosans, chitosans, nod-factors, glycolipids, and/or aglycons, . . . by means of a glycosyltransferase enzyme.

The present invention also describes organisms that do not undergo lactose killing and that can further modify said lactose with enzymes such as but not limited to carbohydrate hydrolases, carbohydrate transferases, carbohydrate synthases, acetylases, acyltransferases, carbohydrate phosphatases, polysaccharide Lyases, kinases, pyruvylases and/or sulfotransferase.

The present invention further describes organisms that do not undergo lactose killing and does not degrade lactose anymore by rendering the lactose hydrolase gene less-functional or non-functional.

The terms 'genes which are rendered less-functional or non-functional' refer to the well-known technologies for a skilled person such as the usage of siRNA, RNAi, miRNA, asRNA, mutating genes, knocking-out genes, transposon mutagenesis, CrispR/CAS etc. . . . which are used to change the genes in such a way that they are less able (i.e. statistically significantly 'less able' compared to a functional wild-type gene) or completely unable (such as knocked-out genes) to produce functional final products. The term '(gene) knockout' thus refers to a gene which is rendered non-functional. The term 'deleted gene' or 'gene deletion' also refers to a gene which is rendered non-functional (2, 4-9, 22, 27, 30, 43, 45, 46, 51, 65, 74).

The present invention describes organisms in which genes are introduced/knocked in/upregulated to produce bioproducts as described above. These genes are found in gene databases such as but not limited to genbank or protein databases such as but not limited to uniprot, or enzyme databases such as but not limited to Brenda enzyme database (16, 23, 38) and pathways towards bioproducts are found in databases such as but not limited to KEGG, Biocyc, Metacyc (20, 44, 47). The pathway towards a certain bioproduct described above can be determined by several mathematical tools described in the art (35, 54, 57, 76).

EXAMPLES

1. Material and methods *Escherichia coli*
Strains and Plasmids

*Escherichia coli* MG1655 [λ$^-$, F$^-$, rph-1] and JM109 were obtained from the Netherlands Culture Collection of Bacteria (NCCB). All mutant strains were created using the method of Datsenko & Wanner (27).

Media

The Luria Broth (LB) medium consisted of 1% tryptone peptone (Difco, Erembodegem, Belgium), 0.5% yeast extract (Difco) and 0.5% sodium chloride (VWR, Leuven, Belgium). Shake flask medium contained 2 g/l NH$_4$Cl, 5 g/l (NH$_4$)$_2$SO$_4$, 2.993 g/l KH$_2$PO$_4$, 7.315 g/l K$_2$HPO$_4$, 8.372 g/l MOPS, 0.5 g/l NaCl, 0.5 g/l MgSO$_4$.7H$_2$O, 15 g/l glycerol (unless stated otherwise), 1 ml/l vitamin solution, 100 μl/l molybdate solution, and 1 ml/l selenium solution. The medium was set to a pH of 7 with 1M KOH.

Vitamin solution consisted of 3.6 g/l FeCl$_2$.4H$_2$O, 5 g/l CaCl$_2$.2H$_2$O, 1.3 g/l MnCl$_2$.2H$_2$O, 0.38 g/l CuCl$_2$.2H$_2$O, 0.5 g/l CoCl$_2$.6H$_2$O, 0.94 g/l ZnCl$_2$, 0.0311 g/l H$_3$BO$_4$, 0.4 g/l Na$_2$EDTA.2H$_2$O and 1.01 g/l thiamine.HCl. The molybdate solution contained 0.967 g/l Na$_2$MoO$_4$.2H$_2$O. The selenium solution contained 42 g/l SeO$_2$.

The minimal medium for fermentations contained 6.75 g/l NH$_4$Cl, 1.25 g/l (NH$_4$)$_2$SO$_4$, 1.15 g/l KH$_2$PO$_4$, 0.5 g/l NaCl, 0.5 g/l MgSO$_4$.7H$_2$O, 30 g/l lactose and 20 g/l sucrose (or different concentrations if stated otherwise), 1 ml/l vitamin solution, 100 μl/l molybdate solution, and 1 ml/l selenium solution with the same composition as described above.

Cultivation Conditions

A preculture, from a single colony on a LB-plate, in 5 ml LB medium was incubated during 8 hours at 37° C. on an orbital shaker at 200 rpm. From this culture, 2 ml was transferred to 100 ml minimal medium in a 500 ml shake flask and incubated for 16 hours at 37° C. on an orbital shaker at 200 rpm. 4% inoculum was used in a 2 or 5 l Biostat B Plus culture vessel with 1.5 l or 4 L working volume (Sartorius Stedim Biotech, Melsungen, Germany). The culture conditions were: 37° C., stirring at 800 rpm, and a gas flow rate of 1.5 l/min. Aerobic conditions were maintained by sparging with air. The pH was maintained at 7 with 0.5 M H$_2$SO4 and 35% M ammonia solution. The exhaust gas was cooled down to 4° C. by an exhaust cooler (Frigomix 1000, Sartorius Stedim Biotech, Melsungen, Germany). 10% solution of silicone antifoaming agent (BDH 331512K, VWR Int Ltd., Poole, England) was added when foaming raised during the fermentation (approximately 10 μl). The off-gas was measured with an EL3020 off-gas analyser (ABB Automation GmbH, 60488 Frankfurt am Main, Germany).

All data was logged with the Sartorius MFCS/win v3.0 system (Sartorius Stedim Biotech, Melsungen, Germany).

Sampling Methodology

The bioreactor contains in its interior a harvest pipe (BD Spinal Needle, 1.2×152 mm (BDMedical Systems, Franklin Lakes, N.J.—USA) connected to a reactor port, linked outside to a Masterflex-14 tubing (Cole-Parmer, Antwerpen, Belgium) followed by a harvest port with a septum for sampling. The other side of this harvest port is connected back to the reactor vessel with a Masterflex-16 tubing. This system is referred to as rapid sampling loop. During sampling, reactor broth is pumped around in the sampling loop. It has been estimated that, at a flow rate of 150 ml/min, the reactor broth needs 0.04 s to reach the harvest port and 3.2 s to re-enter the reactor. At a pO2 level of 50%, there is around 3 mg/l of oxygen in the liquid at 37° C. The pO2 level should never drop below 20% to avoid micro-aerobic conditions. Thus 1.8 mg/l of oxygen may be consumed during transit through the harvesting loop. Assuming an oxygen uptake rate of 0.4 g oxygen/g biomass/h (the maximal oxygen uptake rate found at $\mu_{max}$), this gives for 5 g/l biomass, an oxygen uptake rate of 2 g/l/h or 0.56 mg/l/s, which multiplied by 3.2 s (residence time in the loop) gives 1.8 mg/l oxygen consumption.

In order to quench the metabolism of cells during the sampling, reactor broth was sucked through the harvest port in a syringe filled with 62 g stainless steel beads pre-cooled at −20° C., to cool down 5 ml broth immediately to 4° C. Sampling was immediately followed by cold centrifugation (15000 g, 5 min, 4° C.). During the batch experiments, a sample for $OD_{600\ nm}$ measurement was taken using the rapid sampling loop and the cold stainless bead sampling method.

Analytical Methods

Cell density of the culture was frequently monitored by measuring optical density at 600 nm (Uvikom 922 spectrophotometer, BRS, Brussel, Belgium). Cell dry weight was obtained by centrifugation (15 min, 5000 g, GSA rotor, Sorvall RC-5B, Goffin Meyvis, Kapellen, Belgium) of 20 g reactor broth in pre-dried and weighted falcons. The pellets were subsequently washed once with 20 ml physiological solution (9 g/l NaCl) and dried at 70° C. to a constant weight. To be able to convert $OD_{600\ nm}$ measurements to biomass concentrations, a correlation curve of the $OD_{600\ nm}$ to the biomass concentration was made. The concentrations of glucose and organic acids were determined on a Varian Prostar HPLC system (Varian, Sint-Katelijne-Waver, Belgium), using an Aminex HPX-87H column (Bio-Rad, Eke, Belgium) heated at 65° C., equipped with a 1 cm precolumn, using 5 mM H2SO4 (0.6 ml/min) as mobile phase. A dual-wave UV-VIS (210 nm and 265 nm) detector (Varian Prostar 325) and a differential refractive index detector (Merck LaChrom L-7490, Merck, Leuven, Belgium) was used for peak detection. By dividing the absorptions of the peaks in both 265 and 210 nm, the peaks could be identified. The division results in a constant value, typical for a certain compound (formula of Beer-Lambert).

Glucose, fructose, sucrose, oligosaccharides and glucose-1-phosphate were measured by HPLC with a Hypercarb column and were detected with an MSMS detector (Antonio et al., 2007; Nielsen et al., 2006).

Genetic Methods

The methods used for mutant construction is described below.

Plasmids were maintained in the host E. coli DH5α (F−, φ80dlacZΔM15, Δ(lacZYA-argF)U169, deoR, recA1, endA1, hsdR17(rk−, mk+), phoA, supE44, λ−, thi-1, gyrA96, relA1).

Plasmids. pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were used for the mutant construction. The plasmid pBluescript (Fermentas, St. Leon-Rot, Germany) was used to construct the derivates of pKD3 and pKD4 with a promoter library, or with alleles carrying a point mutation.

Mutations. The mutations consisted in gene disruption (knock-out, KO). They were introduced using the concept of Datsenko and Wanner (27).

Transformants carrying a Red helper plasmid were grown in 10 ml LB media with ampicillin (100 mg/l) and L-arabinose (10 mM) at 30° C. to an $OD_{600\ nm}$ of 0.6. The cells were made electrocompetent by washing them with 50 ml of ice-cold water, a first time, and with 1 ml ice-cold water, a second time. Then, the cells were resuspended in 50 μl of ice-cold water. Electroporation was done with 50 μl of cells and 10-100 ng of linear double-stranded-DNA product by using a Gene Pulser™ (BioRad) (600Ω, 25 μFD, and 250 volts).

After electroporation, cells were added to 1 ml LB media incubated 1 h at 37° C., and finally spread onto LB-agar containing 25 mg/l of chloramphenicol or 50 mg/l of kanamycin to select antibiotic resistant transformants. The selected mutants were verified by PCR with primers upstream and downstream of the modified region and were grown in LB-agar at 42° C. for the loss of the helper plasmid. The mutants were tested for ampicillin sensitivity Linear double-stranded-DNA. The linear ds-DNA amplicons were obtained by PCR using pKD3, pKD4 and their derivates as template. The primers used had a part of the sequence complementary to the template and another part complementary to the side on the chromosomal DNA where the recombination has to take place. For the KO, the region of homology was designed 50-nt upstream and 50-nt downstream of the start and stop codon of the gene of interest. For the KI, the transcriptional starting point (+1) had to be respected. PCR products were PCR-purified, digested with DpnI, repurified from an agarose gel, and suspended in elution buffer (5 mM Tris, pH 8.0).

Elimination of the antibiotic resistance gene. The selected mutants (chloramphenicol or kanamycin resistant) were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistance and of the FLP helper plasmid. The gene knock outs and knock ins are checked with control primers (Fw/Rv-gene-out).

Transformation. Plasmids were transformed in $CaCl_2$ competent cells using the simplified procedure of Hanahan (42) or via electroporation as described above.

2. Material and Methods Yeast 2.1. Strains

Saccharomyces cerevisiae BY4742 was obtained from the Euroscarf culture collection. All mutant strains were created by homologous recombination or plasmid transformation using the method of Gietz (40). Kluyveromyces marxianus lactis was obtained from the culture collection of the Laboratory of Industrial Biotechnology and Biocatalysis.

2.2. Media

Strains are grown on Synthetic Defined yeast medium with Complete Supplement Mixture (SD CSM) or CSM drop-out (SD CSM-Ura) containing 6.7 g·L$^{-1}$ Yeast Nitrogen Base without amino acids (YNB w/o AA, Difco), 20 g·L$^{-1}$ agar (Difco) (solid cultures), 22 g·L$^{-1}$ glucose monohydrate or 20 g·L$^{-1}$ lactose and 0.79 g·L$^{-1}$ CSM or 0.77 g·L$^{-1}$ CSM-Ura (MP Biomedicals).

2.3. Cultivation Conditions

Yeast cultures are first inoculated in 5 mL of the appropriate medium and incubated overnight at 30° C. and 200 rpm. In order to obtain higher volume cultures, 2% (or higher) of the pre-culture is inoculated in 50-200 mL medium. These cultures are again incubated at 30° C. and 200 rpm.

Growth experiments are conducted in 96-well plate or Erlenmeyer scale. In order to obtain single colonies as start material for the growth and production experiments, strains are plated on selective SD CSM plates and incubated for 2-3 days at 30° C. One colony is then picked and transferred to 5 mL medium for the Erlenmeyer studies or to 1 mL medium for the microtiterplate experiments.

For the Erlenmeyer experiments, the pre-cultures are incubated overnight at 30° C. and 200 rpm and 2% of these pre-cultures are added to 100 mL medium in order to start the growth experiments.

For the MTP growth experiments, colonies are added to 150 µL medium and incubated for 24 hours at 30° C. After incubation, 2 µL of the MTP pre-cultures are added to an MTP containing 150 µL fresh media. OD is measured every fifteen minutes for 48 hours with the Infinite® 200 Pro Tecan.

2.4. Sampling Methodology

Samples of both the OD (0.2 mL) and the cellular and supernatant fraction (1 mL) of the culture are taken every two hours until the stationary phase and every couple hours during the stationary phase. The 1 mL sample is first centrifuge (11) after which the cell pellet and the supernatant are separated and stored separately at −20° C. Supernatant is stored for extracellular product analysis while the pellets are used for intracellular metabolite analysis.

2.5. Analytical Methods

Cell density of the culture was frequently monitored by measuring optical density at 600 nm (Uvikom 922 spectrophotometer, BRS, Brussel, Belgium) or with the with the Biochrom Anthos Zenyth 340 Microtiterplate reader. Cell dry weight was obtained by centrifugation (15 min, 5000 g, GSA rotor, Sorvall RC-5B, Goffin Meyvis, Kapellen, Belgium) of 20 g reactor broth in pre-dried and weighted falcons. The pellets were subsequently washed once with 20 ml physiological solution (9 g/l NaCl) and dried at 70° C. to a constant weight. To be able to convert $OD_{600\ nm}$ measurements to biomass concentrations, a correlation curve of the $OD_{600\ nm}$ to the biomass concentration was made. The concentrations of glucose and organic acids were determined on a Varian Prostar HPLC system (Varian, Sint-Katelijne-Waver, Belgium), using an Aminex HPX-87H column (Bio-Rad, Eke, Belgium) heated at 65° C., equipped with a 1 cm precolumn, using 5 mM H2SO4 (0.6 ml/min) as mobile phase. A dual-wave UV-VIS (210 nm and 265 nm) detector (Varian Prostar 325) and a differential refractive index detector (Merck LaChrom L-7490, Merck, Leuven, Belgium) was used for peak detection. By dividing the absorptions of the peaks in both 265 and 210 nm, the peaks could be identified. The division results in a constant value, typical for a certain compound (formula of Beer-Lambert).

Glucose, fructose, sucrose, oligosaccharides and glucose-1-phosphate were measured by HPLC with a Hypercarb column and were detected with an MSMS detector (Antonio et al., 2007; Nielsen et al., 2006).

2.6. Genetic Methods

The methods used for mutant construction is described below.

Plasmids were maintained in the host *E. coli* DH5α (F−, φ80dlacZΔM15, Δ(lacZYA-argF)U169, deoR, recA1, endA1, hsdR17(rk−, mk+), phoA, supE44, λ−, thi-1, gyrA96, relA1).

Plasmids. Yeast expression plasmid p2a_2µ_Lac4 available at the Laboratory of Industrial Biotechnology and Biocatalysis was used to enable growth of *Saccharomyces* on lactose as the sole C-source. This plasmid contains an ampicillin resistance gene and a bacterial origin of replication to allow for selection and maintenance in *E. coli*. The plasmid further contains the 2µ yeast ori and the Ura3 selection marker for selection and maintenance in yeast. Finally, the plasmid contains a β-galactosidase expression cassette (SEQ ID 9, FIG. 15).

Mutations. The mutations consisted in plasmid introduction using p2a_2µ_Lac4 (described above) and gene knock-in (KI) (KI at the rDNA locus) using double stranded linear DNA (described above). Transformants were plated on SD CSM-Ura after transformation with plasmid DNA or on SD CSM-Ura with lactose as the sole C-source after transformation with double stranded linear DNA. The selected plasmid bearing mutants were verified by PCR with primers matching p2a_2µ_Lac4. The selected genomic knock-in mutants were verified by PCR with primers upstream and downstream of the modified region and confirmed by sequencing (performed at LGC Genomics (LGC group, Germany)).

Linear double-stranded-DNA. The linear ds-DNA amplicons were obtained by PCR using plasmid pJet_KI_p1_Lac12_t@rDNA or pJet_KI_p2_Lac12_t@rDNA. These plasmids contain 2 500 bp homology regions (HR1 (SEQ ID 10, FIG. 16) and HR2 (SEQ ID 11, FIG. 17)) flanking SEQ ID 7 and SEQ ID 8, respectively, at the multi-cloning site of the pJET Cloning vector (Thermoscientific). The primers used are homologous to the 5' end of HR1 (forward primer) and the 3' end of HR2 (reverse primer). PCR products were PCR-purified prior to transformation.

Transformations. Plasmids and linear double stranded DNA were transformed using the method Gietz (40).

3. Results

Example 1: Construction of an *E. coli* Lactose Permease lacY Knock in at the agp Locus First the strain MG1655ΔlacY was constructed according to the method of Datsenko and Wanner as described above. To this end MG1655 was transformed with pKD46 and linear DNA was constructed from the base plasmids pKD3 and pKD4 with flanking homologies to the lacY gene. Successful recombinations were then screened with the appropriate antibiotics. To ensure no lactose could be taken up in this strain, the strain was grown on a minimal medium only containing lactose as carbon source. No growth was observed during this experiment, hence this cell could not transport lactose anymore over its membrane.

To further construct a synthetic expression system, a synthetic promoter and RBS were synthesized in combination with the lacY gene (ordered from IDT and Geneart). This sequence is shown in FIG. 3. This sequence was also introduced into the genome at the agp gene locus via an adaptation of the Datsenko and Wanner methodology. Briefly, the lactose permease construct was first assembled with a screening cassette from the pKD3 plasmid, resultin into a novel plasmid, pCX_lacY-kan. From this plasmid linear DNA could be PCR amplified with homologies to the agp genomic region. This obtained linear DNA can then be transformed into an *E. coli* MG1655ΔlacY, in which the pKD46 plasmid is present. This lead to the recombination of the lactose transporter expression cassette into the genome, resulting into a lactose permease expression organism MG1655ΔlacYΔagp::lacY$_{synthetic}$. To ensure growth on lactose was restored, this strain was grown on a lactose minimal medium as described above. This resulted in full restoration of growth on lactose, with a growth rate similar to the wild type.

Figure 2:
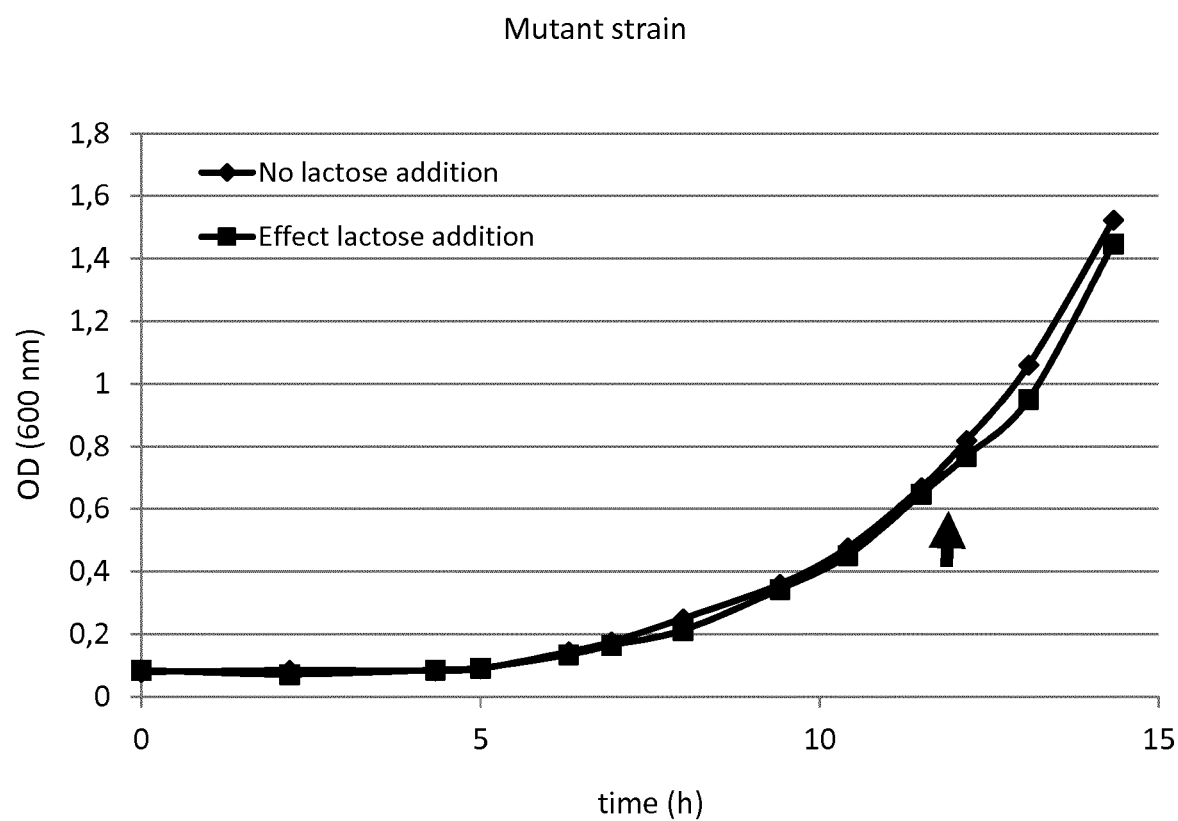
FIG. 2: Effect of lactose on an *E. coli* lactose transporter mutant strain in which lactose transporter expression is altered by means of a synthetic constitutive promoter. The arrow indicates the moment on which lactose was added to the medium in one of the cultures. In this case no effect was observed on growth. Hence, these mutant strains can be selected in this manner.

Example 2: The Effect of Lactose on the Wild Type E. coli Strain and a Mutant E. coli Strain that does not Undergo Lactose Killing A shake flask experiment as described in materials and methods was set up with the wild type MG1655 and MG1655ΔlacYΔagp::lacY$_{synthetic}$. These strains were grown in a glycerol shake flask medium (15 g/l glycerol, as described in the materials and methods) and lactose (200 g/l stock solution was added resulting in a final concentration of 10 g/l) was added mid exponential phase (approximately at OD 0.8). As can be seen in FIG. 1 and FIG. 2, the mutant strain does not undergo lactose killing.

Example 3: The Use of Translational Coupling or Translational Sensors to Ensure Lactose Transporter Expression Because a full lactose permease knock out strain would also not undergo lactose killing and the goal is to obtain a functional, active, expressed lactose permease a screen is needed to ensure lactose permease expression. To this end, sequence variants of promoters, ribozyme binding sites, Kozak sequences, codon usage and transcription terminators can be created. However, these sequence variants may lead to null-expression constructs, hence leading to lactose transporter negative mutant strains. Therefore a system needs to be designed to detect the expression of the lactose transporter, preferably by a easy to screen reporter gene such as lacZ, fluorescent proteins or antibiotic resistance genes.

Construction of a Translational Coupling System that Reinitiates Translation of the Reporter Gene to Detect Lactose Transporter Expression Two genes can be translationally coupled by introducing a translation reinitiation region 3' from the gene of interest and 5' from the reporter gene. Translation can be reinitiated by several codons, such as AUG, UUG, GUG or AUA (63). The sequence of such a construct, which couples the lactose permease gene and the lacZ gene translationally is shown in FIG. 4. To create this sequence, the lacY and lacZ sequence are amplified from the E. coli genome with primers with golden gate restriction sites (BsaI, obtained from NEB). The intergenic region that allows the translational coupling can be ordered from any gene synthesis company, such as IDT or Geneart. All parts are then assembled via the Golden Gate method as described by Engler et al. (2013) (36) into a pUC54 plasmid together with a promoter and RBS sequence as shown in FIG. 3 (for E. coli) or into pGK12 which replicates in Bacillus sp. with a Bacillus promoter and ribosome binding site.

Construction of a Translational Coupling System that Initiates Translation of the Reporter Gene to Detect Lactose Transporter Expression Via the Opening of a Loop on the Ribosome Binding Site A second method to screen for expression via translational coupling is described by Mendez-Perez et al (2012) (58). This method was adapted for the screening of lactose permease expression with a chloramphenicol reporter gene. In this case the lactose transporter lacY is coupled via a HIS-tag and ribosome binding site to the chloramphenicol resistance gene. The sequence parts for this construct are also ordered at IDT or Geneart and assembled via Golden gate assembly. The resulting sequence is given in FIG. 5.

Construction of a Translational Coupling System that Couples the Yeast Lactose Transporter with a Reporter Gene Although yeasts do not use cistrons, it is still possible to screen for expression via translational coupling via viral internal ribosomal entry sites (so called IRES sequences) (56). An example of such a sequence is the T2A sequence (10), which allows fully independent (which means not as a protein fusion), yet coupled translation of two proteins in a cistron. This means that if the last protein of the cistron is expressed, the first protein is also expressed.

In yeasts, the lactose permease gene of for instance Kluyveromyces marxianus can be used to transport lactose in the cell. This gene can be coupled with the T2A sequence to the aph 1 gene, encoding resistance to Geneticin. This sequence is analogously constructed as describe above. The final sequence is given in FIG. 6.

Construction of an Aptamer Coupling System that Introduces an Aptamer into the Messenger RNA of Lactose Permease Lactose permease expression can also be detected on a messenger RNA level. To this end, a (Z)-4-(3,5-difluoro-4-hydroxybenzylidene)-1,2-dimethyl-1H-imidazol-5(4H)-one binding aptamer is cloned after the lactose permease coding sequence as shown in FIG. 7. The expression of this construct is modulated further as described in example 6. After growth of the cells, (Z)-4-(3,5-difluoro-4-hydroxybenzylidene)-1,2-dimethyl-1H-imidazol-5(4H)-one is added to the medium as described by Pothoulakis et al (2013) (64) and the lactose permease expressing mutant strains are selected via a fluorescence-activated cell sorter (FACS).

Figure 8:
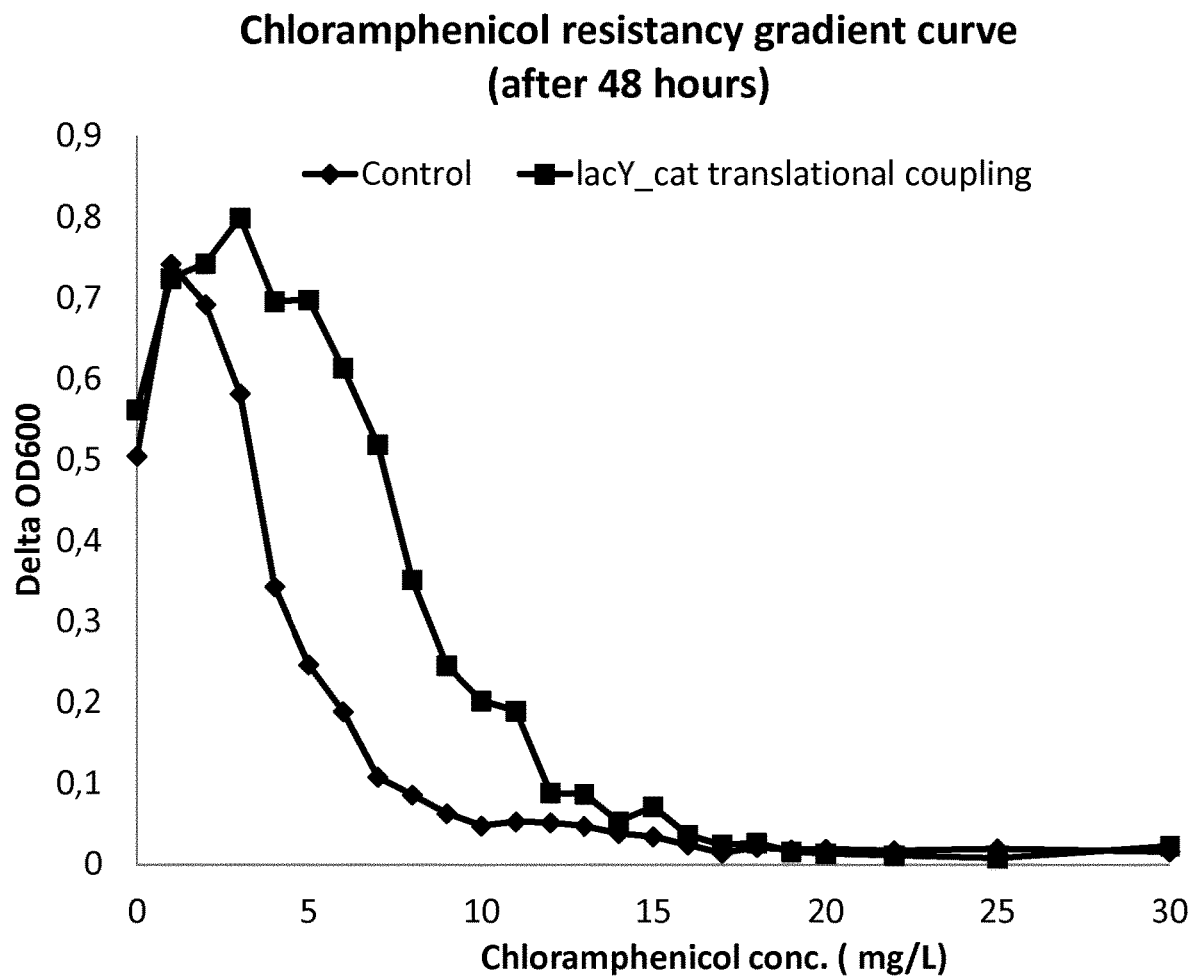
FIG. 8: Chloramphenicol resistance of a reference strain containing a reference plasmid pSC101 without a lactose permease translational coupled to a chloramphenicol resistance gene and a mutant strain with a lactose permease translational coupled to a chloramphenicol resistance gene. The X-axis shows the different chloramphenicol concentrations tested, the Y-axis shows the optical density of the culture after 48 hours of incubation. The reference strain shows growth retardation at a lower chloramphenicol screening than the mutant strain, which proofs that expression of lactose permease can be screened via translational coupling with an antibiotic resistance gene. Lactose permease expressing organisms can hence be selected from a mixture of non-expressing and expressing organisms in this manner.
Figure 9:
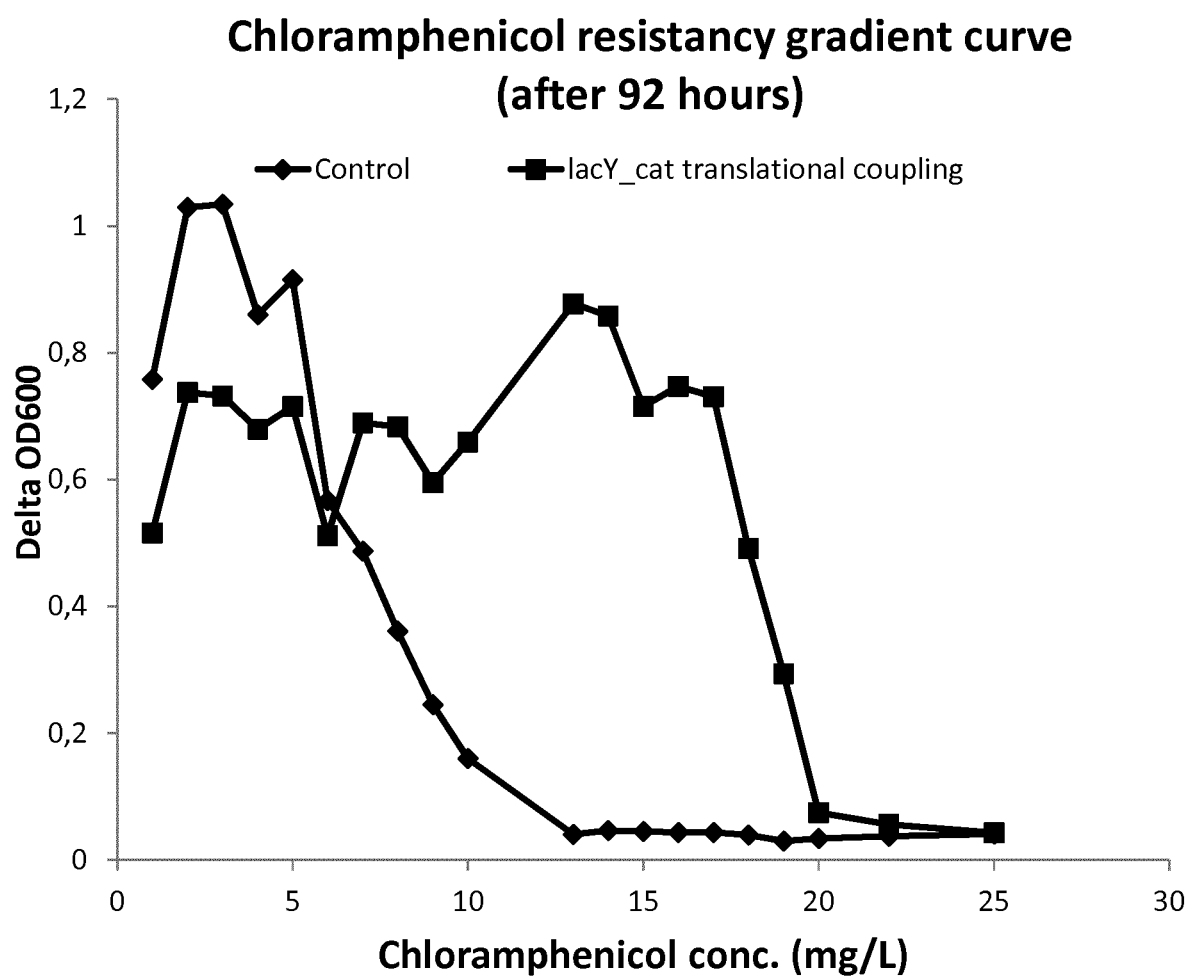
FIG. 9: Chloramphenicol resistance of a reference strain containing a reference plasmid pSC101 without a lactose permease translational coupled to a chloramphenicol resistance gene and a mutant strain with a lactose permease translational coupled to a chloramphenicol resistance gene. The X-axis shows the different chloramphenicol concentrations tested, the Y-axis shows the optical density of the culture after 92 hours of incubation. The reference strain shows growth retardation at a lower chloramphenicol screening than the mutant strain, which proofs that expression of lactose permease can be screened via translational coupling with an antibiotic resistance gene. Lactose permease expressing organisms can hence be selected from a mixture of non-expressing and expressing organisms in this manner.

Example 4: Detection of the Expression of a Lactose Transporter Translational Coupled with a Chloramphenicol Resistance Gene Two strains were constructed in which lactose permease was knockout out from the genome. In both strains a pSC101 plasmid containing a kanamycin resistance gene was transformed, with the difference that one of the plasmids contained a constitutively expressed lactose permease as described in Example 1 and 2, resulting in a reference strain MG1655ΔlacY pSC101_kan and the lacY_cat translational coupled strain MG1655ΔlacY pSC101_kan_lacY$_{synthetic}$_cat as described in Example 4 and FIG. 5. Both strains were grown in a minimal medium as described above at different chloramphenicol concentrations (between 0 and 30 mg/l). FIGS. 8 and 9 show after 48 and 92 hours of growth that the growth of reference strain is inhibited at a lower chloramphenicol concentration than the mutant lacY_cat translational coupled strain, which makes such a system an excellent screen for lactose permease expressing genetic constructs.

Example 5: Screening Procedure for Lactose Permease Expressing Mutants that do not Undergo Lactose Killing Similar to example 2, a mixture of two strains resistant to chloramphenicol were grown, one strain that does not undergo lactose killing and translational coupled to chloramphenicol and one strain with the chloramphenicol cassette but with the natural expression system of lactose permease. Both strains were grown in the medium as described in example 2 and mid exponential phase lactose was added as shown in example 2. The mutant strain that does not undergo lactose killing kept on growing while the other strain, that is lactose killing sensitive, stopped growing. At the end of the exponential phase, 0.1 ml of this culture was inoculated in a second shake flask with a similar medium as described above. Again, at OD 0.8 lactose was added arresting the growth of the lactose killing sensitive strain and further enriching the mutant strain that does not undergo lactose killing. After 5 repeats of this procedure a 99% enrichment of the mutant strain that does not undergo lactose killing was obtained, which is then easily isolated from the culture.

Example 6: Creation of Mutants of Lactose Permease Expression Cassettes

Sequence variants of promoters, ribosome binding sites, Kozak sequences, transcription terminators and lactose permease gene variants (with different codon usages) are ordered at gene synthesis vendors such as IDT, Geneart, Genscript, Gen9, . . . . The design of a promoter library for bacteria are based on the consensus sequence of bacterial promoters, with two conserved regions at −10 and −35 bp of the transcription start. The bases in between, before and after these conserved regions are then varied randomly with A, T, G or C, leading to promoters with different expression strengths. Alternatively, the conserved regions are varied and the surrounding sequence is kept fixed, which also leads to promoters with different strengths. These sequence mixtures are then cloned (via either Gibson Assembly, Golden Gate assembly, Cliva assembly, LCR or restriction ligation) (25, 36, 50, 79) in front of a translational coupled lactose permease leading to a library of expression cassettes of lactose permease that can be screened by means of the screening protocol described in Example 5.

An eukaryotic promoter library is created based on a core promoter (13). For *Saccharomyces cerevisiae* this promoter may be a heterologous TEF promoter pTEF1 which is enhanced with UAS sequences and is mutated to vary promoter strength (12). Such a promoter is ordered and cloned as described above in front of a translational coupled lactose permease and the final construct transformed into a yeast such as *Saccharomyces cerevisiae* on a plasmid or for integration into a chromosome.

The untranslated region consists for prokaryotes of a ribosome binding site and for eukaryotes of a Kozak sequence. Both sequences are randomized and cloned in front of the coding sequence as described above leading to a library of expression cassettes with different translational efficiencies. The randomization can be rationalized with tools such as RBS calculator which calculates the sequence translation efficiency correlation, and reducing the number of variants that have to be included into the library (67).

The codon usage is changed by means of changing the coding sequence of the gene without changing the amino acid sequence of the protein. This is called codon adaptation. The codon usages through the codon sequence is changed in such a way that more or less rare codons are introduced in certain regions, leading to altered expression efficiencies and folding efficiencies. A permease with only rare codons in its sequence (determined on an organism basis by means of the codon usage database (61)) show lower translation rates than permeases with a fully codon optimized sequence (with only codons with high occurrence in the target organism). In addition, the first codons of the coding sequence also influence the Kozak or ribosime binding site efficiency (62, 69, 78).

The transcription terminator region is varied by means of endogenous or exogenous transcription terminator sequences found in database (18, 26). These transcription terminators are also cloned similar to the method described above.

Example 7: Enrichment of Expression Cassettes that Express Lactose Permease and do not Lead to Lactose Killing The expression cassettes are created according to example 3 and 7. This leads to a library of expression cassettes of lactose permease. The expression cassettes that result in the expression of lactose permease are selected according to the methods of example 3 and 4. The expression cassettes, expression lactose permease, that do not lead to lactose killing are selected according to the methods described in Example 2 and 5. The selected expression cassettes are further analysed by sequencing and by the method described in example 2.

Example 8: Fermentative 2-fucosyllactose Production with a Fucosyltransferase Originating from *Helicobacter pylori* with *E. coli*

The mutant strain in which the genes lacZ, glgC, agp, pfkA, pfkB, pgi, arcA, iclR, wcaJ are knocked out and lacY was expressed via constitutive expression as described in example 1 and example 2 to ensure expression under all culturing conditions, was transformed further with a fucosyltransferase originating from *Helicobacter pylori* and a sucrose phosphorylase originating from *Bifidobacterium adolescentis*, which were also constitutively expressed. The constitutive promoters originate from the promoter library described by De Mey et al. 2007. This strain was cultured in a medium as described in the materials and methods, however with 30 g/l of sucrose and 50 g/l of lactose. This resulted in the formation of up to 1.5 g/l 2'-fucosyllactose Example 9: Fed Batch Production of 2-fucosyllactose with *E. coli*

A mutant strain was constructed via the genetic engineering methodologies described above with the following genotype: ΔlacZYAΔglgCΔagpΔpgiΔpfkA-P22-baSPΔpfkBΔarcAΔiclR::slΔwcaJΔlonΔadhE-P14-frk+ pCXP14-FT_*H. pylori* (a vector with sequence SEQ ID No 6, see FIG. 10) With lactose permease expression altered as described in example 1 and example 2. The promoter P22 and P14 originate from the promoter library constructed by De Mey et al (29) and was cloned similar to the methodology described by Aerts et al (1). "::sl" marks a scarless gene deletion, thus without a FRT site that remains in the chromosome.

This strain was cultured in a bioreactor as described above in materials and methods, in the mineral medium with 30 g/l of sucrose and 50 g/l of lactose. After the batch phase the bioreactor was fed with 500 g/l of sucrose, 50 g/l lactose and 1 g/l of magnesium sulphate heptahydrate. This led to the accumulation of 27.5 g/l of fucosyllactose in the supernatant.

Example 10: Production of lactoNtriose with *E. coli*

A mutant strain was constructed via genetic engineering with the methodologies described above expression a UDP-N-acetylglucosamine transferase, a sucrose phosphorylase and a L-glutamine:D-fructose-6-phosphate aminotransferase and a glucosamine uridyltransferase on a pBR322 plasmid with each a constitutive promoter from the promoter library of De Mey et al (29) and with a beta-lactamase selection marker. This vector was transformed in an *E. coli* mutant strain with genotype ΔlacZYAΔglgCΔagp::P14-frk-P22-BaSPΔpgiΔpfkAΔpfkB ΔnagABCDEΔmanAΔnanATEKΔmanXYZ expressing lactose permease constitutively as described above. This strain was cultivated in a shake flask as described above with lactose and sucrose as carbon sources, with or without additional glycerol. This production host did not undergo lactose killing and produced 62.5 and 55.3 mg/l lactoNtriose, respectively, from the added lactose.

Example 11: Construction of a Yeast *K. marxianus* Lactose Permease (p2) Knock in at the rDNA Locus First, plasmid p2a_2μ_Lac4 was used to transform into the *Saccharomyces cerevisiae* BY4742 wild type strain. Transformation was performed using a total of 4 μg of plasmid using the Gietz protocol (40). The transformed yeast cells were plated out on SD-CSM drop-out plates (without uracil). After two days, growth was observed on the plates and the yeast colonies were tested for presence of the desired plasmid. Colony PCR was carried out on all 33 colonies. All colonies tested positive for presence of the plasmid p2a_2μ_Lac4. Colony 5 was selected for further use. This colony was transformed with 2 μg double stranded linear DNA obtained from pJet_KI_p1_Lac12_t@rDNA. The transformed cells were plated on SD-CSM-Ura plates with lactose as the sole C-source. Three days after transformation, several colonies were sufficiently grown on to be tested for the presence of the Lac12 expression cassette in the *Saccharomyces* rDNA. Colony PCR was carried out on all colonies. All colonies tested positive for presence of the Lac12 expression cassette. Colony 6 was selected for further use (*Saccharomyces* KI_p1_Lac12_t@rDNA).

Example 12: Construction of a Yeast *K. marxianus* Lactose Permease (p2) Knock in at the rDNA Locus First, plasmid p2a_2μ_Lac4 was used to transform into the *Saccharomyces cerevisiae* BY4742 wild type strain. Transformation was performed using a total of 4 μg of plasmid using the Gietz protocol (40). The transformed yeast cells were plated out on SD-CSM drop-out plates (without uracil). After two days, growth was observed on the plates and the yeast colonies were tested for presence of the desired plasmid. Colony PCR was carried out on all 33 colonies. All colonies tested positive for presence of the plasmid p2a_2μ_Lac4. Colony 5 was selected for further use. This colony was transformed with 2 μg double stranded linear DNA obtained from pJet_KI_p2_Lac12_t@rDNA. The transformed cells were plated on SD-CSM-Ura plates with lactose as the sole C-source. Three days after transformation, several colonies were sufficiently grown on to be tested for the presence of the Lac12 expression cassette in the *Saccharomyces* rDNA. Colony PCR was carried out on all colonies. All colonies tested positive for presence of the Lac12 expression cassette. Colony 7 was selected for further use (*Saccharomyces* K1_p2_Lac12_t @rDNA).

Example 13: Growth on Lactose of a Wild Type Yeast Strain and 2 Mutant Yeast Strains A shake flask experiment as described in materials and methods was set up with the wild type *Kluyveromyces*, *Saccharomyces* KI_p1_Lac12_t@rDNA and *Saccharomyces* KI_p2_Lac12_t@rDNA. These strains were grown in a shake flask medium containing lactose as the sole C-source (20 g/L). As can be seen in Table 1, the mutant *Saccharomyces* strains grow as fast as the wild type *Kluyveromyces marcianus* lactis, which is known for fast growth on lactose (31). The constitutively expressed lactose permease thus ensures fast and efficient influx of lactose in the yeast cell.

TABLE 1

| Strain | $\mu_{max}$ |
|---|---|
| *Kluyveromyces marxianus lactis* | 0.14 |
| *Saccharomyces* KI_p1_Lac12_t@rDNA | 0.18 |
| *Saccharomyces* KI_p2_Lac12_t@rDNA | 0.18 |

Figure 11:
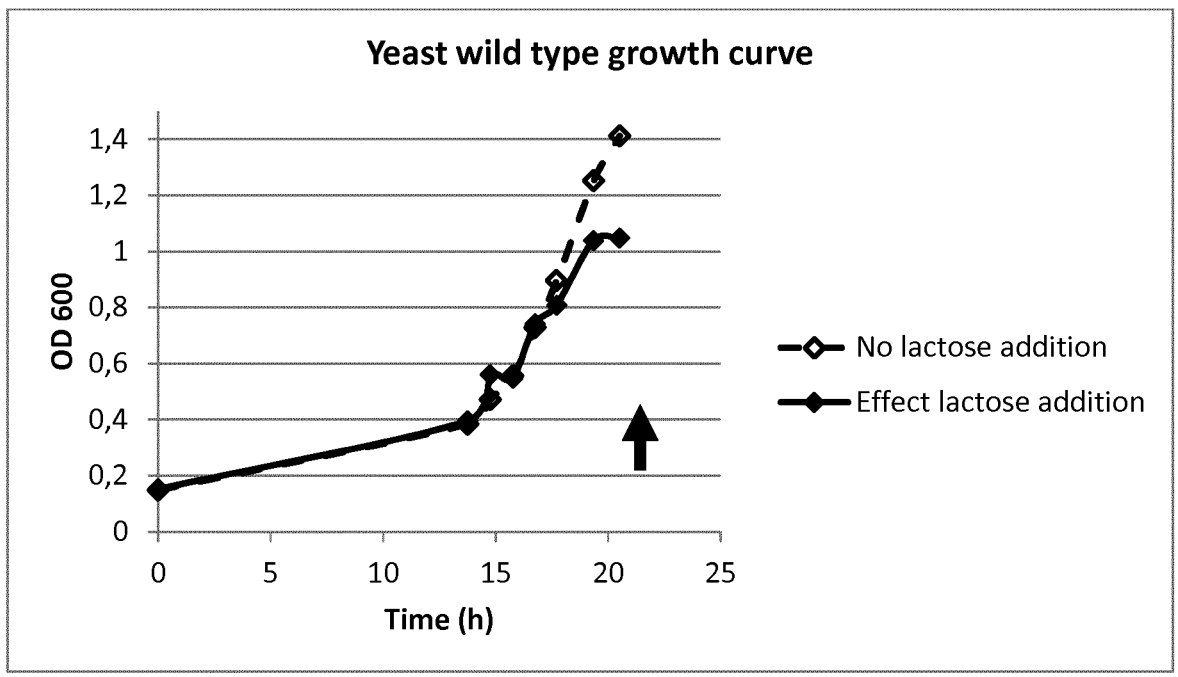
FIG. 11: Effect of lactose on a yeast wild type strain (*Kluyveromyces marxianus lactis*). At the arrow lactose was added to one of the cultures and growth of this culture stopped immediately, while the other strain continued to grow in the other culture.
Figure 12:
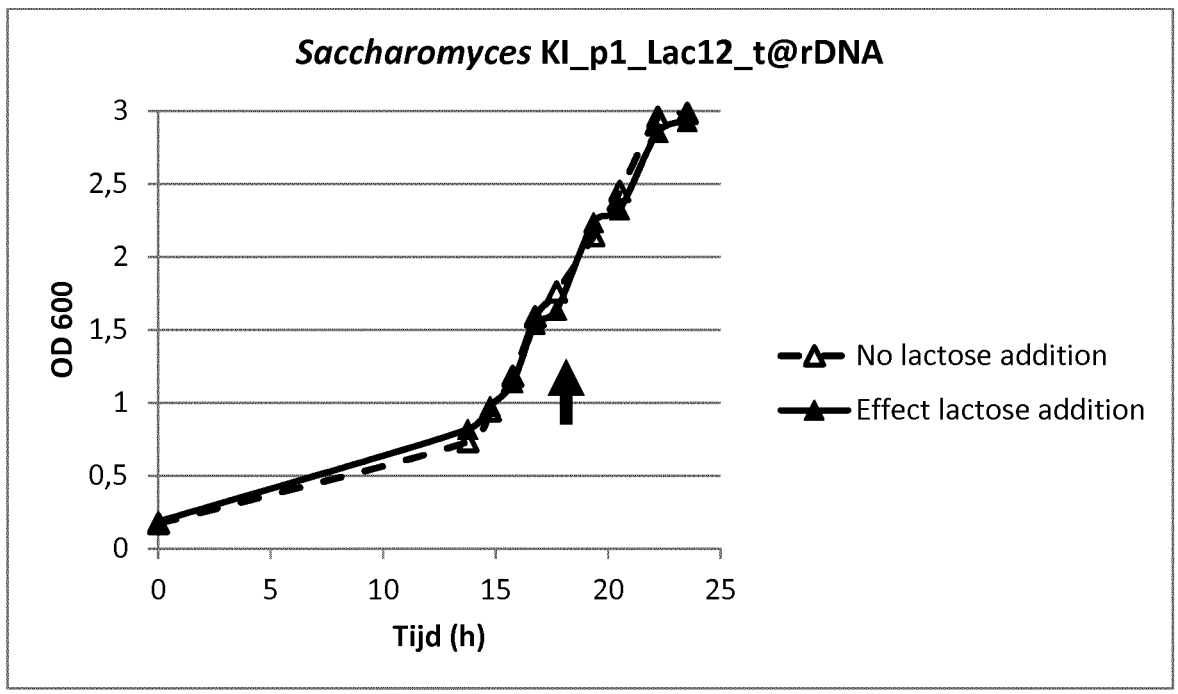
FIG. 12: Effect of lactose on yeast lactose transporter mutant strains (*Saccharomyces cerevisiae*) in which lactose transporter expression is altered by means of a synthetic constitutive promoter. The arrow indicates the moment on which lactose was added to the medium in one of the cultures. In this case no effect was observed on growth. Hence, these mutant strains can be selected in this manner.

Example 14: The Effect of Lactose on the Wild Type Yeast Strain and Mutant Yeast Strains that do not Undergo Lactose Killing A shake flask experiment as described in materials and methods was set up with the wild type *Kluyveromyces*, *Saccharomyces* KI_p1_Lac12_t@rDNA and *Saccharomyces* KI_p2_Lac12_t@rDNA. These strains were grown in a glucose shake flask medium (20 g/L glucose, as described in the materials and methods) and lactose (200 g/L stock solution was added resulting in a final concentration of 10 g/L) was added mid exponential phase. As can be seen in FIG. 11 and FIG. 12, the mutant strains do not undergo lactose killing. Yet, fast and efficient influx of lactose in these yeast cell was proven in example 13.

Example 15: Sequencing of Lactose Permease Expression Cassettes that do not Undergo Lactose Killing 46 colonies originating from the screening described above were sequenced, resulting in SEQ ID No 12-57 (FIG. 18). These sequences are promotor and RBS variants that do not result into lactose killing when expressed in *E. coli*. Note that this is a selection of an enormous amount of colonies that has been sequenced, hence, the screening methodology has resulted in much more sequences than shown in FIG. 18 and alternative library creation methodologies as described above will also lead other sequences than those shown in FIG. 18.

Example 16: Determination of $\mu_{MAX}$ of the Lactose Permease Expression Cassette Mutant Strains All strains were either started from LB-agar plate or started from cryovial and inoculated in 5.0 mL Luria broth medium (10 g Tryptone; 5 g yeast extract; 10 g NaCL). After growing o/n at 37° C., 1 mL of this preculture was added to a 500 mL shaker flask containing 100 mL minimal Lactose media (2.0 g/L NH$_4$Cl; 5.0 g/L; (NH$_4$)$_2$SO$_4$; 3.0 g/L KH$_2$PO$_4$, 7.3 g/L K$_2$HPO$_4$; 8.4 g/L MOPS; 0.5 g/L MgSO4×7H$_2$O; 0.5 g/L NaCL; 10 g/L Lactose; 0.4 mg/L Na$_2$EDTA×2H$_2$O; 0.03 mg/L H$_3$BO$_3$; 1.01 mg/L Thiamine HCL; 0.94 mg/L ZnCL$_2$; 0.5 mg/L CoCL$_2$×6H$_2$O; 0.38 mg/L CuCl$_2$×2H$_2$O; 1.59 mg/L MnCl$_2$×4H$_2$O; 3.6 mg/L CaCL$_2$ and 0.096 mg/L Na$_2$MoO$_4$×2H$_2$O); pH 7.0. After growing o/n at 37° C., both precultures were diluted with minimal lactose media to an OD$_{600}$ of 0.050. The suspension was then transferred to a 96 MTP plate (n=32), covered by an easy seal cover. OD measurements were performed every 10 minutes for 24 hours using the Infinite M200 pro (TECAN) under the following conditions: Temperature:37° C.+/−0.5; shaking 597 seconds; 2 mm shaking amplitude; 280 rpm; wavelength $OD_{600}$; Flash#10; settle time 150 ms).

Example 17: Characterization of Lactose Permease Expression Cassettes

One method to reduce or eliminate lactose killing is to significantly reduce or eliminate the activity of lactose permease (see Example 16). However, in light of the production of lactose or galactose based bioproducts, a high lactose influx into the cell is required. Here we proof that the lactose influx of the lactose killing resistant mutant strains is still comparable, equal or even higher than the lactose influx of the wild type organism that undergoes lactose killing. To this end, the novel lactose permease expression cassettes were introduced into a MG1655ΔlacY strain, which still expresses beta-galactosidase. The growth rate of these new strains are a measure for the lactose influx, because any strain that has a significant reduced expression in lactose permease expression will have a significantly reduced growth rate.

Figure 19:
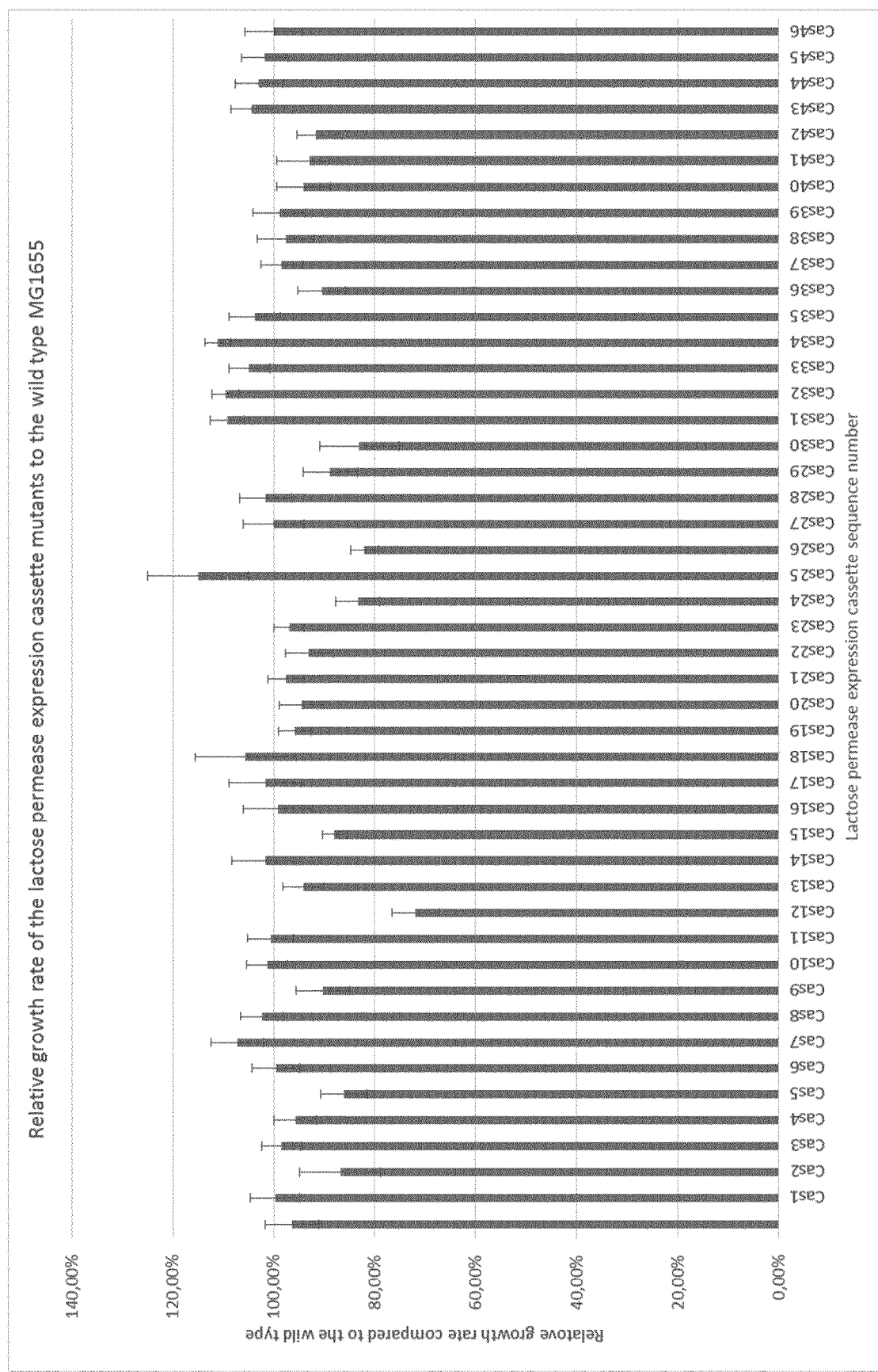
FIG. 19: Relative growth rate of the lactose permease expression cassettes, relative to the wild type. The error bars are standard deviations of at least 3 repeated measurements. The sequences correlating with the sequence numbers in the X-axis are shown in FIG. 18.

The results of this analysis is shown in FIG. 19. Nearly all strains shown in this figure have a growth rate equal or higher than the wild type, indicating a lactose permease activity and expression which is equal or higher than the wild type, however, in contrast to the wild type expression system, these expression cassettes do not result into lactose killing. This method is however limited by the expression of the beta galactosidase gene which becomes the rate limiting step for growth. Therefore, the expression of the lactose permease gene was measured via the above described translational coupling system described above. The minimal inhibition concentration (MIC) for chloramphenicol is indicative for the expression of the lactose permease gene and this was determined for each of the cassettes. The lowest MIC that still resulted into the same growth rate compared to the wild type was used as an indicator for the expression of the wild type lactose permease expression.

The cassettes with the lowest MIC that have the same growth rate as the wild type strain have a MIC of approximately 20 mg/l chloramphenicol. Mutant strains with a slightly lower growth rate have a MIC that ranges between 15 and 20 mg/l and mutant strains with equal or higher growth rate have a MIC between 20 and 80 mg/l. 85% of the sequences fall in the latter category, which means most sequences that were identified as lactose killing negative expression cassettes have a higher lactose permease expression, contrary to what has been previously described in literature.

Example 18: Construction of a lacIq Promoter Expression Cassette

Similar to the methodology described above a placIQ promoter was cloned in front of the lacY gene of *E. coli*. The final sequence of this construct is shown in FIG. 20.

Example 19: Other Used Promoters in Art that Undergo Lactose Killing

Figure 21:
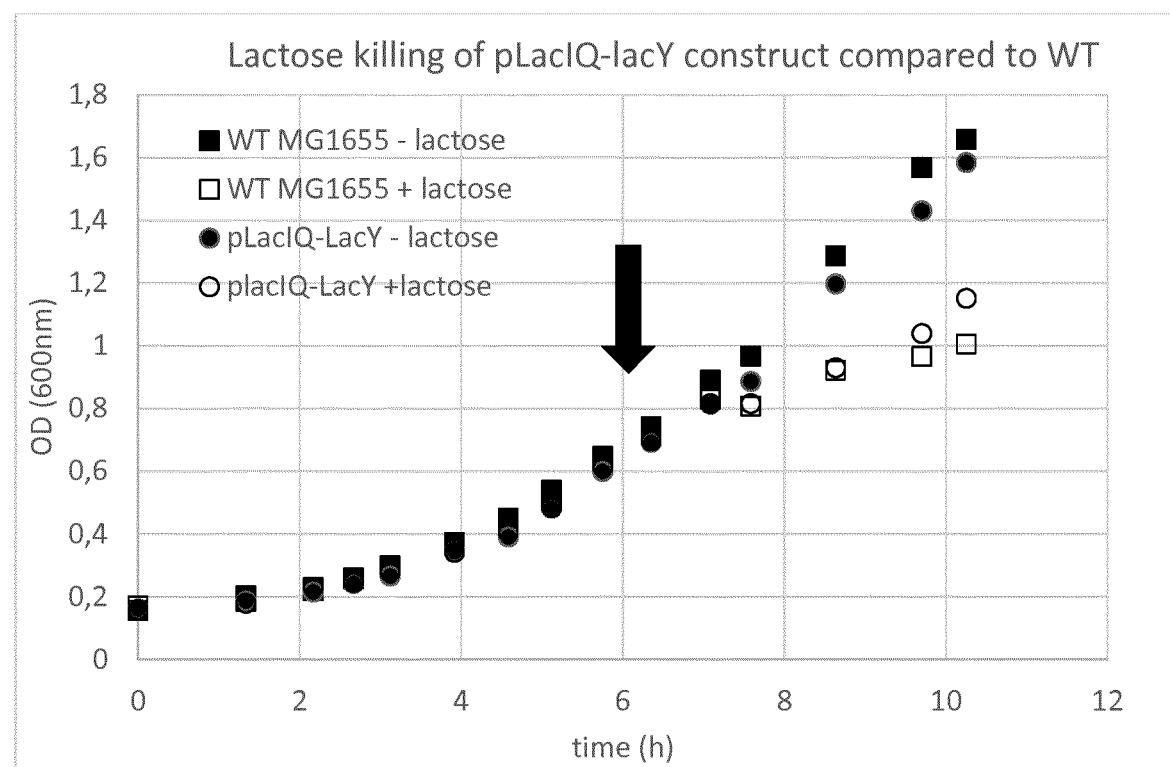
FIG. 21: Effect of lactose on an *E. coli* wild type strain and a placIQ_lacY mutant strain. Both strains were grown with and without the addition of lactose mid exponential phase. The arrow indicates the moment of lactose addition. The growth of both strains was severely impaired by addition of lactose.

The promoter placIQ is a promoter that has been used in the art for the expression of lactose permease in *E. coli*. The use of this promoter resulted into the uptake of lactose into the cell. However, the effect of such uptake was not tested. The growth rate on lactose of the wild type was not significantly different from the lacIq promoter (μmax of 0.1 and 0.11 $h^{-1}$ respectively), hence indicating a similar lactose uptake rate. A lactose killing screen of this lacIQ expression cassette proofed that this promoter also led to lactose killing (see FIG. 21). This proofs that there are specific promoter sequences lead to lactose killing and other sequences that do not lead to lactose killing. Rationalization of the sequences is not possible and trial and error of individual sequences is a laborious job which would lead to enormous costs, hence the methodology described above to identity the expression cassettes that do not undergo lactose killing is the perfect way to avoid lengthy and costly screening work.

Example 20: Production of lactoNtetraose with *S. cerevisiae*

The mutant strains constructed in Example 11 and 12 were transformed further with a β-1,4-galactosyltransferase and a β 1,3-N-acetylglucosaminyltransferase originating from *Neisseria meningitidis*, which were also constitutively expressed, using a standard yeast expression vector, for example as described by Lee et. al. (52). The strains were cultured in a medium as described in the materials and methods, however with 20 g/l of sucrose and 20 g/l of lactose. This resulted in the formation of up to 30 mg/l lactoNtetraose.

Example 21: Production of 2-fucosyllactose with *S. cerevisiae*

The mutant strains constructed in Example 11 and 12 were transformed further with a GDP-fucose synthase and a GDP-mannose 4,6-dehydratase of *E. coli* and a fucosyltransferase originating from *Helicobacter pylori*, which were also constitutively expressed, using a standard yeast expression vector, for example as described by Lee et. al. (52). The strains were cultured in a medium as described in the materials and methods, however with 20 g/l of sucrose and 20 g/l of lactose. This resulted in the formation of up to 10 mg/l 2 fucosyllactose.

REFERENCES

1. Aerts, D., T. Verhaeghe, M. De Mey, T. Desmet, and W. Soetaert. 2010. A constitutive expression system for high throughput screening. Engineering in Life Sciences 10:DOI: 10.1002/elsc.201000065.
2. Agrawal, N., P. V. N. Dasaradhi, A. Mohmmed, P. Malhotra, R. K. Bhatnagar, and S. K. Mukherjee. 2003. RNA Interference: Biology, Mechanism, and Applications. Microbiology and Molecular Biology Reviews 67:657-685.
3. Alper, H., C. Fischer, E. Nevoigt, and G. Stephanopoulos. 2005. Tuning genetic control through promoter engineering. Proceedings of the national academy of sciences of the United States of America 102:12678-12683.
4. Avihoo, A., I. Gabdank, M. Shapira, and D. Barash. 2007. In silico design of small RNA switches. IEEE Transactions on Nanobioscience 6:4-11.
5. Ayres, E. K., V. J. Thomson, G. Merino, D. Balderes, and D. H. Figurski. 1993. Precise deletions in large bacterial genomes by Vector-mediated Excision (VEX): The trfA gene of promiscuous plasmid RK2 is essential for replication in several gram-negative hosts. Journal of Molecular Biology 230:174-185.

6. Balbás, P., M. Alexeyev, I. Shokolenko, F. Bolivar, and F. Valle. 1996. A pBRINT family of plasmids for integration of cloned DNA into the *Escherichia coli* chromosome. Gene 172:65-69.
7. Balbas, P., and G. Gosset. 2001. Chromosomal editing in *Escherichia coli*. Molecular Biotechnology 19:1-12.
8. Barrett, A. R., Y. Kang, K. S. Inamasu, M. S. Son, J. M. Vukovich, and T. T. Hoang. 2008. Genetic tools for allelic replacement in *Burkholderia* species. Applied and Environmental Microbiology 74:4498-4508.
9. Beauprez, J. 2010. Metabolic modelling and engineering of *Escherichia coli* for succinate production. PhD. Ghent University, Ghent.
10. Beekwilder, J., H. M. van Rossum, F. Koopman, F. Sonntag, M. Buchhaupt, J. Schrader, R. D. Hall, D. Bosch, J. T. Pronk, A. J. A. van Maris, and J.-M. Daran. 2014. Polycistronic expression of a β-carotene biosynthetic pathway in *Saccharomyces cerevisiae* coupled to β-ionone production.
11. Biofuge, H. Thermo.
12. Blazeck, J., R. Garg, B. Reed, and H. S. Alper. 2012. Controlling promoter strength and regulation in *Saccharomyces cerevisiae* using synthetic hybrid promoters. Biotechnology And Bioengineering 109:2884-2895.
13. Blount, B. A., T. Weenink, S. Vasylechko, and T. Ellis. 2012. Rational Diversification of a Promoter Providing Fine-Tuned Expression and Orthogonal Regulation for Synthetic Biology. PLoS ONE 7:e33279.
14. Bode, L. 2012. Human milk oligosaccharides: Every baby needs a sugar mama. Glycobiology 22:1147-1162.
15. Bode, L. 2006. Recent Advances on Structure, Metabolism, and Function of Human Milk Oligosaccharides. The Journal of Nutrition 136:2127-2130.
16. Brenda Database 2006, posting date. [Online.]
17. Cabantous, S., T. C. Terwilliger, and G. S. Waldo. 2005. Protein tagging and detection with engineered self-assembling fragments of green fluorescent protein. Nat Biotech 23:102-107.
18. Cambray, G., J. C. Guimaraes, V. K. Mutalik, C. Lam, Q.-A. Mai, T. Thimmaiah, J. M. Carothers, A. P. Arkin, and D. Endy. 2013. Measurement and modeling of intrinsic transcription terminators. Nucleic Acids Research 41:5139-5148.
19. Canton, B., A. Labno, and D. Endy. 2008. Refinement and standardization of synthetic biological parts and devices. Nat Biotech 26:787-793.
20. Caspi, R., T. Altman, R. Billington, K. Dreher, H. Foerster, C. A. Fulcher, T. A. Holland, I. M. Keseler, A. Kothari, A. Kubo, M. Krummenacker, M. Latendresse, L. A. Mueller, Q. Ong, S. Paley, P. Subhraveti, D. S. Weaver, D. Weerasinghe, P. Zhang, and P. D. Karp. 2014. The MetaCyc database of metabolic pathways and enzymes and the BioCyc collection of Pathway/Genome Databases. Nucleic Acids Research 42:D459-D471.
21. Chen, X., and A. Varki. 2009. Advances in the Biology and Chemistry of Sialic Acids. ACS Chemical Biology 5:163-176.
22. Cherepanov, P. P., and W. Wackernagel. 1995. Gene disruption in *Escherichia coli*: TcR and KmR cassettes with the option of Flp-catalyzed excision of the antibiotic-resistance determinant. Gene 158:9-14.
23. Consortium, T. U. 2015. UniProt: a hub for protein information. Nucleic Acids Research 43:D204-D212.
24. Coppa, G. V., L. Zampini, T. Galeazzi, and O. Gabrielli. 2006. Prebiotics in human milk: a review. Digestive and Liver Disease 38:S291-S294.
25. Coussement, P., J. Maertens, J. Beauprez, W. Van Bellegem, and M. De Mey. 2014. One step DNA assembly for combinatorial metabolic engineering, p. 70-77, vol. 23.
26. Curran, K. A., A. S. Karim, A. Gupta, and H. S. Alper. 2013. Use of expression-enhancing terminators in *Saccharomyces cerevisiae* to increase mRNA half-life and improve gene expression control for metabolic engineering applications, p. 88-97, vol. 19.
27. Datsenko, K. A., and B. L. Wanner. 2000. One-step inactivation of chromosomal genes in *Escherichia coli* K-12 using PCR products. Proceedings of the national academy of sciences of the United States of America 97:6640-6645.
28. Davis, S. S. 1997. Biomedical applications of nanotechnology—implications for drug targeting and gene therapy. Trends in Biotechnology 15:217-224.
29. De Mey, M., J. Maertens, G. J. Lequeux, W. K. Soetaert, and E. J. Vandamme. 2007. Construction and model-based analysis of a promoter library for *E. coli*: an indispensable tool for metabolic engineering. BMC Biotechnology 7:34-48.
30. DiCarlo, J. E., J. E. Norville, P. Mali, X. Rios, J. Aach, and G. M. Church. 2013. Genome engineering in *Saccharomyces cerevisiae* using CRISPR-Cas systems. Nucleic Acids Research.
31. Drozdíková, E., M. Garaiová, Z. Csáky, M. Obernauerová, and I. Hapala. 2015. Production of squalene by lactose-fermenting yeast *Kluyveromyces lactis* with reduced squalene epoxidase activity. Letters in Applied Microbiology 61:77-84.
32. Dumon, C., B. Priem, S. L. Martin, A. Heyraud, C. Bosso, and E. Samain. 2001. In vivo fucosylation of lactoN-neotetraose and lactoN-neohexaose by heterologous expression of *Helicobacter pylori* α-1,3 fucosyltransferase in engineered *Escherichia coli*. Glycoconjugate Journal 18:465-474.
33. Dykhuizen, D., and D. Hartl. 1978. Transport by the lactose permease of *Escherichia coli* as the basis of lactose killing. Journal of Bacteriology 135:876-882.
34. Eames, M., and T. Kortemme. 2012. Cost-Benefit Tradeoffs in Engineered lac Operons. Science 336:911-915.
35. Edwards, J. S., R. Ramakrishna, C. H. Schilling, and B. O. Palsson. 1999. Metabolic flux balance analysis. Metabolic Engineering:13-57.
36. Engler, C., R. Gruetzner, R. Kandzia, and S. Marillonnet. 2009. Golden Gate Shuffling: A One-Pot DNA Shuffling Method Based on Type IIs Restriction Enzymes. PLoS ONE 4:e5553.
37. Filonov, G. S., J. D. Moon, N. Svensen, and S. R. Jaffrey. 2014. Broccoli: Rapid Selection of an RNA Mimic of Green Fluorescent Protein by Fluorescence-Based Selection and Directed Evolution. Journal of the American Chemical Society.
38. Galperin, M. Y., and G. R. Cochrane. 2009. Nucleic Acids Research annual Database Issue and the NAR online Molecular Biology Database Collection in 2009. Nucleic Acid Research 37:D1-4.
39. Ghazi, A., H. Therisod, and E. Shechter. 1983. Comparison of lactose uptake in resting and energized *Escherichia coli* cells: high rates of respiration inactivate the lac carrier. Journal of Bacteriology 154:92-103.
40. Gietz, R. D., R. H. Schiestl, A. R. Willems, and R. A. Woods. 1995. Studies on the transformation of intact yeast cells by the LiAc/SS-DNA/PEG procedure. Yeast 11:355-360.

41. Hammer, K., I. Mijakovic, and P. R. Jensen. 2006. Synthetic promoter libraries—tuning of gene expression. TRENDS in Biotechnology 24:53-55.
42. Hanahan, D., J. Jessee, and F. R. Bloom. 1991. Plasmid transformation of *Escherichia coli* and other bacteria. Methods in Enzymology 204:63-113.
43. Hebert, C. G., J. J. Valdes, and W. E. Bentley. 2008. Beyond silencing—engineering applications of RNA interference and antisense technology for altering cellular phenotype. Current opinion in biotechnology 19:500-505.
44. Heinemann, M., A. Kummel, R. Ruinatscha, and S. Panke. 2005. KEGG: Kyoto Encyclopedia of Genes and Genomes In silico genome-scale reconstruction and validation of the *Staphylococcus aureus* metabolic network. Biotechnol Bioeng 92:850-864.
45. Hoang, T. T., R. R. Karkhoff-Schweizer, A. J. Kutchma, and H. P. Schweizer. 1998. A broad-host-range Flp-FRT recombination system for site-specific excision of chromosomally-located DNA sequences: application for isolation of unmarked Pseudomonas aeruginosa mutants. Gene 212:77-86.
46. Jiang, W., D. Bikard, D. Cox, F. Zhang, and L. A. Marraffini. 2013. RNA-guided editing of bacterial genomes using CRISPR-Cas systems. Nat Biotech 31:233-239.
47. Kanehisa, M., M. Araki, S. Goto, M. Hattori, M. Hirakawa, M. Itoh, T. Katayama, S. Kawashima, S. Okuda, T. Tokimatsu, and Y. Yamanishi. 2008. KEGG for linking genomes to life and the environment. Nucleic Acid Research 36:D480-484.
48. Koizumi, S., T. Endo, K. Tabata, and A. Ozaki. 1998. Large-scale production of UDP-galactose and globotriose by coupling metabolically engineered bacteria. Nat Biotech 16:847-850.
49. Kojima, K. K., T. Matsumoto, and H. Fujiwara. 2005. Eukaryotic Translational Coupling in UAAUG Stop-Start Codons for the Bicistronic RNA Translation of the Non-Long Terminal Repeat Retrotransposon SART1. Molecular and Cellular Biology 25:7675-7686.
50. Kok, S. d., L. H. Stanton, T. Slaby, M. Durot, V. F. Holmes, K. G. Patel, D. Platt, E. B. Shapland, Z. Serber, J. Dean, J. D. Newman, and S. S. Chandran. 2014. Rapid and Reliable DNA Assembly via Ligase Cycling Reaction. ACS Synthetic Biology 3:97-106.
51. Kristensen, C. S., L. Eberl, J. M. Sanchez-Romero, M. Givskov, S. Molin, and V. De Lorenzo. 1995. Site-specific deletions of chromosomally located DNA segments with the multimer resolution system of broad-host-range plasmid RP4. Journal of Bacteriology 177:52-58.
52. Lee, M. E., W. C. DeLoache, B. Cervantes, and J. E. Dueber. 2015. A Highly Characterized Yeast Toolkit for Modular, Multipart Assembly. ACS Synthetic Biology 4:975-986.
53. Levin-Karp, A., U. Barenholz, T. Bareia, M. Dayagi, L. Zelcbuch, N. Antonovsky, E. Noor, and R. Milo. 2013. Quantifying Translational Coupling in *E. coli* Synthetic Operons Using RBS Modulation and Fluorescent Reporters. ACS Synthetic Biology 2:327-336.
54. Llaneras, F., and J. Picó. 2008. Stoichiometric modelling of cell metabolism. Journal of Bioscience and Bioengineering 105:1-11.
55. Lodi, T., and C. Donnini. 2005. Lactose-induced cell death of β-galactosidase mutants in *Kluyveromyces lactis*. FEMS Yeast Research 5:727-734.
56. Martin, P., O. Albagli, M. Poggi, K. Boulukos, and P. Pognonec. 2006. Development of a new bicistronic retroviral vector with strong IRES activity. BMC Biotechnology 6:4.
57. McShan, D. C., S. Rao, and I. Shah. 2003. PathMiner: predicting metabolic pathways by heuristic search. Bioinformatics 19:1692-1698.
58. Mendez-Perez, D., S. Gunasekaran, V. J. Orler, and B. F. Pfleger. 2012. A translation-coupling DNA cassette for monitoring protein translation in *Escherichia coli*. Metabolic Engineering 14:298-305.
59. Merighi, M., J. M. Mccoy, and M. I. Heidtman. 2012. Biosynthesis of human milk oligosaccharides in engineered bacteria. WO2012112777
60. Mutalik, V. K., J. C. Guimaraes, G. Cambray, C. Lam, M. J. Christoffersen, Q.-A. Mai, A. B. Tran, M. Paull, J. D. Keasling, A. P. Arkin, and D. Endy. 2013. Precise and reliable gene expression via standard transcription and translation initiation elements. Nat Meth 10:354-360.
61. Nakamura, Y., T. Gojobori, and T. Ikemura. 2000. Codon usage tabulated from international DNA sequence databases: status for the year 2000. Nucleic Acids Research 28:292.
62. Pechmann, S., and J. Frydman. 2012. Evolutionary conservation of codon optimality reveals hidden signatures of cotranslational folding. Nat Struct Mol Biol 20:237-243.
63. Peijnenburg, A. C. M., G. Venema, and S. Bron. 1990. Translational coupling in a penP-lacZ gene fusion in *Bacillus subtilis* and *Escherichia coli*: Use of AUA as a restart codon. 1990 221:267-272.
64. Pothoulakis, G., F. Ceroni, B. Reeve, and T. Ellis. 2014. The Spinach RNA Aptamer as a Characterization Tool for Synthetic Biology. ACS Synthetic Biology 3:182-187.
65. Rasmussen, L., H. Sperling-Petersen, and K. Mortensen. 2007. Hitting bacteria at the heart of the central dogma: sequence-specific inhibition. Microbial Cell Factories 6:24.
66. Rhodius, V. A., V. K. Mutalik, and C. A. Gross. Predicting the strength of UP-elements and full-length *E. coli* SigmaE promoters. Nucleic Acids Research 40:2907-2924.
67. Salis, H. M., E. A. Mirsky, and C. A. Voigt. 2009. Automated design of synthetic ribosome binding sites to control protein expression. Nat Biotech 27:946-950.
68. Seed, B., and J. Holgersson. 1999. Fucosyltransferase genes and uses thereof U.S. Pat. No. 5,858,752
69. Supek, F., \#352, and T. muc. 2010. On Relevance of Codon Usage to Expression of Synthetic and Natural Genes in *Escherichia coli*. Genetics 185:1129-1134.
70. Timblin, C. R., and M. L. Kahn. 1984. Lactose inhibits the growth of *Rhizobium meliloti* cells that contain an actively expressed *Escherichia coli* lactose operon. Journal of Bacteriology 158:1204-1207.
71. Varki, A. 1992. Diversity in the sialic acids. Glycobiology 2:25-40.
72. Waldo, G. S., B. M. Standish, J. Berendzen, and T. C. Terwilliger. 1999. Rapid protein-folding assay using green fluorescent protein. Nat Biotech 17:691-695.
73. Welch, M., S. Govindarajan, J. E. Ness, A. Villalobos, A. Gurney, J. Minshull, and C. Gustafsson. 2009. Design Parameters to Control Synthetic Gene Expression in *Escherichia coli*. PLoS ONE 4:e7002.
74. Williams, J., J. Luke, and C. Hodgson. 2009. Strain engineering by genome mass transfer: Efficient chromosomal trait transfer method utilizing donor genomic DNA and recipient recombineering hosts. Molecular Biotechnology 43:41-51.

75. Wilson, D. M., R. M. Putzrath, and T. H. Wilson. 1981. Inhibition of growth of Escherichia coli by lactose and other galactosides. Biochimica et Biophysica Acta (BBA)—Biomembranes 649:377-384.

76. Xu, X. J., L. M. Cao, and X. Chen. 2008. Elementary flux mode analysis for optimized ethanol yield in anaerobic fermentation of glucose with Saccharomyces cerevisiae. Chinese Journal of Chemical Engineering 16:135-142.

77. Yanase, H., J. Kurii, and K. Tonomura. 1988. Fermentation of lactose by Zymomonas mobilis carrying a Lac+ recombinant plasmid. Journal of Fermentation Technology 66:409-415.

78. Zhou, M., J. Guo, J. Cha, M. Chae, S. Chen, J. M. Barral, M. S. Sachs, and Y. Liu. 2013. Non-optimal codon usage affects expression, structure and function of clock protein FRQ. Nature 495:111-115.

79. Zou, R., K. Zhou, G. Stephanopoulos, and H. P. Too. 2013. Combinatorial Engineering of 1-Deoxy-D-Xylulose 5-Phosphate Pathway Using Cross-Lapping <italic>In Vitro</italic> Assembly (CLIVA) Method. PLoS ONE 8:e79557.

The invention claimed is:

1. A method for producing microorganisms which resist lactose killing when grown in an environment in which lactose is combined with another carbon source, wherein said method comprises:
   (a) mutating a lactose transporter gene within a microorganism, wherein said mutation results in altered expression of said lactose transporter gene compared to expression by corresponding wild-type lactose transporter gene, thereby providing a mutated microorganism;
   (b) growing said mutated microorganism on a medium comprising a carbon source which is not lactose;
   (c) adding lactose to said medium during growth of said mutated microorganism; and
   (d) selecting microorganisms which (i) resist lactose killing when grown on said medium comprising lactose and (ii) retain at least 50% of the lactose influx obtained with the wild-type expression cassette of said lactose transporter gene.

2. The method according to claim 1, wherein step (a) comprises introducing a heterologous promoter in front of the lactose transporter gene.

3. The method according to claim 2, wherein said introducing comprises deleting the endogenous lactose transporters from the genome and reintroducing them at another location within the genome of said microorganism.

4. The method according to claim 1, further comprising the step of detecting expression of said mutated lactose transporter gene via translational coupling with a reporter gene or via aptamer coupling.

5. The method according to claim 4, further comprising the step of detecting expression of said mutated lactose transporter gene via a genetic construct selected from the group consisting of SEQ ID NO: 2, 3, 4, and 5.

6. The method according to claim 1, wherein the lactose transporter encoded by said lactose transporter gene is a lactose permease.

7. The method according to claim 1, wherein said selected microorganism is a bacterium.

8. A microorganism which resists lactose killing when grown in an environment in which lactose is combined with another carbon source(s), and is obtainable by the method according to claim 1.

9. The method according to claim 1, wherein step (a) comprises introducing a lactose transporter expression cassette comprising a heterologous sequence in front of the lactose transporter gene, the lactose transporter expression cassette comprising a sequence as given by SEQ ID NO: 1, 7, 8, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56 or 57.

10. The method according to claim 9, wherein at least one gene of the selected microorganisms coding for at least one enzyme from the lactose degradation pathway and/or the galactose degradation pathway is knocked out.

11. The method according to claim 10, further comprising culturing the selected microorganisms for production of lactose- and/or galactose-based specialty products.

12. The method according to claim 11, wherein said lactose-based specialty products are selected from the group consisting of specialty carbohydrates, specialty glycolipids, specialty galactosylated compounds, and any combination thereof.

13. The method according to claim 12, wherein said specialty carbohydrates are selected from the group consisting of 2-fucosyllactose, 2'-fucosyllactose, 3-fucosyllactose, 2',3-difucosyllactose, lactoNtriose, lacto-N-tetraose, lacto-nN-tetraose, 3'-sialyllactose, and 6'-sialyllactose.

14. The method according to claim 1, wherein step (a) comprises mutating an untranslated region in front of the coding sequence of the lactose transporter gene, said untranslated region comprising a ribosome binding sequence or a Kozak sequence.

15. The method according to claim 1, wherein step (a) comprises modifying codons of the lactose transporter gene to codons used more frequently by the microorganism or to codons used rarely by the microorganism.

16. The method according to claim 1, wherein said selected microorganism is a yeast.

17. The method according to claim 1, wherein said selected microorganism is a fungus cell.

18. The method according to claim 2, wherein said introducing comprises introducing a heterologous promoter in front of the endogenous lactose transporters.

19. The method according to claim 2, wherein said introducing comprises knocking out the endogenous lactose promoter and introducing a heterologous promoter at the same location in the genome of said microorganism.

20. A method for producing a mutant lactose transporter expression cassette which facilitates resistance to lactose killing when microorganisms transformed with the expression cassette are grown in an environment in which lactose is combined with another carbon source, wherein said method comprises:
(a) creating mutants of a lactose transporter expression cassette, wherein said mutant exhibits altered expression of a lactose transporter gene compared to expression by a corresponding wild-type transporter gene;
(b) selecting for mutant expression cassettes of step (a) that ensure lactose transporter expression in a microorganism transformed with the expression cassette;
(c) selecting for mutants of step (b) that do not lead to lactose killing in a microorganism transformed with the expression cassette by growing microorganisms that have been transformed with the expression cassettes in a medium to which lactose is added during the mid exponential phase; and
(d) isolating the expression cassette from the transformed microorganisms of step (c) that (i) resist lactose killing when grown on medium comprising lactose and (ii) retain at least 50% of the lactose influx obtained with the wild-type expression cassette of said lactose transporter gene.

21. The method according to claim 20, wherein lactose transporter expression from the expression cassette is detected via translational coupling with a reporter gene and/or via aptamer coupling.

22. A method to produce microorganisms which resist the phenomenon of lactose killing when grown in an environment in which lactose is combined with another carbon source, wherein said method comprises:
(a) introducing an exogenous lactose transporter gene into the genome of a microorganism which lacks an endogenous lactose transporter gene, thereby providing a mutated microorganism capable of expressing said exogenous lactose transporter;
(b) growing said mutated microorganism on a medium comprising a carbon-source which is not lactose;
(c) adding lactose to said medium during growth of said mutated microorganism; and
(d) selecting microorganisms which (i) exhibit lactose influx and (ii) resist the phenomenon of lactose killing growing on said medium comprising lactose.

23. The method according to claim 22, wherein step (a) comprises introducing the exogenous lactose transporter gene into an operon that is expressed via a heterologous promoter.

24. The method according to claim 22, wherein step (a) comprises introducing into the genome a lactose transporter cassette comprising a heterologous promoter sequence in front of the exogenous lactose transporter gene.

25. The method according to claim 24, wherein the lactose transporter expression cassette comprises a sequence selected from the group consisting of SEQ ID NOs: 1, 7, 8, and 12-57.

26. The method according to claim 22, wherein step (a) comprises introducing into the genome a lactose transporter cassette comprising a mutation in the untranslated region sequence in front of the coding sequence of the exogenous lactose transporter gene, wherein said untranslated region sequence comprises a ribosome binding sequence or a Kozak sequence.

27. The method according to claim 22, wherein the lactose transporter encoded by said exogenous lactose transporter gene is a lactose permease.

28. The method according to claim 22, wherein at least one gene of the selected microorganisms coding for at least one enzyme from the lactose degradation pathway and/or the galactose degradation pathway is knocked out.

29. The method according to claim 28, further comprising culturing the selected microorganisms for production of lactose- and/or galactose-based specialty products.

30. The method according to claim 29, wherein said lactose-based specialty products are selected from the group consisting of specialty carbohydrates, specialty glycolipids, specialty galactosylated compounds, and any combination thereof.

31. The method according to claim 30, wherein said specialty carbohydrates are selected from the group consisting of 2-fucosyllactose, 2'-fucosyllactose, 3-fucosyllactose, 2',3-difucosyllactose, lactoNtriose, lacto-N-tetraose, lacto-nN-tetraose, 3'-sialyllactose, and 6'-sialyllactose.

32. The method according to claim 22, wherein step (a) further comprises modifying codons of the exogenous lactose transporter gene to codons used more frequently by the microorganism or to codons used rarely by the microorganism.

33. The method according to claim 22, wherein said selected microorganism is a bacterium.

34. The method according to claim 22, wherein said selected microorganism is a yeast.

35. The method according to claim 22, wherein said selected microorganism is a fungus cell.

* * * * *